US008012504B2

(12) United States Patent
Davis et al.

(10) Patent No.: US 8,012,504 B2
(45) Date of Patent: *Sep. 6, 2011

(54) SUSTAINED RELEASE OF GUAIFENESIN COMBINATION DRUGS

(75) Inventors: Robert D. Davis, Arlington, TX (US); Ralph W. Blume, Fort Worth, TX (US); Donald Jeffrey Keyser, Southlake, TX (US)

(73) Assignee: Reckitt Benckiser Inc., Parsippany, NJ (US)

( * ) Notice: Subject to any disclaimer, the term of this patent is extended or adjusted under 35 U.S.C. 154(b) by 335 days.

This patent is subject to a terminal disclaimer.

(21) Appl. No.: 10/413,530

(22) Filed: Apr. 15, 2003

(65) Prior Publication Data
US 2003/0215508 A1 Nov. 20, 2003

Related U.S. Application Data

(63) Continuation-in-part of application No. 10/406,557, filed on Apr. 4, 2003, and a continuation-in-part of application No. 10/406,574, filed on Apr. 4, 2003, which is a continuation-in-part of application No. 10/121,706, filed on Apr. 15, 2002, now Pat. No. 6,955,821, which is a continuation-in-part of application No. 09/559,542, filed on Apr. 28, 2000, now Pat. No. 6,372,252.

(51) Int. Cl.
*A61K 9/22* (2006.01)
(52) U.S. Cl. ......... 424/468; 424/452; 424/457; 424/474
(58) Field of Classification Search .................. 424/468
See application file for complete search history.

(56) References Cited

U.S. PATENT DOCUMENTS

| 2,738,303 | A | 3/1956 | Blythe |
| 3,065,143 | A | 11/1962 | Christenson et al. |
| 3,362,880 | A | 1/1968 | Sampson |
| 3,362,881 | A | 1/1968 | Klaus et al. |
| 3,458,622 | A | 7/1969 | Hill |
| 3,555,151 | A | 1/1971 | Kaplan et al. |
| 3,634,584 | A | 1/1972 | Poole |
| 3,870,790 | A | 3/1975 | Lowey et al. |
| 3,981,984 | A | 9/1976 | Signorino |
| 4,122,157 | A | 10/1978 | Huber |
| 4,140,755 | A | 2/1979 | Sheth et al. |
| 4,167,558 | A | 9/1979 | Sheth et al. |
| 4,226,849 | A | 10/1980 | Schor |
| 4,248,857 | A | 2/1981 | DeNeale et al. |
| 4,248,858 | A | 2/1981 | Guley et al. |
| 4,259,314 | A | 3/1981 | Lowey |
| 4,308,251 | A | 12/1981 | Dunn et al. |
| 4,309,404 | A | 1/1982 | DeNeale et al. |
| 4,309,405 | A | 1/1982 | Guley et al. |
| 4,357,469 | A | 11/1982 | Schor |
| 4,369,172 | A | 1/1983 | Schor et al. |
| 4,389,393 | A | 6/1983 | Schor et al. |
| 4,424,235 | A | 1/1984 | Sheth et al. |
| 4,540,566 | A | 9/1985 | Davis et al. |
| 4,543,370 | A | 9/1985 | Porter et al. |
| 4,552,899 | A | 11/1985 | Sunshine et al. |
| 4,680,323 | A | 7/1987 | Lowey |
| 4,695,464 | A | 9/1987 | Alderman |
| 4,699,779 | A | 10/1987 | Palinczar |
| 4,704,285 | A | 11/1987 | Alderman |
| 4,756,911 | A | 7/1988 | Drost et al. |
| 4,795,643 | A | 1/1989 | Seth |
| 4,798,725 | A | 1/1989 | Patel |
| 4,814,179 | A | 3/1989 | Bolton et al. |
| 4,826,688 | A | 5/1989 | Panoz et al. |
| 4,834,965 | A | 5/1989 | Martani et al. |
| 4,834,984 | A | 5/1989 | Goldie et al. |
| 4,851,392 | A | 7/1989 | Shaw et al. |
| 4,871,548 | A | 10/1989 | Edgren et al. |

(Continued)

FOREIGN PATENT DOCUMENTS
EP 0409781 B1 6/1994
(Continued)

OTHER PUBLICATIONS

The Physicians' Desk Reference: For Nonprescription Drugs and Dietary Supplements, 20th edition, 1999, Medical Economics Company, Inc, Montvale, NJ USA.*
Lacy et al (Drug Information Handbook. (1999) p. 481-482.*
FDA (Guidance for Industry—Bioavailability and bioequivalence studies for orally administered drug products—General considerations (Oct. 2000).*

(Continued)

*Primary Examiner* — Jake M. Vu
(74) *Attorney, Agent, or Firm* — Fitzpatrick, Cella, Harper & Scinto

(57) ABSTRACT

The invention relates to a novel pharmaceutical modified release formulation of guaifenesin and dextromethorphan. The formulation may comprise a hydrophilic polymer, preferably a hydroxypropyl methylcellulose, and a water-insoluble polymer, preferably an acrylic resin, in a ratio range of about one-to-one (1:1) to about nine-to-one (9:1), more preferably a range of about three-to-two (3:2) to about six-to-one (6:1), and most preferably in a range of about two-to-one (2:1) to about four-to-one (4:1) by weight. This formulation capable of providing therapeutically effective bioavailability of guaifenesin for at least twelve hours after dosing in a human subject. The invention also relates to a modified release product which has two portions: a first portion having an immediate release formulation of guaifenesin and a second portion having a sustained release formulation of guaifenesin, wherein one or both portions further comprises dextromethorphan. The modified release product has a maximum guaifenesin serum concentration equivalent to that of an immediate release guaifenesin tablet, and is capable of providing therapeutically effective bioavailability of guaifenesin for at least twelve hours after dosing in a human subject.

8 Claims, 45 Drawing Sheets

U.S. PATENT DOCUMENTS

| | | | |
|---|---|---|---|
| 4,900,557 A | 2/1990 | Dell et al. | |
| 4,968,508 A | 11/1990 | Oren et al. | |
| 4,971,805 A | 11/1990 | Kitanishi et al. | |
| 4,980,170 A | 12/1990 | Schneider et al. | |
| 4,983,398 A | 1/1991 | Gaylord et al. | |
| 4,990,341 A | 2/1991 | Goldie et al. | |
| 4,994,276 A | 2/1991 | Baichwal et al. | |
| 5,004,613 A | 4/1991 | Radebaugh et al. | |
| 5,032,406 A * | 7/1991 | Dansereau et al. | 424/472 |
| 5,047,248 A | 9/1991 | Calanchi et al. | |
| 5,085,865 A | 2/1992 | Nayak | |
| 5,098,715 A | 3/1992 | McCabe et al. | |
| 5,133,974 A | 7/1992 | Paradissis et al. | |
| 5,164,398 A | 11/1992 | Sims et al. | |
| 5,186,943 A | 2/1993 | Okada et al. | |
| 5,186,963 A | 2/1993 | Howman | |
| 5,200,193 A | 4/1993 | Radebaugh et al. | |
| 5,260,073 A | 11/1993 | Phipps | |
| 5,286,493 A | 2/1994 | Oshlack et al. | |
| 5,292,534 A | 3/1994 | Valentine et al. | |
| 5,326,571 A | 7/1994 | Wright et al. | |
| 5,368,861 A | 11/1994 | Ushimaru et al. | |
| 5,376,384 A | 12/1994 | Eichel et al. | |
| 5,395,626 A | 3/1995 | Kotwal et al. | |
| 5,403,593 A | 4/1995 | Royce | |
| 5,427,799 A | 6/1995 | Valentine et al. | |
| 5,445,829 A | 8/1995 | Paradissis et al. | |
| 5,451,409 A | 9/1995 | Rencher et al. | |
| 5,472,704 A | 12/1995 | Santus et al. | |
| 5,486,364 A | 1/1996 | King et al. | |
| 5,494,681 A | 2/1996 | Cuca et al. | |
| 5,529,791 A | 6/1996 | Deboeck et al. | |
| 5,576,022 A | 11/1996 | Yang et al. | |
| 5,593,694 A | 1/1997 | Hayashida et al. | |
| 5,650,169 A | 7/1997 | Conte et al. | |
| 5,656,296 A | 8/1997 | Khan et al. | |
| 5,662,933 A | 9/1997 | Baichwal et al. | |
| 5,738,874 A | 4/1998 | Conte et al. | |
| 5,773,031 A | 6/1998 | Shah et al. | |
| 5,780,057 A | 7/1998 | Conte et al. | |
| 5,807,580 A | 9/1998 | Luber | |
| 5,840,329 A | 11/1998 | Bai | |
| 5,945,123 A | 8/1999 | Hermelin | |
| 5,968,554 A | 10/1999 | Beiman et al. | |
| 5,993,858 A | 11/1999 | Crison et al. | |
| 6,120,802 A | 9/2000 | Breitenbach et al. | |
| 6,210,710 B1 | 4/2001 | Skinner | |
| 6,217,903 B1 | 4/2001 | Skinner | |
| 6,294,199 B1 * | 9/2001 | Conley et al. | 424/468 |
| 6,312,724 B1 | 11/2001 | Odidi et al. | |
| 6,372,252 B1 | 4/2002 | Blume et al. | |
| 6,475,521 B1 | 11/2002 | Timmins et al. | |
| 6,623,756 B1 | 9/2003 | Wilber et al. | |
| 6,838,094 B2 | 1/2005 | Grimmett et al. | |
| 6,955,821 B2 | 10/2005 | Davis et al. | |
| 2002/0022058 A1 | 2/2002 | Lovercheck | |
| 2002/0142044 A1 | 10/2002 | Vendola | |
| 2003/0012820 A1 | 1/2003 | Upadhyay | |
| 2003/0039691 A1 | 2/2003 | Waterman | |
| 2003/0091624 A1 | 5/2003 | Szymczak et al. | |
| 2003/0147952 A1 | 8/2003 | Lim et al. | |
| 2004/0018233 A1 | 1/2004 | Davis et al. | |
| 2004/0022851 A1 | 2/2004 | Davis et al. | |
| 2004/0033258 A1 | 2/2004 | Koike | |
| 2004/0156902 A1 | 8/2004 | Lee et al. | |
| 2004/0180085 A1 | 9/2004 | Ohkouchi et al. | |
| 2005/0095288 A1 | 5/2005 | Honea | |
| 2005/0152967 A1 | 7/2005 | Tengler et al. | |
| 2005/0276852 A1 | 12/2005 | Davis et al. | |

FOREIGN PATENT DOCUMENTS

| | | | |
|---|---|---|---|
| EP | 0 875 245 A2 | 9/1999 | |
| GB | 2255344 A | 11/1992 | |
| JP | 7277962 | 10/1995 | |
| WO | WO 87/00044 | 1/1987 | |
| WO | 94/06416 A1 | 3/1994 | |
| WO | 94/27557 A2 | 12/1994 | |
| WO | 95/20946 A1 | 8/1995 | |
| WO | 95/28148 A1 | 10/1995 | |
| WO | 96/04908 A1 | 2/1996 | |
| WO | 97/09042 A1 | 3/1997 | |
| WO | 98/05305 A1 | 2/1998 | |
| WO | 98/22091 A1 | 5/1998 | |
| WO | WO 98/22097 | 5/1998 | |
| WO | WO 00/33818 A1 | 6/2000 | |
| WO | WO 01/19901 A3 | 3/2001 | |

OTHER PUBLICATIONS

Bodmeier, R. et al, "Prolonged Release Multiple-Unit Dosage Forms Based on Water-Soluble Cellulosic Polymers or Aqueous Latexes," *Proceed. Intern. Sump. Control. Rel. Bioact. Mater.*, 18 (1991), Controlled Release Society, Inc.

Bauer et al., "Coated Pharmaceutical Dosage Forms," p. 83 (MedPharm Scientific Publishers 1998).

Request for Reexamination, filed Apr. 20, 2005, USPN 6,372,252, Issued Apr. 16, 2002.

Welling, P.G., "Oral Controlled Drug Administration: Pharmacokinetic Considerations", Drug Dev. Ind. Pharm., 9, 1185-1225 (1983).

Kim, C., "Pharmacokinetic Considerations in the Design of Controlled Release Dosage Forms," Controlled Release Dosage Form Design, ch. 11 (Technomic Publishing Co., Inc. 2000).

International Search Report dated Aug. 19, 2003 for International Application No. PCT/US03/11500, filed Apr. 15, 2003.

Physicians' Desk Reference: For Nonprescription Drugs and Dietary Supplements 807 (Medical Economics Company, Inc., 20th ed. 1999).

Ansel HC and Popovich NG. Pharmaceutical Dosage Forms and Drug Delivery Systems. Fifth Edition. Lea & Febiger. 1990. p. 64.

Bankser GS and Rhodes CT. Modern Pharmaceutics. Fourth Edition. Marcel Dekker, Inc. 2002. p. 83.

Curriculum Vitae of Peter Anthony Crooks, MSc, PhD, FRPharmS, CSci, CChem, FRSC (Jul. 2006).

United Research Laboratories and Mutual Pharmaceutical Company, Press Release: United Research Laboratories/Mutual Pharmaceutical Company Announce ANDA Filing for Guaifenesin Extended-Release Tablets, 600 mg and 1200 mg (Aug. 18, 2006), *at* http://www.urlmutual.com/guaifenesin_pr.htm.

Correspondence from E. Brendan Magrab, Esq., Vice President, Intellectual Property, United Research Laboratories, Inc. and Mutual Pharmaceutical Company, Inc. to Michael J. Valentino, President & Chief Executive Officer, Adams Respiratory Therapeutics, Inc., including Exhibits A and B and additional attachments (Aug. 22, 2006), *available at* http://www.urlmutual.com/guaifenesin2.pdf (excluding the additional attachments).

United Research Laboratories and Mutual Pharmaceutical Company, Press Release: United Research Laboratories/Mutual Pharmaceutical Company Formally Notifies Adams Respiratory Therapeutics of Its ANDA Filing for Guaifenesin Extended-Release Tablets, 600 mg and 1200 mg (Aug. 23, 2006), *at* http://www.urlmutual.com/guaifenesin_pr08232006.htm.

Correspondence from Joseph M. O'Malley, Jr., Esq., Attorney, Fitzpatrick, Cella, Harper & Scinto to E. Brendan Magrab, Esq., Vice President, Intellectual Property, United Research Laboratories, Inc. and Mutual Pharmaceutical Company, Inc., including attachment (Aug. 31, 2006), *available at* http://www.urlmutual.com/guaifenesin3.pdf.

Correspondence from James D. Veltrop, Attorney, Axinn, Veltrop & Harkrider LLP to Joseph M. O'Malley, Jr., Esq., Attorney, Fitzpatrick, Cella, Harper & Scinto, including attachment (Sep. 6, 2006), *available at* http://www.urlmutual.com/guaifenesin4.pdf.

United Research Laboratories and Mutual Pharmaceutical Company, Press Release: United Research Laboratories/Mutual Pharmaceutical Company Views Legal Response From Adams as Excessive and Disingenuous [sic] Attempt to Delay Competition (Sep. 7, 2006), *at* http://www.urlmutual.com/guaftenesin_pr09072006.htm.

Correspondence from James D. Veltrop, Attorney, Axinn, Veltrop & Harkrider LLP to Dominick A. Conde, Attorney, Fitzpatrick, Cella, Harper & Scinto (Sep. 28, 2006), *available at* http://www.urlmutual.com/guaifenesin6.pdf.

Declaration of Harry G. Brittain, Ph.D. (Sep. 28, 2006), *available at* http://www.urlmutual.com/guaifenesin7.pdf.

United Research Laboratories and Mutual Pharmaceutical Company, Press Release: Independent Expert Confirms View That Adams Has No Legal Basis for Pursuing Legal Action Against Mutual Pharmaceutical Company for Its Guaifenesin Extended-Release Tablets, 600 mg and 1200 mg (Sep. 28, 2006), *at* http://www.urlmutual.com/guaifenesin_pr09282006.htm.

*Adams Respiratory Therapeutics, Inc. v. Pharmaceutical Holdings Corp.*, Complaint for Patent Infringement and Certification Pursuant to Local Rule 11.2, including Exhibit A (D.N.J. Oct. 2, 2006).

*Adams Respiratory Therapeutics, Inc. v. Pharmaceutical Holdings Corp.*, Complaint for Patent Infringement, including Exhibit A (E.D. Pa. Oct. 4, 2006).

*Adams Respiratory Therapeutics, Inc. v. Pharmaceutical Holdings Corp.*, Answer and Counterclaims (E.D. Pa. Oct. 10, 2006).

*Adams Respiratory Therapeutics, Inc. v. Pharmaceutical Holdings Corp.*, Defendants' Motion for Summary Judgment (E.D. Pa. Oct. 17, 2006).

*Adams Respiratory Therapeutics, Inc. v. Pharmaceutical Holdings Corp.*, Defendants' Memorandum of Law in Support of a Motion for Summary Judgment (E.D. Pa. Oct. 17, 2006).

United Research Laboratories and Mutual Pharmaceutical Company, Press Release: Mutual Pharmaceutical Company Files Counter Suit Against Adams Respiratory Therapeutics (Oct. 17, 2006), *at* http://www.urlmutual.com/guaifenesin8.pdf.

Gudipati, M., In Vitro/In Vivo Correlation Approach for the Development of Drug Delivery Systems, Chapter 4, pp. 76-199 (University of Texas at Austin, Aug. 1990).

U.S. Department of Health and Human Services, Approved Drug Products with Therapeutic Equivalence Evaluations, pp. ix-x (19th ed. 1999).

The Merck Index, p. 812 (Merck Research Laboratories, 13th ed. 2001).

A. S. Hussain et al., "The Biopharmaceutics Classification System: Highlights of the FDA's Draft Guidance," Dissolution Technologies May 1999 Article #1, pp. 1-4 and Biopharmaceutics Classification Figures 1-3, pp. 1-2 (found at http://www.dissolutiontech.com/DTresour/599articles/Biopharm_Class2_copy.html and http://www.dissolutiontech.com/DTresour/599articles/BiopharmFig1-3.html on Oct. 15, 2009).

L. Kalantzi et al., "Biowaiver Monographs for Immediate Release Solid Oral Dosage Forms: Acetaminophen (Paracetamol)," J. Pharm. Sciences 95(1):4-14 (2006).

Lydia C. Kaus et al., "The Effect of in Vivo Dissolution, Gastric Emptying Rate, and Intestinal Transit Time on the Peak Concentration and Area-Under-the Curve of Drugs with Different Gastrointestinal Permeabilities," Pharm. Research 16(2):272-280 (1999).

Th. Knapp, "Der Einfluss von Guajakolderivaten auf die Ausscheidung der Glukuronsäure," J. Suisse de Chimie et Pharmacie LX(17):229-231, 245-248, 257-262 (1911), with certified translation.

Leszek Krowczynski, Extended-Release Dosage Forms 4-6, 51-58 (Dorota Porebska Brozyna trans. 1987).

C. Gordon Law, "Dose Proportionality," in Encyclopedia of Biopharmaceutical Statistics 295-297 (Shein-Chung Chow ed., 2d ed., revised and expanded, 2003).

Mark A. Longer & Joseph R. Robinson, "Sustained-Release Delivery Systems," in Remington's Pharmaceutical Sciences 1644-1661 (Alfonso R. Gennaro ed., 17th ed. 1985).

R. D. Maier, "Zum Nachweis von Guaiphenesin, einem Inhaltsstoff einiger Rezeptfreier Schlafmittel," Archives of Toxicology 45:123-131 (1980) PGFSN 054573-054583.

Carol N. Manners et al., "Distribution Coefficient, a Convenient Term for the Relation of Predictable Physico-Chemical Properties to Metabolic Processes," Xenobiotica 18(3):331-350 (1988) PGFSN 054769-054790.

Marilyn N. Martinez & Gordon L. Amidon, "A Mechanistic Approach to Understanding the Factors Affecting Drug Absorption: A Review of Fundamentals," J. Clin. Pharmacol. 42:620-643 (2002).

William R. Maynard, Jr. & Robert B. Bruce, "GLC Determination of Guaiacol Glyceryl Ether in Blood," J. Pharm. Sciences 59(9):1346-1348 (1970) PGFSN 054808-054811.

Hussain Y. Mohammed & Frederick F. Cantwell, "Liquid Chromatographic Analysis of Pharmaceutical Syrups Using Pre-Columns and Salt-Adsorption on Amberlite XAD-2," Analytical Chemistry 50(3):491-496 (1978) PFGSN 054812-054817.

Sakae Obara et al, "Evaluation of Several Grades of Hydroxypropyl Methylcellulose for Use in a Sustained-Release Tablet Matrix," Advances in Pharmaceutics and Pharm. Tech., pp. 212-219 (1989).

Rebecca L. Oberle & Gordon L. Amidon, "The Influence of Variable Gastric Emptying and Intestinal Transit Rates on the Plasma Level Curve of Cimetidine; An Explanation for the Double Peak Phenomenon," J. Pharmacokinetics & Biopharmaceutics 15(5):529-544 (1987).

Eugene L. Parrott, "Solid Dosage Forms," in Prescription Pharmacy, Dosage Formulation and Pharmaceutical Adjuncts 103-162 (Joseph B. Sprowls, Jr. ed., 2d ed. 1970) PGFSN 053056-053116.

James E. Polli et al., "Summary Workshop Report: Biopharmaceutics Classification System—Implementation Challenges and Extension Opportunities," J. Pharm. Sciences 93(6):1375-1381 (2004).

W. Steven Pray, Nonprescription Product Therapeutics 225-231 (1999).

Gurvinder Singh Rekhi et al., "Identification of Critical Formulation and Processing Variables for Metoprolol Tartrate Extended-Release (ER) Matrix Tablets," J. Controlled Release 59:327-342 (1999).

Manford Robinson et al., "Sustained Action Dosage Forms," in The Theory and Practice of Industrial Pharmacy 439-465 (Leon Lachman et al. eds., 2d ed. 1976) PGFSN 053001-053029.

P. E. Rolan, "The Assessment of Pharmacokinetics in Early Phase Drug Evaluation," in Handbook of Phase I/II Clinical Drug Trials 169-175 (John O'Grady & Pieter H. Joubert eds. 1997).

Earl Rosen & Joseph V. Swintosky, "Preparation of a 35S Labelled Trimeprazine Tartrate Sustained Action Product for Its Evaluation in Man," J. Of Pharmacy and Pharmacology, XII Supp.:237T-244T (1960) PGFSN 052992-053000.

Edward M. Rudnic & Mary Kathryn Kottke, "Tablet Dosage Forms," in Modern Pharmaceutics 333, 359-364 (Gilbert S. Banker & Christopher T. Rhodes eds., 3d ed., revised and expanded, 1996).

H. Rupprecht & D. Regensburg, "XIV. Silicium Dioxide and Silicates in Drug Delivery," in Controlled Drug Delivery 197-225 (Bernd W. Muller ed. 1987).

Leroy A. Shervington & Amal Shervington, "Guaifenesin," in Analytical Profiles of Drug Substances and Excipients 121-164 (Harry G. Brittain ed. 1998) PGFSN 054626-054671.

Patrick J. Sinko & Gordon L. Amidon, "Characterization of the Oral Absorption of β-Lactam Antibiotics. I. Cephalosporins: Determination of Intrinsic Membrane Absorption Parameters in the Rat Intestine In Situ," Pharm. Research 5(10) 645-650 (1988).

J. P. Skelly et al., "Scaleup of Oral Extended-Release Dosage Forms," Pharm. Research 10(12):1800-1805 (1993).

Dennis Smith et al., "Design of Drugs Involving the Concepts and Theories of Drug Metabolism and Pharmacokinetics," Medicinal Research Reviews 16(3):243-266 (1996) PGFSN 054600-054625.

Dennis Smith, "Can We Design Drugs with Low Variability," in Variability in Human Drug Response 251-261 (G.T. Tucker ed. 1999) PGFSN 054727-054737.

Dennis Smith & Barry Jones, "Variability in Drug Response as a Factor in Drug Design," Current Opinion in Drug Discovery & Development 2(1):33-41 (1999) PGFSN 054672-054681.

Joel T. Smith & Dutt V. Vinjamoori, "Rapid Determination of Logarithmic Partition Coefficients Between n-Octanol and Water Using Micellar Electrokinetic Capillary Chromatography," J. Chromatography B: Biomed. Applications 669(1):59-66 (1995) PGFSN 054759-054768.

David O. Thueson, Thueson's Guide to Over-The-Counter Drugs 54-57 (1995).

Klara Valkó et al., "Chromatographic Hydrophobicity Index by Fast-Gradient RP-HPLC: A High-Throughput Alternative to log P/log D," Anal. Chem. 69:2022-2029 (1997).

Daniel L. Wagner & Vikram S. Patel, "Steady-State Human Pharmacokinetics and Bioavailability of Guaifenesin and Pseudoephedrine in a Sustained-Release Tablet Relative to Immediate-Release Liquids," Int'l J. Pharmaceutics 114:171-176 (1995) PGFSN 053117-053122.

Zheng Wang et al., "In-Vivo and In-Vitro Evaluations of a Modified-Release Oral Dosage Form of Nifedipine by Hybridization of Hydroxypropyl-β-Cyclodextrin and Hydroxypropylcelluloses in Dogs," J. Pharm. Pharmacol. 46:505-507 (1994) PGFSN 052869-52871.

Hong Gi Yi et al., "Formulation of a Extended Release Tablet Containing Dexibuprofen," Arch. Pharm. Res. 31(12):1637-1643 (2008).

Lawrence X. Yu & Gordon L. Amidon, "A Compartmental Absorption and Transit Model for Estimating Oral Drug Absorption," Int'l J. Pharmaceutics 186:119-125 (1999).

Excipients and Delivery Systems for Pharmaceutical Formulations 123-124, 186-190 (D. R. Karsa & R. A. Stephenson eds. 1995).

Handbook of Pharmaceutical Excipients 252-261, 280-282, 424-427 (Ainley Wade & Paul J. Weller eds., 2d ed. 1994).

Handbook of Pharmaceutical Excipients 188-191 (Raymond C. Rowe et al. eds., 5th ed. 2006).

The Merck Index 716-717 (Susan Budavari et al. eds., 11th ed. 1989) PGFSN 054754-054758.

The Merck Index 776-777 (Susan Budavari et al. eds., 12th ed. 1996) PGFSN 054749-054753.

Pharmaceutical Dosage Forms, vol. 1, pp. 2, 241, 247-284 (Herbert A. Lieberman et al. eds., 2d ed., revised and expanded, 1989).

Pharmaceutical Dosage Forms, vol. 2, pp. 7-11, 13-20, 60-67 (Herbert A. Lieberman et al. eds., 2d ed., revised and expanded, 1990).

Physicians' Desk Reference to Pharmaceutical Specialties and Biologicals 216, 490-491 (5th ed. 1951) PGFSN 053917-053921.

Physicians' Desk Reference to Pharmaceutical Specialties and Biologicals 248, 517, 522, 570 (9th ed. 1955) PGFSN 053922-053927.

Physicians' Desk Reference to Pharmaceutical Specialties and Biologicals, passim (14th ed. 1960) PGFSN 053928-053941.

Physicians' Desk Reference to Pharmaceutical Specialties and Biologicals, passim (25th ed. 1971) PGFSN 053942-053983.

Physicians' Desk Reference to Pharmaceutical Specialties and Biologicals, passim (34th ed. 1980) PGFSN 053984-054044.

Physicians' Desk Reference to Pharmaceutical Specialties and Biologicals, passim (39th ed. 1985) PGFSN 054045-054130.

Physicians' Desk Reference to Pharmaceutical Specialties and Biologicals, passim (40th ed. 1986) PGFSN 054131-054206.

Physicians' Desk Reference to Pharmaceutical Specialties and Biologicals, passim (46th ed. 1992) PGFSN 054207-054265.

Physicians' Desk Reference to Pharmaceutical Specialties and Biologicals, passim (50th ed. 1996) PGFSN 054266-054360.

Physicians' Desk Reference to Pharmaceutical Specialties and Biologicals, passim (51st ed. 1997) PGFSN 054361-054442.

Physicians' Desk Reference to Pharmaceutical Specialties and Biologicals, passim (52d ed. 1998) PGFSN 054443-054508.

Physicians' Desk Reference to Pharmaceutical Specialties and Biologicals, passim (53d ed. 1999) PGFSN 054509-054572.

Random House Unabridged Dictionary 1780 (2d ed. 1993).

Textbook of Therapeutics: Drug and Disease Management 1255 (Eric T. Herfindal & Dick R. Gourley eds., 6th ed. 1996) PGFSN 054880-054882.

The United States Pharmacopeia / The National Formulary 19-20, 724-725 (USP 23/ NF 18 1995) PGFSN 054594-054599.

Webster's New World/Stedman's Concise Medical Dictionary 345 (1987).

Wilson and Gisvold's Textbook of Organic Medicinal and Pharmaceutical Chemistry 948-956 (John H. Block & John M. Beale, Jr. eds.,11th ed. 2004) PGFSN 054738-054748.

The Dow Chemical Company, Formulating Sustained Release Pharmaceutical Products With Methocel (1982).

Thomson Reuters Press Release, "Thomson Healthcare Launches PDRhealth.com" pp. 1-3 (Nov. 5, 2007) (found at http://thomsonreuters.com/content/press_room/tsh/mdx_ThomHcareLaunchesPDRhealth on Mar. 31, 2010).

47 FR 30002-30010 (Jul. 9, 1982) PGFSN 053860-053880.

54 FR 8494-8509 (Feb. 28, 1989) & PGFSN 053881-053916.

Food and Drug Administration, Compliance Program Guidance Manual, Program 7361.003, Chapter 61—OTC Drug Evaluation (May 2007).

Food and Drug Administration, Inspections, Compliance, Enforcement, and Criminal Investigations, CPG Sec. 450.200 Drugs—General Provisions and Administrative Procedures for Recognition as Safe and Effective (CPG 7132b.15) (found at fda.gov/ICECI/.../ucm074388.htm on Oct. 15, 2009).

U.S. Department of Health and Human Services, Food and Drug Administration, Center for Devices and Radiological Health, Guidance for Industry and FDA Staff, "Format for Traditional and Abbreviated 510(k)s" (Aug. 12, 2005).

U.S. Department of Health and Human Services, Food and Drug Administration, Center for Drug Evaluation and Research (CDER), Guidance for Industry, "Extended Release Oral Dosage Forms: Development, Evaluation, and Applications of In Vitro/In Vivo Correlations" (Sep. 1997).

U.S. Department of Health and Human Services, Food and Drug Administration, Center for Drug Evaluation and Research (CDER), Guidance for Industry, "SUPAC-MR: Modified Release Solid Oral Dosage Forms, Scale-Up and Postapproval Changes: Chemistry, Manufacturing, and Controls; In Vitro Dissolution Testing and In Vivo Bioequivalence Documentation" (Sep. 1997).

U.S. Department of Health and Human Services, Food and Drug Administration, Center for Drug Evaluation and Research (CDER), Guidance for Industry, "Waiver of In Vivo Bioavailability and Bioequivalence Studies for Immediate Release Solid Oral Dosage Forms Containing Certain Active Moieties/Active Ingredients Based on a Biopharmaceutics Classification System," Draft Guidance (Jan. 1999) PGFSN 054706-054719.

U.S. Department of Health and Human Services, Food and Drug Administration, Center for Drug Evaluation and Research (CDER), Guidance for Industry, "Statistical Approaches to Establishing Bioequivalence" (Jan. 2001).

U.S. Department of Health and Human Services, Food and Drug Administration, Center for Drug Evaluation and Research (CDER), Guidance for Industry, "Food-Effect Bioavailability and Fed Bioequivalence Studies" (Dec. 2002).

U.S. Department of Health and Human Services, Food and Drug Administration, Center for Drug Evaluation and Research (CDER), Guidance for Industry, "Power Blends and Finished Dosage Units—Stratified In-Process Dosage, Unit Sampling and Assessment," Draft Guidance (Oct. 2003).

U.S. Department of Health and Human Services, Food and Drug Administration, Center for Drug Evaluation and Research (CDER), Guidance for FDA Staff and Industry, "Marketed Unapproved Drugs—Compliance Policy Guide, Sec. 440.100 Marketed New Drugs Without Approved NDAs or ANDAs" (Jun. 2006).

Correspondence from David J. Horowitz, Esq., Director, Office of Compliance, Center for Drug Evaluation and Research, Food and Drug Administration to 45 entities, Guaifenesin single product Warning Letters (Oct. 11, 2002).

Correspondence from David J. Horowitz, Esq., Director, Office of Compliance, Center for Drug Evaluation and Research, Food and Drug Administration to 26 entities, Guaifenesin multiple products Warning Letters (Oct. 11, 2002).

Correspondence from Salomon Stavchansky Ph.D., Professor of Pharmaceutics and Alcon Centennial Professor of Pharmacy to R. Andrew Morgan, R.Ph., Adams Laboratories, Inc., Regulatory Affairs, including attachment (Feb. 1, 1994).

STN Search Report 1-5 (Oct. 7, 2009).

*Adams Respiratory Therapeutics, Inc., et al. v. Perrigo Company, et al.*, Plaintiffs' Opening Memorandum of Law on Claim Construction (W.D. Mich. May 21, 2009).

*Adams Respiratory Therapeutics, Inc., et al. v. Perrigo Company, et al.*, Declaration of Dr. Thomas Foster (W.D. Mich. May 21, 2009).

*Adams Respiratory Therapeutics, Inc., et al. v. Perrigo Company, et al.*, Defendants' Markman Brief in Support of Their Proposed Claim Construction (W.D. Mich. May 21, 2009).

*Adams Respiratory Therapeutics, Inc., et al. v. Perrigo Company, et al.*, Declaration of Walter G. Chambliss, Ph.D. (W.D. Mich. May 20, 2009).

*Adams Respiratory Therapeutics, Inc., et al.* v. *Perrigo Company, et al.*, Plaintiffs' Responsive Memorandum of Law on Claim Construction (W.D. Mich. Jun. 22, 2009).
*Adams Respiratory Therapeutics, Inc., et al.* v. *Perrigo Company, et al.*, Supplemental Declaration of Dr. Thomas Foster (W.D. Mich. Jun. 22, 2009).
*Adams Respiratory Therapeutics, Inc., et al.* v. *Perrigo Company, et al.*, Defendants' Responsive Brief to Plaintiffs' Opening Memorandum of Law on Claim Construction (W.D. Mich. Jun. 22, 2009).
*Adams Respiratory Therapeutics, Inc., et al.* v. *Perrigo Company, et al.*, Plaintiffs' Reply Memorandum of Law on Claim Construction (W.D. Mich. Jul. 8, 2009).
*Adams Respiratory Therapeutics, Inc., et al.* v. *Perrigo Company, et al.*, Second Supplemental Declaration of Dr. Thomas Foster (W.D. Mich. Jul. 8, 2009).
*Adams Respiratory Therapeutics, Inc., et al.* v. *Perrigo Company, et al.*, Defendants' Reply in Support of Defendants' Markman Brief in Support of Their Proposed Claim Construction (W.D. Mich. Jul. 8, 2009).
*Adams Respiratory Therapeutics, Inc., et al.* v. *Perrigo Company, et al.*, Supplemental Declaration of Walter G. Chambliss, Ph.D. (W.D. Mich. Jul. 7, 2009).
*Adams Respiratory Therapeutics, Inc., et al.* v. *Perrigo Company, et al.*, Order and Proposed Construction of Disputed Terms (W.D. Mich. Jul. 24, 2009).
*Adams Respiratory Therapeutics, Inc., et al.* v. *Perrigo Company, et al.*, Submission in Response to the Court's Proposed Construction of Disputed Terms (W.D. Mich. Aug. 7, 2009).
*Adams Respiratory Therapeutics, Inc., et al.* v. *Perrigo Company, et al.*, Defendants' Response to the Court's Jul. 24, 2009 Proposed Construction of Disputed Terms (W.D. Mich. Aug. 7, 2009).
*Adams Respiratory Therapeutics, Inc., et al.* v. *Perrigo Company, et al.*, Order Adopting Proposed Claim Construction (W.D. Mich. Aug. 24, 2009).
*Adams Respiratory Therapeutics, Inc., et al.* v. *Perrigo Company, et al.*, Memorandum in Support of Plaintiffs' Motion for Reconsideration of Court's Aug. 24, 2009 Order Regarding Claim Construction of the Term "Fully Bioavailable in the Subject's Stomach"—Redacted (W.D. Mich. Dec. 4, 2009).
*Adams Respiratory Therapeutics, Inc., et al.* v. *Perrigo Company, et al.*, Defendants' Opposition to Plaintiffs' Motion for Reconsideration of the Court's Aug. 24, 2009 Order Construing the Term "Fully Bioavailable in the Subject's Stomach"—Redacted (W.D. Mich. Dec. 14, 2009).
*Adams Respiratory Therapeutics, Inc., et al.* v. *Perrigo Company, et al.*, Defendants' Memorandum in Support of Their Motion for Summary Judgment of Non-Infringement—Redacted (W.D. Mich. Nov. 16, 2009).
*Adams Respiratory Therapeutics, Inc., et al.* v. *Perrigo Company, et al.*, Plaintiffs' Memorandum of Law in Opposition to Defendants' Motion for Summary Judgment of Non-Infringement—Redacted (W.D. Mich. Dec. 14, 2009).
*Adams Respiratory Therapeutics, Inc., et al.* v. *Perrigo Company, et al.*, Defendants' First Supplemental Responses and Objections to Adams' Second Set of Interrogatories (Nos. 13-14) (W.D. Mich. Jun. 30, 2009).
*Adams Respiratory Therapeutics, Inc., et al.* v. *Perrigo Company, et al.*, Expert Report of Walter G. Chambliss—Redacted (W.D. Mich. Aug. 10, 2009).
*Adams Respiratory Therapeutics, Inc., et al.* v. *Perrigo Company, et al.*, Rule 26 Expert Report of John T. Goolkasian, Esq. (W.D. Mich. Aug. 4, 2009).
*Adams Respiratory Therapeutics, Inc., et al.* v. *Perrigo Company, et al.*, Expert Report of Michael Mayersohn, Ph.D. (W.D. Mich. Aug. 7, 2009).
*Adams Respiratory Therapeutics, Inc., et al.* v. *Perrigo Company, et al.*, Responsive Expert Report of Dr. Gordon Amidon—Redacted (W.D. Mich. Sep. 18, 2009).
*Adams Respiratory Therapeutics, Inc., et al.* v. *Perrigo Company, et al.*, Responsive Expert Report of Dr. Thomas S. Foster—Redacted (W.D. Mich. Sep. 18, 2009).
*Adams Respiratory Therapeutics, Inc., et al.* v. *Perrigo Company, et al.*, Expert Report of Charles E. Van Horn (W.D. Mich. Sep. 18, 2009).
*Adams Respiratory Therapeutics, Inc., et al.* v. *Perrigo Company, et al.*, Reply Expert Report of Walter G. Chambliss, Ph.D.—Redacted (W.D. Mich. Oct. 9, 2009).
*Adams Respiratory Therapeutics, Inc., et al.* v. *Perrigo Company, et al.*, Reply Expert Report of John T. Goolkasian, Esq. (W.D. Mich. Oct. 7, 2009).
*Adams Respiratory Therapeutics, Inc., et al.* v. *Perrigo Company, et al.*, Reply Expert Report of Michael Mayersohn, Ph.D.—Redacted (W.D. Mich. Oct. 8, 2009).
*Adams Respiratory Therapeutics, Inc., et al.* v. *Perrigo Company, et al.*, Supplemental Expert Report of Dr. Gordon Amidon—Redacted (W.D. Mich. Nov. 14, 2009).
*Adams Respiratory Therapeutics, Inc., et al.* v. *Perrigo Company, et al.*, Second Supplemental Expert Report of Dr. Gordon Amidon—Redacted (W.D. Mich. Nov. 15, 2009).
J.B. Aluri & S. Stavchansky, "Determination of Guaifenesin in Human Plasma by Liquid Chromatography in the Presence of Pseudoephedrine," J. of Pharm. & Biomed. Analysis 11(9):803-808 (1993) PGFSN 053048-053055.
Gordon L. Amidon et al., "Estimating Human Oral Fraction Dose Absorbed: A Correlation Using Rat Intestinal Membrane Permeability for Passive and Carrier-Mediated Compunds," Pharm. Research 5(10):651-654 (1988).
Gordon L. Amidon et al., "Effects of Gravity on Gastric Emptying, Intestinal Transit, and Drug Absorption," J. Clin. Pharmacol. 31:968-973 (1991).
Gordon L. Amidon et al., "A Theoretical Basis for a Biopharmaceutic Drug Classification: The Correlation of in Vitro Drug Product Dissolution and in Vivo Bioavailability," Pharm. Research 12(3):413-420 (1995).
Howard C. Ansel et al., Pharmaceutical Dosage Forms and Drug Delivery Systems 213-225 (6th ed. 1995).
Howard C. Ansel et al., Pharmaceutical Dosage Forms and Drug Delivery Systems 229-243 (7th ed. 1999).
A. Arancibia et al., "Pharmacokinetics and Bioavailability of a Controlled Release Amoxicillin Formulation," Int'l J. of Clin. Pharmacol., Therapy and Toxicology 25(2):97-100 (1987).
B. Huet De Barochez et al., "Influence of Drug Solubility in the Formulation of Hydrophilic Matrices," Drug Development and Industrial Pharmacy 15(14-16):2197-2212 (1989).
Joeby Bass et al., "An Evaluation of the Effect of Food on the Oral Bioavailability of Sustained-Release Morphine Sulfate Tablets (Oramorph SR) After Multiple Doses," J. Clin. Pharmacol. 32(11):1003-1007 (1992).
Henning H. Blume & Barbara S. Schug, "The Biopharmaceutics Classification System (BCS): Class III Drugs—Better Candidates for BA/BE Waiver?" European J. Pharm. Sciences 9:117-121 (1999) PGFSN 054720-054726.
Rudolph H. Blythe, "The Formulation and Evaluation of Sustained Release Products," Drug Standards 26(1):1-7 (1958) PGFSN 053162-053170.
Gerald W. Bottenfield et al., "Safety and Tolerability of a New Formulation (90mg/kg/day Divided Every 12 h) of Amoxicillin/Clavulanate (Augmentin®) in the Empiric Treatment of Pediatric Acute Otitis Media Caused by Drug-Resistant *Streptococcus pneumoniae*," Pediatr. Infect. Dis. J. 17(10):963-968 (1998).
Harold G. Boxenbaum, "Physiological and Pharmacokinetic Factors Affecting Performance of Sustained Release Dosage Forms," Drug Dev. & Industrial Pharmacy 8(1):1-25 (1982).
David E. Bugay & W. Paul Findlay, Pharmaceutical Excipients 289 (1999).
Xianhua Cao et al., "Permeability Dominates in Vivo Intestinal Absorption of P-gp Substrate with High Solubility and High Permeability," Molecular Pharmaceutics 2(4):329-340 (2005).
Rong-Kun Chang & Joseph R. Robinson, "Sustained Drug Release from Tablets and Particles Through Coating," in Pharmaceutical Dosage Forms, vol. 3, pp. 199-302 (Herbert A. Lieberman et al. eds., 2d ed., revised and expanded, 1990).

Jun Chen et al., "Superporous Hydrogels as a Platform for Oral Controlled Drug Delivery," in Handbook of Pharmaceutical Controlled Release Technology 211-224 (Donald L Wise et al. eds. 2000).
Charles S. L. Chiao & Joseph R. Robinson, "Sustained-Release Drug Delivery Systems," in Remington: The Science and Practice of Pharmacy 1660-1675 (Alfonso R. Gennaro ed., 19th ed. 1995).
Yie W. Chien, Novel Drug Delivery Systems 747-776 (2d ed., revised and expanded, 1992).
Ferenc Csizmadia et al., "Prediction of Distribution Coefficient from Structure. 1. Estimation Model," J. Pharm. Sciences 86(7):865-871 (1997).
S. S. Davis et al., "Transit of Pharmaceutical Dosage Forms Through the Small Intestine," Gut 27:886-892 (1986).
J.G. Devane et al., "Pharmacokinetic and In-Vitro Characteristics of Sustained Release Verapamil Products," Drug Development and Industrial Pharmacy 16(7):1233-1248 (1990).
John Devane, "Oral Drug Delivery Technology: Addressing the Solubility/Permeability Paradigm," Pharm. Tech. 22(11):68-80 (1998).
John G. Devane & John G. Kelly, "Effect of Food on the Bioavailability of a Multiparticulate Sustained-Release Verapamil Formulation," Advances in Therapy 8(1):48-53 (1991).
M. R. Dobrinska & P. G. Welling, "Blood Levels from a Sustained-Release Dosage Form," J. Pharm. Sciences 17(10):1728-1729 (1998).
J.B. Dressman et al., "Physichemical Model for Dose-Dependent Drug Absorption," J. Pharm. Sciences 73(9):1274-1279 (1984).
J.B. Dressman et al., "Absorption Potential: Estimating the Fraction Absorbed for Orally Administered Compounds," J. Pharm. Sciences 74(5):588-589 (1985).
Natalie D. Eddington et al., "Development and Internal Validation of an In Vitro—In Vivo Correlation for a Hydrophilic Metoprolol Tartrate Extended Release Tablet Formulation," Pharm. Research 15(3):466-473 (1998).
M. El-Khawas et al., "Phenylpropanolamine Controlled-Release Tablets," Pharm. Ind. 55(4):392-395 (1993) PGFSN 052986-052991.
Mark G. Eller & Andrew A. Della-Coletta, "Absence of Effect of Food on Alprazolam Absorption from Sustained Release Tablets," Biopharmaceutics & Drug Disposition 11:31-37 (1990).
David Fleisher et al., "Drug, Meal and Formulation Interactions Influencing Drug Absorption After Oral Administration," Clin. Pharmacokinetics 36(3):233-254 (1999) PGFSN 05682-054705.
Arthur C. Guyton & John E. Hall, Textbook of Medical Physiology 793-802, 833-844 (9th ed. 1996).
Lester I. Harrison, "Kinetics of Absorption of a new Once-a-Day Formulation of Theophylline in the Presence and Absence of Food," J. Pharm. Sciences 82(6):644-648 (1993).
A.K. Hilton & P.B. Deasy, "In Vitro and In Vivo Evaluation of an Oral Sustained-Release Floating Dosage Form of Amoxycillin Trihydrate," Int 'l J. Pharmaceutics 86:79-88 (1992).
A.K. Hilton & P.B. Deasy, "Use of Hyroxypropyl Methylcellulose Acetate Succinate in an Enteric Polymer Matrix to Design Controlled-Release Tablets of Amoxicillin Trihydrate," J. Pharm. Sciences 82(7):737-743 (1993).
J. Hirtz, "The Gastrointestinal Absorption of Drugs in Man: A Review of Current Concepts and Methods of Investigation," Br. J. Clin. Pharmac. 19:77S-83S (1985).
Ammon Hoffman et al., "Pharmacodynamic and Pharmacokinetic Rationales for the Development of an Oral Controlled-Release Amoxicillin Dosage Form," J. Controlled Release 54:29-37 (1998).
H. E. Huber et al., "Utilization of Hydrophilic Gums for the Control of Drug Release from Tablet Formulations I. Disintegration and Dissolution Behavior," J. Pharm. Sciences 55(9):974-976 (1966).
*Adams Respiratory Therapeutics, Inc., et al.* v. *Perrigo Company, et al.*, Defendants' Reply Memorandum in Support of Their Motion for Summary Judgment of Non-Infringement (W.D. Mich. Dec. 28, 2009).
*Adams Respiratory Therapeutics, Inc., et al.* v. *Perrigo Company, et al.*, Opinion [regarding Plaintiffs' motion for reconsideration and Defendants' motion for summary judgment] (W.D. Mich. Feb. 11, 2010).
*Adams Respiratory Therapeutics, Inc., et al.* v. *Perrigo Company, et al.*, Order Reconsidering and Vacating in Part Opinion and Order Regarding Claim Construction (W.D. Mich. Mar. 3, 2010).
*Adams Respiratory Therapeutics, Inc., et al.* v. *Perrigo Company, et al.*, Non-Confidential Brief of Plaintiffs—Appellants Adams Respiratory Therapeutics, Inc., Adams Respiratory Operations, Inc., and Adams Respiratory Products, Inc. (Fed. Cir. Mar. 24, 2010).
*Reckitt Benckiser Inc.* v. *Watson Laboratories, Inc.*—Florida & Watson Pharmaceuticals, Inc., Amended Complaint for Patent Infringement (S.D. Fla. Oct. 23, 2009).
*Reckitt Benckiser Inc.* v. *Watson Laboratories, Inc.*—Florida & Watson Pharmaceuticals, Inc., Defendants Watson Laboratories, Inc.—Florida and Watson Pharmaceuticals, Inc.'s Answer and Counterclaims to Plaintiff's Amended Complaint (S.D. Fla. Oct. 29, 2009).
*Reckitt Benckiser Inc.* v. *Watson Laboratories, Inc.*—Florida & Watson Pharmaceuticals, Inc., Reckitt Benckiser's Answer to Watson Laboratories, Inc.—Florida and Watson Pharmaceuticals, Inc.'s Oct. 29, 2009 Counterclaims (S.D. Fla. Nov. 23, 2009).
Drituss G and Q-Bid LA, Qualitest 011, produced by Perrigo Company et al. in the *Adams Respiratory Therapeutics, Inc. et al.* v. *Perrigo Company et al.* (W.D. Mich.) litigation in Aug. 2008.
Q-Bid LA label, Qualitest 015, Apr. 1994.
Q-Bid LA label, Qualitest 017, May 1999.
Drituss G and Q-Bid LA, Vintage 011, produced by Perrigo Company et al. in the *Adams Respiratory Therapeutics, Inc. et al.* v. *Perrigo Company et al.* (W.D. Mich.) litigation in Aug. 2008.
Drituss G label, Vintage 012, Dec. 2001.
Drituss G label, Vintage 013, Dec. 2001.
Guaifenesin Long-Acting Tablets, Vintage 014, Dec. 2001.
Q-Bid LA label, Vintage 015, Apr. 1994.
Q-Bid LA label, Vintage 016, Feb. 1999.
Q-Bid LA label, Vintage 017, May 1999.
Guaifenesin Sustained-Release Tablets and Guaifenesin/Dextromethorphan Hydrobromide Sustained-Release Tablets, Vintage 018, Mar. 2001.
*Adams Respiratory Therapeutics, Inc., et al.* v. *Perrigo Company, et al.*, NonConfidential Brief for Defendants-Appellees (Fed. Cir. Apr. 23, 2010).
*Adams Respiratory Therapeutics, Inc., et al.* v. *Perrigo Company, et al.*, Non-Confidential Reply Brief of Plaintiffs-Appellants (Fed. Cir. May 3, 2010).
*Adams Respiratory Therapeutics, Inc., et al.* v. *Perrigo Company, et al.*, Opinion (Fed. Cir. Aug. 5, 2010).
*Reckitt Benckiser Inc.* v. *Watson Laboratories, Inc.*—Florida, Defendant Watson Laboratories, Inc—Florida's [Redacted] Amended Answer and Counterclaims to Plaintiffs Amended Complaint (S.D. Fla. Aug. 2, 2010).
*Reckitt Benckiser Inc.* v. *Watson Laboratories, Inc.*—Florida & Watson Pharmaceuticals, Inc., Defendant Watson Laboratories, Inc.—Florida's Claim Construction Brief (S.D. Fla. Sep. 10, 2010).
*Reckitt Benckiser Inc.* v. *Watson Laboratories, Inc.*—Florida & Watson Pharmaceuticals, Inc., Declaration of Thomas Dowling, Pharm.D., Ph.D., In Support of Defendant Watson Laboriatories [sic], Inc.—Florida's Claim Construction Brief (S.D. Fla. Sep. 10, 2010).
*Reckitt Benckiser Inc.* v. *Watson Laboratories, Inc.*—Florida & Watson Pharmaceuticals, Inc., Declaration of Gilbert S. Baker Ph.D., D.Sc., In Support of Defendant Watson Laboratories, Inc.—Florida's Claim Construction Brief (S.D. Fla. Sep. 10. 2010).
*Reckitt Benckiser Inc.* v. *Watson Laboratories, Inc.*—Florida, Plaintiffs Opening Memorandum of Law in Support of Its Motion for a Markman Hearing and to Construe Certain Language of the Asserted Claims (S.D. Fla. Sep. 10, 2010).
*Reckitt Benckiser Inc.* v. *Watson Laboratories, Inc.*—Florida, Declaration of Dr. Thomas Foster (S.D. Fla. Sep. 10, 2010).
*Reckitt Benckiser Inc.* v. *Watson Laboratories, Inc.*—Florida, Declaration of Dr. Gordon Amidon (S.D. Fla. Sep. 10, 2010).
*Reckitt Benckiser Inc.* v. *Watson Laboratories, Inc.*—Florida, Plaintiffs Memorandum of Law in Response to Watson's Sep. 10 Markman Brief, Public Version (S.D. Fla. Sep. 24, 2010).
*Reckitt Benckiser Inc.* v. *Watson Laboratories, Inc.*—Florida, Supplemental Declaration of Dr. Gordon Amidon, Public Version (S.D. Fla. Sep. 24, 2010).
*Reckitt Benckiser Inc.* v. *Watson Laboratories, Inc.*—Florida, Supplemental Declaration of Dr. Thomas Foster, Public Version (S.D. Fla. Sep. 24, 2010).

*Reckitt Benckiser Inc.* v. *Watson Laboratories, Inc.*—Florida & Watson Pharmaceuticals, Inc., Defendant Watson Laboratories, Inc.—Florida's Opposition to Plaintiffs Motion for a Markman Hearing and to Construe Certain Language of the Asserted Claims (S.D. Fla. Sep. 24, 2010).

*Reckitt Benckiser Inc.* v. *Watson Laboratories, Inc.*—Florida, Plaintiffs Memorandum of Law in Reply to Watson's Sep. 24 Opposition Markman Brief, Public Version (S.D. Fla. Oct. 1, 2010).

*Reckitt Benckiser Inc.* v. *Watson Laboratories, Inc.*—Florida & Watson Pharmaceuticals, Inc., Defendant Watson Laboratories, Inc.—Florida's Reply in Support of Claim Construction Brief (S.D. Fla. Oct. 1, 2010).

*Reckitt Benckiser Inc.* v. *Watson Laboratories, Inc.*—Florida & Watson Pharmaceuticals, Inc., Declaration of Thomas Dowling, Pharm.D., Ph.D., In Support of Defendant Watson Laboriatories [sic], Inc.—Florida's Claim Construction Brief (S.D. Fla. Oct. 1, 2010).

*Reckitt Benckiser Inc.* v. *Watson Laboratories, Inc.*—Florida, Reckitt Benckiser Inc.'s Reply to Watson Laboratories, Inc.—Florida's Amended Counterclaims (S.D. Fla. Nov. 12, 2010).

*Reckitt Benckiser Inc.* v. *Watson Laboratories, Inc.*—Florida, Order of Partial Dismissal (S.D. Fla. Dec. 6, 2010).

*Reckitt Benckiser Inc.* v. *Watson Laboratories, Inc.*—Florida, Claim Construction Order (S.D. Fla. Jan. 12, 2010).

*Reckitt Benckiser Inc.* v. *Watson Laboratories, Inc.*—Florida, Redacted Findings of Fact and Conclusions of Law (S.D. Fla. Feb. 18, 2011).

*Reckitt Benckiser Inc.* v. *Watson Laboratories, Inc.*—Florida, Non-Confidential Brief on Behalf of Plaintiff-Appellant Reckitt Benckiser, Inc. (Fed. Cir. Mar. 17, 2011).

*Reckitt Benckiser Inc.* v. *Watson Laboratories, Inc.*—Florida, Non-Confidential Brief For Defendant—Appellee Watson Laboratories, Inc.—Florida (Fed. Cir. Apr. 18, 2011).

\* cited by examiner

SUSTAINED RELEASE OF GUAIFENESIN COMBINATION DRUGS

CROSS-REFERENCE TO RELATED APPLICATIONS

This application is a continuation-in-part of U.S. patent application Ser. No. 10/406,557 which was filed on Apr. 4, 2003 and U.S. patent application Ser. No. 10/406,574 which was filed on Apr. 4, 2003 both of which are a continuation-in-part of U.S. patent application Ser. No. 10/121,706 which was filed on Apr. 15, 2002 now U.S. Pat. No. 6,955,821 which is a continuation-in-part of U.S. Pat. No. 6,372,252 which was filed on Apr. 28, 2000 as application Ser. No. 09/559,542 and issued on Apr. 16, 2002 all of which are hereby incorporated in their entirety by reference.

BACKGROUND OF THE INVENTION

The invention is directed to a modified release formulation for oral administration comprising combinations of guaifenesin and optionally at least one additional drug and methods of manufacture thereof. In particular, the invention is directed to a sustained release formulation which maintains a therapeutically effective blood concentration of guaifenesin and optionally the additional drug for a duration of about twelve hours. The invention further relates to combinations which demonstrate a maximum serum concentration equivalent to an immediate release tablet, while maintaining therapeutically effective blood concentration for about twelve hours.

Sustained release pharmaceutical formulations provide a significant advantage over immediate release formulations to both clinicians and their patients. Sustained release dosage forms provide for fewer daily dose administrations than their immediate release counterparts. For example, a standard dosage regimen for a 400 mg immediate release drug with a short half-life, such as guaifenesin, requires administration three times within twelve hours to maintain adequate bioavailability to achieve the desired therapeutic effect. This results in a series of three serum concentration profiles in the patient showing a rapid increase of drug followed by a similar rapid decrease. As a result, patients are provided with only a short window of the appropriate blood concentration of the medicament for optimum therapy. A 1200 mg sustained release dosage form, on the other hand, may require administration once every twelve hours to achieve therapeutic effect. Sustained release dosage forms generally control the rate of drug absorption, to avoid excessive drug absorption while maintaining effective blood concentration of the drug to provide a patient with a consistent therapeutic effect over an extended duration of time.

Besides reducing the frequency of dosing and providing a more consistent therapeutic effect, sustained release dosage forms generally help reduce side effects caused by a drug. Because sustained release dosage forms deliver the drug in slow, incremental amounts versus the cyclic high and low concentrations of immediate release formulations, it is easier for a patient's body to digest the drug, thereby avoiding undesirable side-effects. For patients who self-administer therapies, sustained release dosage forms generally result in greater compliance due to the lower frequency of dosing, lower quantity of dosage units to be consumed, and reduced undesired side-effects.

Generally, sustained release formulations contain drug particles mixed with or covered by a polymer material, or blend of materials, which is resistant to degradation or disintegration in the stomach and/or in the intestine for a selected period of time. Release of the drug may occur by leeching, erosion, rupture, diffusion or similar actions depending upon the nature of the polymer material or polymer blend used.

Conventionally, pharmaceutical manufacturers have used hydrophilic hydrocolloid gelling polymers such as hydroxypropyl methylcellulose (hydroxypropyl methylcellulose is also known as hypromellose and is used interchangeably throughout the application), hydroxypropyl cellulose, or Pullulan to formulate sustained release tablets or capsules. These polymers first form a gel when exposed to an aqueous environment of low pH thereby slowly diffusing the active medicament that is contained within the polymer matrix. When the gel enters a higher pH environment such as that found in the intestines, however, it dissolves resulting in a less controlled drug release. To provide better sustained release properties in higher pH environments, some pharmaceutical manufacturers use polymers which dissolve only at higher pHs, such as acrylic resins, acrylic latex dispersions, cellulose acetate phthalate, and hydroxypropyl methylcellulose phthalate, either alone or in combination with hydrophilic polymers.

Generally, these formulations are prepared by combining the medicament with a finely divided powder of the hydrophilic polymer, or the hydrophilic and water-insoluble polymers. These ingredients are mixed and granulated with water or an organic solvent and the granulation is dried. The dry granulation is then usually further blended with various pharmaceutical additives and compressed into tablets.

Although these types of formulations have been successfully used to manufacture dosage forms that demonstrate sustained release properties, these formulations generally do not have the desired release profile or serum concentration of medicament over an extended period of time. These sustained release formulations generally result in a delay in the appearance of drug in the blood stream, thereby delaying therapeutic effect. Additionally, when the drug does appear, its maximum serum concentration ($C_{max}$) is lower than the maximum concentration required for the most effective therapeutic result. Furthermore, most formulations that claim twelve hour potency release almost all of their drug within six to eight hours, making the formulation less therapeutically effective towards the end of the twelve hour period. To prevent blood serum concentrations of drug from falling below a therapeutically effective level ($C_{min}$) at extended time periods, many manufacturers increase the drug strength of the dosage form. The increase in drug strength, however, results in a concomitant increase in side-effects.

Other pharmaceutical manufacturers have made tablets and capsules containing a combination of an immediate release formulation and a sustained release formulation to improve the release profile of certain sustained release dosage forms. Although this solution improves the $C_{max}$ and length of time before the drug appears in the blood stream in some formulations, the extended therapeutic effect is not improved.

Furthermore, medicaments have different solubility properties and pH dependencies, which affect dissolution rate and bioavailability. Bioavailability can also be affected by a number of factors such as the amounts and types of adjuvants used, the granulation process, compression forces (in tablet manufacturing), surface area available for dissolution and environmental factors such as agitation in the stomach and the presence or absence of food. Due to these numerous factors, specific formulations play an important role in the preparation of prolonged action solid dosage forms, particularly in the preparation of solid dosage forms that achieve appropriate bioavailability for optimum therapeutic effect.

Guaifenesin, 3-(2-methoxyphenoxy)-1,2-propanediol, is an expectorant that increases respiratory tract fluid secretions and helps to loosen phlegm. By reducing the viscosity of secretions, guaifenesin increases the efficiency of a cough reflex and of ciliary action in removing accumulated secretions from trachea and bronchi. Guaifenesin is readily absorbed from the intestinal tract and is rapidly metabolized and excreted in urine. Guaifenesin has a typical plasma half-life of approximately one hour. The rapid metabolism and excretion of guaifenesin provides only a short window of therapeutic effectiveness when immediate release dosage is used.

Pseudoephedrine hydrochloride is an orally active sympathomimetic amine and exerts a decongestant action on the nasal mucosa. Pseudoephedrine produces peripheral effects similar to those of ephedrine and central effects similar to, but less intense than, amphetamines. It has the potential for excitatory effects. At the recommended oral dose, it has little or no pressor effect in normotensive adults. Pseudoephedrine has been shown to have a mean elimination half-life of 4-6 hours.

Dextromethorphan acts centrally to elevate the threshold for coughing. It has no analgesic or addictive properties. The major circulating metabolite is dextrorphan.

The need exists for a sustained release dosage form of guaifenesin alone and in combinations, which are capable of sustaining therapeutic effective for extended periods of time. Further the need exists for sustained release dosage forms of guaifenesin alone and in combination which results in a $C_{max}$ equivalent to that of an immediate release formulation, appears in the blood stream as quickly as an immediate release formulation, and sustains the therapeutic effect.

SUMMARY OF THE INVENTION

The invention relates to strategies and designs in formulations of modified release guaifenesin and guaifenesin combination dosage forms. This invention provides sustained release pharmaceutical formulation comprising guaifenesin and at least one additional drug. The sustained release formulation (SR) may comprise a combination of at least one hydrophilic polymer and at least one water-insoluble polymer. The total weight ratio of hydrophilic polymer to water-insoluble polymer may be in a range of about one-to-one (1:1) to about nine-to-one (9:1), more preferably in a range of about three-to-two (3:2) to about six-to-one (6:1), and most preferably in a range of about two-to-one (2:1) to about four-to-one (4:1). When a tablet comprising the sustained release formulation is exposed to an aqueous medium of low pH, such as that found in the stomach, the polymer combination gels causing guaifenesin and the drug(s) to diffuse from the gel. When the tablet passes to the intestines where an aqueous medium of higher pH is present, the gel begins to dissolve, thereby releasing guaifenesin and/or the drug(s) in controlled amounts. The tablet is capable of releasing therapeutically effective amounts of guaifenesin over an extended period, e.g. twelve or more hours and at least one additional drug immediately, over an extended period, or both.

This invention also encompasses a modified release composition which comprises two portions (e.g. a bi-layer tablet, or capsule), an immediate release formulation (IR) and a sustained release formulation (SR). Each formulation comprises a specific quantity of guaifenesin and may optionally contain at least one additional drug. The immediate release formulation is formulated to dissolve in aqueous acidic medium, such as that found in the stomach, to quickly release guaifenesin contained within the portion, and optionally quickly release the at least one additional drug. The sustained release portion may comprise a combination of hydrophilic polymer and a water-insoluble polymer in a ratio range of about one-to-one (1:1) to about nine-to-one (9:1), more preferably a range of about three-to-two (3:2) to about six-to-one (6:1), and most preferably from about two-to-one (2:1) to about four-to-one (4:1). Likewise, the sustained release portion may also contain the additional drug(s).

The invention also relates to sustained release preparations of the type described above in the form of capsules having beads or granules of both immediate release formulation and beads or granules of sustained release formulation. The beads may comprise a mixture of discrete beads each having only one of the SR or IR formulations or may comprise beads containing both SR and IR formulations associated in a single bead, or combinations of the foregoing. Alternatively, the sustained release formulation may comprise a core that is coated by a layer of the immediate release formulation to form a single tablet. For purpose of illustration only, the invention will be described in detail in the context of the bi-layered tablet embodiment. It should be understood that for either the immediate release and/or the sustained release portion the guaifenesin and optionally the additional drug may be mixed within the same matrix portion or comprise separate release portions which are then either compressed or mixed for capsules (e.g. comprise separate beads or granules) etc.

A bi-layer tablet demonstrates a maximum serum concentration ($C_{max}$) and time of availability in the blood stream that are equivalent to an immediate release tablet. The bi-layer tablet also provides sustained release of guaifenesin over about a twelve hour period from one dose. The bi-layer tablet further maintains serum concentration levels of guaifenesin at a therapeutically effective level for about a twelve hour period without an increase in dosage strength. As the bi-layer tablet may also contain at least one additional drug, the additional drug can be formulated within the sustained release formulation, immediate release formulation, or both. In one embodiment, the bi-layer tablet maintains serum concentration levels of at least one additional drug at a therapeutically effective level for about a twelve hour period without an increase in dosage strength.

In another embodiment, the tablets and capsules of the invention provide a $C_{min}$ which is above the necessary therapeutically effective level for a period of 10 hours, more preferably 12 or more hours. In a more preferred embodiment, a tablet or capsule of the invention provides the above describe $C_{min}$ characteristics and provides the necessary $C_{max}$ to mimic an immediate release product to obtain symptom relief. In a more preferred embodiment, the delivery system provides the above describe $C_{min}$ characteristics and provides the necessary $C_{max}$ to mimic an immediate release product to obtain symptom relief within a substantially similar $T_{max}$ period to an immediate release profile.

In another embodiment of the invention, the delivery system provides a $C_{max}$ which does not result in an equivalent $C_{max}$ of an immediate release product but does provide a $C_{max}$ which is therapeutically effect to relieve systems while reducing the likelihood of side effects due to an increased $C_{max}$.

The invention also relates to methods of manufacturing sustained release formulations and bi-layer tablets. An example of a manufacturing method for a sustained release formulation comprises mixing a hydrophilic polymer and active ingredients in a mixer, adding water to the mixture and continuing to mix and chop, drying the mixture to obtain hydrophilic polymer encapsulated granules, milling and screening the resulting granulation, and blending it with various pharmaceutical additives, additional hydrophilic polymer, and water insoluble polymer. The formulation may then be tableted and may further be film coated with a protective coating which rapidly dissolves or disperses in gastric juices.

An example of a bi-layer tablet manufacturing method comprises blending a quantity of guaifenesin and optionally, at least one drug with various excipients, colorants, and/or other pharmaceutical additives to form an immediate release formulation, separately blending another quantity of guaifenesin and optionally at least one drug with a hydrophilic polymer, a water-insoluble polymer, and various excipients, colorants, and/or other pharmaceutical additives to form a sustained release formulation, and compressing a quantity of the immediate release formulation with a quantity of the sustained release formulation to form a bi-layer tablet. The tablet may then optionally be coated with a protective coating which rapidly dissolves or disperses in gastric juices.

Other objects, advantages and embodiments of the invention are described below and will be obvious from this description and practice of the invention.

BRIEF DESCRIPTION OF THE DRAWINGS

FIG. 20 is a graph demonstrating the plasma concentration of three different 120 mg pseudoephedrine dosages for treatments A, B, and C of example 13.

FIG. 21 depicts guaifenesin concentrations of various formulations and dosage strength.

DETAILED DESCRIPTION OF THE INVENTION

Figure 1:
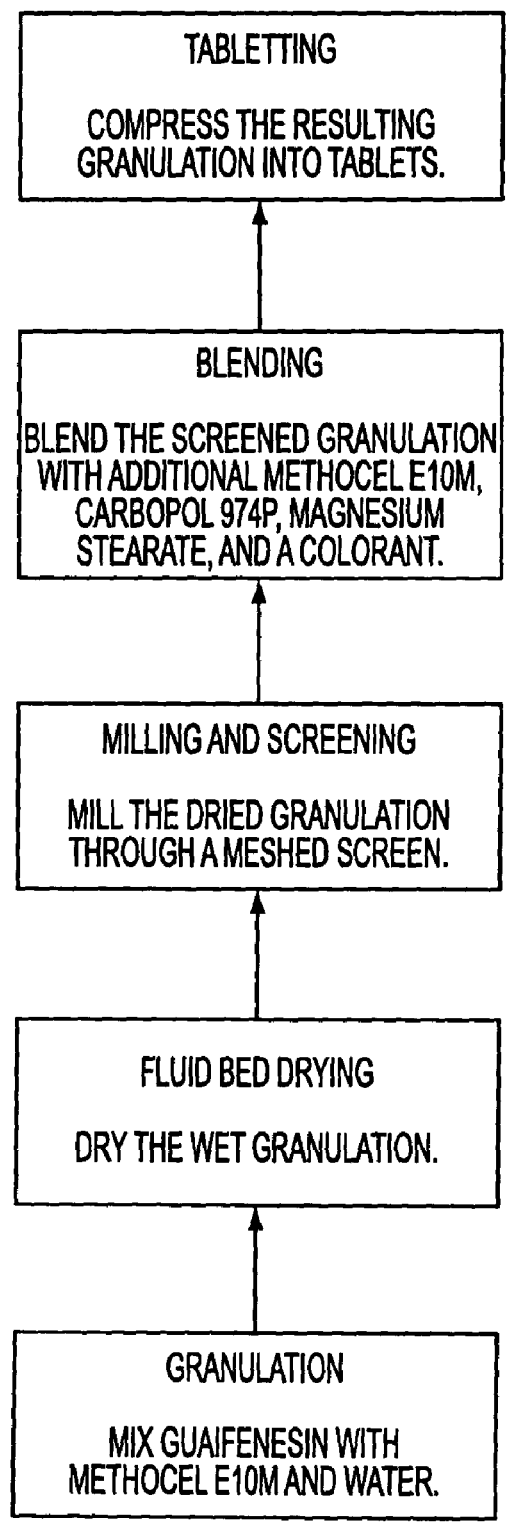
FIG. 1 is a flow diagram depicting steps in a wet granulation method for manufacturing the sustained release formulation.
Figure 2:
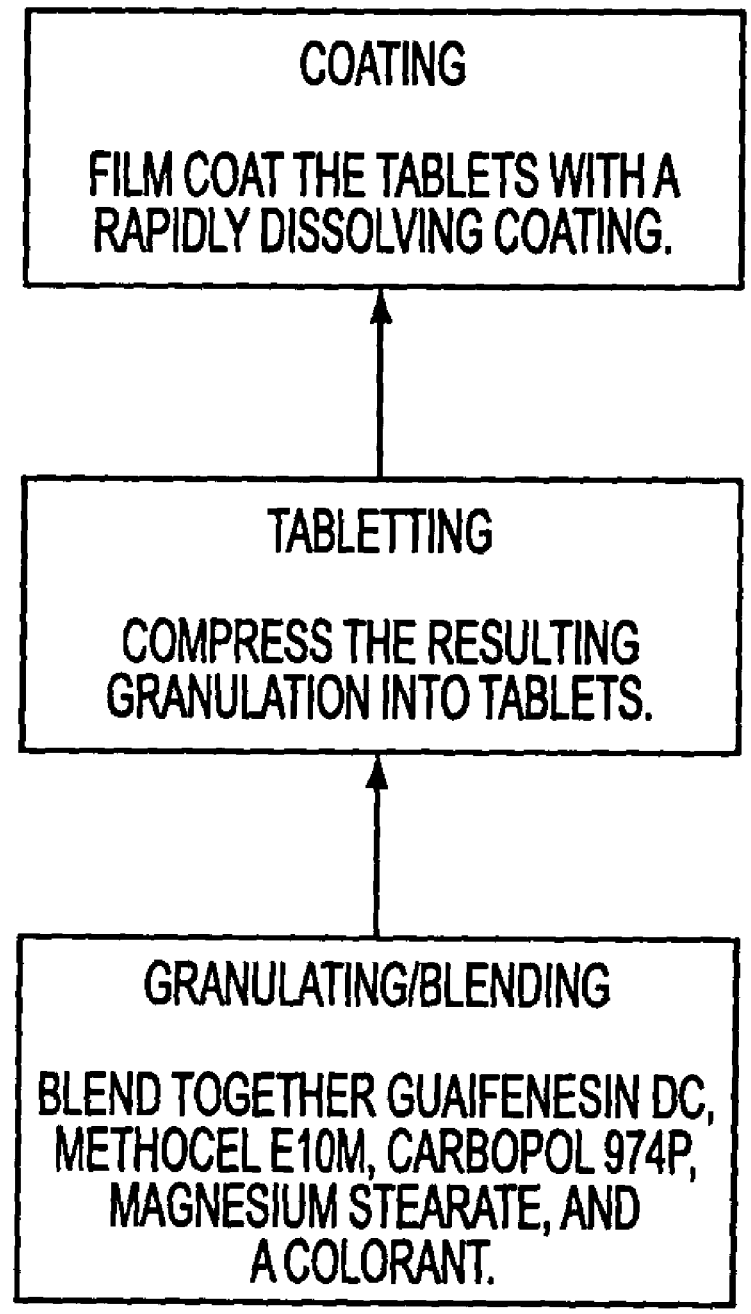
FIG. 2 is a flow diagram depicting steps in a dry granulation method for manufacturing the sustained release formulation.
Figure 3:
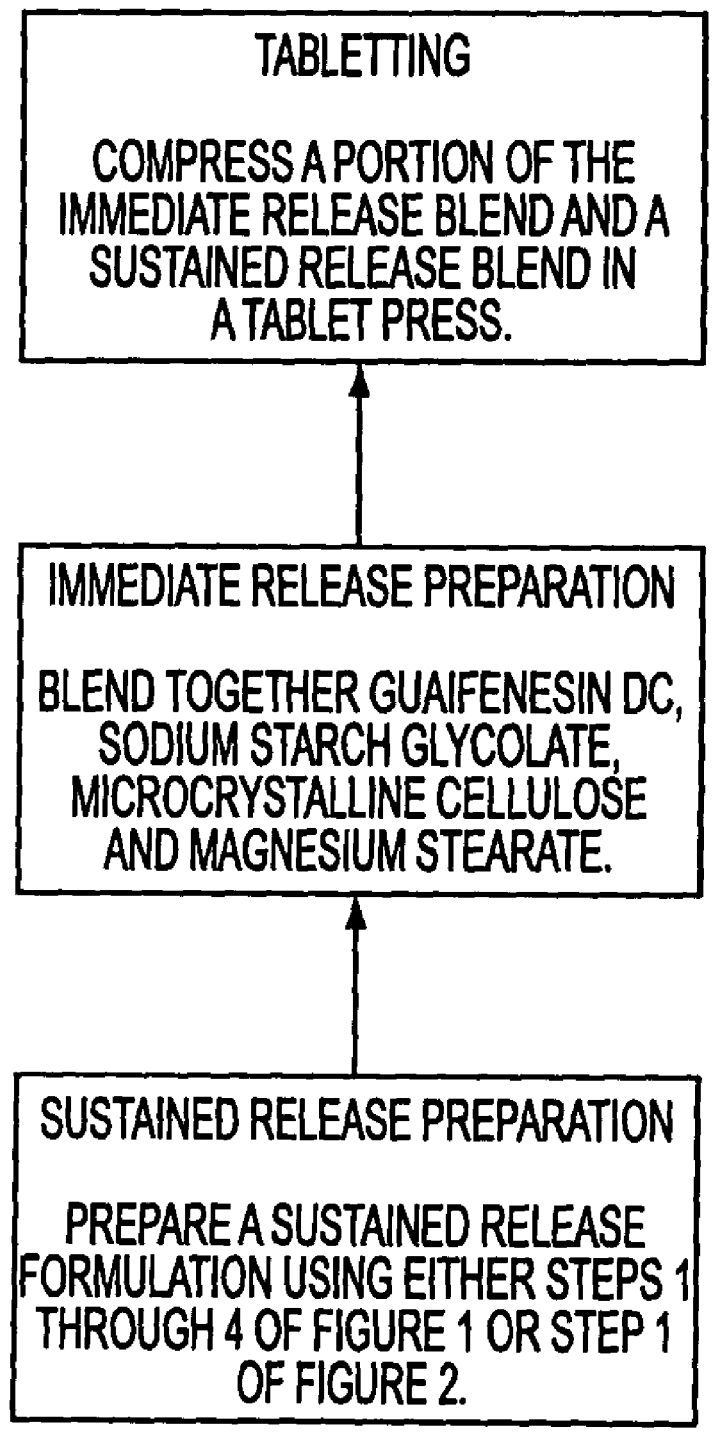
FIG. 3 is a flow diagram depicting steps in a method for manufacturing the bi-layer tablet.

The invention relates to sustained release formulations of guaifenesin. In a preferred embodiment, the formulations also comprise at least one additional drug in immediate release form, sustained release form, or both. Each formulation comprises a specific quantity of guaifenesin and may optionally contain at least one additional drug. The immediate release formulation is formulated to dissolve in aqueous acidic medium, such as that found in the stomach, to provide rapid release of the guaifenesin and optionally the at least one additional drug. In a preferred embodiment, the sustained release formulation comprises a combination of a hydrophilic polymer and a water-insoluble polymer in a ratio range of about one-to-one (1:1) to about nine-to-one (9:1), more preferably a range of about three-to-two (3:2) to about six-to-one (6:1), and most preferably in a range of about two-to-one (2:1) to about four-to-one (4:1).

In a preferred embodiment the hydrophilic polymers are selected from acacia, gum tragacanth, locust bean gum, guar gum, or karaya gum, methylcellulose, hydroxomethylcellulose, hydroxypropyl methylcellulose, hydroxypropyl cellulose, hydroxyethylcellulose, carboxymethylcellulose, agar, pectin, carrageen, alginates, carboxypolymethylene, gelatin, casein, zein, bentonite, magnesium aluminum silicate, polysaccharides, and modified starch derivatives. In a more preferred embodiment the hydrophilic polymers are selected from cellulose ethers. In a most preferred embodiment the hydrophilic polymers are selected from hydroxypropyl methylcelluloses such as Methocel (E10M). Preferred total amounts of the hydrophilic polymer include more than 0.5% and less than 10% by weight for a 1200 mg tablet. More preferably hydrophilic polymer amounts includes more than 1.0% and less than 7.0%, more than 2% and less than 6.0%. These amounts include the hydrophilic polymer in the Guaifenesin DC described below. The hydrophilic polymer added separately to form the release-delaying matrix is preferably from about 0.5% to 4.0% and more preferably from about 1.0% to 2.0%. It should be recognized that these amounts may be proportionally present in a 600 mg tablet or any desired formulation strength.

In a preferred embodiment the water-insoluble polymers are selected from polyacrylic acids, acrylic resins, acrylic latex dispersions, cellulose acetate phthalate, polyvinyl acetate phthalate, hydroxypropyl methylcellulose phthalate. In a more preferred embodiment the water-insoluble polymers are selected from acrylic resins. In a most preferred embodiment the water-insoluble polymers are selected from Carbomer acrylic resins such as Carbomer 934P. Preferred amounts of the water-insoluble polymer include more than about 0.5% and less than about 2.5% by weight for a 1200 mg tablet. More preferably hydrophilic polymer amounts includes more than about 0.75% and less than about 1.5%, and most preferably more than about 0.9% and less than 1.25%. It should be recognized that these amounts may be proportionally present in a 600 mg tablet or any desired formulation strength.

The invention also relates to sustained release preparations of the type described above in the form of bi-layered tablets or capsules having a combination of beads or granules of immediate release formulation and beads or granules of sustained release formulation. Alternatively, the sustained release formulation may comprise a core that is coated by a layer of immediate release formulation to form a single tablet. For purpose of illustration only, the invention will be described in detail in the context of the bi-layered tablet embodiment. When the embodiment is a bi-layered tablet, the tablet is made of two portions: one portion comprising a sustained release formulation and a second portion comprising an immediate release formulation. In a preferred embodiment, the at least one additional drug can be present within the sustained release formulation, the immediate release formulation, or both depending upon the desired effect.

For instance, a preferred embodiment of the present invention has the following ingredients and proportions in the sustained release layer (mg/tablet): 1052.6 mg Guaifenesin DC (95%) [1000.0 mg of Guaifenesin, USP and 52.6 mg of hydroxypropyl methylcellulose, USP]; 120.0 mg Pseudoephedrine HCL, USP; 30.0 mg hydroxypropyl methylcellulose, USP [Methocel E10M, USP]; 15.0 mg Carbomer 934P, NF [Carbopol 974P]; 0.4 mg FD&C Red #40 Aluminum Lake (14-16%); and 10.0 mg magnesium stearate, NF for a total sustained release weight of 1228.0 mg. In a preferred embodiment the immediate release layer has the following proportions: 210.5 mg Guaifenesin DC (95%) [200.0 mg of guaifenesin, USP and 10.5 mg of hydroxypropyl methylcellulose, USP]; 117.5 mg of microcrystalline cellulose, NF [Avicel PH102]; 30.0 mg of sodium starch glycolate, NF [EXPLOTAB]; and 1.0 mg magnesium stearate, NF for a total immediate release weight of 359.0 mg.

In another preferred embodiment a 1200 mg Guaifenesin/120 mg Pseudoephedrine Tablet has the following ingredients and proportions:

| Component | Amount (mg/tablet) | Representative Batch (kg)[1] IR Layer | Representative Batch (kg)[1] SR Layer |
|---|---|---|---|
| Guaifenesin DC (95%)[2] | 1263.1 | 280.00 | 947.376 |
| Hydroxypropyl methylcellulose (Methocel ™) | 30.0 | N/A | 27.000 |
| Pseudoephedrine hydrochloride | 120.0 | N/A | 108.0 |
| Microcrystalline cellulose | 117.50 | 156.28 | N/A |
| Sodium starch glycolate | 30.0 | 39.90 | N/A |
| Carbomer 934P | 15.0 | N/A | 13.500 |
| Magnesium stearate | 11.0 | 1.33 | 9.000 |
| FD&C Red #40 Aluminum Lake (14-16%) | 0.4 | N/A | 0.360 |
| Water, purified | N/A[3] | N/A[3] | N/A[3] |
| Total Weight | 1587.0 | 477.51 | 1105.236 |

[1]Based on batch size of 900,000 tablets
[2]Guaifenesin direct compression used in the manufacturing process consists of 95% Guaifenesin, USP, 5% hydroxypropyl methylcellulose, USP (Methocel ™ E10M) granulated with Purified water, USP (49.21 Kg).
[3]Water is removed during processing of Guaifenesin DC 95%.

In another preferred embodiment a 600 mg Guaifenesin/60 mg Pseudoephedrine Tablet has the following ingredients and proportions:

| Component | Amount (mg/tablet) | Representative Batch (kg)[1] IR Layer | Representative Batch (kg)[1] SR Layer |
|---|---|---|---|
| Guaifenesin DC (95%)[2] | 631.55 | 280.00 | 947.376 |
| Hydroxypropyl methylcellulose (Methocel ™) | 15.0 | N/A | 27.000 |
| Pseudoephedrine hydrochloride, USP | 60.0 | N/A | 108.0 |
| Microcrystalline cellulose | 58.75 | 156.28 | N/A |
| Sodium starch glycolate | 15.0 | 39.90 | N/A |
| Carbomer 934P | 7.5 | N/A | 13.500 |
| Magnesium stearate | 5.50 | 1.33 | 9.000 |
| D&C Yellow #6 Aluminum Lake (15-18%) | 0.8 | N/A | 1.440 |
| Water, purified | N/A[3] | N/A[3] | N/A[3] |
| Total Weight | 794.1 | 477.51 | 1106.316 |

[1]Based on batch size of 1,800,000 tablets
[2]guaifenesin direct compression used in the manufacturing process consists of 95% guaifenesin, USP, 5% hydroxpropyl methylcellulose, USP (Methocel ™ E10M) granulated with purified water, USP (49.21 Kg).
[3]Water is removed during processing of Guaifenesin DC 95%.

In another example, a 1200 mg Guaifenesin/120 mg Pseudoephedrine Tablet may also have the following properties:

| | |
|---|---|
| Description | 1200 mg bi-layer tablet |
| Average Tablet Weight | 1587.0 mg ± 3% (1539.4 mg-1634.6 mg) |
| Tablet Thickness | 0.321"-0.341" |
| Tablet Hardness | 25-45 SCU |
| Friability | NMT 0.8% |
| Loss on Drying (moisture) | NMT 2.0% NMT 31.74 mg/unit dose |
| Assay-guaifenesin | 1140.0-1260.0 mg/tablet (95.0-105.0%) |
| Assay-Pseudoephedrine hydrochloride | 116.6 to 128.4 mg/tablet (93.0-107.0%) |
| Guaifenesin Identification A | The retention time of the peak obtained from the Assay preparation matches that of the Standard preparation. |
| Guaifenesin (Identification B) | A deep-cherry red to purpose color is produced. |
| Pseudoephedrine hydrochloride Identification A | The retention time of the peak obtained from the Assay preparation matches that of the Standard preparation. |
| Pseudoephedrine hydrochloride Identification B | The IR spectrum matches that of the standard in the 2510 $cm^{-1}$ to 2400 range $cm^{-1}$ |
| Dose Uniformity | % RSD NMT 6.0% (% RSD NMT 7.8% for Level II) All individual values between 85.0-115.0% (For Level II, one value is allowed outside 85.0-115.0%, but none outside 75.0-125.0%) |
| Dissolution: Guaifenesin | 1 Hour: NMT 45% 2 Hour: 36-56% 6 Hour: 61-81% 12 Hour: NLT 85% |
| Dissolution: Pseudoephedrine hydrochloride | 1 Hour: NMT 53% 2 Hour: 48-68% 6 Hour: NLT 75% 12 Hour: NLT 85% |

In another example, a 600 mg Guaifenesin/60 mg Pseudoephedrine Tablet may also have the following properties:

| | |
|---|---|
| Description | 600 mg bi-layer tablet |
| Average Tablet Weight | 794.1 mg ± 3% (766.4mg-821.8 mg) |
| Tablet Thickness | 0.247"-0.262" |
| Tablet Hardness | 17-32 SCU |
| Friability | NMT 0.8% |
| Loss on Drying (moisture) | NMT 2.0% NMT 15.88 mg/unit dose |
| Assay-Guaifenesin | 570.0-630.0 mg/tablet(95.0-105.0%) |
| Assay-Pseudoephedrine hydrochloride | 58.2 to 61.8 mg/tablet (93.0-107.0%) |
| Guaifenesin Identification A | The retention time of the peak obtained from the Assay preparation matches that of the Standard preparation. |
| Guaifenesin Identification B | A deep-cherry red to purpose color is produced. |
| Pseudoephedrine hydrochloride Identification A | The retention time of the peak obtained from the Assay preparation matches that of the Standard preparation. |
| Pseudoephedrine hydrochloride Identification B | The IR spectrum matches that of the standard in the 2510 $cm^{-1}$ to 2400 range $cm^{-1}$. |
| Dose Uniformity | % RSD NMT 6.0% (% RSD NMT 7.8% for Level II) All individual values between 85.0-115.0% (For Level II, one value is allowed outside 85.0-115.0%, but none outside 75.0-125.0%) |
| Dissolution: Guaifenesin | 1 Hour: NMT 48% 2 Hour: 41-61% 6 Hour: 73-93% 12 Hour: NLT 90% |
| Dissolution: Pseudoephedrine hydrochloride | 1 Hour: NMT 58% 2 Hour: 56-76% 6 Hour: NLT 80% 12 Hour: NLT 85% |

In one embodiment, the 1200/60 mg guaifenesin/dextromethorphan weight specification is 1530.4 mg±3.0%, corresponding to a range of 1484.5-1576.3 mg. For the 600/30 mg tablet, the weight specification is 765.2 mg±3.0%, corresponding to a range of 742.2-788.2 mg. This specification range of ±3.0% of the theoretical weight is similar to the guaifenesin alone 1200 mg and 600 mg tablets, respectively.

The proposed hardness and thickness specifications for the 1200/60 mg guaifenesin/dextromethorphan tablet are 15-65 SCU and 0.310"-0.340", respectively. Tablets pressed at 527 tpm at the minimum hardness parameter (12LB86A) ranged from 0.329"-0.334" and 17-23 SCU. The friability ranged from 0.20-0.33%. Tablets pressed at 737 tpm at the minimum hardness parameter (12LB86B) ranged from 0.331"-0.335" and 15-24 SCU. The friability ranged from 0.20-0.39%. Dissolution testing was performed for each test condition (527 tpm and 737 tpm) within one hour of compression. No significant difference was seen in the release profile between the test samples and the pilot batches.

Further tablets pressed as thin and as hard as the press would allow at speeds of 527 tpm (12LB86C) and 737 tpm (12LB86D) provided a thickness range of 0.303"-0.312" with a corresponding initial hardness range of 39-47 SCU at 527 tpm. The friability ranged from 0.07-0.13%. A thickness range of 0.304"-0.313" was obtained with a corresponding initial hardness range of 38-47 SCU at 737 tpm. The friability ranged from 0.06-0.13%. Historically, it has been noted that these tablets harden during the first few days after compression. Therefore, these 'hard' tablets were tested for dissolution at least 5 days after compression. The hardness range on the fifth day after compression was 52-60 SCU for the tablets pressed at 527 tpm. The hardness range on the fifth day after compression was 48-56 SCU for the tablets pressed at 737 tpm. Again, the dissolution profile for the test samples corresponded closely with that seen in the pilot batches. Additionally, a tablet hardness range of 60-79 SCU was reported for PB01-H30 at the 3-month real-time stability time point. No significant difference in the dissolution profile from "$T_0$" was noted.

The proposed hardness and thickness specifications for the 600/30 mg guaifenesin/dextromethorphan tablet were 15-65 SCU and 0.220"-0.260" respectively. Tablets pressed at the minimum hardness parameter at 527 tpm (12LB85A) ranged from 0.257"-0.260" and 8-13 SCU. The friability ranged from 0.13-0.26%. Tablets pressed at the minimum hardness parameter at 840 tpm (12LB85B) ranged from 0.258"-0.261" and 8-13 SCU. The friability ranged from 0.13-0.26%. Dissolution testing was performed for each test condition (527 tpm and 840 tpm) within one hour of compression. No significant difference was seen in the release profile between the test samples and the pilot batches.

Tablets were then pressed as thin and as hard as the press would allow. A range of 0.232"-0.241" was obtained at compression with a corresponding hardness ranging from 25-30 SCU at 527 tpm (12LB85C). The friability ranged from 0.13-0.78%. The hardness on the seventh day after compression ranged from 28-34 SCU. A range of 0.230"-0.241" was obtained at compression with a corresponding hardness ranging from 23-30 SCU at 840 tpm (12LB85D). The friability ranged from 0.00-0.13%. The hardness on the seventh day after compression ranged from 28-33 SCU. Again, the dissolution profile for the test samples (seven days after compression) corresponded closely with that seen in the pilot batches. Additionally, a tablet hardness range of 37-51 SCU was reported for lot PB10-H54 at the 3-month real-time stability time point. No significant difference in the dissolution profile from "$T_0$" was noted.

The preferred 1200 mg guaifenesin/60 mg dextromethorphan tablets have an average tablet thickness of 0.305"-0.335", an average tablet hardness of 25-35 SCU (in process), and average tablet hardness 20-79 SCU (at time of release).

The preferred 600 mg guaifenesin/30 mg dextromethorphan tablets have an average tablet thickness of 0.230"-0.260", an average tablet hardness of 20-30 SCU (in process), and an average tablet hardness of 10-51 SCU (at time of release through expiration date).

The specification of NMT 0.8% set for the friability of both guaifenesin/dextromethorphan tablet strengths is based on the limit established with the guaifenesin alone tablets. The specification for Loss on Drying is comparable to guaifenesin alone, i.e. NMT 2.0%. The moisture limit is 2.0% of the total theoretical tablet weight, recorded in mg/unit dose.

The range for the specification for guaifenesin is based on the labeled amount, 1200 mg or 600 mg±4.0%. For the 1200/60 mg guaifenesin/dextromethorphan tablet, the range is 1152.0-1248.0 mg per tablet. For the 600/30 mg guaifenesin/dextromethorphan tablet, the range is 576.0-624.0 mg per tablet. The range for the specification for dextromethorphan HBr is based on the labeled amount, 60 mg or 30 mg±4.0%. For the 1200/60 mg tablet, the range is 57.6-62.4 mg per tablet. For the 600/30 mg tablet, the range is 28.8-31.2 mg per tablet.

Other embodiments of the invention, include a SCU that is preferably less than 43, more preferably less than 41, more preferably less than 38, more preferably less than 37, and more preferably between 32 and 35. SCU is also preferably greater than 21, more preferably greater than 24, more preferably greater than 28, and more preferably greater than 31.

The weight of 10 bi-layer guaifenesin/pseudoephedrine tablets (1200 mg/120 mg) is preferably less than 16.4 g, more preferably less than 16.35 g, more preferably less than 16.29 g, more preferably less than 16.22 g, more preferably less than 16.16 g, more preferably less than 16.10 g, more preferably less than 16.04 g, and more preferably between 15.71 g and 16.03 g. The weight of 10 bi-layer tablets is also preferably greater than 15.35 g, more preferably greater than 15.40 g, more preferably greater than 15.46 g, more preferably greater than 15.53 g, more preferably greater than 15.59 g, more preferably greater than 15.65 g.

Other embodiments and characteristics of the invention are described in further detail below.

Sustained Release Formulation

In one embodiment of the invention, a sustained release formulation comprises guaifenesin and optionally at least one drug both mixed with a polymer blend which comprises at least one hydrophilic polymer and at least one water-insoluble polymer. In a further embodiment, the sustained release formulation may comprise a combination of guaifenesin and at least one additional drug, wherein the additional drug may be selected from, but is not limited to, an antitussive such as dextromethorphan hydrobromide, codeine, hydrocodone, a decongestant such as phenylephrine hydrochloride, phenylpropanolamine hydrochloride, pseudoephedrine hydrochloride or ephedrine, an antihistamine such as chlorpheniramine maleate, brompheniramine maleate, phenindamine tartrate, pyrilamine maleate, doxylamine Succinate, phenyltoloxamine citrate, diphenhydramine hydrochloride, promethazine, and clemastine fumerate, an analgesic such as aspirin, ibuprofen, naprosin, and acetaminophen, or combinations thereof. Preferably, the drug is dextromethorphan hydrobromide, pseudoephedrine hydrochloride, or a combination thereof.

The sustained release matrix utilizes polymers as described below to achieve the required delay release profile in vivo. To obtain the release profile proper mixing and formulation is required. For instance, too much hydrophilic polymer will result in too quick of a release and not allow for 12 hour relief while too much hydrophobic polymer will result in inadequate $C_{max}$ for relief of symptoms. Therefore, the selection of polymers, the amounts utilized in total and the amount utilized in comparison to each other provide a matrix which is then formulated according to the below methods to provide the appropriate release profile.

Hydrophilic polymers suitable for use in the sustained release formulation include: one or more natural or partially or totally synthetic hydrophilic gums such as acacia, gum tragacanth, locust bean gum, guar gum, or karaya gum, modified cellulosic substances such as methylcellulose, hydroxomethylcellulose, hydroxypropyl methylcellulose, hydroxypropyl cellulose, hydroxyethylcellulose, carboxymethylcellulose; proteinaceous substances such as agar, pectin, carrageen, and alginates; and other hydrophilic polymers such as carboxypolymethylene, gelatin, casein, zein, bentonite, magnesium aluminum silicate, polysaccharides, modified starch derivatives, and other hydrophilic polymers known to those of skill in the art or a combination of such polymers.

These hydrophilic polymers gel and dissolve slowly in aqueous acidic media thereby allowing the guaifenesin and at least one drug to diffuse from the gel in the stomach. When the gel reaches the intestines, where the guaifenesin and the drug are fairly absorbable, it dissolves in controlled quantities in the higher pH medium to allow sustained release of guaifenesin and at least one drug throughout the digestive tract. Preferred hydrophilic polymers are the hydroxypropyl methylcelluloses such as those manufactured by The Dow Chemical Company and known as Methocel ethers. In one preferred embodiment of a sustained release formulation the hydrophilic polymer is a Methocel ether known as Methocel E10M.

Water-insoluble polymers, which are suitable for use in the sustained release formulation, are polymers which generally do not dissolve in solutions of a pH below 5, and dissolve more slowly in basic solutions than the hydrophilic polymer. Because the polymer is insoluble in low pH environments such as those found in gastric fluid, it aids in retarding drug release in those regions. Likewise, because the polymer dissolves more slowly in solutions of higher pH than hydrophilic polymers, it aids in retarding drug release throughout the intestines. This overall delayed release results in a more uniform serum concentration of guaifenesin.

The water-insoluble polymers suitable for use in this invention include for example: polyacrylic acids, acrylic resins, acrylic latex dispersions, cellulose acetate phthalate, polyvinyl acetate phthalate, hydroxypropyl methylcellulose phthalate, and other polymers common to those of skill in the art. In a preferred embodiment, a sustained release formulation comprises the acrylic resin Carbopol 974P supplied by BF Goodrich.

A sustained release formulation of invention may further comprise pharmaceutical additives including, but not limited to: lubricants such as magnesium stearate, calcium stearate, zinc stearate, powdered stearic acid, hydrogenated vegetable oils, talc, polyethylene glycol, and mineral oil; colorants; binders such as sucrose, lactose, gelatin, starch paste, acacia, tragacanth, povidone polyethylene glycol, Pullulan and corn syrup; glidants such as colloidal silicon dioxide and talc; surface active agents such as sodium lauryl sulfate, dioctyl sodium sulfosuccinate, triethanolamine, polyoxyethylene sorbitan, poloxalkol, and quarternary ammonium salts; preservatives and stabilizers; excipients such as lactose, mannitol, glucose, fructose, xylose, galactose, sucrose, maltose, xylitol, sorbitol, chloride, sulfate and phosphate salts of potassium, sodium, and magnesium; and/or any other pharmaceutical additives known to those of skill in the art. Colorants include, but are not limited to, Emerald Green Lake, FD&C Red No. 40, FD&C Yellow No. 6, D&C Yellow No. 10, or FD&C Blue No. 1 and other various certified color additives (See 21 CFR, Part 74). In one preferred embodiment, a sustained release formulation further comprises magnesium stearate and Emerald Green Lake. In another preferred embodiment, a sustained release formulation further comprises magnesium stearate and FD&C Blue No. 1 Aluminum Lake Dye.

In another embodiment the modified release formulation comprises at least two drugs, one of which is guaifenesin, at least one hydrophilic polymer, at least one water-insoluble polymer, and at least one pharmaceutical additive which permits dissolution of drugs in a therapeutically effective profile for an extended period of time. It is preferred that the drug profile provides a therapeutically effective profile for greater than 10 hours, more preferably greater than 12 hours, and most preferably greater than 14 hours. In a preferred embodiment, a modified release formulation comprises from about 75% to about 95% guaifenesin by weight, from about 1% to about 15% by weight of an additional drug, from about 0.5% to about 10% hydroxypropyl methylcellulose, from about 0.5% to about 2.5% acrylic resin, from about 0.4% to about 1.5% magnesium stearate, and from about 0.01% to about 1% colorant by weight. In a more preferred embodiment, a modified release formulation comprises from about 75% to about 80% guaifenesin by weight, from about 3% to about 10% by weight of an additional drug, from about 3% to about 6% hydroxypropyl methylcellulose, from about 1% to about 1.5% acrylic resin, from about 0.7% to about 1% magnesium stearate, and from about 0.03% to about 0.13% colorant by weight.

The sustained release formulation controls the release of guaifenesin and optionally at least one additional drug into the digestive tract over an extended period of time resulting in an improved profile when compared to immediate release combinations. guaifenesin solubility is effected by the pH of the environment in which it is present (i.e. stomach versus intestinal tract). In a more acidic environment, such as the stomach, guaifenesin is less soluble while in a higher pH environment, such as the intestines, guaifenesin is readily soluble. The pH changes throughout the digestive tract effect the dissolution rate of guaifenesin and are partially determinate of the concentrations of guaifenesin attained in the blood and tissues.

To maintain a blood concentration of guaifenesin which provides good therapeutic effect, the release, or dissolution, of guaifenesin from a formulation matrix is preferably retarded and/or controlled through the intestines. The hydrophilic and water-insoluble polymers of the sustained release formulation gel when exposed to media of low pH. This gel matrix allows the sustained release drugs, e.g. guaifenesin alone or in combination with a second drug to diffuse at a controlled rate when exposed to a higher pH environment.

When using drugs approved by the Food and Drug Administration (FDA), the sustained release formulation may be formulated to mimic the blood serum profile of guaifenesin and optionally the additional drug(s) as described in the clinical documents filed with the FDA or as required by the FDA. In other words, the sustained release formulation releases at least one additional drug at a similar rate to the commercially available formulation, thereby providing a therapeutically effective amount of the additional drug.

In a preferred embodiment, a sustained release formulation comprises a hydrophilic polymer and a water-insoluble polymer in a ratio of about one-to-one (1:1) to about nine-to-one (9:1), more preferably the range is about three-to-two (3:2) to about six-to-one (6:1), and most preferably the range of hydrophilic polymer to water-insoluble polymer is about two-to-one (2:1) to about four-to-one (4:1). In another embodiment, the sustained release formulation comprises not more than about 10% hydrophilic polymer, preferably, not more than 6%, and in a more preferred embodiment, the sustained release formulation also comprises not more than 2.5% of the water-insoluble polymer by weight. In another preferred embodiment, the water-hydrophilic polymer is hydroxypropyl methylcellulose and the water-insoluble polymer is acrylic resin. The ratios result in a serum concentration profile of guaifenesin that provides an optimal therapeutic concentration for about twelve hours.

A sustained release formulation may be manufactured according to any appropriate method known to those of skill in the art of pharmaceutical manufacture. In one embodiment, guaifenesin and a hydrophilic polymer may be mixed in a mixer with an aliquot of water to form a wet granulation. The granulation may be dried to obtain hydrophilic polymer encapsulated granules of guaifenesin. The resulting granulation may be milled, screened, and then blended with various pharmaceutical additives, water insoluble polymer, and additional hydrophilic polymer. The formulation may then tableted and may further be film coated with a protective coating which rapidly dissolves or disperses in gastric juices.

In a preferred embodiment the method of preparing a sustained release formulation comprises loading approximately 126 kg of guaifenesin and about 2 kg of Methocel E10M into a high shear mixer. The Methocel E10M and guaifenesin may be mixed for about seven minutes at a mixing speed of about 150 RPM and a chopper speed of about 2000 RPM. The mixing and chopping speeds may then be increased to about 200 RPM and 3000 RPM respectively for about five minutes while about 49 kg of water are added to the mixer contents. The mixer may be run for two additional minutes to complete granulation. In a further preferred embodiment, the shut off for the mixer load is set to 21 kilowatts.

The wet granulation may be emptied into a fluid bed bowl and placed into a fluid bed dryer set to a dryer air flow of 900 CFM and an inlet temperature of about 50° C. to about 55° C. until the outlet temperature increases at a rate of 1° C. per minute. The air flow may then be decreased to 600 CFM, and the inlet temperature may be decreased to 43° C. until the granulation is dried to a moisture content of no more than 0.5%. In another preferred embodiment, the outlet temperature is set to a cut-off of 48° C. In yet another preferred embodiment, an agitator in the fluid bed bowl may be run intermittently during drying. The dried granulation may be passed through a mill fitted with a suitable screen size so that not more than about 30% of the resulting granulation comes through a 100 mesh screen and not more than about 10% of the resulting granulation is retained on a 10 mesh screen. In one preferred embodiment, the dried granulation may be passed through a mill fitted with a 0.109" size screen at a mill speed of about 500 to about 1500 RPM and a screw feed rate of about 35 to about 45 RPM. The resulting screened granulation is about 95% guaifenesin and is called G Guaifenesin DC (Direct Compressed) herein after. Screened granulation may be transferred to a 10 cubic foot V blender, combined with about another 0.6 kg of Methocel E10M, about 0.3 kg of a colorant such as Emerald Green Lake or FD&C BLUE No. 1, about 0.7 kg of magnesium stearate, and about 1.3 kg of Carbopol 974P. The combination may be blended for about three minutes.

In another preferred embodiment the method of preparing a sustained release formulation comprises loading about 101 kg to about 150 kg of guaifenesin, about 4.5 kg to about 18 kg of the additional drug, about 4.5 kg to about 5 kg of Methocel E10M, about 1.5 kg to about 2.25 kg of Carbopol® 974P, and about 40 g to about 240 g of colorant into a high shear mixer. If at this time water is to be added, then about 1 kg to about 1.5 kg of magnesium stearate is added as well. The ingredients may be mixed for about ten to about 12 minutes at a mixing speed of about 150 RPM and a chopper speed of about 2000 RPM. The mixing and chopping speeds may then be increased to about 200 RPM and 3000 RPM, respectively, for about five minutes while optionally about 29 kg of water are added to the mixer contents. If no water is added, then from about 1 kg to about 1.5 kg of magnesium stearate can be added at this time. The mixer may be run for ten additional minutes to complete granulation. In a further preferred embodiment, the shut off for the mixer load is set to 21 kilowatts.

The wet granulation may be emptied into a fluid bed bowl and placed into a fluid bed dryer set to a dryer air flow of 900 CFM and an inlet temperature of about 38° C. to about 48° C. until the outlet temperature increases at a rate of 1° C. per minute. The air flow may then be decreased to 600 CFM, and the inlet temperature may be decreased to 43° C. until the granulation is dried to a moisture content of no more than 0.5%. In another preferred embodiment, the outlet temperature is set to a cut-off of 48° C. In yet another preferred embodiment, an agitator in the fluid bed bowl may be run intermittently during drying. The dried granulation may be passed through a mill fitted with a suitable screen size so that not more than about 30% of the resulting granulation comes through a 100 mesh screen and not more than about 10% of the resulting granulation is retained on a 10 mesh screen. In one preferred embodiment, the dried granulation may be passed through a mill fitted with a size screen of about 0.109" to about 0.125" at a mill speed of about 500 to about 1500 RPM and a screw feed rate of about 35 to about 45 RPM.

The resulting formulations may further be compressed on a tablet compressor machine using tooling to form tablets. The tablets may be any appropriate weight, size, and shape depending on the desired dosage strength of tablet. In one embodiment, these tablets may further be loaded into a coating pan and film coated with Opadry Y-S-3-714 (supplied by Colorcon, Inc.) and air dried in the pan.

In another embodiment, the method of preparing a sustained release formulation comprises blending the drugs, hydrophilic polymer, water insoluble polymer, and any pharmaceutical additives. The resulting blend may then be compressed into tablets and, if desired, film coated with a protective coating which rapidly dissolves or disperses in gastric juices. In a preferred embodiment of such a method, about 126 kg of Guaifenesin DC (about 95% purity), about 2.6 kg of Methocel E10M, about 1.3 kg of Carbopol 974P and about 0.333 kg of a colorant such as Emerald Green Lake or FD&C BLUE No. 1 may be loaded into a 10 cubic foot V Blender. The ingredients may be blended for about 20 minutes at which time about 0.6 kg of magnesium stearate may be added to the blended ingredients. This mixture may be blended for about another 10 minutes. The resulting formulation may further be compressed on a tablet compressor machine using tooling to form tablets. The tablets may be any appropriate weight, size, and shape depending on the desired dosage strength of the tablet. These tablets may further be loaded into a coating pan and film coated with Opadry Y-S-3-714 (supplied by Colorcon, Inc.) and air dried in the pan.

One embodiment of the invention uses the following general methods of manufacturing. To make the Guaifenesin DC (95%) intermediate granulation is conducted. The granulator is charged with purified water USP. The guaifenesin USP is added into the granulator. Next the hydroxypropyl methylcellulose USP (Methocel El OM) is added. The guaifenesin intermediate is dried with the air inlet temperature set about 5° C., until the air outlet temperature reached approximately 48° C. A sample may then be taken for in-process control testing (moisture analysis). After the material reaches the target moisture level, discharge the blend and proceed to milling. The dried granulation is then added to the milling machine and the milling process initiated. Again a sample may be taken for in-process control testing (moisture and sieve analysis). The milled material is collected into tared fiber drums, double-lined with plastic bags and containing a desiccant pouch between the inner and outer plastic bags, then transferred to blending. The batches are blended in a 60-cu. foot blender for at least 10 minutes. Again, a sample may be taken for in-process control testing (description, moisture, blend assay and sieve analysis). The final sieve analysis for milled Guaifenesin DC preferably will be as follows: not more than about 2 to 10% retained on a 10-mesh screen (2.00 mm), not less than about 50 to 60% retained on the 20-mesh through 100-mesh screens (150 µm), not less than about 4 to 6% will pass through a 100-mesh screen, and not more than about 15-20% will pass through a 140-mesh screen (106 µm). When at least 50%, and preferably at least 60% of the Guaifenesin DC has a particle size in the range of from about 2 mm to about 150 µm, this facilitates both processability and achievement of the desired in vivo release profiles for the single entity and combination drugs described herein. The final Guaifenesin DC (95%) granulation is collected into tared fiber drums, double-lined with double-lined with plastic bags and containing a desiccant pouch between the inner and outer plastic bags.

In one embodiment the immediate release layer is produced according to the following general procedures. The released components, Guaifenesin DC (95%) and microcrystalline cellulose, NF (Avicel® PH102), are weighed and blended in a PK V-blender for about 20 minutes. Then sodium starch glycolate, NF (Explotab®), is added to the blender and blend for about 10 minutes. Next magnesium stearate, NF, is added to the blender and blended for approximately an additional 10 minutes. Sample may then be taken for in-process control testing (description, blend assay and sieve analysis).

In one embodiment the sustained release layer is produced according to the following general procedures. The released components, Guaifenesin DC (95%) and pseudoephedrine HCl, USP, previously screened through a No. 20 screen, are weighed and blended for ten minutes with hydroxypropyl methylcellulose, USP (Methocel E10M), Carbomer 934P and the appropriate colorant (FD & C Red No. 40 aluminum lake dye for 1200 mg guaifenesin/120 mg pseudoephedrine HCl tablets or FD & C Yellow No. 6 aluminum lake dye for 600 mg guaifenesin/60 mg pseudoephedrine HCl tablets). Next, an additional amount of Guaifenesin DC (95%), previously screened through a No. 10 screen, is added and blended for about ten minutes. Then magnesium stearate, NF, previously screened through a No. 20 screen, is added and blended for about ten minutes. Again, samples may be taken for in-process control testing (description, sieve analysis, and blend assay for both guaifenesin and pseudoephedrine HCl). Tablet Compression involved loading each blend (IR and SR) into its respective hopper on the bi-layer tablet compressor and then compressed according to the described parameters.

In another embodiment 1200 mg guaifenesin and 60 mg dextromethorphan HBr tablets are manufactured using the following protocol. The manufacturing process yields 600,000 tablets per batch for the 1200 mg guaifenesin and 60 mg dextromethorphan HBr or 1,200,000 tablets for 600 mg guaifenesin and 30 mg dextromethorphan HBr tablets. The components for the immediate release layer (IR layer) for both strength tablets are identical. The components for the sustained release layer (SR layer) for both strength tablets are also identical.

For the SR layer (for 1200 mg guaifenesin and 60 mg dextromethorphan HBr tablets), the guaifenesin and dextromethorphan HBr (previously screened through a 20-mesh screen), are granulated together with carbomer 934P, hydroxypropyl methylcellulose (Methocel E10M), and FD&C blue #1, aluminum lake (11-13%) using purified water as the granulating fluid in a Day mixer. The wet mass is evenly spread onto paper-lined trays and dried in a drying oven set at 109±10° F. for approximately 25 hours until the average moisture is not more than 1.5%. The process for the SR layer for 600 mg guaifenesin and 30 mg dextromethorphan HBr tablets is identical to the process for the 1200 mg guaifenesin and 60 mg dextromethorphan HBr extended release tablets with the exception of the dye used. The dye used in the half strength tablet is D&C yellow #10, aluminum lake (14-18%) while the dye in the full strength tablet is FD&C Blue #1, aluminum lake (11-13%). The dried granulation is milled using a Fitzpatrick Mill fitted with a 0.125" round-hole screen, knives forward at a "fast" speed. The granulation is fed into the mill using an automatic feeder. The six sublots (112.04 kg per sublot, granulated, dried, and milled as described above) are then blended together in a 60-cu. foot blender with magnesium stearate for ten minutes.

For the IR layer, the guaifenesin and dextromethorphan HBr (previously screened through a 20-mesh screen), are granulated together with sodium starch glycolate (Explotab), microcrystalline cellulose (Avicel PH102), and hydroxypropyl methylcellulose (Methocel E10M) using purified water as the granulating fluid in a Day mixer. The wet mass is evenly spread onto paper-lined trays and dried in a drying oven set at 109±10° F. for approximately 26 hours until the average moisture is not more than 2.0%. The IR layer process is the same for both tablet strengths. The dried granulation is passed through a Sweco equipped with 10-mesh screen. The granulation retained on the 10-mesh screen is milled using a Fitzpatrick Mill fitted with a 0.125" round-hole screen, knives forward at a "medium" speed. The granulation is fed into the mill using an automatic feeder. The milled material is later blended with the material that passed through the 10-mesh screen. The three sublots (95.52 kg per sublot, granulated, dried, and milled as described above) are then blended together in a 60 cu.-foot blender with magnesium stearate for ten minutes. Each blend is then loaded into their respective hoppers and compressed into bi-layer tablets.

Figure 4:
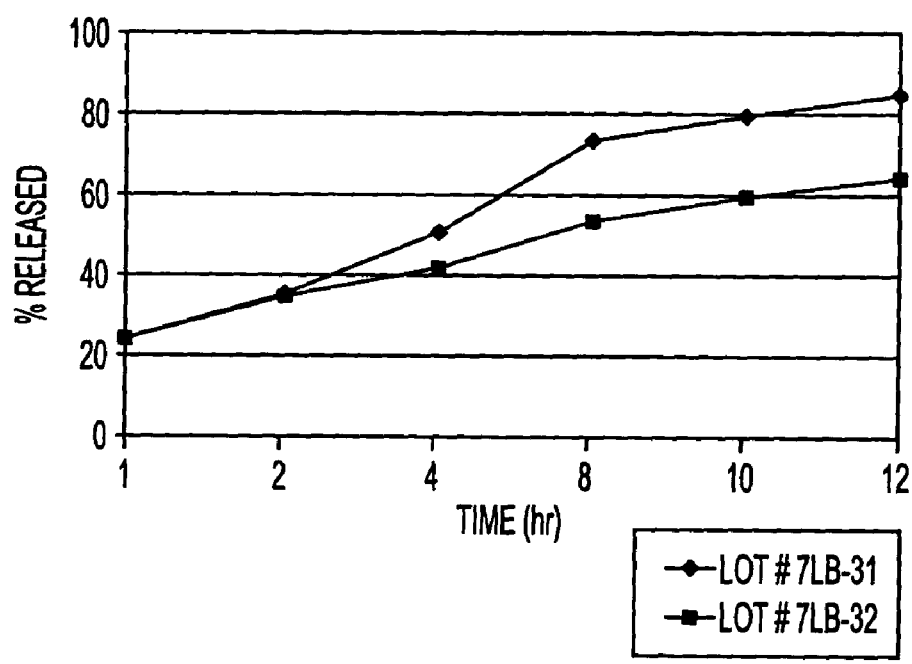
FIG. 4 is a graph demonstrating the dissolution profiles of tablets comprising two different sustained release formulations.

Tablets comprising a sustained release formulation were prepared and tested for both in vitro and in vivo release characteristics as described in Examples 1, 2, and 3 below. In the in vitro testing, the dissolution rates of these tablets were compared against modified release tablets formulated without acrylic resin (Example 1), and three commercially available tablets, one being an immediate release formulation and the other two being modified release formulations. Tablets comprising the sustained release formulation demonstrated a slower, more controlled release of guaifenesin over a twelve hour period than any of the other tablets (see e.g., Example 1 and 2, and FIGS. 4 and 5).

Figure 6:
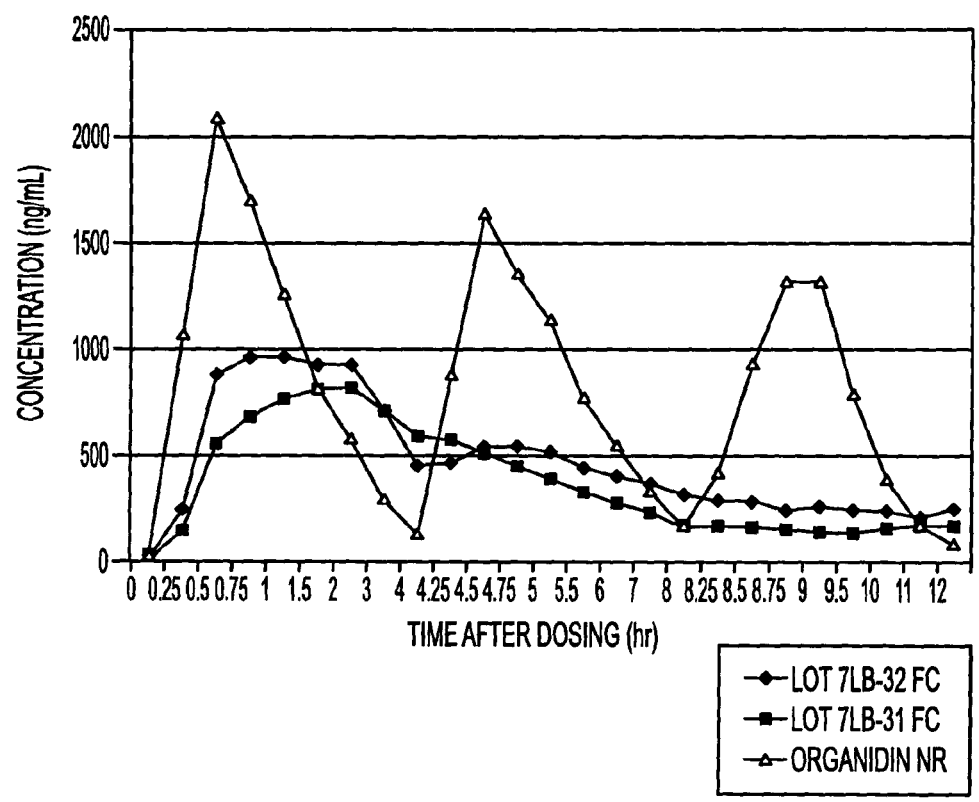
FIG. 6 is a graph demonstrating the plasma concentration of guaifenesin over time in healthy human volunteers who were dosed with three different guaifenesin formulations; a commercial immediate release formulation, and two different sustained release formulations (Lot 7B-32 and Lot 7B-31).

In the in vivo testing, serum concentrations of subjects taking tablets comprising the sustained release formulation were compared with serum concentrations of subjects taking immediate release guaifenesin tablets and modified release guaifenesin tablets formulated without acrylic resin (see Example 3 and FIG. 6). Tablets comprising the sustained release formulation demonstrated improved sustained release and therapeutic concentration over an extended time period compared to the other two formulations. Additionally, in the subjects taking tablets comprising the sustained release formulation, it took longer for guaifenesin to appear in the blood stream and the maximum guaifenesin serum concentration ($C_{max}$) was less than half that of the subjects who took the immediate release tablets.

Modified Release Formulation

To improve the $C_{max}$ and guaifenesin appearance speed in patients while maintaining therapeutic effect for about twelve hours, a portion of a sustained release formulation as described above may be combined with a portion of an immediate release formulation in a modified release product. In a preferred embodiment, at least one additional drug can be present within the sustained release formulation, the immediate release formulation, or both depending upon the desired effect. When using drugs approved by the Food and Drug Administration (FDA), the sustained release formulation, immediate release formulation, or both may be formulated to mimic the blood serum profile of the additional drug as described in the clinical documents filed with the FDA or as required by the FDA. In other words, the sustained and/or immediate release formulations of the modified release formulation may release the at least one additional drug at a similar rate to the commercially available formulation, thereby providing a therapeutically effective amount of the additional drug.

The modified release formulation can be in the form of bi-layered tablets, capsules having a combination of beads or granules of immediate release formulation and sustained release formulation, or a tablet wherein the sustained release formulation comprises a core that is coated by a layer of the immediate release formulation. For purpose of illustration only, the invention will be described in detail in the context of the bi-layered tablet embodiment.

The immediate release formulation may comprise guaifenesin and various pharmaceutical additives such as lubricants, colorants, binders, glidants, surface active agents, preservatives, stabilizers, as described above and/or any other pharmaceutical additives known to those of skill in the art. In one embodiment, the immediate release layer comprises at least one drug. In another embodiment, the immediate release layer comprises at least two drugs. In a more preferred embodiment, an immediate release formulation comprises guaifenesin, microcrystalline cellulose, sodium starch glycolate, and magnesium stearate. In another more preferred embodiment, an immediate release formulation comprises guaifenesin, at least one additional drug, microcrystalline cellulose, hydroxypropyl methylcellulose, sodium starch glycolate, and magnesium stearate. In yet another preferred embodiment, an immediate release formulation may comprise about 47% to about 58% guaifenesin, about 32% to about 42% microcrystalline cellulose, about 3% to about 8% sodium starch glycolate, and about 0.3% to about 0.5% magnesium stearate by weight. In yet another preferred embodiment, an immediate release formulation comprises about 47% to about 58% guaifenesin, about 3% to about 5% of at least one additional drug, about 32% to about 42% microcrystalline cellulose, about 2% to about 5% hydroxypropyl methylcellulose, about 3% to about 8% sodium starch glycolate, and about 0.3% to about 0.5% magnesium stearate by weight.

The bi-layer tablet may be manufactured according to any method known to those of skill in the art. The resulting tablet comprises the two portions compressed against one another so that the face of each portion is exposed as either the top or bottom of the tablet, or the resulting tablet may comprise the sustained release portion in the center coated by the immediate release portion so that only the immediate release portion is exposed. In a preferred embodiment, a bi-layer tablet comprises the two portions compressed against one another so that the face of each portion is exposed.

In a preferred method of manufacturing the bi-layer tablets, a sustained release formulation is prepared according to either a wet granulation or dry granulation method as described above. The immediate release formulation may be prepared by simply blending the guaifenesin with any pharmaceutical additives. If at least one additional drug is present, then water may be added to the formulation, as described above. In a further preferred embodiment, appropriate quantities of Guaifenesin DC, microcrystalline cellulose, and sodium starch glycolate are blended in a 10 cubic foot blender for about twenty minutes. An appropriate quantity of magnesium stearate is then added to the ingredients and blended for about ten more minutes to make an immediate release formulation. Portions of the sustained release formulation and immediate release formulation are then compressed by a tablet compressor machine capable of forming bi-layer tablets. In one embodiment, these tablets may further be coated with a protective film which rapidly disintegrated or dissolves in gastric juices.

The tablets may be made with any ratio of guaifenesin to at least one additional drug which results in a blood profile demonstrating appropriate therapeutic effect over extended time periods. As discussed above, the additional drug may be present in an amount sufficient to mimic the blood serum profile of the commercially available formulation of the drug and not to exceed the maximum dose approved by the FDA for the treatment, prevention, or amelioration of a particular illness or disease. In one embodiment, the ratio of total guaifenesin to at least one additional drug is about 1:1 to about 30:1, more preferably about 1:1 to 25:1, and more preferably about 20:1 by weight. Alternatively, the ratio is about 2:1 to about 15:1 by weight, and more preferably, the ratio of guaifenesin to at least one additional drug is about 8:1 to about 12:1 by weight. When present in the immediate release layer, the amount of the at least one additional drug should be sufficient to match the drug release profile of the additional drug within the sustained release profile.

In a preferred embodiment, the tablets are made with any ratio of guaifenesin to pseudoephedrine which results in a blood profile demonstrating appropriate therapeutic effect over extended time periods. As discussed above, the pseudoephedrine is present in an amount sufficient to mimic the blood serum profile of the commercially available formulation of the drug and not to exceed the maximum dose approved by the FDA for the treatment, prevention, or amelioration of a particular illness or disease. In one embodiment, the ratio of total guaifenesin to pseudoephedrine is about 1:1 to about 30:1, more preferably about 1:1 to 25:1, and more preferably about 20:1 by weight. Alternatively, the ratio of guaifenesin to pseudoephedrine is about 8:1 to about 12:1 by weight. In another embodiment the pseudoephedrine is only present in the immediate release layer.

In a preferred embodiment, the tablets are made with any ratio of guaifenesin to dextromethorphan which results in a blood profile demonstrating appropriate therapeutic effect over extended time periods. As discussed above, the dextromethorphan is present in an amount sufficient to mimic the blood serum profile of the commercially available formulation of the drug and not to exceed the maximum dose approved by the FDA for the treatment, prevention, or amelioration of a particular illness or disease. In one embodiment, the ratio of total guaifenesin to dextromethorphan is about 1:1 to about 30:1, more preferably about 1:1 to 25:1, and more preferably about 20:1 by weight. Alternatively, the ratio of guaifenesin to dextromethorphan is about 8:1 to about 12:1 by weight.

The tablets may be made with any ratio of sustained release to immediate release formulation which results in a blood profile demonstrating appropriate therapeutic effect over extended time periods. In one embodiment, the bi-layer tablets comprise guaifenesin distributed within the sustained release formulation and the immediate release formulation wherein the ratio of guaifenesin in the SR to guaifenesin in the IR is about 1:1 to about 20:1, more preferably about 1:1 to about 1:15 by weight, preferably the ratio is about 3:2 to about 11:1, and more preferably, the ratio of guaifenesin distributed within the sustained release formulation and the immediate release formulation is about 5:1 to about 9:1 by weight, respectively. For example, in a 1200 mg bi-layer modified release guaifenesin tablet, there may be about 200 mg of guaifenesin in the immediate release layer and about 1000 mg of guaifenesin in the sustained release layer.

The tablets may be made with at least one additional drug only within the sustained release formulation or with the additional drug only in the immediate release formulation. Optionally, the tablets may be made with at least one additional drug distributed within the sustained release formulation and the immediate release formulation. In one embodiment, the bi-layer tablets comprise an additional drug distributed within the sustained release formulation and immediate release formulation wherein the ratio of additional drug in the SR to additional drug in the IR is about 1:1 to about 20:1, more preferably about 1:1 to about 1:15 by weight, preferably the ratio is about 3:2 to about 9:1, and more preferably the ratio is about 3:1 to about 4:1 by weight, respectively. Alternatively the weight ratio for the additional drug is sustained release portion to immediate release portion is about 4:1 to about 1:1, more preferably about 1:1 to about 2:1.

In one preferred embodiment of manufacturing a 1200 mg bi-layer sustained release guaifenesin tablet, about 105 kg of Guaifenesin DC, about 2.5 kg of Methocel E10M, about 1.25 kg of Carbopol 974P, and about 0.333 kg of Emerald Green Lake or FD&C Blue No. 1 in a 10 cubic foot P.K. blender for about twenty minutes. About 0.6 kg of magnesium stearate may then be added and blending continued for about another ten minutes to prepare the sustained release formulation. Approximately 21 kg of Guaifenesin DC, approximately 11.75 kg of microcrystalline cellulose, and approximately 3 kg of sodium starch glycolate may be blended in a 3 cubic foot P.K. blender for about twenty minutes. Approximately 0.1 kg of magnesium stearate may then be added and blending continued for about another ten minutes to prepare the immediate release formulation. The two formulations may then be compressed to make bi-layer tablets wherein about 75% of each tablet may be sustained release formulation and about 25% of each tablet may be immediate release formulation. The tablets may be any dosage strength, size, or shape. In a preferred embodiment, 1200 mg tablets are round and about ⅝ inch in diameter, about 0.28 inch-0.31 inch in thickness, weigh about 1.46 grams and have a hardness range of about 15-40 SCU. In another preferred embodiment, 600 mg tablets are round and about ½ inch in diameter, about 0.218 inch-0.230 inch in thickness, weigh about 0.729 grams and have a hardness range of about 12-30 SCU.

In another preferred embodiment of manufacturing a 1200 mg bi-layer sustained release guaifenesin tablet, about 101 kg of Guaifenesin DC, about 4.5 kg of at least one additional drug such as dextromethorphan, about 5 kg of Methocel E10M, about 1.5 kg of Carbopol 974P, and about 0.04 kg of FD&C Blue No. 1 are blended in a 10 cubic foot Day mixer for about twelve minutes. Thereafter, about 29 kg of water is added and the mixture is blended for an additional 10 minutes, followed by drying. About 1 kg of magnesium stearate may then be added and blending continued for about another ten minutes to prepare the sustained release formulation. About 45.6 kg of GUAIFENESIN, about 3.6 kg of at least one additional drug such as dextromethorphan, about 40.32 kg of microcrystalline cellulose, and approximately 3 kg of sodium starch glycolate are blended in a 3 cubic foot Day mixer for about 12 minutes. Thereafter, about 36 kg of water is added and the mixture is blended for an additional 10 minutes, followed by drying. About 0.48 kg of magnesium stearate may then be added and blending continued for about another ten minutes to prepare the immediate release formulation. The two formulations may then be compressed to make bi-layer tablets wherein about 75% of each tablet may be sustained release formulation and about 25% of each tablet may be immediate release formulation. The tablets may be any dosage strength, size, or shape. In a preferred embodiment, 1200 mg tablets are round and about ⅝ inch in diameter, about 0.31 inch-0.34 inch in thickness, weigh about 15.3 grams and have a hardness range of about 15-35 SCU. In another preferred embodiment, 600 mg tablets are round and about ½ inch in diameter, about 0.22 inch-0.26 inch in thickness, weigh about 7.65 grams and have a hardness range of about 15-65 SCU.

The immediate release portion of the bi-layer tablet is formulated to dissolve in aqueous media of low pH, such as that found in the stomach, to quickly release the guaifenesin contained within the portion. This results in rapid bioavailability of a high concentration of guaifenesin. As demonstrated in Example 6 and FIGS. 9 and 10 below, the immediate release portion of the bi-layer tablet results in a maximum serum concentration ($C_{max}$) and time of maximum serum concentration ($T_{max}$) equivalent to the $C_{max}$ obtained when the first of three doses of a standard immediate release formulation having one third the amount of guaifenesin is dosed every four hours over a 12 hour period.

The sustained release portion gels when exposed to media of low pH allowing the sustained release portion of the tablet to be passed into the intestinal tract. In the intestines, the gelled sustained release portion is exposed to a higher pH environment, causing the gel to slowly dissolve, thereby allowing guaifenesin to diffuse and dissolve out of the gelled matrix. This results in controlled bioavailability over an extended time period (i.e. eight to twelve or more hours) causing the tablet to provide extended therapeutic effect. As shown in Example 6 and FIGS. 9 and 10, the half-life of the modified release bi-layer tablet is increased to more than 3 hours and the tablet has an $AUC_{inf}$ (the area under a plasma concentration versus time curve from time 0 to infinity) of greater than 8000 hr-ng/mL.

Figure 11:
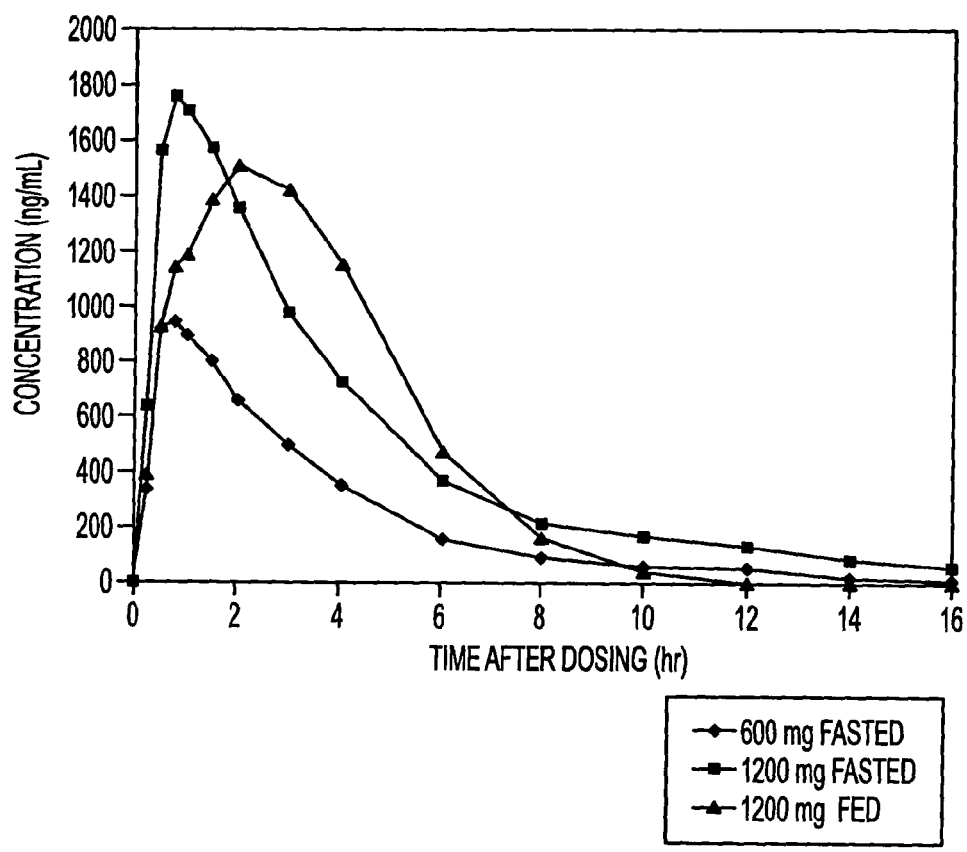
FIG. 11 is a graph demonstrating the averaged plasma concentration of guaifenesin over a 16 hour period in 27 healthy human volunteers from 600 mg bi-layered modified release tablets of the invention administered to fasting volunteers, 1200 mg bi-layered modified release tablets of the invention administered to fasting volunteers, and 1200 mg bi-layered modified release tablets of the invention administered to volunteers who had been fed a high fat meal.

As demonstrated in Example 7 and FIG. 11, the bi-layer tablets of the invention had a further surprising result in that a 600 mg tablet had a $T_{max}$ equivalent to that of a 1200 mg and a $C_{max}$ and $AUC_{inf}$ approximately half of a 1200 mg tablet. Thus, without adjusting or changing the composition of the sustained release formulation or bi-layer tablet, a lower dosage strength guaifenesin tablet of the invention exhibits a plasma concentration profile that is approximately directly proportional to that of a higher dosage strength guaifenesin tablet. As further demonstrated in Example 7 and FIG. 11, the bi-layer tablets resulted in that the $C_{max}$ and $AUC_{inf}$ of a 1200 mg tablet administered to volunteers who had been fasting and the $C_{max}$ and $AUC_{inf}$ of a 1200 mg tablet administered to volunteers who had consumed a high fat meal were approximately equivalent. Thus, a bi-layer tablet of the invention demonstrates a reduced food effect, being approximately equally effective when administered to a patient on an empty or full stomach. Similar results were obtained for combination formulations for instance as described in Examples 8-21.

Several combination formulations were also compared to commercial drugs for bioavailability. For instance, Example 8 shows three batches of the 1200 mg guaifenesin/60 mg dextromethorphan HBr which were dissolved to determine the amount of dextromethorphan HBr released over time. Generally, the formulations had 1200 mg of guaifenesin and 60 mg dextromethorphan HBr and were studied over a 12 hour period. The released amount of dextromethorphan HBr was determined as a weight percent of dissolved dextromethorphan in contrast to the total weight of dextromethorphan prior to dissolution. After 1 hour about 46% to 47% of the dextromethorphan had dissolved. After 2 hours the about 59% to 60% had dissolved, after 6 hours 73% to 76% had dissolved, and after 12 hours about 86% to 89% by weight of the dextromethorphan had dissolved. Thus, the formulations of the invention reproducibly release dextromethorphan over time. (see, FIG. 12). While, example 9, for instance demonstrates the in vivo bioavailability of a sustained release guaifenesin with dextromethorphan.

Various combination guaifenesin/pseudoephedrine compositions were also examined to determine their dissolution rates and bioavailability. Examples 10 and 11, provide a formulations of guaifenesin and pseudoephedrine in the sustained release portion of a bi-layered tablet. Results demonstrated that combining the drugs into a single tablet according to methods of the invention did not effect their dissolution profile or their in vivo release profile.

The two prototype lots of example 12 showed similar in vitro release to market Mucinex™ and Sudafed®. In particular, Formulation B (lot PB01-K61) produced optimal bioavailability for both guaifenesin and pseudoephedrine and was therefore used in subsequent bioavailability studies.

Example 13 compared combination products for guaifenesin/pseudoephedrine HCL) of 1200/120 mg strength, Formulation B (lot PB01-M65A2) and of 600/60 mg strength, Formulation C (lot PB10-A12A) to commercial Mucinex™ and Sudafed® 12 Hour. The 1200/120 mg strength showed bioequivalence for ratios of both $C_{max}$ and $AUC_{inf}$ with a 90% confidence interval, which is contained in the 80-125% range. Further, the 600/60 mg strength demonstrated proportional dosage pharmacokinetics.

Example 14 compared reference Mucinex™ and Sudafed® 12 Hour to a 1200/120 mg strength test formulation (lot PB01-M65A3) for steady-state bioavailability in an 11 day twice-daily dose regime. The test formulation was bioequivalent (within the 80-125% range with a 90% confidence interval) when compared to the reference formulation. Therefore, for both guaifenesin and pseudoephedrine, the steady state for $C_{max}$ and $AUC_{ss}$ were bioequivalent.

Examples 15 and 17 compared the effect of a high fat meal for both reference formulations and combination formulations of the invention. The test formulation (lot PB01-M65) was not bioequivalent with regard to $C_{max}$ for guaifenesin but was for the pseudoephedrine portion when compared to the reference. However, the $AUC_{inf}$ was bioequivalent for both guaifenesin and pseudoephedrine within the 80-125% range.

Example 16 compared single-dose relative bioavailability and interaction potential of guaifenesin and pseudoephedrine administered as Mucinex™ and Sudafed® 12 Hour alone or in combination. The results demonstrate that the pharmacokinetics of guaifenesin and pseudoephedrine are unaffected with regard to both $AUC_{inf}$ and $C_{max}$ in the presence or absence of one another (ratios within 80-125%). This further confirms the results of the other examples which demonstrate bioequivalence for the combination formulations of the invention.

Example 18 compared the bioavailability of guaifenesin and dextromethorphan from an experimental formulation containing both guaifenesin and dextromethorphan as compared to reference guaifenesin and dextromethorphan. The pharmacokinetics of guaifenesin and dextromethorphan were not affected by the presence of the other component and the pharmacokinetics of dextromethorphan were linear over the range studied.

Example 19 compared the relative bioavailability of guaifenesin and dextromethorphan from an experimental formulation, containing both guaifenesin and dextromethorphan, as compared to reference guaifenesin and dextromethorphan. The guaifenesin in the experimental tablet was clearly bioequivalent to that of the Reference, Mucinex, in terms of $C_{max}$, $AUC_{0-t}$ or $AUC_{inf}$. Dextromethorphan hydrobromide in the experimental tablet was also found to be bioequivalent to both 30 mg dextromethorphan hydrobromide every 6 hours, and 20 mg every 4 hours, in terms of $C_{max}$, $AUC_{0-t}$ or $AUC_{inf}$.

Example 20 compared the relative bioavailability of guaifenesin and dextromethorphan from an experimental formulation containing both guaifenesin and dextromethorphan following the consumption of a high fat meal as compared to following an overnight fast. There was no food effect on the absorption of guaifenesin from the experimental tablet. There was an effect of food on the rate of absorption of dextromethorphan from the experimental tablet formulation (a small increase in the rate of absorption) but not on the extent of absorption.

Example 21 compared the relative bioavailability of guaifenesin and dextromethorphan from an experimental formulation containing both guaifenesin and dextromethorphan, as compared to reference guaifenesin and dextromethorphan products. The guaifenesin in the experimental tablet was bioequivalent to that of the Reference, Mucinex, in terms of $C_{max}$ and $AUC_{ss}$ within 80% to 125%. Dextromethorphan hydrobromide in the experimental tablet was bioequivalent to both 30 mg dextromethorphan hydrobromide every 6 hours, and 20 mg every 4 hours, in terms of $C_{max}$ and $AUC_{ss}$ within 80% to 125%.

These studies demonstrate the compositions of the invention provide systemic levels of drug over a 12-hour period. Additionally, the studies demonstrate the bioequivalence of the combination formulations.

Comparison to FDA Approved Drugs

Figure 31:
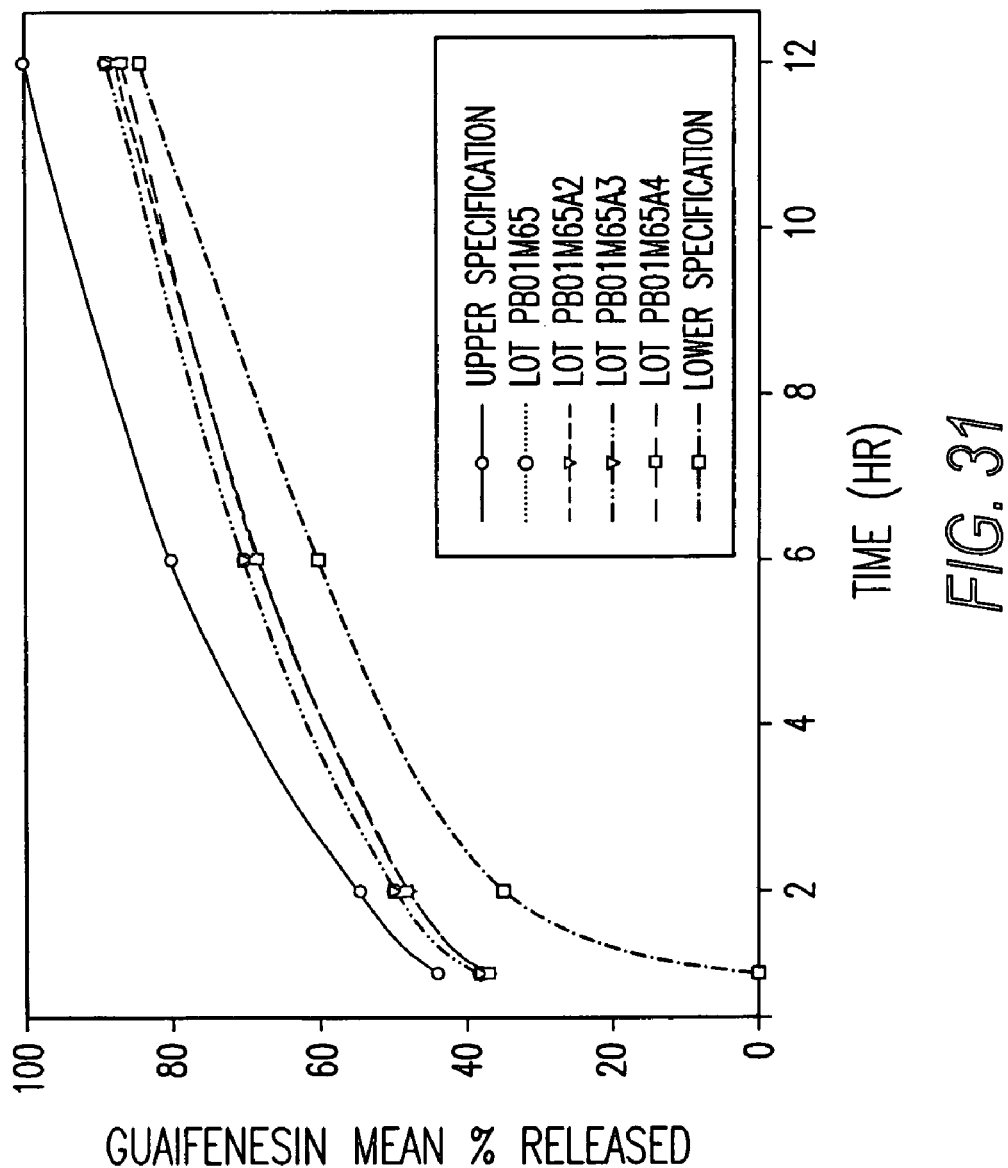
FIG. 31 depicts guaifenesin dissolution profiles for various batches associated with the studies.
Figure 32:
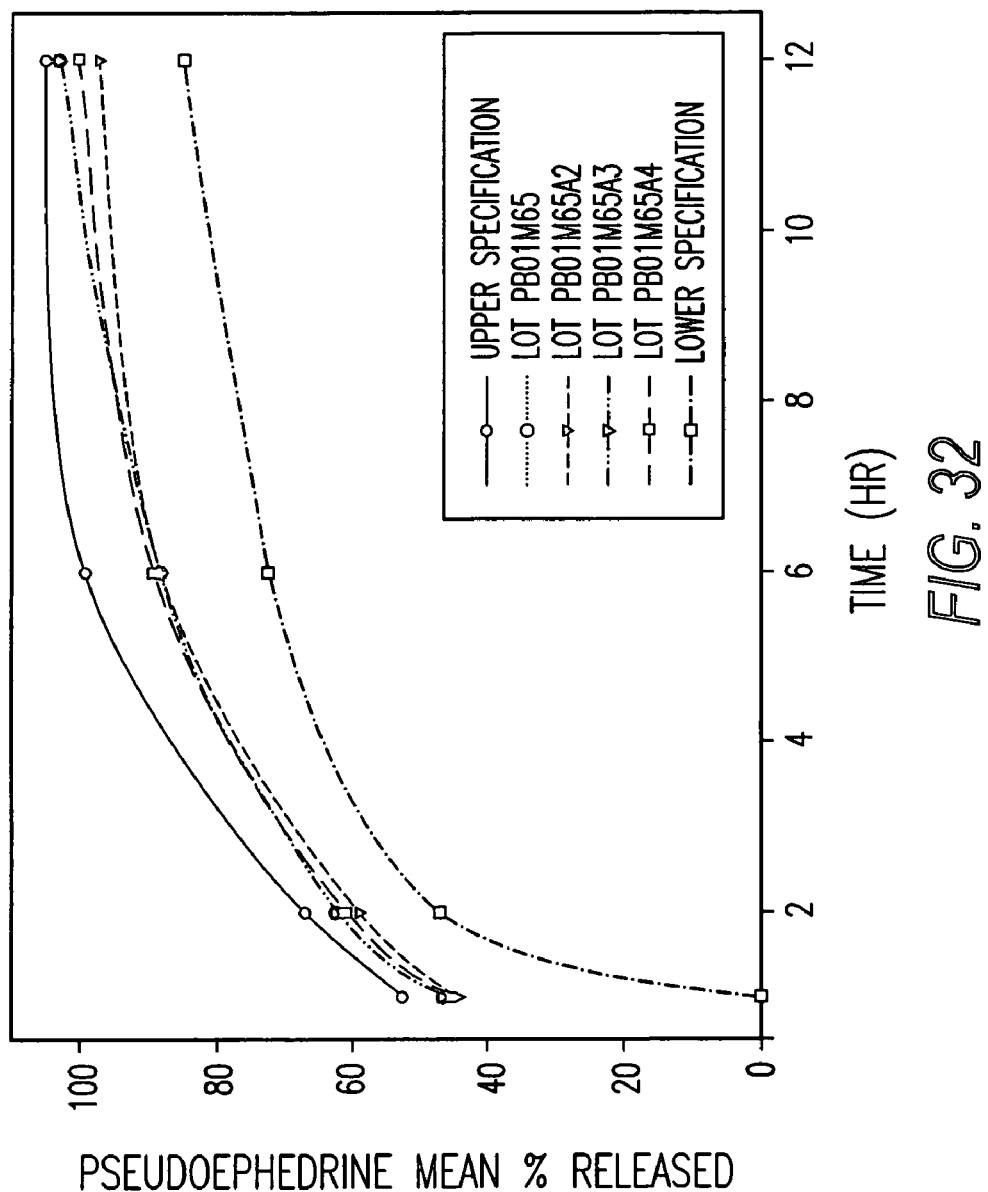
FIG. 32 depicts pseudoephedrine dissolution profiles for various batches associated with the studies.

When using drugs approved by the Food and Drug Administration (FDA), the sustained release formulation alone or in combination with an immediate release component may be formulated to mimic the blood serum profile of guaifenesin and optionally the additional drug(s) as described in the clinical documents filed with the FDA or as required by the FDA. This information may be found at http://www.fda.gov/cder/foi/nda/2002/21-282_Mucinex.htm which is hereby incorporated by reference in its entirety. For instance, a single dose 400 mg immediate release tablet has a $C_{max}$ of 2,463±1033, a $T_{max}$ of 0.5, an $AUC_{0-12}$ 8,382±3,282, an $AUC_{inf}$ 8,529±3,362, and a $T_{1/2}$ of 0.78±0.09. Alternatively, multiple doses of a 400 mg immediate release tablet has a $C_{max}$ of 2,278±791, a $T_{max}$ of 0.5, an $AUC_{0-12}$ 7,751±2,697, $C_{min0}$ 112±52, and a $C_{min12}$ 137±98. Preferably, the formulations result in a maximum serum concentration ($C_{max}$) and/or time of maximum serum concentration ($T_{max}$) equivalent to the $C_{max}$ obtained when the first of three doses of a standard immediate release formulation having one third the amount of guaifenesin is dosed every four hours over a 12 hour period. In other words, the sustained release formulation releases both the guaifenesin and at least one additional drug at a similar rate to the commercially available formulation, thereby providing a therapeutically effective amount of both drugs. Alternatively, the parameters may be calculated through any of the following or combinations thereof: $C_{max}$, $C_{min}$, $T_{max}$, $AUC_{inf}$, $AUC_{0-t}$, $AUC_{ss}$ and $T_{1/2}$. Unless otherwise specified, all reference to $AUC_{0-t}$ in the specification and claims shall refer to data which corresponds to a time (t) of 24 hours. The parameters may also be calculated from in vivo studies such as those presented herein where equivalence is determined from the mean and an 80-125% range with a 90% confidence level and/or one standard deviation from the mean. The parameters may also be calculated from in vivo studies such as those presented herein where equivalence is determined from the median and an 80-125% range with a 90% confidence level and/or one standard deviation from the median. Due to the extreme variability for dextromethorphan, as recognized by the FDA and the inherent variability of measuring plasma serum levels at the picogram level the equivalence is determined from the mean and a 50-150% range, more preferably the equivalence is determined from the mean and a 60-140% range, and most preferably the equivalence is determined from the mean and a 80-125% range with a 90% confidence level. FIGS. 31 and 32 demonstrate specification ranges for various batch compositions of the invention.

Additionally the $C_{max}$ for either guaifenesin, the additional drug(s) or both is preferably between 80% and 125% of the FDA approved mean, more preferably between 90% and 115%, and most preferably between 95% and 115%. These ranges do not have to adjust commensurately, that is to say the mean may for instance preferably be between 90% and 125% of the FDA mean depending on the formulation. Alternatively, the low end of the $C_{max}$ for guaifenesin is preferably greater than 640 ng/mL, more preferably 700 ng/mL, more preferably 800 ng/mL, more preferably 900 ng/mL, more preferably 1000 ng/mL, more preferably 1100 ng/mL, and most preferably 1250 ng/mL depending on the formulation. The high end of the $C_{max}$ for guaifenesin is preferably less than 3750 ng/mL, more preferably 3500 ng/mL, more preferably 3250 ng/mL, more preferably 3000 ng/mL, more preferably 2750 ng/mL, and most preferably 2500 ng/mL depending on the formulation. For a 1200 mg tablet the range is preferably between 1000 ng/mL and 3750 ng/mL, 1200 ng/mL and 3500 ng/mL, 1350 ng/mL and 3000 ng/mL, and 1450 ng/mL and 2750 ng/mL. For a 600 mg tablet the range is preferably between 320 ng/mL and 1875 ng/mL, 400 ng/mL and 1500 ng/mL, 500 ng/mL and 1375 ng/mL, and 625 ng/mL and 1250 ng/mL.

Alternatively, the low end of the $C_{max}$ for pseudoephedrine is preferably greater than 150 ng/mL, more preferably 175 ng/mL, more preferably 200 ng/mL, and most preferably 250 ng/mL depending on the formulation. The high end of the $C_{max}$ for pseudoephedrine is preferably less than 500 ng/mL, more preferably 450 ng/mL, more preferably 400 ng/mL, and most preferably 375 ng/mL depending on the formulation. For a 120 mg tablet the range is preferably between 150 ng/mL and 500 ng/mL, 175 ng/mL and 500 ng/mL, 200 ng/mL and 450 ng/mL, 250 ng/mL and 400 ng/mL, and 300 ng/mL and 375 ng/mL. For a 60 mg tablet the range is preferably between 75 ng/mL and 250 ng/mL, 88 ng/mL and 250 ng/mL, 100 ng/mL and 225 ng/mL, 125 ng/mL and 200 ng/mL, and 150 ng/mL and 188 ng/mL.

Alternatively, the low end of the $C_{max}$ for dextromethorphan is preferably greater than 3840 pg/mL, more preferably 5,500 pg/mL, more preferably 6,600 pg/mL, more preferably 7,000 pg/mL, more preferably 7,700 pg/mL, more preferably 8,000 pg/mL, more preferably 8,800 pg/mL, more preferably 9,900 pg/mL, and most preferably 10,000 pg/mL depending on the formulation. The high end of the $C_{max}$ for dextromethorphan is preferably less than 22,500 pg/mL, more preferably 16,500 pg/mL, more preferably 15,400 pg/mL, more preferably 14,300 pg/mL, more preferably 13,200 pg/mL, and most preferably 12,100 pg/mL depending on the formulation. For a 60 mg tablet the range is preferably between 9,600 pg/mL and 15,000 pg/mL, 10,800 pg/mL and 13,500 pg/mL, 10,800 pg/mL and 12,000 pg/mL, and 12,000 pg/mL and 13,500 pg/mL. For a 30 mg tablet the range is preferably between 7,200 pg/mL and 11,250 pg/mL, 8,100 pg/mL and 10,125 pg/mL, 8,100 pg/mL and 9,000 pg/mL, and 9,000 pg/mL and 10,125 pg/mL. In an alternative embodiment the low end of the $C_{max}$ for dextromethorphan is preferably greater than 1300 pg/mL, more preferably 1,550 pg/mL, more preferably 1,860 pg/mL, more preferably 2,170 pg/mL, more preferably 2,480 pg/mL, and most preferably 2,790 pg/mL depending on the formulation. The high end of the $C_{max}$ for dextromethorphan is preferably less than 5,400 pg/mL, more preferably 4,650 pg/mL, more preferably 4,350 pg/mL, more preferably 4,000 pg/mL, more preferably 3,750 pg/mL, and most preferably 3,400 pg/mL depending on the formulation.

The $C_{min}$ is another aspect which is often not met by various extended release drugs found on the market. Formulations of the invention provide a $C_{min}$ which maintains it therapeutic effectiveness for a period of at least 10 hours, more preferably 12 hours and most preferably 14 or more hours. Additionally the $C_{min}$ for either guaifenesin, the additional drug(s) or both is preferably between 80% and 125% of the FDA approved mean, more preferably between 90% and 115%, and most preferably between 95% and 115%. These ranges do not have to adjust commensurately, that is to say the mean may for instance preferably be between 90% and 125% of the FDA mean depending on the formulation. Alternatively, the low end of the $C_{min}$ for guaifenesin is preferably greater than 40 ng/mL, more preferably 50 ng/mL, more preferably 60 ng/mL, and most preferably 70 ng/mL depending on the formulation. The high end of the $C_{min}$ for guaifenesin is preferably less than 200 ng/mL, more preferably 175 ng/mL, more preferably 150 ng/mL, and most preferably 125 ng/mL depending on the formulation. The $C_{min}$ range for either a 1200 or a 600 mg tablet may be selected from 50 ng/mL and 150 ng/mL, 50 ng/mL and 125 ng/mL, 60 ng/mL, 125 ng/mL, 70 ng/mL and 125 ng/mL, 80 ng/mL and 125 ng/mL, between 35 ng/mL and 75 ng/mL, 40 ng/mL and 70 ng/mL, 45 ng/mL and 65 ng/mL, and 50 ng/mL and 60 ng/mL.

Alternatively, the low end of the $C_{min}$, for pseudoephedrine is preferably greater than 75 ng/mL, more preferably 100 ng/mL, more preferably 125 ng/mL, and most preferably 150 ng/mL depending on the formulation. The high end of the $C_{min}$ for pseudoephedrine is preferably less than 300 ng/mL, more preferably 250 ng/mL, more preferably 225 ng/mL, and most preferably 200 ng/mL depending on the formulation. The $C_{min}$ range for either a 120 mg or 60 mg tablet may be selected from 75 ng/mL and 300 ng/mL, 100 ng/mL and 250 ng/mL, 125 ng/mL and 225 ng/mL, 150 ng/mL and 200 ng/mL.

Alternatively, the low end of the $C_{min}$ for dextromethorphan is preferably greater than 1,250 pg/mL, more preferably 1,500 pg/mL, more preferably 1,700 pg/mL, more preferably 2,000 pg/mL, and most preferably 2,250 pg/mL. Alternatively, the high end of the $C_{min}$ for dextromethorphan is preferably less than 3,750 pg/mL, more preferably 3,500 pg/mL, more preferably 3,250 pg/mL, more preferably 3,000 pg/mL, and most preferably 2,750 pg/mL depending on the formulation. Alternatively, the $C_{min}$ range for a 60 mg tablet may be selected from 7,200 pg/mL and 11,250 pg/mL, 8,100 pg/mL and 10,125 pg/mL, 8,100 pg/mL and 9,000 pg/mL, and 9,000 pg/mL and 10,125 pg/mL. The $C_{min}$ range for a 30 mg tablet may be selected from 5,400 pg/mL and 8,400 pg/mL, 6,075 pg/mL and 7,600 pg/mL, 6,075 pg/mL and 6,750 pg/mL, and 6,750 pg/mL and 7,600 pg/mL. In another embodiment the low end of the $C_{min}$ for dextromethorphan is preferably greater than 1,050 pg/mL, more preferably 1,250 pg/mL, more preferably 1,450 pg/mL, more preferably 1,650 pg/mL, and most preferably 1,850 pg/mL. The high end of the $C_{min}$ for dextromethorphan is preferably less than 3,150 pg/mL, more preferably 2,950 pg/mL, more preferably 2,700 pg/mL, more preferably 2,500 pg/mL, and most preferably 2,300 pg/mL depending on the formulation.

Formulations of the invention provide a $T_{max}$ for either guaifenesin, the additional drug(s) or both which is preferably between 80% and 125% of the FDA approved mean, more preferably between 90% and 115%, and most preferably between 95% and 115%. These ranges do not have to adjust commensurately, that is to say the mean may for instance preferably be between 90% and 125% of the FDA mean depending on the formulation. Alternatively, the low end of the $T_{max}$ for guaifenesin is preferably greater than 0.6 hours, more preferably 0.8 hours, more preferably 0.9 hours, more preferably 1.0 hours, and most preferably 1.1 hours depending on the formulation. The high end of the $T_{max}$ for guaifenesin is preferably less than 3.0 hours, more preferably 2.5 hours, more preferably 2.25 hours, and most preferably 2 hours depending on the formulation. The $T_{max}$ range may also be selected from between 0.6 hours and 3.0 hours, 0.8 hours and 2.5 hours, 0.9 hours and 2.25 hours, 1.0 hours and 2 hours, and 1.1 hours and 2 hours.

Alternatively, the low end of the $T_{max}$ for pseudoephedrine is preferably greater than 3.75 hours, more preferably 4.0 hours, more preferably 4.25 hours, more preferably 4.5 hours, and most preferably 4.75 hours depending on the formulation. The high end of the $T_{max}$ for pseudoephedrine is preferably less than 9.0 hours, more preferably 8.5 hours, more preferably 8.0 hours, and most preferably 7.5 hours depending on the formulation. The $T_{max}$ range may also be selected from between 3.75 hours and 9.0 hours, 4.0 hours and 8.5 hours, 4.25 hours and 8.0 hours, 4.5 hours and 7.5 hours, and 4.75 hours and 7.5 hours.

Alternatively, the low end of the $T_{max}$ for dextromethorphan is preferably greater than 3.3 hours, more preferably 3.9 hours, more preferably 4.6 hours, more preferably 5.2 hours, and most preferably 5.85 hours depending on the formulation. The high end of the $T_{max}$ for dextromethorphan is preferably less than 10.6 hours, more preferably 9.8 hours, more preferably 9.1 hours, more preferably 8.8 hours, more preferably 8.5 hours, more preferably 7.8 hours and most preferably 7.2 hours depending on the formulation. The $T_{max}$ range may also be selected from between 6.2 hours and 9.7 hours, 6.7 hours and 8.8 hours, 6.7 hours and 7.75 hours, and 7.75 hours and 8.8 hours for a 60 mg tablet. The $T_{max}$ range may also be selected from between 4.6 hours and 7.25 hours, 5.2 hours and 6.5 hours, 5.2 hours and 5.8 hours, and 5.8 hours and 6.5 hours for a 30 mg tablet.

Formulations of the invention provide a $AUC_{inf}$ for either guaifenesin, the additional drug(s) or both which is preferably between 80% and 125% of the FDA approved mean, more preferably between 90% and 115%, and most preferably between 95% and 115%. These ranges do not have to adjust commensurately, that is to say the mean may for instance preferably be between 90% and 125% of the FDA mean depending on the formulation. Alternatively, the low end of the $AUC_{inf}$ for guaifenesin is preferably greater than 4,000 hr-ng/mL, more preferably 5,000 hr-ng/mL, more preferably 5,500 hr-ng/mL, and most preferably 6,000 hr-ng/mL depending on the formulation. The high end of the $AUC_{inf}$ for guaifenesin is preferably less than 12,500 hr-ng/mL, more preferably 10,000 hr-ng/mL, more preferably 9,500 hr-ng/mL, and most preferably 9,000 hr-ng/mL depending on the formulation. For a 1200 mg tablet the $AUC_{inf}$ range may be selected from between 4,000 hr-ng/mL and 12,500 hr-ng/mL, 5,000 hr-ng/mL and 10,000 hr-ng/mL, 5,500 hr-ng/mL and 9,500 hr-ng/mL, and 6,000 hr-ng/mL and 9,000 hr-ng/mL. For a 600 mg tablet the $AUC_{inf}$ range may be selected from between 2,000 hr-ng/mL and 6,250 hr-ng/mL, 2,500 hr-ng/mL and 5,000 hr-ng/mL, 2,250 hr-ng/mL and 4,750 hr-ng/mL, and 3,000 hr-ng/mL and 4,500 hr-ng/mL.

Alternatively, the low end of the $AUC_{inf}$ for pseudoephedrine is preferably greater than 2,500 hr-ng/mL, more preferably 2,800 hr-ng/mL, more preferably 3,500 hr-ng/mL, and most preferably 3,750 hr-ng/mL depending on the formulation. The high end of the $AUC_{inf}$ for pseudoephedrine is preferably less than 6,000 hr-ng/mL, more preferably 5,800 hr-ng/mL, more preferably 5,500 hr-ng/mL, and most preferably 5,000 hr-ng/mL depending on the formulation. For a 120 mg tablet the $AUC_{inf}$ may be selected from between 2,500 hr-ng/mL and 6,000 hr-ng/mL, 2,800 hr-ng/mL and 5,800 hr-ng/mL, 3,500 hr-ng/mL and 5,500 hr-ng/mL, and 3,750 hr-ng/mL and 5,000 hr-ng/mL. For a 60 mg tablet the $AUC_{inf}$ may be selected from between 1,250 hr-ng/mL and 3,000 hr-ng/mL, 1,400 hr-ng/mL and 2,900 hr-ng/mL, 1,750 hr-ng/mL and 2,750 hr-ng/mL, and 1,875 hr-ng/mL and 2,500 hr-ng/mL.

Alternatively, the low end of the $AUC_{inf}$ for dextromethorphan is preferably greater than 55,200 hr-ng/mL, more preferably 145,000 hr-ng/mL, more preferably 174,000 hr-ng/mL, more preferably 192,000 hr-ng/mL, more preferably 203,000 hr-ng/mL, more preferably 216,000 hr-ng/mL, more preferably 232,000 hr-ng/mL, more preferably 240,000 hr-ng/mL, and most preferably 261,000 hr-ng/mL depending on the formulation. The high end of the $AUC_{inf}$ for dextromethorphan is preferably less than 587,500 hr-ng/mL, more preferably 435,000 hr-ng/mL, more preferably 405,000 hr-ng/mL, more preferably 400,000 hr-ng/mL, more preferably 377,000 hr-ng/mL, more preferably 360,000 hr-ng/mL, more preferably 348,000 hr-ng/mL, and most preferably 320,000 hr-ng/mL depending on the formulation. For a 60 mg tablet the $AUC_{inf}$ may be selected from between 256,000 hr-ng/mL and 400,000 hr-ng/mL, 288,000 hr-ng/mL and 360,000 hr-ng/mL, 288,000 pg/mL and 320,000 hr-ng/mL, and 320,000 hr-ng/mL and 360,000 hr-ng/mL. For a 30 mg tablet the $AUC_{inf}$ may be selected from between 192,000 hr-ng/mL and 300,000 hr-ng/mL, 216,000 hr-ng/mL and 270,000 hr-ng/mL, 216,000 hr-ng/mL and 240,000 hr-ng/mL, and 240,000 hr-ng/mL and 270,000 hr-ng/mL. In another embodiment the low end of the $AUC_{inf}$ for dextromethorphan is preferably greater than 15,000 hr-ng/mL, more preferably 18,000 hr-ng/mL, more preferably 21,000 hr-ng/mL, more preferably 24,000 hr-ng/mL, and most preferably 27,000 hr-ng/mL depending on the formulation. The high end of the $AUC_{inf}$ for dextromethorphan is preferably less than 46,900 hr-ng/mL, more preferably 45,000 hr-ng/mL, more preferably 42,000 hr-ng/mL, more preferably 39,000 hr-ng/mL, more preferably 36,000 hr-ng/mL, and most preferably 33,000 hr-ng/mL depending on the formulation.

Formulations of the invention provide a $AUC_{0-t}$ for either guaifenesin, the additional drug(s) or both which is preferably between 80% and 125% of the FDA approved mean, more preferably between 90% and 115%, and most preferably between 95% and 115%. These ranges do not have to adjust commensurately, that is to say the mean may for instance preferably be between 90% and 125% of the FDA mean depending on the formulation. Alternatively, the low end of the $AUC_{0-t}$ for guaifenesin is preferably greater than 3,200 hr-ng/mL, more preferably 3,700 hr-ng/mL, more preferably 4,000 hr-ng/mL, and most preferably 4,500 hr-ng/mL depending on the formulation. The high end of the $AUC_{0-t}$ for guaifenesin is preferably less than 11,250 hr-ng/mL, more preferably 10,500 hr-ng/mL, more preferably 9,500 hr-ng/mL, more preferably 9,000 hr-ng/mL, and most preferably 8,500 hr-ng/mL depending on the formulation. For a 1200 mg tablet the $AUC_{0-t}$ may be selected from between 3,200 hr-ng/mL and 11,250 hr-ng/mL, 3,700 hr-ng/mL and 10,500 hr-ng/mL, 4,000 hr-ng/mL and 9,500 hr-ng/mL, 4,250 hr-ng/mL and 9,000 hr-ng/mL, and 4,500 hr-ng/mL and 8,500 hr-ng/mL. For a 600 mg tablet the $AUC_{0-t}$ may be selected from between 1,600 hr-ng/mL and 5,625 hr-ng/mL, 1,850 hr-ng/mL and 5,250 hr-ng/mL, 2,000 hr-ng/mL and 4,750 hr-ng/mL, 2,125 hr-ng/mL and 4,500 hr-ng/mL, and 2,250 hr-ng/mL and 4,250 hr-ng/mL.

Alternatively, the low end of the $AUC_{0-t}$ for pseudoephedrine is preferably greater than 2,000 hr-ng/mL, more preferably 2,200 hr-ng/mL, more preferably 2,500 hr-ng/mL, and most preferably 2,800 hr-ng/mL depending on the formulation. The high end of the $AUC_{0-t}$ for pseudoephedrine is preferably less than 6,000 hr-ng/mL, more preferably 5,750 hr-ng/mL, more preferably 5,500 hr-ng/mL, more preferably 5,250 hr-ng/mL, and most preferably 5,000 hr-ng/mL depending on the formulation. For a 120 mg tablet the $AUC_{0-t}$ may be selected from between 2,000 hr-ng/mL and 6,000 hr-ng/mL, 2,200 hr-ng/mL and 5,750 hr-ng/IL, 2,500 hr-ng/mL and 5,500 hr-ng/mL, 2,700 hr-ng/mL and 5,250 hr-ng/mL, and 2,800 hr-ng/mL and 5,000 hr-ng/mL. For a 60 mg tablet the $AUC_{0-t}$ may be selected from between 1,000 hr-ng/mL and 3,000 hr-ng/mL, 1,100 hr-ng/mL and 2,875 hr-ng/mL, 1,250 hr-ng/mL and 2,750 hr-ng/mL, 1,350 hr-ng/mL and 2,625 hr-ng/mL, and 1,400 hr-ng/mL and 2,500 hr-ng/mL.

Alternatively, the low end of the $AUC_{0-t}$ for dextromethorphan is preferably greater than 59,000 hr-ng/mL, more preferably 119,000 hr-ng/mL, more preferably 143,000 hr-ng/mL, more preferably 162,000 hr-ng/mL, more preferably 166,000 hr-ng/mL, more preferably 182,000 hr-ng/mL, more preferably 190,000 hr-ng/mL, more preferably 202,000 hr-ng/mL, and most preferably 214,000 hr-ng/mL depending on the formulation. The high end of the $AUC_{0-t}$ for dextromethorphan is preferably less than 475,000 hr-ng/mL, more preferably 360,000 hr-ng/mL, more preferably 337,500 hr-ng/mL, more preferably 333,000 hr-ng/mL, more preferably 309,000 hr-ng/mL, more preferably 300,000 hr-ng/mL, more preferably 286,000 hr-ng/mL, more preferably 270,000 hr-ng/mL, and most preferably 262,000 hr-ng/mL depending on the formulation. For a 60 mg tablet the $AUC_{0-t}$ may be selected from between 216,000 hr-ng/mL and 337,500 hr-ng/mL, 243,000 hr-ng/mL and 300,000 hr-ng/mL, 243,000 hr-ng/mL and 270,000 hr-ng/mL, and 270,000 hr-ng/mL and 300,000 hr-ng/mL. For a 30 mg tablet the $AUC_{0-t}$ may be selected from between 162,000 hr-ng/mL and 250,000 hr-ng/mL, 182,000 hr-ng/mL and 230,000 hr-ng/mL, 182,000 hr-ng/mL and 202,000 hr-ng/mL, and 202,000 hr-ng/mL and 230,000 hr-ng/mL. In another embodiment the low end of the $AUC_{0-t}$ for dextromethorphan is preferably greater than 15,000 hr-ng/mL, more preferably 18,000 hr-ng/mL, more preferably 21,000 hr-ng/mL, more preferably 24,000 hr-ng/mL, and most preferably 27,000 hr-ng/mL depending on the formulation. The high end of the $AUC_{0-t}$ for dextromethorphan is preferably less than 47,300 hr-ng/mL, more preferably 45,000 hr-ng/mL, more preferably 42,000 hr-ng/mL, more preferably 39,000 hr-ng/mL, more preferably 36,000 hr-ng/mL, and most preferably 33,000 hr-ng/mL depending on the formulation.

Formulations of the invention provide a $AUC_{ss}$ for either guaifenesin, the additional drug(s) or both which is preferably between 80% and 125% of the FDA approved mean, more preferably between 90% and 115%, and most preferably between 95% and 115%. These ranges do not have to adjust commensurately, that is to say the mean may for instance preferably be between 90% and 125% of the FDA mean depending on the formulation. Alternatively, the low end of the $AUC_{ss}$ for guaifenesin is preferably greater than 5000 hr-ng/mL, more preferably 5600 hr-ng/mL, more preferably 6000 hr-ng/mL, and most preferably 6500 hr-ng/mL depending on the formulation. The high end of the $AUC_{ss}$ for guaifenesin is preferably less than 9000 hr-ng/mL, more preferably 8750 hr-ng/mL, more preferably 8250 hr-ng/mL, and most preferably 8000 hr-ng/mL depending on the formulation. The $AUC_{ss}$ for a 1200 mg tablet may be selected from between 5000 hr-ng/mL and 9000 hr-ng/mL, 5600 hr-ng/mL and 8750 hr-ng/mL, 6000 hr-ng/mL and 8000 hr-ng/mL, and 6500 hr-ng/mL and 8250 hr-ng/mL. The $AUC_{ss}$ for a 600 mg tablet may be selected from between 2,500 hr-ng/mL and 4,500 hr-ng/mL, 2,800 hr-ng/mL and 4,375 hr-ng/mL, 3,000 hr-ng/mL and 4,000 hr-ng/mL, and 3,250 hr-ng/mL and 4,125 hr-ng/mL.

Alternatively, the low end of the $AUC_{ss}$ for pseudoephedrine is preferably greater than 2,100 hr-ng/mL, more preferably 2,400 hr-ng/mL, more preferably 2,650 hr-ng/mL, and most preferably 2,800 hr-ng/mL depending on the formulation. The high end of the $AUC_{ss}$ for pseudoephedrine is preferably less than 5,500 hr-ng/mL, more preferably 5,000 hr-ng/mL, more preferably 4,500 hr-ng/mL, and most preferably 4,000 hr-ng/mL depending on the formulation. The $AUC_{ss}$ for a 120 mg tablet may be selected from between 2,100 hr-ng/mL and 5,500 hr-ng/mL, 2,400 hr-ng/mL and 5,000 hr-ng/mL, 2,650 hr-ng/mL and 4,500 hr-ng/mL, and 2,800 hr-ng/mL 4,000 hr-ng/mL. The $AUC_{ss}$ for a 60 mg tablet may be selected from between 1,050 hr-ng/mL and 2,250 hr-ng/mL, 1,200 hr-ng/mL and 2,500 hr-ng/mL, 1,325 hr-ng/mL and 2,250 hr-ng/mL, and 1,400 hr-ng/mL 2,000 hr-ng/mL.

Alternatively, the low end of the $AUC_{ss}$ for dextromethorphan is preferably greater than 87,750 hr-ng/mL, more preferably 105,000 hr-ng/mL, more preferably 120,000 hr-ng/mL, more preferably 132,000 hr-ng/mL, more preferably 140,000 hr-ng/mL, and most preferably 158,000 hr-ng/mL depending on the formulation. The high end of the $AUC_{ss}$ for dextromethorphan is preferably less than 263,000 hr-ng/mL, more preferably 245,000 hr-ng/mL, more preferably 228,000 hr-ng/mL, more preferably 220,000 hr-ng/mL, more preferably 210,000 hr-ng/mL, more preferably 197,000 hr-ng/mL, and most preferably 193,000 hr-ng/mL depending on the formulation. The $AUC_{ss}$ for a 60 mg tablet may be selected from between 140,000 hr-ng/mL and 220,000 hr-ng/mL, 157,500 hr-ng/mL and 197,000 hr-ng/mL, 157,500 hr-ng/mL and 175,000 hr-ng/mL, and 175,000 hr-ng/mL and 197,000 hr-ng/mL. The $AUC_{ss}$ for a 30 mg tablet may be selected from between 105,000 hr-ng/mL and 165,000 hr-ng/mL, 120,000 hr-ng/mL and 149,000 hr-ng/mL, 120,000 hr-ng/mL and 132,000 hr-ng/mL, and 132,000 hr-ng/mL and 149,000 hr-ng/mL. In another embodiment the low end of the $AUC_{ss}$ for dextromethorphan is preferably greater than 19,000 hr-ng/mL, more preferably 22,800 hr-ng/mL, more preferably 26,600 hr-ng/mL, more preferably 30,500 hr-ng/mL, and most preferably 34,000 hr-ng/mL depending on the formulation. The high end of the $AUC_{ss}$ for dextromethorphan is preferably less than 57,000 hr-ng/mL, more preferably 53,000 hr-ng/mL, more preferably 49,500 hr-ng/mL, more preferably 45,600 hr-ng/mL, and most preferably 41,800 hr-ng/mL depending on the formulation.

Formulations of the invention provide a $T_{1/2}$ for either guaifenesin, the additional drug(s) or both which is preferably between 80% and 125% of the FDA approved mean, more preferably between 90% and 115%, and most preferably between 95% and 115%. These ranges do not have to adjust commensurately, that is to say the mean may for instance preferably be between 90% and 125% of the FDA mean depending on the formulation. Alternatively, the low end of the $T_{1/2}$ for guaifenesin is preferably greater than 0.7 hours, more preferably 0.9 hours, more preferably 1.1 hours, more preferably 1.3 hours, and most preferably 1.4 hours depending on the formulation. The high end of the $T_{1/2}$ for guaifenesin is preferably less than 7.25 hours, more preferably 6.0 hours, more preferably 5.0 hours, and most preferably 3.5 hours depending on the formulation. The $T_{1/2}$ for a 1200 mg tablet may be selected from between 0.7 hours and 7.25 hours, 0.9 hours and 6.0 hours, 1.1 hours and 5.0 hours, 1.3 hours and 3.5 hours, and 1.4 hours and 3.5 hours. The $T_{1/2}$ for a 600 mg tablet may be selected from between 0.35 hours and 3.63 hours, 0.45 hours and 3.0 hours, 0.55 hours and 2.5 hours, 0.65 hours and 1.75 hours, and 0.70 hours and 1.75 hours.

Alternatively, the low end of the $T_{1/2}$ for pseudoephedrine is preferably greater than 3.2 hours, more preferably 3.6 hours, more preferably 4.0 hours, more preferably 4.2 hours, and most preferably 4.5 hours depending on the formulation. The high end of the $T_{1/2}$ for pseudoephedrine is preferably less than 8.0 hours, more preferably 7.5 hours, more preferably 7.0 hours, and most preferably 6.25 hours depending on the formulation. The $T_{1/2}$ for a 120 mg tablet may be selected from between 3.2 hours and 8.0 hours, 3.6 hours and 7.5 hours, 4.0 hours and 7.0 hours, 4.2 hours and 6.25 hours, and 4.5 hours and 6.25 hours. The $T_{1/2}$ for a 60 mg tablet may be selected from between 1.60 hours and 4.0 hours, 1.80 hours and 3.75 hours, 2.0 hours and 3.5 hours, 2.1 hours and 3.13 hours, and 2.25 hours and 3.13 hours.

Alternatively, the low end of the $T_{1/2}$ for dextromethorphan is preferably greater than 4.6 hours, more preferably 5.6 hours, more preferably 6.5 hours, more preferably 7.0 hours, more preferably 7.4 hours, more preferably 7.9 hours, more preferably 8.4 hours, and most preferably 8.8 hours depending on the formulation. The high end of the $T_{1/2}$ for dextromethorphan is preferably less than 15.75 hours, 14.7 hours, more preferably 13.0 hours, more preferably 13.0 hours, more preferably 12.1 hours, more preferably 11.75 hours, more preferably 11.2 hours, and most preferably 10.2 hours depending on the formulation. The $T_{1/2}$ for a 60 mg tablet may be selected from between 9.4 hours and 14.7 hours, 10.6 hours and 13.2 hours, 10.6 hours and 11.75 hours, and 11.75 hours and 13.2 hours. The $T_{1/2}$ for a 60 mg tablet may be selected from between 7.0 hours and 11.0 hours, 7.9 hours and 9.9 hours, 7.9 hours and 8.8 hours, and 8.8 hours and 9.9 hours.

Examples of other sustained release/immediate release formulations with and without additional drugs are discussed further in the examples which follow.

EXAMPLES

The invention is further defined by reference to the following examples describing in detail the compositions and methods of the invention. It will be apparent to those skilled in the art that many modifications, both to materials and methods, may be practiced without departing from the purpose and interest of this invention.

For the in vivo study portions, the following general procedures were used for sample analysis unless otherwise indicated. Blood samples (5-10 mLs with sodium heparin as anticoagulant) were taken prior to dosing and at specific intervals after dosing. All blood samples were chilled and centrifuged within 30 minutes of being drawn. The plasma was separated, transferred to a polypropylene tube, frozen at −20° C. or below and stored frozen until being shipped for drug analysis. The plasma samples were then analyzed by a fully validated HPLC method. This resulting plasma concentration v. time data was subjected to pharmacokinetic analysis using non-compartmental analysis with Winnonlin 1.5.

When necessary, volunteers were then given at least a seven day washout period (where no guaifenesin was administered to them under the study) prior to being crossed-over to the next treatment group. Generally, the subjects weighed within 15% of their Ideal Body Weight as defined by the 1983 Metropolitan Life chart.

Example 1

A batch of sustained release guaifenesin tablets, LotNo. 7LB-31FC, with the following composition was prepared:

| Components | Weight per Tablet |
| --- | --- |
| Guaifenesin DC | 1260 mg |
| Methocel E10M | 30 mg |
| Emerald Green Lake | 4 mg |
| Magnesium Stearate | 6.8 mg |
| Opadry Y-S-3-7413 | 13.01 mg |

Another batch of sustained release guaifenesin tablets, Lot No. 7LB-32FC, with the following composition was prepared:

| Components | Weight per Tablet |
| --- | --- |
| Guaifenesin DC | 1260 mg |
| Methocel E10M | 30 mg |
| Carbopol 974P | 15 mg |
| Emerald Green Lake | 4 mg |
| Magnesium Stearate | 6.8 mg |
| Opadry Y-S-3-7413 | 13.16 mg |

Six tablets from Lot 7LB-31FC and six tablets from Lot 7LB-32FC were tested for in vitro guaifenesin release using an Acid/Base dissolution (slightly modified USP 23/NF 18 <711> Drug Release using Apparatus 2). Six dissolution vessels of a USP calibrated Hanson dissolution bath, equipped with shafts and paddles, and were filled with 675 mL of 0.1N hydrochloric acid at 37.0° C. The bath and vessels were maintained at a temperature of 37.0±0.5° C. throughout the 12 hour dissolution test. The paddles were set to rotate at 50 RPM and slowly lowered into the vessels. One tablet of lot 7LB-31 was then dropped into each vessel.

At the one hour and two hour intervals of testing, 5 mL samples of dissolution solution were withdrawn from each vessel and filtered through a 10 micron polyethylene filter into glass HPLC vials. Immediately after the two hour samples were withdrawn, 225 mL of 0.2M sodium phosphate tribasic was added to each vessel to increase the solution pH to about 6.8. The dissolution was run for ten additional hours, 2.0 mL samples being withdrawn from each vessel at the four, eight 10, and 12 hour intervals. The filtered samples were then run on an HPLC to determine percent guaifenesin released.

The same dissolution testing procedure was performed for lot 7LB-32 FC. The lots gave dissolution profiles shown below and depicted in FIG. 4.

Lot 7LB-31

| Vessel No. | 1 hr. | 2 hr. | 4 hr. | 8 hr. | 10 hr. | 12 hr. |
|---|---|---|---|---|---|---|
| 1 | 26 | 38 | 55 | 77 | 84 | 88 |
| 2 | 27 | 39 | 54 | 75 | 81 | 86 |
| 3 | 22 | 37 | 50 | 73 | 78 | 85 |
| 4 | 23 | 33 | 47 | 64 | 73 | 79 |
| 5 | 25 | 36 | 52 | 75 | 81 | 86 |
| 6 | 24 | 35 | 49 | 74 | 81 | 87 |
| Average | 24.5 | 36.3 | 51.2 | 73.0 | 79.7 | 85.2 |

Lot 7LB-32FC

| Vessel No. | 1 hr. | 2 hr. | 4 hr. | 8 hr. | 10 hr. | 12 hr. |
|---|---|---|---|---|---|---|
| 1 | 25 | 36 | 42 | 54 | 59 | 64.0 |
| 2 | 24 | 35 | 42 | 55 | 61 | 66 |
| 3 | 26 | 38 | 45 | 59 | 65 | 69 |
| 4 | 24 | 35 | 42 | 54 | 60 | 65 |
| 5 | 24 | 36 | 43 | 54 | 59 | 64 |
| 6 | 23 | 34 | 38 | 50 | 55 | 59 |
| Average | 24.3 | 35.7 | 42.0 | 54.3 | 59.8 | 64.5 |

Both formulations demonstrated sustained release of guaifenesin over a 12 hour period. Lot 7LB-32FC demonstrated identical release properties to Lot 7LB-31FC in 0.1N HCl. In buffered solution, however, Lot 7LB-32FC, the lot comprising a 2:1 ratio of Methocel E10M to Carbopol 974P, demonstrated a statistically slower release than Lot 7LB-31FC, comprising Methocel E10M and no Carbopol 974P. A slower release rate in vitro translates to a slower, more controlled release with longer drug action in vivo—a favorable characteristic for pharmaceutical products containing a high concentration of an active ingredient with a short half-life (e.g. guaifenesin).

Example 2

Figure 5:
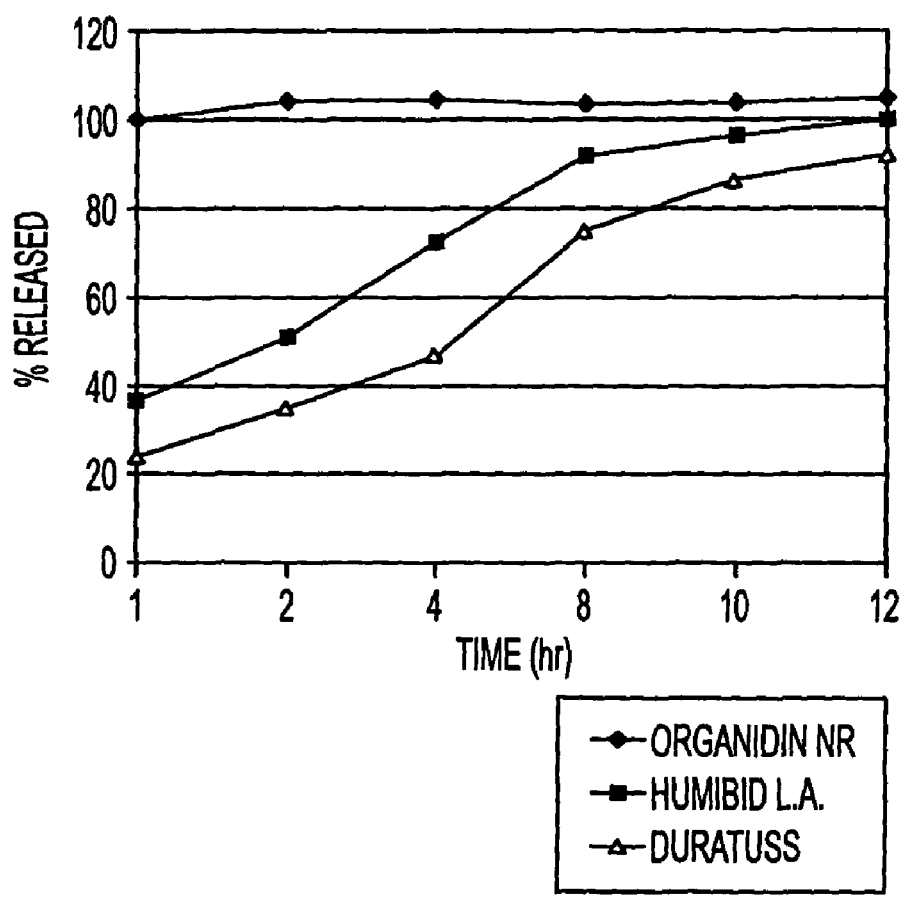
FIG. 5 is a graph demonstrating the dissolution profiles of a commercially available immediate release dosage form and two sustained release dosage forms of guaifenesin.

A dissolution study was run to compare dissolution profiles of lots 7LB-32FC and 7LB-31FC with currently available guaifenesin dosage forms. One immediate release tablet, ORGANIDIN NR, and two sustained release tablets, HUMIBID L.A. and DURATUSS, were subjected to the same dissolution study as described for lots 7LB-31FC and 7LB-32FC in Example 1 above. The following is a summary of the results which are also depicted in FIG. 5.

| | Organidin NR % guaifenesin released | Humibid LA % guaifenesin released | Duratuss % guaifenesin released |
|---|---|---|---|
| 1 hr. | 100 | 36 | 24 |
| 2 hr. | 103 | 51 | 35 |
| 4 hr. | 104 | 72 | 47 |
| 8 hr. | 103 | 91 | 75 |
| 10 hr. | 103 | 96 | 86 |
| 12 hr. | 105 | 100 | 92 |

The immediate release Organidin released 100% of guaifenesin content within the first hour of dissolution. The two commercial sustained release dosage forms demonstrated a slower release of guaifenesin. However, both the Humibid LA and Duratuss released guaifenesin more rapidly than either Lot 7LB-31FC or 7LB-32FC, particularly after the eight hour interval. Both Humibid LA and Duratuss would, therefore, exhibit a faster rate of release and thus a shorter lived therapeutic effect in vivo.

Example 3

The in vivo behavior of sustained release tablets of Lot 7LB-31FC and Lot 7LB-32FC from Example 1 were compared to the in vivo behavior of an immediate release formulation (Organidin NR). The open-label study involved 9 healthy volunteers averaging 38±11.01 years of age with a range of 23 years to 55 years of age. The subjects weighed 175.56±24.22 lbs. with a range of 143 to 210 lbs. One subject was female and the remainder was male. Each subject received either one 1200 mg dose of 7LB-31FC, 7LB-32FC or a commercial 400 mg immediate release tablet (every four hours for 3 doses).

The results of the pharmacokinetic parameters analysis are described below and depicted in FIG. 6.

| Subject | Formulation | $T_{max}$ (hr.) | $C_{max}$ (ng/mL) | $AUC_{0-12}$ (hr-ng/mL) | $T_{1/2}$ (hrs.) | $AUC_{inf}$ (hr-ng/mL) |
|---|---|---|---|---|---|---|
| 1 | 7LB-31FC | 2.00 | 827.02 | 4817.20 | 4.64 | 6339.25 |
| 2 | 7LB-31FC | 1.50 | 834.65 | 4695.89 | 2.71 | 5291.71 |
| 3 | 7LB-31FC | 1.50 | 802.44 | 4142.14 | 3.44 | 4728.33 |
| 4 | 7LB-32FC | 0.75 | 625.48 | 3034.31 | 5.78 | 5134.35 |
| 5 | 7LB-32FC | 1.00 | 1052.00 | 5872.46 | 5.99 | 8298.33 |
| 6 | 7LB-32FC | 2.00 | 1372.00 | 7924.35 | 5.53 | 9557.78 |
| 7 | Organidin NR | 0.50 | 2140.00 | 6921.94 | 0.86 | 7009.68 |
| 8 | Organidin NR | 4.25 | 18.17.00 | 6598.26 | 0.73 | 6674.65 |
| 9 | Organidin NR | 0.50 | 2831.00 | 9389.76 | 0.81 | 9570.91 |
| Mean | 7LB-31FC | 1.67 | 821.37 | 4551.74 | 3.59 | 5453.10 |
| Mean | 7LB-32FC | 1.25 | 1016.49 | 5610.37 | 5.77 | 7663.49 |
| Mean | Organidin NR | 1.75 | 2262.67 | 7636.65 | 0.80 | 7751.74 |
| Ratio (%) | 7LB-31FC/IR | 95.43 | 36.30 | 59.60 | 448.27 | 70.35 |
| Ratio (%) | 7LB-32FC/IR | 71.43 | 44.92 | 73.47 | 718.92 | 98.86 |

Subjects given the 1200 mg formulation 7LB-32FC reached maximum plasma guaifenesin concentrations of 1016 ng/mL in 1.25 hours and had an $AUC_{inf}$ of 7663 hr-ng/mL. The subjects given formulation 7LB-31FC reached maximum plasma guaifenesin concentrations of 821 ng/mL in 1.67 hours and had an $AUC_{inf}$ of 5453 hr-ng/mL. The subjects given the immediate release formulation, Organidin NR, reached maximum plasma guaifenesin concentrations of 2263 ng/mL in 1.75 hours (2 subjects peaked at 0.5 hours after the first dose and the third peaked at 0.25 hours after the second dose at 4 hours) and had an $AUC_{inf}$ of 7752 hr-ng/mL. The two controlled release formulations demonstrated sustained release in that their half-lives were longer, 5.77 hours for the 7LB-32FC and 3.59 hours for the 7LB-31 FC compared to 0.8 hours for the immediate release formulation, Organidin NR.

Both formulations 7LB-32FC (with both Methocel E10M and Carbopol 974P) and 7LB-31FC (with Methocel E10M only) control the release of guaifenesin from the tablet compared to the immediate release Organidin NR. Formulation 7LB-32FC, the formulation containing a 6:1 ratio of Methocel E10M to Carbopol 974P, had the longest half life at 5.77 hours with the largest $AUC_{inf}$ between the two sustained release formulation. However, both sustained release formulations have a $C_{max}$ less than half of the $C_{max}$ of the immediate release Organidin NR.

Example 4

Three different sustained release tablet lots of guaifenesin alone were prepared:
i) Formulation I—1200 mg SR; ii) Formulation II—400 mg IR and 800 mg SR; and iii) Formulation III—600 mg IR and 600 mg SR.

Non-Layered Tablet (Sustained Release)

| Components | Formulation I Weight per Tablet |
| --- | --- |
| Guaifenesin DC | 1260 mg |
| Methocel E10M | 40 mg |
| Carbopol 974P | 20 mg |
| Emerald Green Lake | 4 mg |
| Magnesium Stearate | 6.8 mg |

Bi-Layered Tablets (Sustained Release and Immediate Release)

Immediate Release Layer

| Components | Formulation II Weight per Tablet | Formulation III Weight per Tablet |
| --- | --- | --- |
| Guaifenesin DC | 421 mg | 630.8 mg |
| Microcrystalline Cellulose (Avicel) | 40 mg | 353 mg |
| Sodium Starch Glycolate (Explotab) | 60 mg | 90.1 mg |
| Magnesium Stearate | 2 mg | 3 mg |

Sustained Release Layer

| Components | Formulation II Weight per Tablet | Formulation III Weight per Tablet |
| --- | --- | --- |
| Guaifenesin DC | 842 mg | 630.8 mg |
| Methocel E10M | 27 mg | 40 mg |
| Carbopol 974P | 13.5 mg | 20 mg |
| Emerald Green Lake | 3 mg | 4 mg |
| Magnesium Stearate | 4.5 mg | 6.8 mg |

The in vivo behavior of each of the three sustained release tablets and a commercial immediate release formulation (Organidin NR) were compared. The open-label study involved 15 healthy volunteers averaging 31.67±11.89 years of age with a range of 20 years to 51 years of age. The subjects weighed 162.00±25.05 lbs. with a range of 123 to 212 lbs. All 15 subjects were administered 400 mg of the immediate release formulation every 4 hours for a total of 12 hours in on one day. On another day, 5 subjects were administered Sustained Formulation I, another 5 subjects were administered Sustained Formulation II, and yet another 5 subjects were administered Sustained Formulation III.

Figure 7:
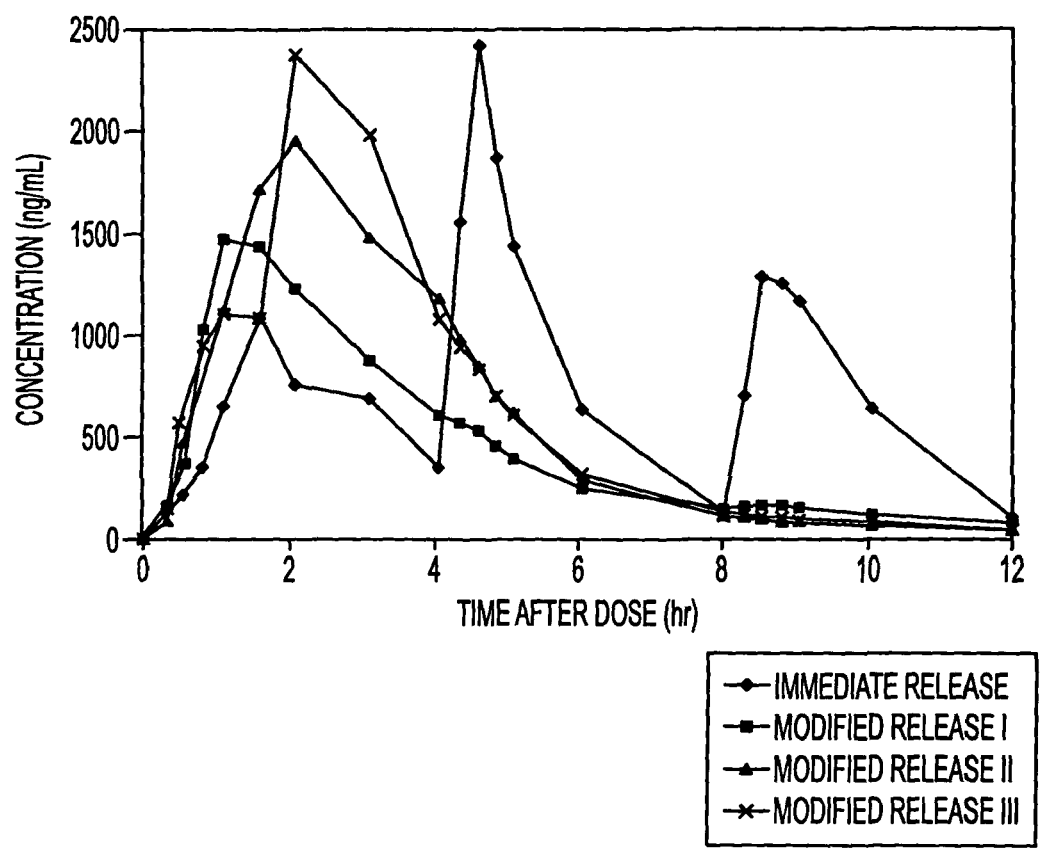
FIG. 7 is a graph demonstrating the plasma concentration of guaifenesin over time in healthy human volunteers from a commercially available immediate release tablet, a non-layered modified release tablet of the invention, and two bi-layered modified release tablets of the invention (one comprising 600 mg of immediate release formulation and 600 mg of sustained release formulation and the other one comprising 400 mg of immediate release formulation and 800 mg of sustained release formulation).

The results of the pharmacokinetic parameters analysis are described below and depicted in FIG. 7.

| | Formulation | $T_{max}$ (hr.) | $C_{max}$ (ng/mL) | $AUC_{0-12}$ (hr-ng/mL) | $T_{1/2}$ (hrs.) | $AUC_{inf}$ (hr-ng/mL) |
| --- | --- | --- | --- | --- | --- | --- |
| Mean | Organidin NR | 0.90 | 2609.40 | 8768.40 | 1.28 | 9082.78 |
| Mean | Formulation I | 2.30 | 1631.40 | 5549.30 | 2.88 | 6044.93 |
| Mean | Formulation II | 2.30 | 2415.40 | 7304.38 | 1.48 | 7509.78 |
| Mean | Formulation III | 1.95 | 2938.00 | 8904.62 | 2.05 | 9161.03 |

Sustained Formulations II and III exhibited a $C_{max}$ more comparable to the immediate release formulation and an increased $AUC_{inf}$ from that of the non-layered Sustained Formulation I. The half-lives of both Sustained Formulation II and III were reduced from the half-life of Sustained Formulation I. These bi-layer tablets, however, showed an improved serum concentration of guaifenesin and an increased overall concentration with time.

Example 5

A dissolution study was run to compare dissolution profiles of Formulation I, Formulation II and Formulation III prepared as defined in Example 4 above, and Formulation IV, a bi-layer tablet lot with 200 mg IR and 1000 mg SR prepared with the following composition:

Immediate Release Layer

| Components | Formulation IV Weight per Tablet |
| --- | --- |
| Guaifenesin DC | 211 mg |
| Microcrystalline Cellulose (Avicel) | 118 mg |
| Sodium Starch Glycolate (Explotab) | 30 mg |
| Magnesium Stearate | 1 mg |

Sustained Release Layer

| Components | Formulation IV Weight per Tablet |
| --- | --- |
| Guaifenesin DC | 1053 mg |
| Methocel E10M | 25 mg |
| Carbopol 974P | 12.5 mg |
| Emerald Green Lake | 3.3 mg |
| Magnesium Stearate | 5.7 mg |

Figure 8:
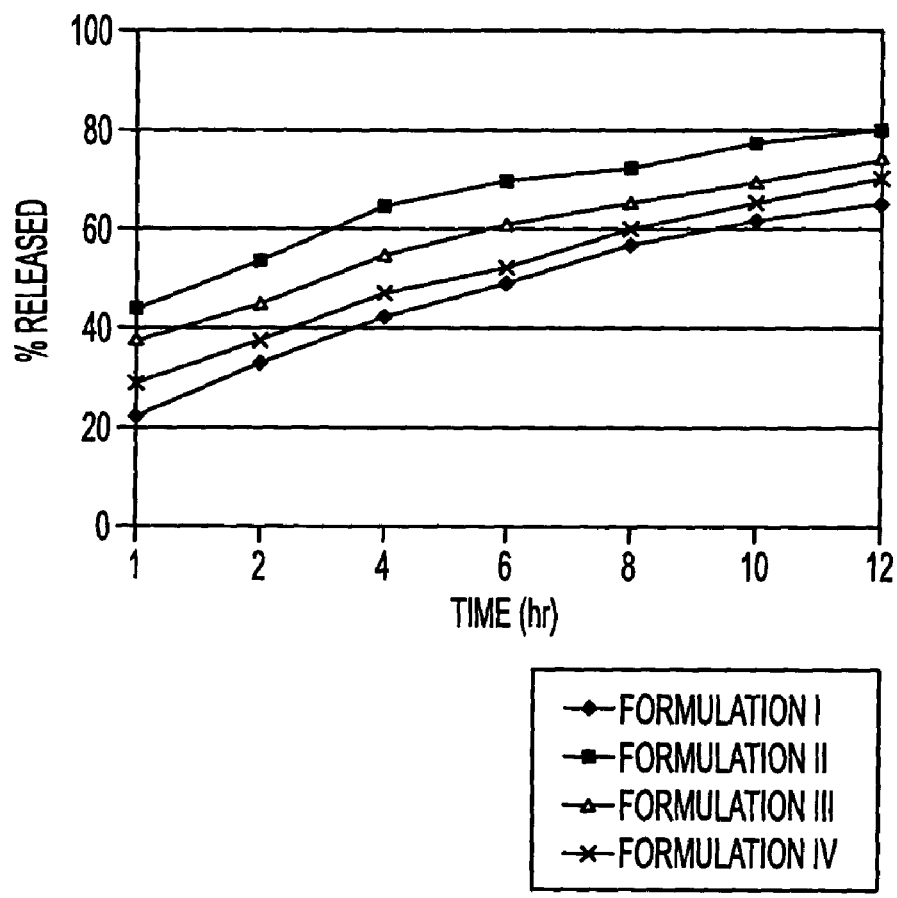
FIG. 8 is a graph demonstrating the dissolution profiles of four sustained release tablets: one tablet is non-layered, comprising 1200 mg of sustained release formulation; another tablet is bi-layered, comprising 600 mg of sustained release formulation and 600 mg of immediate release formulation; another tablet is bi-layered, comprising 800 mg of sustained release formulation and 400 mg of immediate release formulation; and yet another tablet is bi-layered comprising 1000 mg of sustained release formulation and 200 mg of immediate release formulation.

The following is a summary of the results which are also depicted in FIG. 8.

|  | Formulation I % released | Formulation II % released | Formulation III % released | Formulation IV % released |
| --- | --- | --- | --- | --- |
| 1 hr. | 22 | 45 | 38 | 29 |
| 2 hr. | 34 | 54 | 46 | 38 |
| 4 hr. | 43 | 65 | 56 | 48 |
| 6 hr. | 50 | 70 | 61 | 53 |
| 8 hr. | 58 | 73 | 66 | 60 |
| 10 hr. | 62 | 78 | 70 | 66 |
| 12 hr. | 66 | 81 | 75 | 71 |

Formulation I, the non bi-layered tablet, demonstrated the slowest release of guaifenesin. Formulation II and Formulation III had the fastest rates of release and would, therefore, exhibit a faster rate of release and thus a shorter lived therapeutic effect in vivo. Formulation IV has a rate of release which was faster than Formulation I, comprising no immediate release blend, but slower than Formulation II and Formulation III, both comprising more immediate release blend than Formulation IV.

Example 6

The in vivo behavior of Formulation IV bi-layered tablets, prepared as described above in Example 5, was compared to an immediate release formulation (Organidin NR). The open-label, multiple dose, randomized, 2-way crossover study involved 26 healthy volunteers averaging 31.31±9.81 years of age with a range of 19 years to 50 years of age. The subjects weighed 166.77±29.83 lbs. The subjects were placed into one of two treatment groups. Group 1 received Formulation IV tablet with 240 mL of water after an overnight fast every 12 hours for 5 days and a single dose on day 6. Group 2 received 400 mg of Organidin NR (2×200 mg tablets) with 240 mL of water every 4 hours for 5 days and one 400 mg dose every four hours for a total of 3 doses on day 6.

Blood samples (5 mL with sodium heparin as anticoagulant) were taken prior to dosing on days 1, 4, 5, and 6. On Day 1, additional blood samples (5 mL with sodium heparin as anticoagulant) were also obtained at 0.5, 0.75, 1, 1.5, 2, 3, 4, 4.5, 4.75, 5, 5.5, 6, 7, 8, 8.5, 8.75, 9, 9.5, 10. 11, and 12 hours after the initial dose. On Day 6, additional blood samples (5 mL with sodium heparin as anticoagulant) were also obtained at 0.5, 0.75, 1, 1.5, 2, 3, 4, 4.5, 4.75, 5, 5.5, 6, 7, 8, 8.5, 8.75, 9, 9.5, 10, 11, 12, 14, 16, and 24 hours after the initial dose.

The results of the pharmacokinetic parameters analysis are below.

Averaged Testing—11 Twelve-Hour Intervals

|  | Formulation | $T_{max}$ (hr.) | $C_{max}$ (ng/mL) | $AUC_{0-12}$ (hr-ng/mL) | $T_{1/2}$ (hrs.) | $AUC_{inf}$ (hr-ng/mL) |
| --- | --- | --- | --- | --- | --- | --- |
| Mean | Organidin NR | 1.69 | 2463.20 | 8381.93 | 0.78 | 8528.51 |
| Mean | Formulation IV | 1.05 | 2111.38 | 7875.68 | 3.31 | 8686.08 |

Figure 9:
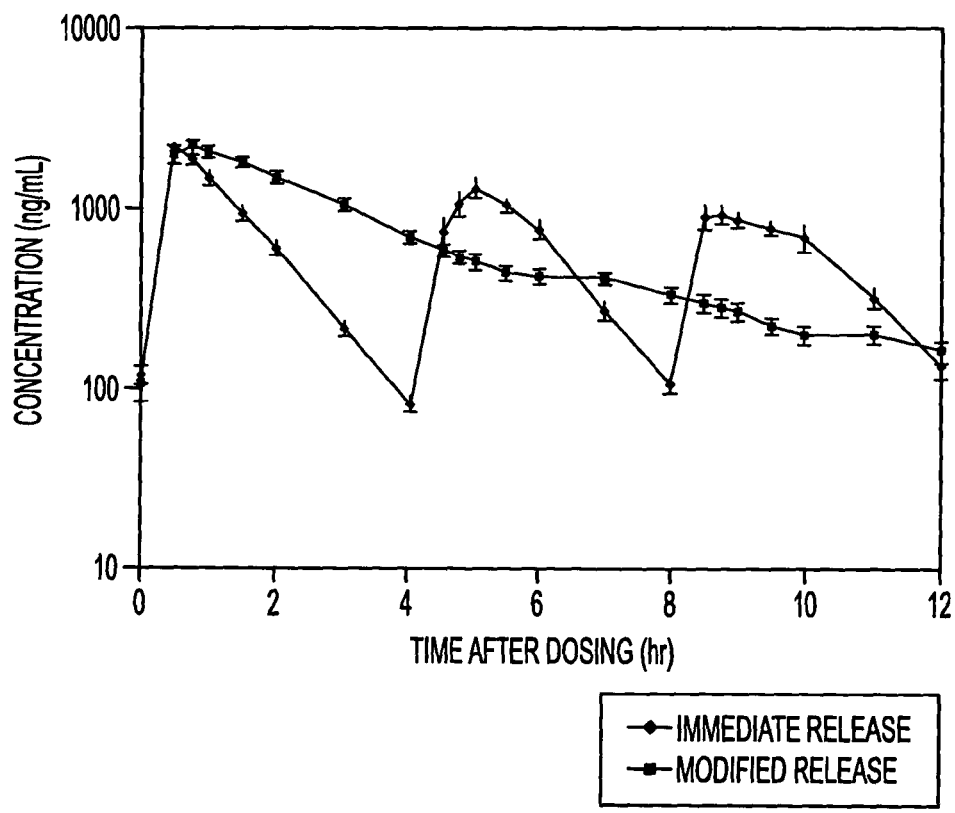
FIG. 9 is a graph demonstrating the plasma concentration of guaifenesin over an averaged 12 hour interval (taken from 11 twelve hour intervals over 5.5 days) in healthy human volunteers from an immediate release tablet and a bi-layered modified release tablet of the invention.

The results of the testing are depicted in FIG. 9.

Steady State Testing

|  | Formulation | $T_{max}$ (hr.) | $C_{max}$ (ng/mL) | $AUC_{0-12}$ (hr-ng/ mL) | $T_{1/2}$ (hrs.) | $AUC_{inf}$ (hr-ng/mL) |
| --- | --- | --- | --- | --- | --- | --- |
| Mean | Organidin NR | 2.03 | 2278.20 | 7751.23 | 0.88 | 7962.14 |
| Mean | Formulation IV | 0.86 | 2349.6 | 8202.47 | 3.61 | 9259.24 |

Figure 10:
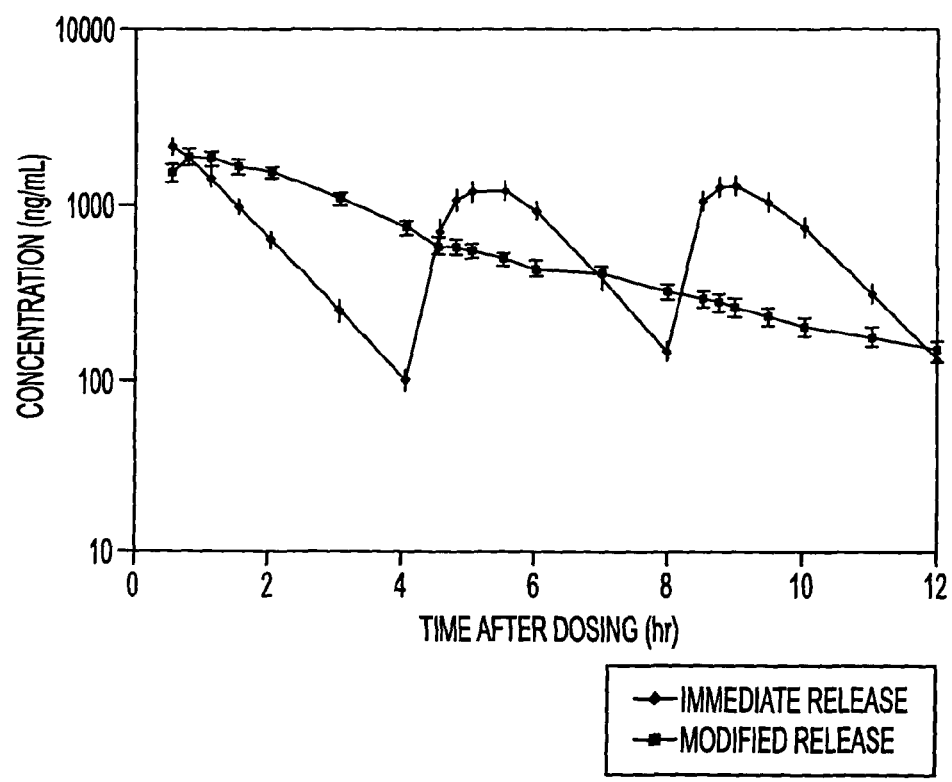
FIG. 10 is a graph demonstrating the plasma concentration of guaifenesin over time (the last twelve hour interval of the 11 twelve hour intervals described above) in healthy human volunteers from an immediate release tablet and a bi-layered modified release tablet of the invention.

The results of the testing are depicted in FIG. 10.

The 200/1000 mg bi-layered tablet exhibited a $C_{max}$ and a $AUC_{inf}$ equivalent to that of the immediate release blend, a short $T_{max}$ and an extended half-life. Thus, a bi-layered tablet with 200 mg guaifenesin in the immediate release formulation and 1000 mg of guaifenesin in the sustained release formulation results in a tablet which delivers a high serum concentration in a short period of time, yet maintains an effective concentration of guaifenesin in the blood stream for a full twelve hours.

Example 7

A study was performed to examine the relative bioavailability of two different dosage strengths of modified release guaifenesin formulations of the invention as well as the effect of food on the relative bioavailability of a guaifenesin formulation of the invention in normal, healthy male and/or female volunteers. Two batches of guaifenesin bi-layer tablets, one 600 mg and one 1200 mg, were prepared.

Immediate Release Layer

| Components | 600 mg Tablet Weight per 200,000 Tablets | 1200 mg Tablet Weight per 100,000 Tablets |
| --- | --- | --- |
| Guaifenesin DC | 21.05 kg | 21.05 kg |
| Microcrystalline Cellulose (Avicel PH102) | 11.75 kg | 11.75 kg |
| Sodium Starch Glycolate (Explotab) | 3.00 kg | 3.00 kg |
| Magnesium Stearate | 0.10 kg | 0.10 kg |

Sustained Release Layer

| Components | 600 mg Tablet Weight per 200,000 Tablets | 1200 mg Tablet Weight per 100,000 Tablets |
| --- | --- | --- |
| Guaifenesin DC | 105.27 kg | 105.27 kg |
| Hydroxypropyl Methyl Cellulose (Methocel E10M) | 2.50 kg | 2.50 kg |
| Carbomer (Carbopol 974P) | 1.25 kg | 1.25 kg |
| FD&C Blue No. 1 Aluminum Lake Dye | 0.33 kg | 0.33 kg |
| Magnesium Stearate | 0.57 kg | 0.57 kg |

The 600 mg and 1200 mg tablets were similarly prepared, the with the exception of the number of tablets produced from the amount of materials used.

The in vivo behaviors of a 600 mg tablet administered to volunteers in the fasting state (about 10 hours pre-dose until about 4 hours after dosing), the 1200 mg tablet administered to volunteers in the fasting state (about 10 hours pre-dose until about 4 hours after dosing), and the 1200 mg tablet administered to volunteers after a high fat meal (consumed within 30 minutes of dosing) were compared. The open-label study involved 27 healthy volunteers between the ages of 18 and 55. The 27 volunteers were divided into 3 treatment groups, 9 receiving the 600 mg tablet, 9 receiving the 1200 mg tablet while fasting, and 9 receiving a 1200 mg tablet after consuming a high fat meal for Period 1 of the trial. After completion of Period 1, the volunteers were crossed-over for Period 2 (e.g. so that the 9 volunteers who had been receiving the 600 mg tablet in Period 1 received the 1200 mg tablet while fasting in Period 2). After completion of Period 2, the volunteers were crossed-over again into their 3rd and final treatment group (i.e. the 9 volunteers who received the 1200 mg tablet while fasting in Period 2 and the 600 mg tablet while fasting in Period 1 received the 1200 mg tablet after consumption of a high fat meal in Period 3). Each volunteer was administered one dose of the appropriate tablet and then monitored over a 16 hour period.

Blood samples were taken about one hour prior to dosing and at specific intervals up to 16 hours after dosing (at 0.25, 0.5, 0.75, 1, 1.5, 2, 3, 4, 6, 8, 10, 12, 14, and 16 hours). The results of the pharmacokinetic parameters analysis are described below and in FIG. 11.

|  | Formulation | $T_{max}$ (hr.) | $C_{max}$ (ng/mL) | $AUC_{0-12}$ (hr-ng/mL) | $T_{1/2}$ (hrs.) | $AUC_{inf}$ (hr-ng/mL) |
|---|---|---|---|---|---|---|
| Mean | 600 mg Fasted | 0.81 | 1074.26 | 3623.03 | 2.33 | 3676.23 |
| Mean | 1200 mg Fasted | 0.94 | 1948.62 | 7483.20 | 3.33 | 7912.61 |
| Mean | 1200 mg Fed | 2.18 | 1988.08 | 7424.20 | 0.91 | 7425.29 |

The 600 mg tablet demonstrated a serum profile approximately directly proportional to the serum profile of the 1200 mg tablet. The $C_{max}$ of the 600 mg tablet was about 55% that of the 1200 mg tablet. The $AUC_{0-12}$ of the 600 mg tablet was about 48% that of the 1200 mg tablet and the $AUC_{inf}$ of the 600 mg tablet was about 46% that of the 1200 mg. improved serum concentration of guaifenesin and an increased overall concentration with time, their half-life was compromised.

The 1200 mg tablet demonstrated that the bi-layer tablets of the invention greatly reduce the food effect in bioavailability and serum concentration of guaifenesin. The $C_{max}$ of the 1200 mg tablet administered after a high fat meal (fed tablet) was about 102% of the $C_{max}$ of the 1200 mg tablet administered after fasting (fasted tablet). The $AUC_{0-12}$ of the 1200 mg fed tablet was about 99% that of the fasted tablet and the $AUC_{inf}$ of the 1200 mg fed tablet was about 94% that of the fasted tablet.

Example 8

In an example of a combination drug formulation, two batches of guaifenesin/dextromethorphan HBr bi-layer tablets were prepared: i) 600 mg/30 mg dextromethorphan and ii) 1200 mg/60 mg. In the 30 mg dextromethorphan tablet 7.5 mg was within the immediate release layer and 22.5 mg within the sustained release layer. The 60 mg dextromethorphan tablet comprised double the dextromethorphan respectively.

Sustained Release Layer

| Components | 600 mg/30 mg Weight per 200,000 tablets (kg) | 1200 mg/60 mg Weight per 100,000 tablets (kg) |
|---|---|---|
| Guaifenesin, USP | 101.00 | 101.00 |
| Dextromethorphan HBr | 4.50 | 4.50 |
| Carbopol 974P, NF | 1.50 | 5.00 |
| Microcrystalline Cellulose (Methocel E10M) | 5.00 | 1.50 |
| D&C Yellow No. 10 Aluminum Lake (14-18%) | 0.04 | 0.04 |
| Magnesium Stearate | 1.00 | 1.0 |

Immediate Release Layer

| Components | 600 mg/30 mg Weight per 480,000 tablets (kg) | 1200 mg/60 mg Weight per 240,000 tablets (kg) |
|---|---|---|
| Guaifenesin, USP | 45.60 | 45.60 |
| Dextromethorphan HBr | 3.60 | 3.60 |
| Sodium Starch Glycolate, NF (Explotab) | 3.60 | 3.60 |
| Microcrystalline Cellulose (Avicel PH102) | 40.32 | 40.32 |
| Methocel E10M, USP | 2.40 | 2.40 |
| Magnesium Stearate, NF | 0.48 | 0.48 |

Figure 12:
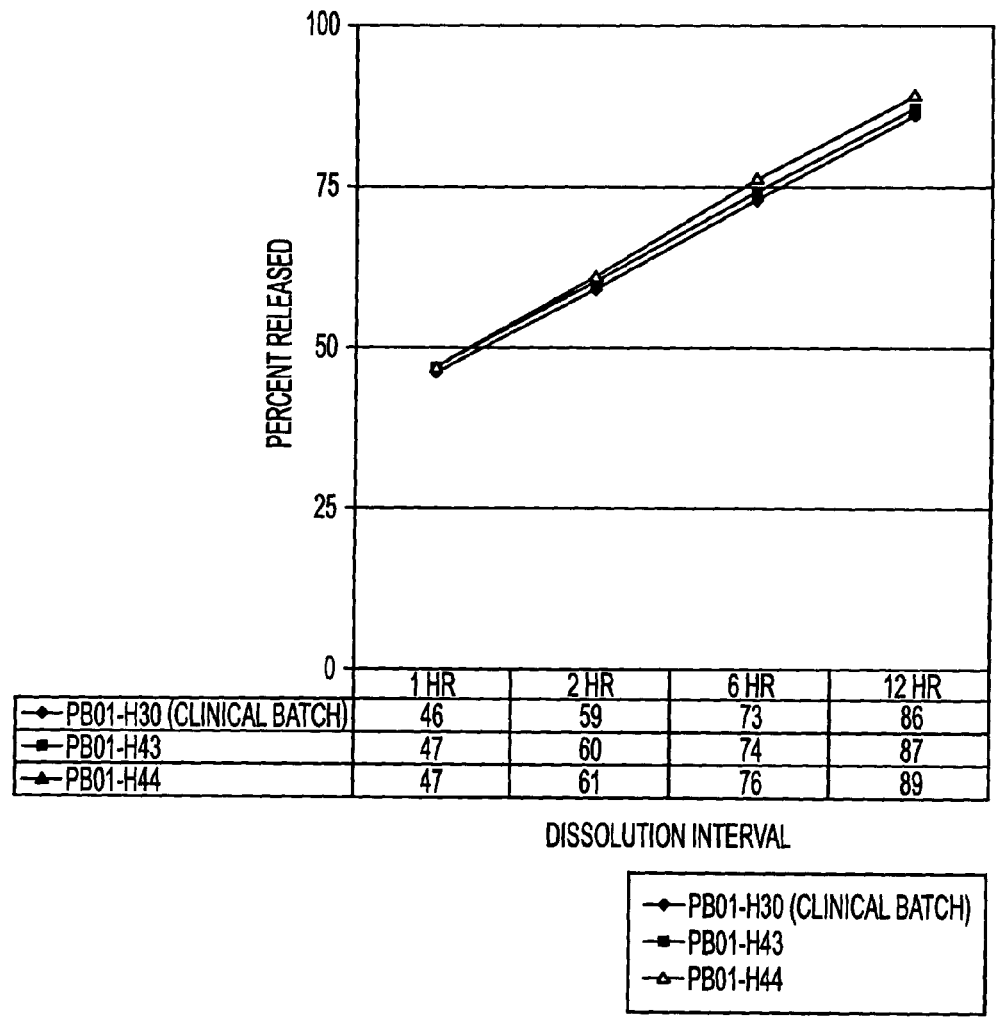
FIG. 12 is a graph demonstrating the dissolution profile of dextromethorphan HBr as measured by three different batches of a 1200 mg guaifenesin—60 mg dextromethorphan tablet over a 12 hour period as measured by the weight percentage of dextromethorphan HBr dissolved over time.

The following is a summary of 1200 mg guaifenesin/60 mg dextromethorphan HBr Dissolution Rate for three different batches also depicted in FIG. 12.

|  | PB01-H30 (clinical batch) % released | PB01-H43 % released | PB01-H44 % released |
|---|---|---|---|
| 1 hr | 46 | 47 | 47 |
| 2 hr | 59 | 60 | 61 |
| 6 hr | 73 | 74 | 76 |
| 12 hr | 86 | 87 | 89 |

Figure 13:
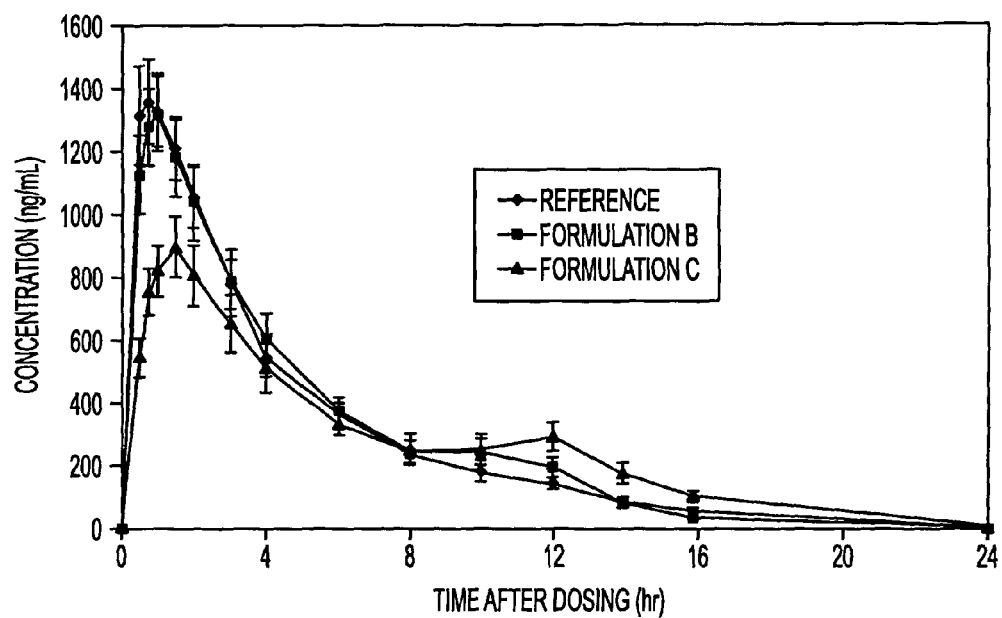
FIG. 13 is a graph demonstrating the plasma concentration of guaifenesin following the administration of 1200 mg guaifenesin and 60 mg dextromethorphan HBr to volunteers separately and in formulations of the invention.
Figure 14:
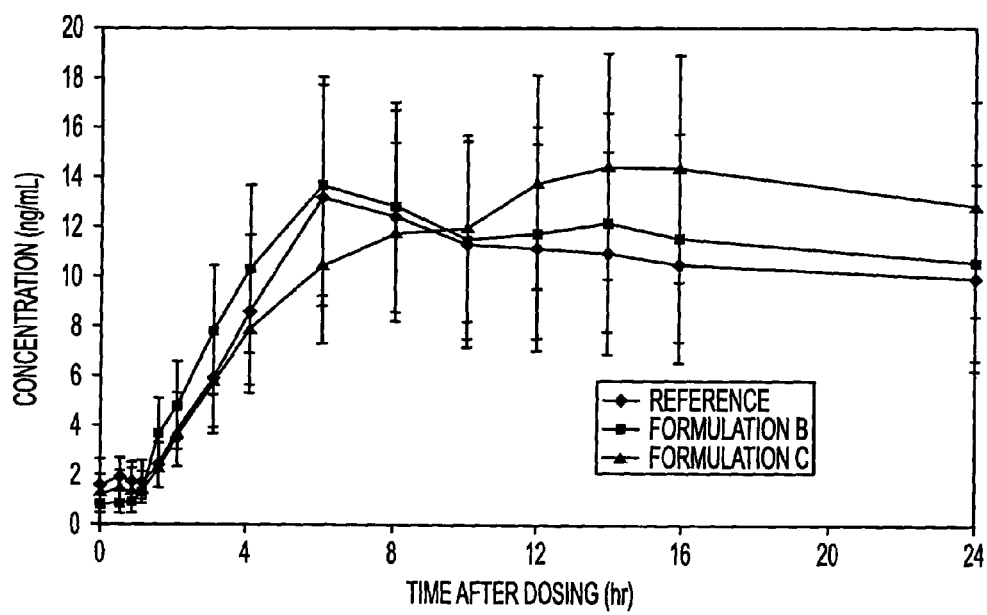
FIG. 14 is a graph demonstrating the plasma concentrations of dextromethorphan HBr following the administration of 1200 mg guaifenesin and 60 mg dextromethorphan HBr to volunteers in three different formulations.
Figure 15:
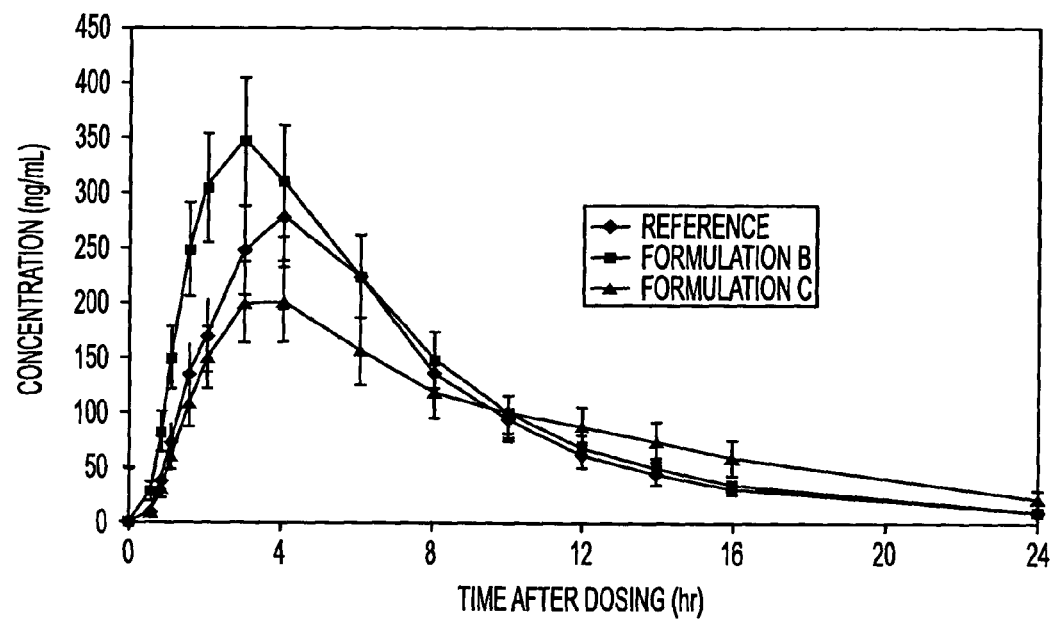
FIG. 15 is a graph demonstrating the plasma concentrations of the metabolite dextrorphan following the administration of 1200 mg guaifenesin and 60 mg dextromethorphan HBr to volunteers in three different formulations.

The in vivo behavior of the 1200 mg guaifenesin and 60 mg tablet was studied by measuring the plasma concentration of guaifenesin, dextromethorphan HBr, and the metabolite dextrorphan. FIGS. 13-15 illustrate the plasma concentration for each drug or metabolite in two formulations, Formulation B and Formulation C, during a 24 hour period. Immediately after administration the plasma concentration of guaifenesin peaks in about an hour, followed by a gradual plasma concentration decrease over 24 hours. Immediately after administration, guaifenesin plasma concentration never decreased to less than 200 ng/mL over 12 hours. Thereafter, guaifenesin plasma concentration gradually decreased over the next 12 hours. Plasma concentration of dextromethorphan HBr peaks at about 6 hours at about 12 ng/mL and the concentration is maintained for the following 19 hours.

Formulations B and C of FIG. 13, exhibited guaifenesin release profiles similar to the reference formulation. The reference formulation for FIG. 13 was Formulation IV of Example 5. Formulation B comprised 77% guaifenesin by weight, 3.8% by weight dextromethorphan, 9.1% by weight microcrystalline cellulose, 1.9% by weight Methocel E10M, and 0.9% Carbopol® 974P. Formulation C comprised 76.5% by weight guaifenesin, 3.8% by weight dextromethorphan, 9.7% by weight microcrystalline cellulose, 1.9% by weight Methocel E10M, and 0.9% by weight Carbopol® 974P. Formulations B and C exhibited similar behavior and had a guaifenesin release profile similar to the reference formulation. Accordingly, the combination formulations of the invention did not interfere with the release of guaifenesin. In particular, after 12 hours Formulation C released a greater dose of guaifenesin than the reference formulation.

Formulations B and C of FIG. 13 were compared against a reference consisting of an extended release formulation of dextromethorphan commercially available under the name Delsym sold by Celitech. The comparison was carried out to determine the behavior of guaifenesin-dextromethorphan formulations of the invention as compared to separately administered combination formulations of dextromethorphan. Formulations B and C had longer dextromethorphan release profiles than the reference, as shown in FIG. 14. Additionally, the combined formulations of the inventions had no detrimental effect upon the release profile of dextromethorphan.

Another method to monitor dextromethorphan plasma concentrations is to measure the plasma concentration of the metabolite dextrorphan. The plasma concentration of dextrorphan metabolite of the reference formulation and Formulations B and C of FIG. 14 were plotted in FIG. 15. Generally, the formulations exhibited similar dextrorphan concentrations, with Formula C exhibiting the highest dextrorphan concentration after 12 hours. FIG. 15 demonstrates that the formulations of the invention containing guaifenesin do not inhibit the release of dextromethorphan, as determined by measuring the presence of the metabolite dextrorphan.

Example 9

A study was performed to examine the relative bioavailability of a sustained release guaifenesin with dextromethorphan formulation of the invention with normal, healthy male and/or female volunteers. A batch of guaifenesin and dextromethorphan bi-layer tablet, 1200 mg, was prepared according to the composition described above for Example 8.

The in vivo behaviors of the 1200 mg tablet administered to volunteers in the fasting state (about 10 hours pre-dose until about 4 hours after dosing) was determined. The open-label study involved 29 healthy volunteers between the ages of 18 and 55. The 29 volunteers were divided into two treatment groups half receiving the 1200 mg tablet while fasting for Period I of the trial. Each volunteer was administered one dose of the appropriate tablet and then monitored over a 16 hour period.

Blood samples (7 mL with sodium heparin as anticoagulant) were taken about one hour prior to dosing and at specific intervals up to 16 hours after dosing (at 0.25, 0.5, 0.75, 1, 1.5, 2, 3, 4, 6, 8, 10, 12, 14, and 16 hours). The results of the pharmacokinetic parameters analysis for guaifenesin include a $T_{max}$ of 1.48 hr, $C_{max}$ (ng/mL) of 2196, $AUC_{0-12}$ (hr-ng/mL) of 8702, $T_{1/2}$ of 1.32 hrs., and an $AUC_{inf}$ (hr-ng/mL) of 8732.5. The results of the pharmacokinetic parameters analysis for dextromethorphan include a $T_{max}$ of 5.0 hrs, $C_{max}$ (pg/mL) of 5157, $AUC_{0-12}$ (hr-pg/mL) of 74209, $T_{1/2}$ of 7.93 hrs., and an $AUC_{inf}$ (hr-pg/mL) of 75016.

Example 10

In another example of a combination formulation, two batches of guaifenesin-pseudoephedrine HCl bi-layer tablets, one 600 mg and one 1200 mg, were prepared in the following amounts.

Sustained Release Layer

| Components | 600 mg/60 mg Weight per 300,000 tablets (kg) | 1200 mg/120mg Weight per 150,000 tablets (kg) |
|---|---|---|
| Guaifenesin DC (95%) | 157.90 | 157.89 |
| Pseudoephedrine HCl | 18.0 | 18.00 |
| Hydroxypropyl Methylcellulose (Methocel E10M) | 4.50 | 4.50 |
| Carbopol 974P, NF | 2.25 | 2.25 |
| FD&C Yellow No. 6 Aluminum Lake (15-18%) | 0.24 | 0.06 |
| Magnesium Stearate | 1.50 | 1.50 |

Immediate Release Layer

| Components | 600 mg/60 mg Weight per 300,000 tablets (kg) | 1200 mg/120 mg Weight per 150,000 tablets (kg) |
|---|---|---|
| Guaifenesin DC (95%) | 39.476 | 39.476 |
| Microcrystalline Cellulose (Avicel PH102) | 22.028 | 22.028 |
| Sodium Starch Glycolate | 5.626 | 5.626 |
| Magnesium Stearate, NF | 0.188 | 0.188 |

Figure 16:
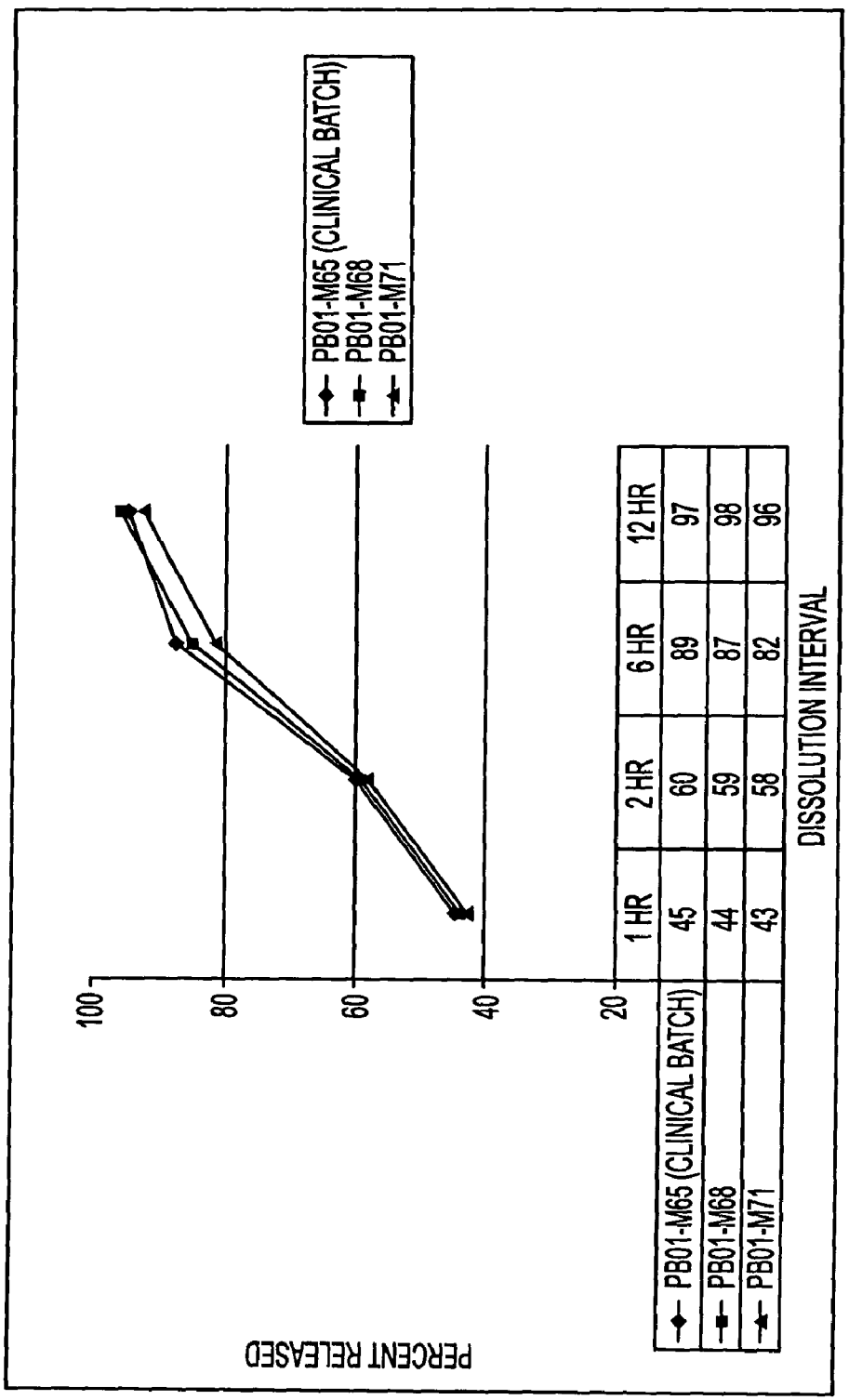
FIG. 16 is a graph demonstrating the dissolution profile of pseudoephedrine HCl in three different batches of a 1200 mg guaifenesin—120 mg pseudoephedrine HCl tablet formulation over a 12 hour period as measured by the percent pseudoephedrine HCl dissolved over time.

The following is a summary of 1200 mg guaifenesin/120 mg pseudoephedrine dissolution rates also depicted in FIG. 16.

| | PB01-M65 (clinical batch) % released | PB01-M68 % released | PB01-M71 % released |
|---|---|---|---|
| 1 hr | 45 | 44 | 43 |
| 2 hr | 60 | 59 | 58 |
| 6 hr | 89 | 87 | 82 |
| 12 hr | 97 | 98 | 96 |

The in vivo behavior of the 1200 mg guaifenesin and 120 mg pseudoephedrine tablet was studied by measuring the plasma concentration of guaifenesin, and pseudoephedrine HCl. The three batches of the 1200 mg guaifenesin/120 mg pseudoephedrine HCl formulation were dissolved to determine the amount of pseudoephedrine HCl released over time. Generally, the formulations had 1200 mg of guaifenesin and 120 mg pseudoephedrine HCl and were studied over a 12 hour period. The released amount of pseudoephedrine HCl was determined as a weight percent of dissolved pseudoephedrine HCl in contrast to the total weight of pseudoephedrine HCl prior to dissolution. After 1 hour about 43% to 45% of the pseudoephedrine HCl had dissolved. After 2 hours the about 58% to 60% dissolved, after 6 hours 82% to 89% had dissolved, and after 12 hours about 96% to 97% by weight of the pseudoephedrine HCl had dissolved. (See FIG. 16).

Figure 17:
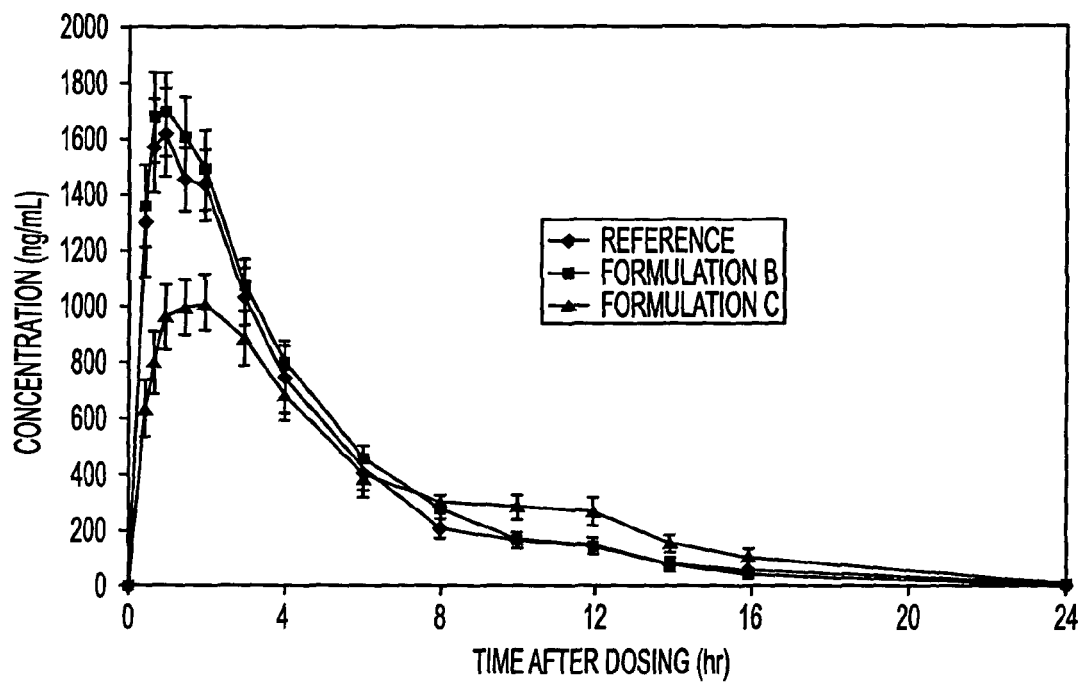
FIG. 17 is a graph demonstrating the plasma concentration of guaifenesin following the administration of 1200 mg guaifenesin and 120 mg pseudoephedrine HCl to volunteers separately and in formulations of the invention.
Figure 18:
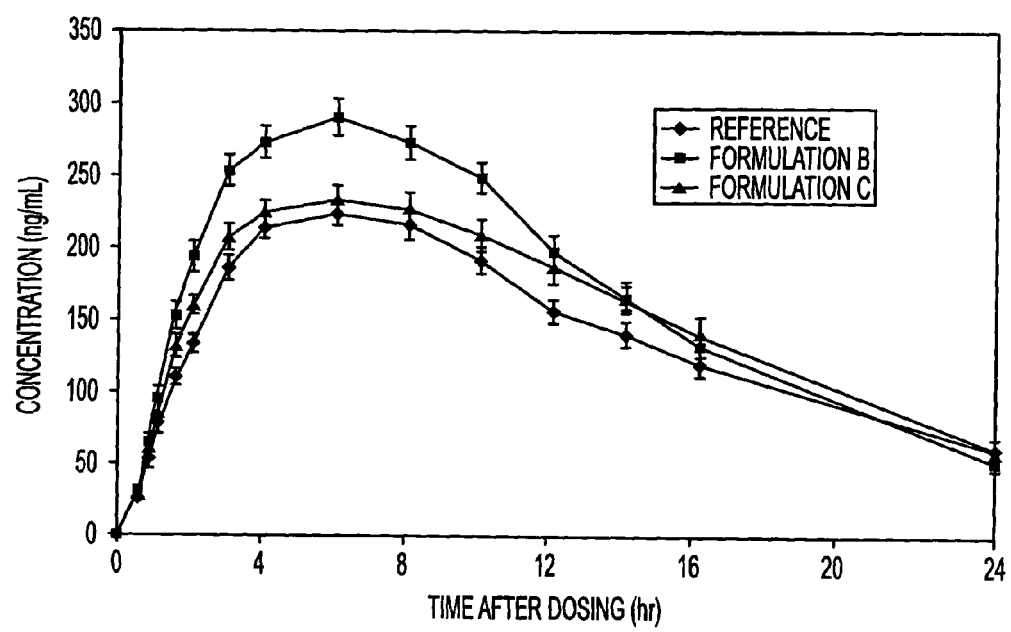
FIG. 18 is a graph demonstrating the plasma concentration of pseudoephedrine HCl following the administration of 1200 mg guaifenesin and 120 mg pseudoephedrine HCl to volunteers in three different formulations.

Three formulations of guaifenesin, two containing an additional drug, pseudoephedrine, were compared to determine whether an additional drug affects the release profile of guaifenesin. FIGS. 17-18 illustrate the plasma concentration for each drug (Formulation B and Formulation C) during a 24 hour period. Immediately after administration the plasma concentration of guaifenesin peaks in about an hour, followed by a gradual plasma concentration decrease over 24 hours. Immediately after administration, guaifenesin plasma concentration never decreased below 200 ng/mL over 12 hours. Thereafter, guaifenesin plasma concentration gradually decreased over the next 12 hours. Plasma concentration of pseudoephedrine HCl peaked at about 6 hours and gradually decreased over the next 18 hours. The plasma concentration of pseudoephedrine HCl never decreased to less than 50 ng/mL after 30 minutes of administration.

In FIG. 17, the reference formulation included formulation IV of Example 5 and a separate Sudafed® 12 hour formulation available from Pfizer Inc. 201 Tabor Road, Morris Plains, N.J., 07950. The reference formulation was compared to Formulation B and Formulation C of the invention. Formulation B comprised a sustained release formulation having 86% by weight Guaifenesin DC, 9.8% by weight pseudoephedrine HCl, 2.4% by weight hydroxypropyl methylcellulose, and 1.2% by weight Carbopol® 974P, and an immediate release formulation having 52% by weight Guaifenesin DC and 39% by weight microcrystalline cellulose by weight. Formulation C comprised 77% by weight Guaifenesin DC, 7.7% by weight pseudoephedrine, 9% by weight microcrystalline cellulose, 1.8% by weight Methocel E10M, and 0.9% by weight Carbopol® 974P. Formulations B and C exhibited similar behavior to separately administered formulations, thus demonstrating that formulations of the invention did not interfere with the profile release of pseudoephedrine.

The plasma concentration for pseudoephedrine HCl was studied to determine whether the formulations of the invention interfered with the release profile of pseudoephedrine. The pseudoephedrine plasma concentrations for the formulations of FIG. 17 were plotted over a 24 hour period. As illustrated in FIG. 18, Formulations B and C of FIG. 17 exhibited higher pseudoephedrine concentrations than the reference formulation. Thus, the combined formulations of the invention release pseudoephedrine in comparable or better release profiles than formulations containing pseudoephedrine alone.

Example 11

A study was performed to examine the relative bioavailability of sustained release guaifenesin with pseudoephedrine formulations of the invention in normal, volunteers. A batch of guaifenesin and pseudoephedrine bi-layer tablets, 1200 mg, was prepared according to the composition described above for Example 10.

The in vivo behaviors of a 1200 mg tablet administered to volunteers in the fasting state (about 10 hours pre-dose until about 4 hours after dosing) were compared. The open-label study involved 29 healthy volunteers between the ages of 18 and 55. The 29 volunteers were divided into two treatment groups, half receiving the 1200 mg tablet while fasting for Period 1 of the trial. Each volunteer was administered one dose of the appropriate tablet and then monitored over a 16 hour period.

Blood samples (7 mL with sodium heparin as anticoagulant) were taken about one hour prior to dosing and at specific intervals up to 16 hours after dosing (at 0.25, 0.5, 0.75, 1, 1.5, 2, 3, 4, 6, 8, 10, 12, 14, and 16 hours). The results of the pharmacokinetic parameters analysis for guaifenesin include a $T_{max}$ of 1.48 hr, $C_{max}$ (ng/mL) of 2196, $AUC_{0-12}$ (hr-ng/mL) of 8702, $T_{1/2}$ of 1.32 hrs., and an $AUC_{inf}$ (hr-ng/mL) of 8732.5. The results of the pharmacokinetic parameters analysis for pseudoephedrine include a $T_{max}$ of 6 hrs, $C_{max}$ (ng/mL) of 300, $AUC_{0-12}$ (hr-ng/mL) of 4201, $T_{1/2}$ of 5.98 hrs., and an $AUC_{inf}$ (hr-ng/mL) of 4709.

Example 12

Guaifenesin and pseudoephedrine sustained release formulations were compared to commercial controlled release guaifenesin and pseudoephedrine products in healthy volunteers in an open label, single dose, randomized, 3-way crossover study in 15 subjects.

The subjects were randomized and placed into one of three treatment groups. Group A was given Formulation A, one 1200 mg controlled release guaifenesin product (Mucinex) plus a 120 mg controlled release pseudoephedrine hydrochloride product (Sudafed-12 Hour) with 240 mL of water after an overnight fast. Group B received Formulation B (lot PB10-K61), an experimental controlled release tablet containing 1200 mg guaifenesin and 120 mg of pseudoephedrine hydrochloride with 240 mL of water after an overnight fast. Group C received Formulation C (lotCB00-01A), another experimental controlled release tablet containing 1200 mg guaifenesin and 120 mg pseudoephedrine hydrochloride with 240 mL of water after an overnight fast. There was at least a 7-day washout between doses.

The volunteers averaged 26.4±10.57 years of age (Mean±Standard Deviation) with a range of 18 years to 50 years of age. They were 66.93±4.37 inches tall with a range of 60 to 74 inches. They weighed 160.87±26.22 pounds with a range of 118 to 222 pounds. Seven were male (47%) and eight female (53%). Ten (67%) of the subjects had a large frame size, three (20%) had a medium frame and two (13%) had a small frame. Thirteen volunteers (87%) were Caucasian and two (13%) were Multiracial. Blood (10 mL, sodium heparin anticoagulant) was obtained at the following times: Pre dose, 0.5, 0.75, 1, 1.5, 2, 3, 4, 6, 8, 10, 12, 14, 16 and 24 hours post dose.

Subjects given 1200 mg of guaifenesin as guaifenesin ER (reference) reached a $C_{max}$ of 1847 ng/mL in 0.78 hours and had an $AUC_{inf}$ of 7302 hr-ng/mL. Subjects given 1200 mg guaifenesin as Formulation B reached a $C_{max}$ of 1784 ng/mL (103% of that of the reference) in 0.82 hour (113% of that of the reference) and had an $AUC_{inf}$ of 7602 hr-ng/mL (109% of that of the reference). Subjects given 1200 mg guaifenesin as Formulation C reached a $C_{max}$ of 1154 ng/mL (65% of that of the reference) in 1.22 hours (179% of that of the reference) and had an $AUC_{inf}$ of 7128 hr-ng/mL (100% of that of the reference).

Subjects given 120 mg pseudoephedrine hydrochloride as Sudafed-12 Hour (reference) reached a $C_{max}$ of 300 ng/mL (mean±standard deviation) in 6 hours and had an $AUC_{inf}$ of 4710 hr-ng/mL. Subjects given 120 mg pseudoephedrine hydrochloride as Formulation B reached a $C_{max}$ of 285 ng/mL (99% of that of the reference) in 6 hours (101% of that of the reference) and had an $AUC_{inf}$ of 4449 hr-ng/mL (100% of that of the reference). Subjects given 120 mg pseudoephedrine hydrochloride as Formulation C reached a $C_{max}$ of 256 ng/mL (86% of that of the reference) in 8 hours (151% of that of the reference) and had an $AUC_{inf}$ of 4444 hr-ng/mL (97% of that of the reference).

Figure 19:
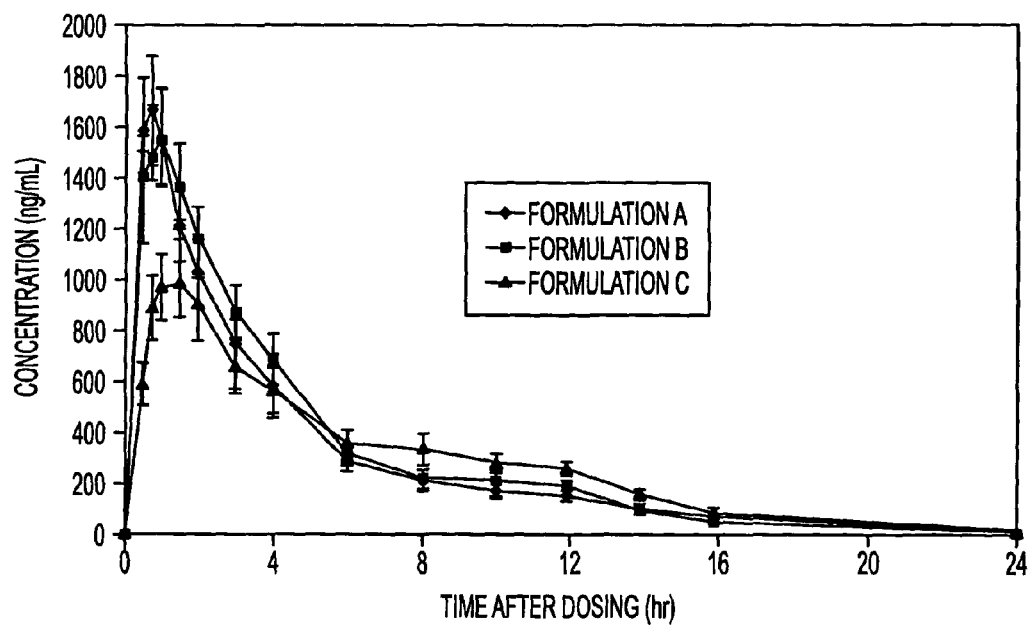
FIG. 19 is a graph demonstrating the plasma concentration of three different 1200 mg guaifenesin dosages in groups A, B, and C of example 12.

The plasma concentrations of guaifenesin are depicted in FIG. 19. The resulting pharmacokinetic data is shown in Tables 1 through 4. The maximum plasma concentrations of guaifenesin following a 1200 mg oral dose as Mucinex were 1847±686.6 ng/mL and occurred in 0.78±0.28 hours. The resulting area under the plasma concentration vs. time curve ($AUC_{inf}$ was 7302±2866.4 hr-ng/mL. The maximum plasma concentrations of guaifenesin following a 1200 mg oral dose as Formulation B were 1784±549.9 ng/mL (102.93%±36.57% of that of the reference formulation) and occurred in 0.82±0.27 hours (112.78%±43.29% that of the reference formulation). The resulting $AUC_{inf}$ was 7602±2492.8 hr-ng/mL (108.67%±23.93% of that of the reference formulation). The maximum plasma concentrations of guaifenesin following a 1200 mg oral dose as Formulation C were 1154±523.3 ng/mL (64.56%±28.03% of that of the reference formulation) and occurred in 1.22±0.45 hours (178.9%±100.64% that of the reference formulation). The resulting $AUC_{inf}$ was 7128±3166.0 hr ng/mL (99.81%±34.23% of that of the reference formulation).

TABLE 1

Guaifenesin Pharmacokinetic Variables Following the Administration of 1200 mg Guaifenesin as Mucinex along with Sudafed 12 Hour to Normal Volunteers

| Subject | $C_{max}$ (ng/mL) | $T_{max}$ (hr) | $AUC_{0-t}$ (hr-ng/mL) | $AUC_{inf}$ (hr-ng/mL) | Half-life (hr) | Clearance (L/hr) |
|---|---|---|---|---|---|---|
| Mean | 1847 | 0.78 | 7143 | 7302 | 3.60 | 188.98 |
| Median | 1530 | 0.75 | 5776 | 5863 | 3.21 | 204.68 |
| Standard Deviation | 686.63 | 0.28 | 2793.41 | 2866.39 | 2.05 | 74.55 |
| Standard Error | 183.51 | 0.08 | 746.57 | 766.08 | 0.55 | 19.92 |
| % CV | 37.18 | 35.92 | 39.11 | 39.26 | 56.94 | 39.45 |
| Maximum | 1847 | 0.78 | 7143 | 7302 | 3.60 | 188.98 |
| Minimum | 1530 | 0.75 | 5776 | 5863 | 3.21 | 204.68 |

TABLE 2

Guaifenesin Pharmacokinetic Variables Following the Administration of 1200 mg Guaifenesin and 120 mg Pseudoephedrine Hydrochloride as Formulation B to Normal Volunteers

| Subject | $C_{max}$ (ng/mL) | $T_{max}$ (hr) | $AUC_{0-t}$ (hr-ng/mL) | $AUC_{inf}$ (hr-ng/mL) | Half-life (hr) | Clearance (L/hr) |
|---|---|---|---|---|---|---|
| Mean | 1784 | 0.82 | 7557 | 7602 | 1.59 | 172.56 |
| Median | 1730 | 0.75 | 7297 | 7349 | 1.35 | 163.30 |
| Standard Deviation | 549.90 | 0.27 | 2487.33 | 2492.75 | 0.59 | 49.49 |
| Standard Error | 146.97 | 0.07 | 664.77 | 666.22 | 0.16 | 13.23 |
| % CV | 30.82 | 33.67 | 32.91 | 32.79 | 37.09 | 28.68 |
| Maximum | 1800 | 0.75 | 5818 | 5842 | 1.35 | 205.42 |
| Minimum | 1120 | 0.5 | 4952 | 4979 | 1.14 | 241.01 |

TABLE 3

Guaifenesin Pharmacokinetic Variables Following the Administration of 1200 mg Guaifenesin and 120 mg Pseudoephedrine Hydrochloride as Formulation C to Normal Volunteers

| Subject | $C_{max}$ (ng/mL) | $T_{max}$ (hr) | $AUC_{0-t}$ (hr-ng/mL) | $AUC_{inf}$ (hr-ng/mL) | Half-life (hr) | Clearance (L/hr) |
|---|---|---|---|---|---|---|
| Mean | 1154 | 1.22 | 6989 | 7128 | 2.40 | 202.57 |
| Median | 1050 | 1.00 | 6291 | 6314 | 2.38 | 190.05 |
| Standard Deviation | 523.29 | 0.45 | 3078.23 | 3165.98 | 1.06 | 89.63 |
| Standard Error | 139.86 | 0.12 | 822.69 | 846.14 | 0.28 | 23.96 |
| % CV | 45.35 | 37.14 | 44.04 | 44.41 | 44.30 | 44.25 |
| Maximum | 612 | 0.75 | 3157 | 3205 | 1.25 | 374.38 |
| Minimum | 781 | 0.75 | 4902 | 4949 | 2.49 | 242.46 |

TABLE 4

Ratio of Guaifenesin Pharmacokinetic Variables Following the Administration of 1200 mg Guaifenesin and 120 mg Pseudoephedrine Hydrochloride as Formulation B Compared to that of the Reference Formulation to Normal Volunteers (%)

| Subject | $C_{max}$ (ng/mL) | $T_{max}$ (hr) | $AUC_{0-t}$ (hr-ng/mL) | $AUC_{inf}$ (hr-ng/mL) | Half-life (hr) | Clearance (L/hr) |
|---|---|---|---|---|---|---|
| Mean | 102.93 | 112.78 | 110.31 | 108.67 | 66.51 | 95.42 |
| Median | 90.59 | 100.00 | 102.28 | 100.45 | 50.76 | 99.55 |
| Standard Deviation | 36.57 | 43.29 | 23.94 | 23.93 | 65.61 | 16.90 |
| Standard Error | 9.77 | 11.57 | 6.40 | 6.40 | 17.53 | 4.52 |
| % CV | 35.53 | 38.38 | 21.70 | 22.02 | 98.64 | 17.72 |
| Maximum | 165.14 | 75 | 122.87 | 121.60 | 83.97 | 82.24 |
| Minimum | 80 | 50 | 87.60 | 84.93 | 17.70 | 117.75 |

Figure 20:
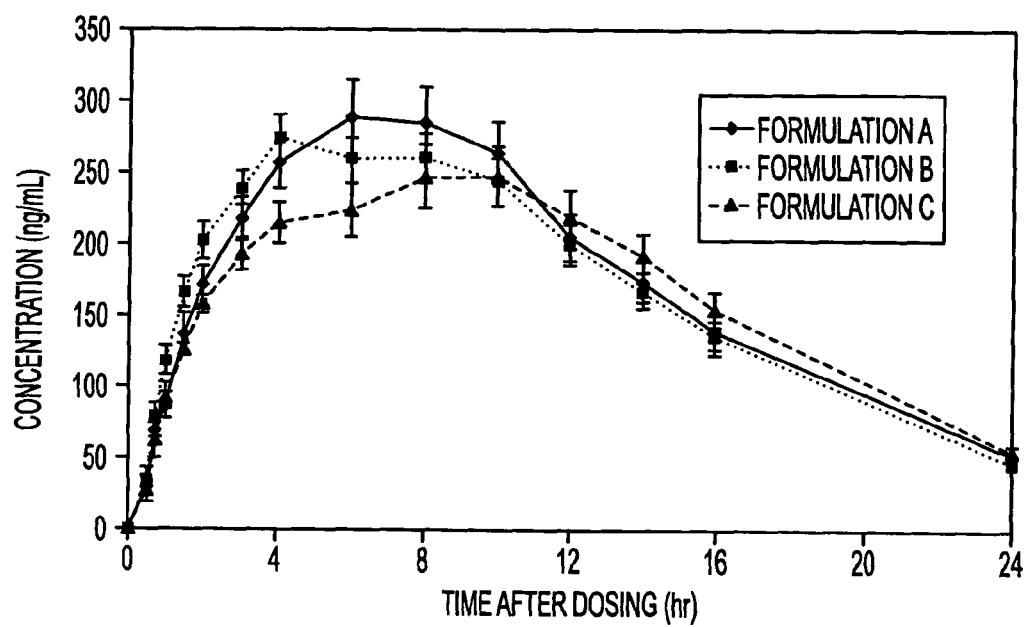
FIG. 20 is a graph demonstrating the plasma concentration of three different 120 mg pseudoephedrine dosages in groups A, B, and C of example 12.

The plasma concentrations of pseudoephedrine are depicted in FIG. 20. The resulting pharmacokinetic data is shown in Tables 5 through 9. The maximum plasma concentrations of pseudoephedrine following a 120 mg oral dose as Sudafed-12 Hour (reference) were 300.3±91.44 ng/mL and occurred in 6±1.69 hours. The resulting $AUC_{inf}$ was 4710±1394.5 hr-ng/mL. The maximum plasma concentrations of pseudoephedrine following a 120 mg oral dose as Formulation B were 285.3±53.28 ng/mL (99.31%±20.39% of that of the reference formulation) and occurred in 5.80±2.40 hours (101.11%±41.77% of that of the reference formulation). The resulting $AUC_{inf}$ was 4449±1079.6 hr-ng/mL (99.87%±26.40% of that of the reference formulation). The maximum plasma concentrations of pseudoephedrine following a 120 mg oral dose as Formulation C were 256.4±80.7 ng/mL (86.37%±14.38% of that of the reference formulation) and occurred in 8.27±2.71 hours (51.11%±73.25% of that of the reference formulation). The resulting $AUC_{inf}$ was 4444±1212.1 hr-ng/mL (96.78%±17.90% of that of the reference formulation).

TABLE 5

Pseudoephedrine Pharmacokinetic Variables Following the Administration of 120 mg Pseudoephedrine Hydrochloride as Sudafed-12 Hour along with 1200 mg Guaifenesin as Mucinex to Normal Volunteers

| Subject | $C_{max}$ (ng/mL) | $T_{max}$ (hr) | $AUC_{0-t}$ (hr-ng/mL) | $AUC_{inf}$ (hr-ng/mL) | Half-life (hr) | Clearance (L/hr) |
|---|---|---|---|---|---|---|
| Mean | 300.27 | 6.00 | 4201.62 | 4709.88 | 5.98 | 22.93 |
| Median | 287.00 | 6.00 | 4042.53 | 4601.31 | 5.19 | 21.37 |
| Standard Deviation | 91.44 | 1.69 | 1182.92 | 1394.49 | 1.68 | 7.77 |
| Standard Error | 24.44 | 0.45 | 316.15 | 372.69 | 0.45 | 2.08 |
| % CV | 30.45 | 28.17 | 28.15 | 29.61 | 28.01 | 33.87 |
| Maximum | 523 | 8 | 6518.45 | 7137.33 | 10.18 | 38.94 |
| Minimum | 183 | 4 | 2419.97 | 2524.37 | 4.29 | 13.77 |

TABLE 6

Pseudoephedrine Pharmacokinetic Variables Following the Administration of 120 mg Pseudoephedrine Hydrochloride and 1200 mg Guaifenesin as Formulation B to Normal Volunteers

| Subject | $C_{max}$ (ng/mL) | $T_{max}$ (hr) | $AUC_{0-t}$ (hr-ng/mL) | $AUC_{inf}$ (hr-ng/mL) | Half-life (hr) | Clearance (L/hr) |
|---|---|---|---|---|---|---|
| Mean | 285.33 | 5.80 | 4080.27 | 4448.85 | 5.40 | 23.41 |
| Median | 269.00 | 6.00 | 3985.05 | 4463.18 | 5.21 | 22.03 |
| Standard Deviation | 53.28 | 2.40 | 946.92 | 1079.61 | 1.01 | 6.06 |
| Standard Error | 14.24 | 0.64 | 253.07 | 288.54 | 0.27 | 1.62 |
| % CV | 18.67 | 41.32 | 23.21 | 24.27 | 18.64 | 25.88 |
| Maximum | 387 | 10 | 6003.14 | 6799.07 | 7.44 | 37.40 |
| Minimum | 215 | 2 | 2381.18 | 2628.19 | 3.85 | 14.46 |

TABLE 7

Pseudoephedrine Pharmacokinetic Variables Following the Administration of 120 mg Pseudoephedrine Hydrochloride and 1200 mg Guaifenesin as Formulation C to Normal Volunteers

| Subject | $C_{max}$ (ng/mL) | $T_{max}$ (hr) | $AUC_{0-t}$ (hr-ng/mL) | $AUC_{inf}$ (hr-ng/mL) | Half-life (hr) | Clearance (L/hr) |
|---|---|---|---|---|---|---|
| Mean | 256.40 | 8.27 | 4008.32 | 4444.09 | 5.39 | 23.85 |
| Median | 226.00 | 10.00 | 3888.93 | 4266.92 | 5.15 | 23.04 |
| Standard Deviation | 80.71 | 2.71 | 1084.90 | 1212.13 | 1.10 | 7.16 |
| Standard Error | 21.57 | 0.72 | 289.95 | 323.96 | 0.29 | 1.91 |
| % CV | 31.48 | 32.80 | 27.07 | 27.28 | 20.41 | 30.03 |
| Maximum | 448 | 10 | 6200.18 | 6756.67 | 8.66 | 40.05 |
| Minimum | 162 | 2 | 2360.01 | 2454.79 | 4.09 | 14.55 |

TABLE 8

Ratio of Pseudoephedrine Pharmacokinetic Variables Following the Administration of 120 mg Pseudoephedrine Hydrochloride and 1200 mg Guaifenesin as Formulation B Compared to that of the Reference Formulation to Normal Volunteers (%)

| Subject | $C_{max}$ (ng/mL) | $T_{max}$ (hr) | $AUC_{0-t}$ (hr-ng/mL) | $AUC_{inf}$ (hr-ng/mL) | Half-life (hr) | Clearance (L/hr) |
|---|---|---|---|---|---|---|
| Mean | 99.31 | 101.11 | 101.58 | 99.87 | 93.38 | 109.24 |
| Median | 94.74 | 100.00 | 104.95 | 101.63 | 90.66 | 98.40 |
| Standard Deviation | 20.39 | 41.77 | 24.96 | 26.40 | 17.54 | 40.60 |
| Standard Error | 5.45 | 11.16 | 6.67 | 7.06 | 4.69 | 10.85 |
| % CV | 20.53 | 41.31 | 24.57 | 26.44 | 18.79 | 37.13 |
| Maximum | 140.40 | 200 | 139.07 | 144.72 | 120.84 | 234.43 |
| Minimum | 65.97 | 25 | 50.46 | 42.66 | 60.12 | 69.10 |

TABLE 9

Ratio of Pseudoephedrine Pharmacokinetic Variables Following the Administration of 120 mg Pseudoephedrine Hydrochloride and 1200 mg Guaifenesin as Formulation C Compared to that of the Reference Formulation to Normal Volunteers (%)

| Subject | $C_{max}$ (ng/mL) | $T_{max}$ (hr) | $AUC_{0-t}$ (hr-ng/mL) | $AUC_{inf}$ (hr-ng/mL) | Half-life (hr) | Clearance (L/hr) |
|---|---|---|---|---|---|---|
| Mean | 86.37 | 151.11 | 96.79 | 96.78 | 93.98 | 107.04 |
| Median | 85.66 | 133.33 | 98.75 | 99.37 | 96.77 | 100.63 |
| Standard Deviation | 14.38 | 73.25 | 14.24 | 17.90 | 21.06 | 22.01 |
| Standard Error | 3.84 | 19.58 | 3.80 | 4.78 | 5.63 | 5.88 |
| % CV | 16.65 | 48.48 | 14.71 | 18.49 | 22.41 | 20.56 |
| Maximum | 115.30 | 250 | 126.82 | 132.10 | 129.45 | 153.94 |
| Minimum | 62.60 | 50 | 75.98 | 64.96 | 51.20 | 75.70 |

The data indicates that both formulations produce optimum guaifenesin bioavailability (although Formulation B appears to more closely match the reference) and Formulation B produces optimal pseudoephedrine bioavailability.

Example 13 bioavailability of a sustained release combination formulation of 1200 mg guaifenesin and 120 mg Pseudoephedrine Hydrochloride was used to examine the dose proportionality of Pseudoephedrine normal volunteers compared to reference guaifenesin and Pseudoephedrine Hydrochloride in an open label, single dose, randomized, 3-way crossover study with 36 subjects. The example also demonstrates the dose proportionality of pseudoephedrine.

The subjects were randomized and placed into one of three treatment groups. Group 1 received Treatment A, a 1200 controlled release guaifenesin product (Mucinex) plus a 120 mg controlled release pseudoephedrine product (Sudafed® 12 Hour) with 240 mL of water after an overnight fast (Reference). Group 2 received Treatment B (PB01-M65A2), an experimental controlled release formulation containing 1200 mg guaifenesin and 120 mg pseudoephedrine hydrochloride with 240 mL of water after an overnight fast (test). Group 3 received Treatment C (PB01-A12A), an experimental controlled release formulation containing 600 mg guaifenesin and 60 mg pseudoephedrine with 240 mL of water after an overnight fast.

The volunteers averaged 23.06±7.05 years of age (Mean±Standard Deviation) with a range of 18 years to 48 years of age. They were 70.58±3.08 inches tall with a range of 64 to 75 inches. They weighed 167.42±26.14 pounds with a range of 114 to 229 pounds. Twenty-four were male (67%) and twelve female (33%). Sixteen (44%) of the subjects had a large frame size, thirteen (36%) had a medium frame and seven (19%) had a small frame. Thirty-two volunteers (89%) were Caucasian, three (8%) were Black and one (3%) Multi-racial. Blood (10 mL, sodium heparin anticoagulant) was obtained at the following times: Pre-dose, 0.5, 0.75, 1, 1.5, 2, 3, 4, 6, 8, 10, 12, 14, 16 and 24 hours post dose (the total blood loss for guaifenesin and pseudoephedrine analysis will be 450 mL).

Subjects given 1200 mg of guaifenesin as Mucinex and 120 mg pseudoephedrine hydrochloride as Sudafed® 12 Hour (Treatment A, Reference) reached a $C_{max}$ of 1940 ng/mL in 0.77 hours and had an $AUC_{inf}$ of 8061 hr-ng/mL. Subjects given 1200 mg guaifenesin and 120 mg pseudoephedrine hydrochloride as Treatment B (Test) reached a $C_{max}$ of 1813 ng/mL (98% of that of the reference) in 1.04 hour (140% of that of the reference) and had an $AUC_{0-\infty}$ of 8124 hr ng/mL (101% of that of the reference). Subjects given 600 mg guaifenesin and 60 mg pseudoephedrine hydrochloride as Treatment C reached a $C_{max}$ of 920 ng/mL (54% of that of the reference) in 0.99 hours (116% of that of the reference) and had an $AUC_{inf}$ of 3565 hr-ng/mL (46% of that of the reference).

Subjects given 120 mg pseudoephedrine hydrochloride as Sudafed® 12 Hour and 1200 mg guaifenesin as Mucinex (Treatment A, Reference) reached a mean $C_{max}$ of 250 ng/mL in 6 hours and had an $AUC_{inf}$ of 3847 hr-ng/mL. Subjects given 120 mg pseudoephedrine and 1200 mg guaifenesin as an experimental formulation (Treatment B, Test) reached a of 263 ng/mL (107% of that of the reference) in 5 hours (85% of that of the reference) and had an $AUC_{inf}$ of 3884 hr-ng/mL (103% of that of the reference). Subjects given 60 mg pseudoephedrine hydrochloride and 600 mg guaifenesin in an experimental formulation (Treatment C) reached a $C_{max}$ of 141 ng/mL (54% of that of Formulation B) in 5 hours (100% of that of Formulation B) and had an $AUC_{inf}$ of 1968 hr-ng/mL (50% of that of Formulation B).

Blood (10 mL, sodium heparin anticoagulant) was obtained at the following times: Pre-dose, 0.5, 0.75, 1, 1.5, 2, 3, 4, 6, 8, 10, 12, 14, 16 and 24 hours post dose. Bioequivalence was examined between the test (Treatment B—guaifenesin or pseudoephedrine hydrochloride experimental formulation) and the reference (Treatment A—guaifenesin or pseudoephedrine hydrochloride reference formulations) groups. The dose response relationship was also examined between the test (Treatment B—guaifenesin or pseudoephedrine hydrochloride experimental formulation) and the reference (Treatment C—guaifenesin or pseudoephedrine hydrochloride reference formulations) groups.

Figure 21:
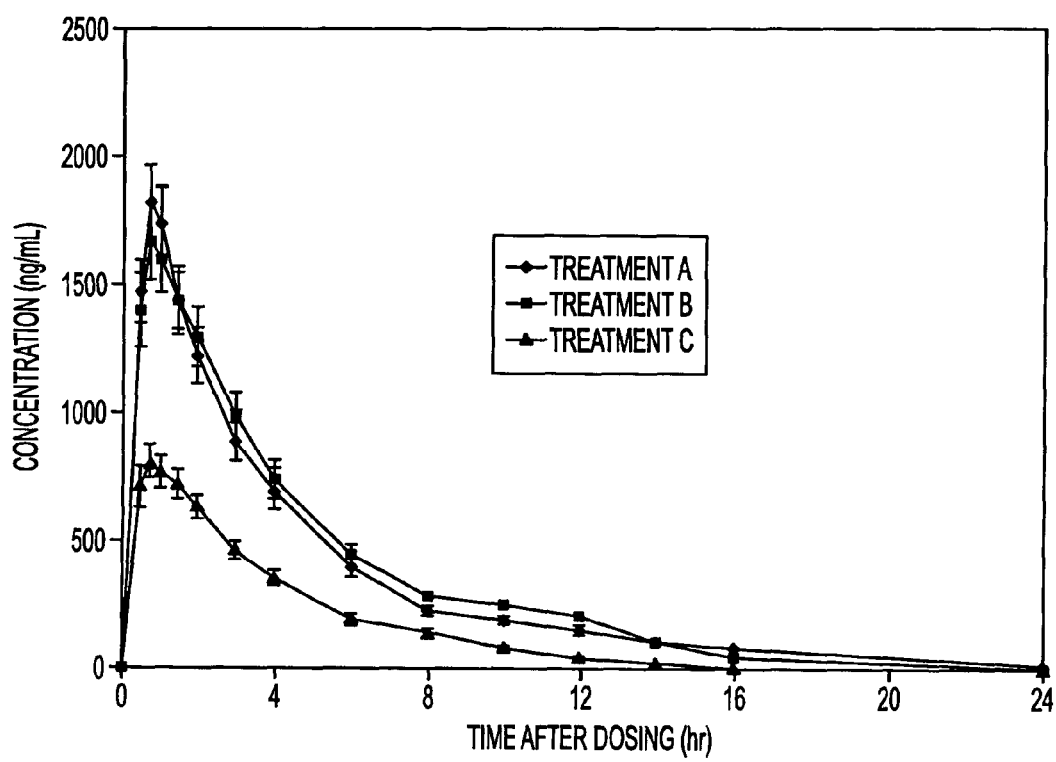
FIG. 21 is a graph demonstrating the plasma concentration of three different 1200 mg guaifenesin dosages for treatments A, B, and C of example 13.

The plasma concentrations of guaifenesin is depicted in FIG. 21. The resulting pharmacokinetic data is shown in Tables 10 through 14. The maximum plasma concentrations of guaifenesin following a 1200 mg oral dose as Mucinex and 120 mg pseudoephedrine hydrochloride as Sudafed® 12 Hour were 1940±889 ng/mL and occurred in 0.77±0.22 hours. The resulting area under the plasma concentration vs. time curve ($AUC_{inf}$ was 8061±3329 hr-ng/mL. The maximum plasma concentrations of guaifenesin following a 1200 mg oral dose as Treatment B were 1813±900 ng/mL (98.1%±35.8% of that of the reference formulation) and occurred in 1.04±0.49 hours (140%±65.3% that of the reference formulation). The resulting $AUC_{inf}$ was 8124±3677 hr-ng/mL (101%±19.3% of that of the reference formulation). The maximum plasma concentrations of guaifenesin following a 600 mg oral dose as Treatment C were 920±481 ng/mL (54.3%±20.2% of that of the reference formulation) and occurred in 0.99±0.46 hours (116%±78.7% that of the reference formulation). The resulting $AUC_{inf}$ was 3565±1442 hr-ng/mL (45.6%±10.2% of that of the reference formulation).

TABLE 10

Guaifenesin Pharmacokinetic Variables Following the Administration of 1200 mg guaifenesin Mucinex along with Sudafed 12 Hour to Normal Volunteers (%)

| Subject | $C_{max}$ (ng/mL) | $T_{max}$ (hr) | $AUC_{0-t}$ (hr-ng/mL) | $AUC_{inf}$ (hr-ng/mL) | Half-life (hr) | Clearance (L/hr) |
|---|---|---|---|---|---|---|
| Mean | 1847 | 0.78 | 7143 | 7302 | 3.60 | 188.98 |
| Median | 1530 | 0.75 | 5776 | 5863 | 3.21 | 204.68 |
| Standard Deviation | 686.63 | 0.28 | 2793.41 | 2866.39 | 2.05 | 74.55 |
| Standard Error | 183.51 | 0.08 | 746.57 | 766.08 | 0.55 | 19.92 |
| % CV | 37.18 | 35.92 | 39.11 | 39.26 | 56.94 | 39.45 |
| Maximum | 1847 | 0.78 | 7143 | 7302 | 3.60 | 188.98 |
| Minimum | 1530 | 0.75 | 5776 | 5863 | 3.21 | 204.68 |

TABLE 11

Guaifenesin Pharmacokinetic Variables Following the Administration of 1200 mg guaifenesin and 120 mg Pseudoephedrine Hydrochloride as an Experimental Formulation to Normal Volunteers (Treatment B, Test)

| Subject | $C_{max}$ (ng/mL) | $T_{max}$ (hr) | $AUC_{0-t}$ (hr-ng/mL) | $AUC_{inf}$ (hr-ng/mL) | Half-life (hr) | Clearance (L/hr) |
|---|---|---|---|---|---|---|
| Mean | 1813 | 1.04 | 8002 | 8124 | 2.21 | 175 |
| Median | 1530 | 0.75 | 7036 | 7083 | 1.99 | 169 |
| Standard Deviation | 900 | 0.49 | 3677 | 3677 | 1.19 | 68.2 |
| Standard Error | 154 | 0.08 | 631 | 631 | 0.20 | 11.7 |
| % CV | 49.6 | 46.9 | 45.9 | 45.3 | 53.9 | 38.9 |

TABLE 12

Guaifenesin Pharmacokinetic Variables Following the Administration of 600 mg Guaifenesin and 60 mg Pseudoephedrine Hydrochloride to Normal Volunteers (Treatment C)

| Subject | $C_{max}$ (ng/mL) | $T_{max}$ (hr) | $AUC_{0-t}$ (hr-ng/mL) | $AUC_{inf}$ (hr-ng/mL) | Half-life (hr) | Clearance (L/hr) |
|---|---|---|---|---|---|---|
| Mean | 920 | 0.99 | 3529 | 3565 | 1.76 | 192 |
| Median | 721 | 0.75 | 3078 | 3098 | 1.47 | 194 |
| Standard Deviation | 481 | 0.46 | 1437 | 1442 | 0.92 | 66.5 |
| Standard Error | 81.3 | 0.08 | 243 | 244 | 0.16 | 11.2 |
| % CV | 52.3 | 46.0 | 40.7 | 40.4 | 52.4 | 34.5 |

TABLE 13

Ratio of Guaifenesin Pharmacokinetic Variables Following the Administration of 1200 mg Guaifenesin and 120 mg Pseudoephedrine Hydrochloride as Formulation B Compared to that of the Reference Formulation (Treatment A) to Normal Volunteers (%)

| Subject | $C_{max}$ (ng/mL) | $T_{max}$ (hr) | $AUC_{0-t}$ (hr-ng/mL) | $AUC_{inf}$ (hr-ng/mL) | Half-life (hr) | Clearance (L/hr) |
|---|---|---|---|---|---|---|
| Mean | 98.1 | 140 | 104 | 101 | 66.2 | 103 |
| Median | 96.8 | 133 | 106 | 100 | 53.1 | 99.5 |
| Standard Deviation | 35.8 | 65.3 | 20.3 | 19.3 | 42.0 | 24.2 |
| Standard Error | 6.14 | 11.2 | 3.48 | 3.31 | 7.20 | 4.16 |
| % CV | 36.5 | 46.5 | 19.5 | 19.1 | 63.4 | 23.5 |

TABLE 14

Ratio of Guaifenesin Pharmacokinetic Variables Following
the Administration of 600 mg Guaifenesin and 60 mg Pseudoephedrine
Hydrochloride (Treatment C) Compared to that of
(Treatment B) to Normal Volunteers (%)

| Subject | $C_{max}$ (ng/mL) | $T_{max}$ (hr) | $AUC_{0-t}$ (hr-ng/mL) | $AUC_{inf}$ (hr-ng/mL) | Half-life (hr) | Clearance (L/hr) |
|---|---|---|---|---|---|---|
| Mean | 54.3 | 116 | 45.9 | 45.6 | 97.0 | 114 |
| Median | 48.8 | 100 | 43.9 | 44.0 | 86.1 | 114 |
| Standard Deviation | 20.2 | 78.7 | 10.6 | 10.2 | 61.6 | 23.2 |
| Standard Error | 3.47 | 13.50 | 1.82 | 1.75 | 10.57 | 3.98 |
| % CV | 37.3 | 67.9 | 23.1 | 22.4 | 63.5 | 20.3 |

Figure 22:
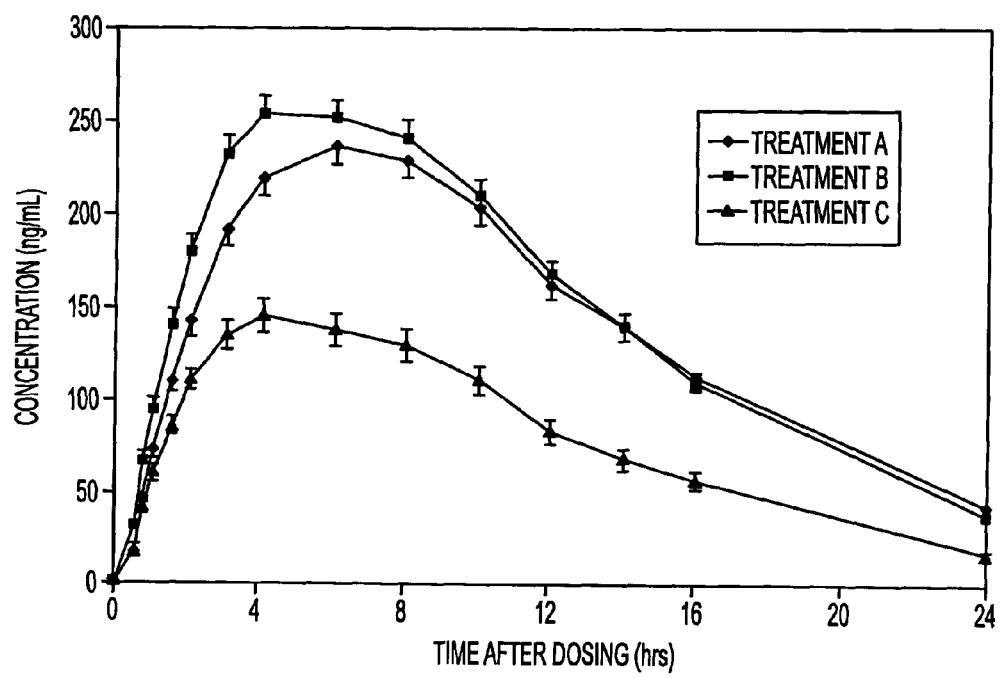
FIG. 22 depicts pseudoephedrine plasma concentrations following administration of two different dose strengths of pseudoephedrine, as well as, different formulations.

The plasma concentrations of pseudoephedrine are depicted in FIG. 22. The resulting pharmacokinetic data is shown in Tables 15 through 19. The maximum plasma concentrations of pseudoephedrine following a 120 mg oral dose as Sudafed® 12 Hour and 1200 mg guaifenesin as Mucinex (Treatment A, Reference) were 250±53.4 ng/mL and occurred in 6.29±1.76 hours. The resulting $AUC_{inf}$ was 3847±910 hr-ng/mL. The maximum plasma concentrations of pseudoephedrine following a 120 mg oral dose as an experimental formulation (Treatment B) were 263±58.5 ng/mL (107%±18.9% of that of the reference formulation) and occurred in 5.11±1.78 hours (85.2%±31.5% of that of the reference formulation). The resulting $AUC_{inf}$ was 3884±911 hr-ng/mL (103%±20.2% of that of the reference formulation). The maximum plasma concentrations of pseudoephedrine following a 60 mg oral dose as an experimental formulation (Treatment C) were 141±30.3 ng/mL (53.5%±6.52% of that of Formulation B) and occurred in 4.94±1.60 hours (99.5%±25.9% of that of Formulation B). The resulting $AUC_{inf}$ was 1968±477 hr-ng/mL (50.5%±8.77% of that of Formulation B).

TABLE 15

Pseudoephedrine Pharmacokinetic Parameters Following
the Administration of 120 mg Pseudoephedrine Hydrochloride as
Sudafed ® 12 Hour and 1200 mg Guaifenesin as Mucinex to Normal
Volunteers (Treatment A)

| Subject | $C_{max}$ (ng/mL) | $T_{max}$ (hr) | $AUC_{0-t}$ (hr-ng/mL) | $AUC_{inf}$ (hr-ng/mL) | Half-life (hr) | Clearance (L/hr) |
|---|---|---|---|---|---|---|
| Mean | 250 | 6.29 | 3479 | 3847 | 5.75 | 27.1 |
| Median | 252 | 6 | 3381 | 3652 | 5.42 | 26.9 |
| Standard Deviation | 53.4 | 1.76 | 805 | 910 | 1.02 | 7.11 |
| Standard Error | 9.16 | 0.30 | 138 | 156 | 0.18 | 1.22 |
| % CV | 21.3 | 28.0 | 23.2 | 23.7 | 17.8 | 26.2 |

TABLE 16

Pseudoephedrine Pharmacokinetic Following the Administration
120 mg Pseudoephedrine Hydrochloride and 1200 mg Guaifenesin
in an Experimental Formulation to Normal Volunteers (Treatment B)

| Subject | $C_{max}$ (ng/mL) | $T_{max}$ (hr) | $AUC_{0-t}$ (hr-ng/mL) | $AUC_{inf}$ (hr-ng/mL) | Half-life (hr) | Clearance (L/hr) |
|---|---|---|---|---|---|---|
| Mean | 263 | 5.11 | 3591 | 3884 | 5.22 | 26.7 |
| Median | 257 | 4.00 | 3507 | 3824 | 5.19 | 25.7 |
| Standard Deviation | 58.5 | 1.78 | 824 | 911 | 0.89 | 6.23 |
| Standard Error | 10.0 | 0.31 | 141 | 156 | 0.15 | 1.07 |
| % CV | 22.3 | 34.8 | 23.0 | 23.5 | 16.9 | 23.3 |

TABLE 17

Pseudoephedrine Pharmacokinetic Parameters Following
the Administration of 60 mg Pseudoephedrine Hydrochloride and
600 mg Guaifenesin in an Experimental Formulation to
Normal Volunteers (Treatment C)

| Subject | $C_{max}$ (ng/mL) | $T_{max}$ (hr) | $AUC_{0-t}$ (hr-ng/mL) | $AUC_{inf}$ (hr-ng/mL) | Half-life (hr) | Clearance (L/hr) |
|---|---|---|---|---|---|---|
| Mean | 141 | 4.94 | 1781 | 1968 | 5.57 | 26.5 |
| Median | 134 | 4.00 | 1696 | 1855 | 5.38 | 26.5 |
| Standard Deviation | 30.3 | 1.60 | 445 | 477 | 1.02 | 6.58 |
| Standard Error | 5.12 | 0.27 | 75.1 | 80.6 | 0.17 | 1.11 |
| % CV | 21.5 | 32.4 | 25.0 | 24.2 | 18.4 | 24.9 |

TABLE 18

Ratio of the Pseudoephedrine Pharmacokinetic Parameters
Following the Administration of 120 mg Pseudoephedrine
Hydrochloride and 1200 mg Guaifenesin as an Experimental
Formulation (Treatment B) Compared to that
Following the Administration of 120 mg Pseudoephedrine
Hydrochloride as Sudafed ® 12 Hour and
120 mg Guaifenesin as Mucinex (Treatment A) (%)

| Subject | $C_{max}$ (ng/mL) | $T_{max}$ (hr) | $AUC_{0-t}$ (hr-ng/mL) | $AUC_{inf}$ (hr-ng/mL) | Half-life (hr) | Clearance (L/hr) |
|---|---|---|---|---|---|---|
| Mean | 107 | 85.2 | 105 | 103 | 92.1 | 101 |
| Median | 106 | 75.0 | 102 | 101 | 93.7 | 98.7 |
| Standard Deviation | 18.9 | 31.5 | 19.39 | 20.16 | 15.19 | 22.03 |
| Standard Error | 3.24 | 5.41 | 3.33 | 3.46 | 2.61 | 3.78 |
| % CV | 17.7 | 37.0 | 18.4 | 19.5 | 16.5 | 21.8 |

TABLE 19

Ratio of Pseudoephedrine Pharmacokinetic Parameters
Following the Administration of 60 mg Pseudoephedrine
Hydrochloride and 600 mg Guaifenesin as an Experimental
Formulation (Treatment C) Relative to that Following
the Administration of 120 mg Pseudoephedrine Hydrochloride
and 1200 mg Guaifenesin in an Experimental Formulation
(Treatment B) (%)

| Subject | $C_{max}$ (ng/mL) | $T_{max}$ (hr) | $AUC_{0-t}$ (hr-ng/mL) | $AUC_{inf}$ (hr-ng/mL) | Half-life (hr) | Clearance (L/hr) |
|---|---|---|---|---|---|---|
| Mean | 53.5 | 99.5 | 49.1 | 50.5 | 108 | 102 |
| Median | 52.6 | 100 | 46.7 | 48.0 | 105 | 104 |
| Standard Deviation | 6.52 | 25.9 | 7.80 | 8.77 | 17.4 | 16.2 |

TABLE 19-continued

Ratio of Pseudoephedrine Pharmacokinetic Parameters
Following the Administration of 60 mg Pseudoephedrine
Hydrochloride and 600 mg Guaifenesin as an Experimental
Formulation (Treatment C) Relative to that Following
the Administration of 120 mg Pseudoephedrine Hydrochloride
and 1200 mg Guaifenesin in an Experimental Formulation
(Treatment B) (%)

| Subject | $C_{max}$ (ng/mL) | $T_{max}$ (hr) | $AUC_{0-t}$ (hr-ng/mL) | $AUC_{inf}$ (hr-ng/mL) | Half-life (hr) | Clearance (L/hr) |
|---|---|---|---|---|---|---|
| Standard Error | 1.12 | 4.44 | 1.34 | 1.50 | 2.98 | 2.78 |
| % CV | 12.2 | 26.0 | 15.9 | 17.4 | 16.2 | 15.9 |

In conclusion, the experimental formulation containing 1200 mg guaifenesin and 120 mg pseudoephedrine hydrochloride is bioequivalent to the reference formulations given is separate doses. In addition the pharmacokinetics of guaifenesin and pseudoephedrine are linear over the range studied.

Example 14

The effects of a high fat meal on the bioavailability of a combination formulation were tested. The bioavailability of a 1200 mg guaifenesin and 120 mg Pseudoephedrine Hydrochloride formulation volunteers was compared to reference drug bioavailability in an open-label, single-dose, randomized, 2-way-crossover study using 36 subjects.

The subjects were randomized and placed into one of two treatment groups. Group 1 received a 1200-mg controlled-release guaifenesin product (Mucinex) and 120 mg pseudoephedrine hydrochloride (Sudafed® 12 Hour) with 240 mL of water, 30 minutes after the beginning of the consumption of a high-fat breakfast (Reference). Group 2 received an experimental formulation containing 1200 mg guaifenesin and 120 mg pseudoephedrine hydrochloride with 240 mL of water, 30 minutes after the beginning of the consumption of a high-fat breakfast (Test)(PB01-M65A3).

Blood (10 mL, sodium heparin anticoagulant) was obtained at the following times: Pre dose, 0.5, 0.75, 1, 1.5, 2, 3, 4, 6, 8, 10, 12, 14, 16 and 24 hours post dose (the total blood loss for guaifenesin and pseudoephedrine analysis was 300 mL).

Subjects given 1200 mg of guaifenesin as Mucinex (Reference) reached a $C_{max}$ of 2207 ng/mL in 1.85 hours and had an $AUC_{inf}$ of 8067 hr-ng/mL. Subjects given 1200 mg guaifenesin as an experimental formulation (Treatment B) reached a of 1649 ng/mL (79% of that of the Reference) in 1.84 hour (118% of that of the Reference) and had an $AUC_{inf}$ of 7663 hr-ng/mL (93% of that of the Reference).

Subjects given 120 mg pseudoephedrine hydrochloride as Sudafed® 12 Hour (Reference) reached a $C_{max}$ of 268 ng/mL in 6.38 hours and had an $AUC_{inf}$ of 3636 hr-ng/mL. Subjects given 120 mg pseudoephedrine hydrochloride as an experimental formulation (Treatment B) reached a $C_{max}$ of 274 ng/mL (103% of that of the Reference) in 4.80 hours (76.5% of that of the Reference) and had an $AUC_{inf}$ of 3528 hr-ng/mL (96.5% of that of the Reference).

Additionally, bioequivalence data was examined between the Test group (Treatment B—1200 mg guaifenesin and 120 mg pseudoephedrine hydrochloride as an experimental formulation) and the Reference group (Treatment A—the reference 1200 mg guaifenesin and 120 mg pseudoephedrine hydrochloride formulations).

Figure 23:
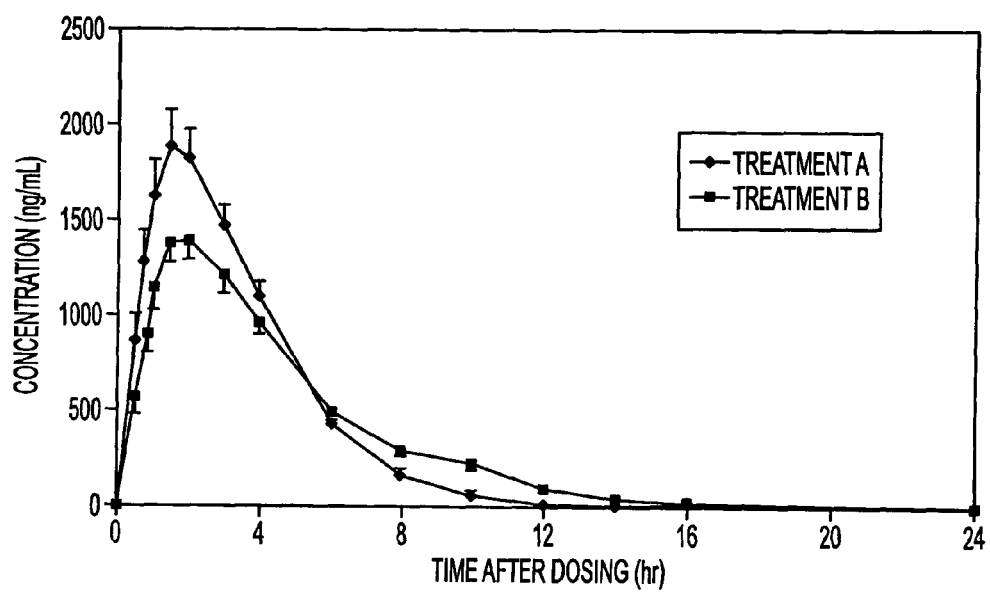
FIG. 23 depicts guaifenesin concentrations following administration of 1200 mg of guaifenesin with 120 mg pseudoephedrine hydrochloride in two different formulations following a high-fat meal.

The plasma concentrations of guaifenesin are depicted in FIG. 23. The resulting pharmacokinetic data are shown in Tables 20 through 22. The maximum plasma concentrations of guaifenesin following a 1200 mg oral dose as Mucinex were 2207±952 ng/mL and occurred in 1.85±1.06 hours. The resulting area under the plasma concentration vs. time curve ($AUC_{inf}$ was 8067±2663 hr-ng/mL. The maximum plasma concentrations of guaifenesin following a 1200-mg oral dose as an experimental formulation (Treatment B) was 1649±690 ng/mL (79%±31.5% of the Reference formulation) and occurred in 1.84±0.818 hours (118%±68.8% of the Reference formulation). The resulting $AUC_{inf}$ was 7663±2864 hr-ng/mL (93%±17.6% of that of the Reference formulation).

TABLE 20 guaifenesin Pharmacokinetic Parameters Following
the Administration of 1200 mg Guaifenesin as Mucinex
Along with 120 mg Pseudoephedrine Hydrochloride
as Sudafed ® 12 Hour to Normal Volunteers Following
the Consumption of a High-Fat Meal (Treatment A, Reference)

| Subject | $C_{max}$ (ng/mL) | $T_{max}$ (hr) | $AUC_{0-t}$ (hr-ng/mL) | $AUC_{inf}$ (hr-ng/mL) | Half-life (hr) | Clearance (L/hr) |
|---|---|---|---|---|---|---|
| Mean | 2207 | 1.85 | 8049 | 8067 | 1.22 | 168 |
| Median | 2140 | 1.50 | 8160 | 8196 | 0.983 | 146 |
| Standard Deviation | 952 | 1.06 | 2666 | 2663 | 0.621 | 64.4 |
| Standard Error | 166 | 0.184 | 464 | 464 | 0.108 | 11.2 |
| % CV | 43.2 | 57.2 | 33.1 | 33.0 | 51.1 | 38.3 |

TABLE 21

Guaifenesin Pharmacokinetic Parameters Following
the Administration of 1200 mg Guaifenesin and 120 mg
Pseudoephedrine Hydrochloride in an Experimental Formulation
to Normal Volunteers Following the Consumption of a High-Fat Meal
(Treatment B, Test)

| Subject | $C_{max}$ (ng/mL) | $T_{max}$ (hr) | $AUC_{0-t}$ (hr-ng/mL) | $AUC_{inf}$ (hr-ng/mL) | Half-life (hr) | Clearance (L/hr) |
|---|---|---|---|---|---|---|
| Mean | 1649 | 1.84 | 7611 | 7663 | 1.40 | 181 |
| Median | 1580 | 2.00 | 7474 | 7485 | 1.07 | 160 |
| Standard Deviation | 690 | 0.818 | 2816 | 2864 | 0.793 | 77.6 |
| Standard Error | 118 | 0.140 | 483 | 491 | 0.136 | 13.3 |
| % CV | 41.9 | 44.4 | 37.0 | 37.4 | 56.6 | 42.9 |

TABLE 22

Ratio of Guaifenesin Pharmacokinetic Parameters Following
the Administration of 1200 mg Guaifenesin and 120 mg
Pseudoephedrine Hydrochloride in an Experimental Formulation
Compared to those of Treatment A (Reference) to Normal
Volunteers Following the Consumption of a High-Fat Meal (%)

| Subject | $C_{max}$ (ng/mL) | $T_{max}$ (hr) | $AUC_{0-t}$ (hr-ng/mL) | $AUC_{inf}$ (hr-ng/mL) | Half-life (hr) | Clearance (L/hr) |
|---|---|---|---|---|---|---|
| Mean | 79 | 118 | 93 | 93 | 135 | 109.9 |
| Median | 73 | 100 | 91 | 91 | 99 | 109.8 |
| Standard Deviation | 31.5 | 68.8 | 17.5 | 17.6 | 97.1 | 16.8 |
| Standard Error | 5.57 | 12.2 | 3.09 | 3.12 | 17.2 | 2.96 |
| % CV | 39.8 | 58.3 | 18.8 | 18.9 | 72.0 | 15.3 |

Figure 24:
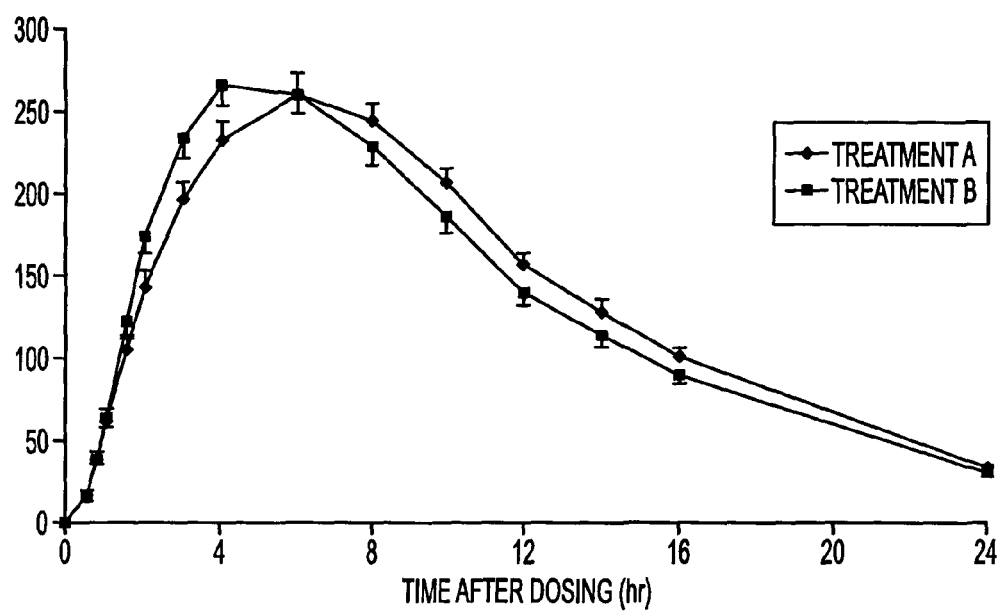
FIG. 24 depicts pseudoephedrine concentrations following administration of 1200 mg of guaifenesin with 120 mg pseudoephedrine hydrochloride in two different formulations following a high-fat meal.

The plasma concentrations of pseudoephedrine are depicted in FIG. 24. The resulting pharmacokinetic data are shown in Tables 23 through 25. The maximum plasma concentrations of pseudoephedrine following a 120 mg oral dose as Sudafed® 12 Hour (Reference) was 268±69.7 ng/mL and occurred in 6.38±1.26 hours. The resulting $AUC_{inf}$ was 3636±940 hr-ng/mL. The maximum plasma concentrations of pseudoephedrine following a 120 mg oral dose as an experimental formulation (Treatment B) was 274±72.3 ng/mL (103%±10.3% of that of the Reference formulation) and occurred in 4.80±1.28 hours (76.5%±23.1% of that of the Reference formulation). The resulting $AUC_{inf}$ was 3528±962 hr-ng/mL (96.5%±11.7% of that of the Reference formulation).

TABLE 23

Pseudoephedrine Pharmacokinetic Parameters Following the Administration of 120 mg Pseudoephedrine Hydrochloride as Sudafed ® 12 Hour Along with 1200 mg Guaifenesin as Mucinex to Normal Volunteers Following the Consumption of a High-Fat Meal (Treatment A, Reference)

| Subject | $C_{max}$ (ng/mL) | $T_{max}$ (hr) | $AUC_{0-t}$ (hr-ng/mL) | $AUC_{inf}$ (hr-ng/mL) | Half-life (hr) | Clearance (L/hr) |
|---|---|---|---|---|---|---|
| Mean | 268 | 6.38 | 3362 | 3636 | 5.28 | 28.8 |
| Median | 249 | 6.00 | 3238 | 3545 | 4.97 | 27.7 |
| Standard Deviation | 69.7 | 1.26 | 847 | 940 | 1.08 | 7.55 |
| Standard Error | 12.1 | 0.219 | 147 | 164 | 0.188 | 1.31 |
| % CV | 26.03 | 19.67 | 25.18 | 25.86 | 20.42 | 26.19 |

TABLE 24

Pseudoephedrine Pharmacokinetic Parameters Following the Administration of 120 mg of Pseudoephedrine Hydrochloride and 1200 mg Guaifenesin in an Experimental Formulation to Normal Volunteers Following the Consumption of a High-Fat Meal (Treatment B, Test)

| Subject | $C_{max}$ (ng/mL) | $T_{max}$ (hr) | $AUC_{0-t}$ (hr-ng/mL) | $AUC_{inf}$ (hr-ng/mL) | Half-life (hr) | Clearance (L/hr) |
|---|---|---|---|---|---|---|
| Mean | 274 | 4.80 | 3273 | 3528 | 5.26 | 30.0 |
| Median | 268 | 4.00 | 3198 | 3448 | 5.31 | 28.5 |
| Standard Deviation | 72.3 | 1.28 | 876 | 962 | 1.02 | 8.48 |
| Standard Error | 12.2 | 0.216 | 148 | 163 | 0.172 | 1.43 |
| % CV | 26.4 | 26.6 | 26.8 | 27.3 | 19.4 | 28.3 |

TABLE 25

Ratio of Pseudoephedrine Pharmacokinetic Parameters Following the Administration of 120 mg Pseudoephedrine Hydrochloride and 1200 mg Guaifenesin in an Experimental Formulation Compared to those of Treatment A (Reference) to Normal Volunteers Following the Consumption of a High-Fat Meal (%)

| Subject | $C_{max}$ (ng/mL) | $T_{max}$ (hr) | $AUC_{0-t}$ (hr-ng/mL) | $AUC_{inf}$ (hr-ng/mL) | Half-life (hr) | Clearance (L/hr) |
|---|---|---|---|---|---|---|
| Mean | 103 | 76.5 | 96.5 | 96.5 | 101 | 105 |
| Median | 103 | 66.7 | 95.7 | 94.2 | 99.5 | 106 |
| Standard Deviation | 10.3 | 23.1 | 10.6 | 11.7 | 17.9 | 12.6 |
| Standard Error | 1.82 | 4.09 | 1.88 | 2.06 | 3.17 | 2.23 |
| % CV | 10.0 | 30.3 | 11.0 | 12.1 | 17.7 | 12.0 |

The rate of absorption of guaifenesin from the experimental formulation, as assessed by $C_{max}$ is not bioequivalent to the test formulation in the presence of a high fat meal with a 95% confidence interval between 67.9% and 81.8%. The extent of absorption of guaifenesin from the experimental tablet, as assessed by $AUC_{inf}$ is equivalent to the test formulation in the presence of a high fat meal.

In conclusion, the rate of guaifenesin absorption from the experimental formulation is not bioequivalent to the Reference formulations; whereas the extent of guaifenesin absorption is bioequivalent to the Reference formulation in the presence of a high-fat meal. The rate and extent of pseudoephedrine absorption from the experimental formulation are bioequivalent to the Reference formulation in the presence of a high-fat meal.

Example 15

A combination guaifenesin and Pseudoephedrine formulation was tested for steady state pharmacokinetics as compared to references in an open-label, multiple-dose, randomized, 2-way-crossover study using 36 subjects. The subjects were randomly placed into one of two treatment groups. Group 1 received a 1200 mg controlled-release guaifenesin product (Mucinex) plus a 120 mg controlled-release pseudoephedrine product (Sudafed® 12 Hour) with 240 mL of water after an overnight fast and again 12 hours later for 11 doses (Reference). Group 2 received an experimental controlled-release formulation comprising 1200 mg guaifenesin and 120 mg pseudoephedrine hydrochloride with 240 mL of water after an overnight fast and again 12 hours later for 11 doses (Test)(PB01-M65).

Blood (10 mL, sodium heparin anticoagulant) was obtained at the following times: Pre dose blood sample before the AM dose on Days 1, 4, 5 and 6. On Day 6 additional blood samples (5 mL, sodium heparin anticoagulant) were also obtained at 0.5, 0.75, 1, 1.5, 2, 3, 4, 6, 8, 10, 12, 14, 16 and 24 hours after the last dose (total blood loss for guaifenesin determination was 380 mL).

The subjects given 1200 mg guaifenesin, as Mucinex every 12 hours for 11 doses, reached a maximum steady-state plasma guaifenesin concentration of 1960 ng/mL at 0.81 hours after the last dose (120.81 hours after the first dose). The mean $AUC_{ss}$ was 7209 hr-ng/mL and the mean $C_{min}$ was 52 ng/mL. Those subjects given 1200 mg guaifenesin, as an experimental formulation every 12 hours for 11 doses, reached a maximum steady-state plasma guaifenesin concentration of 1983 ng/mL (103% of the Reference formulation) at 0.96 hours after the last dose (120.96 hours after the first dose, 100% of that of the Reference formulation). The mean $AUC_{ss}$ was 8183 hr-ng/mL (114% of that of the Reference formulation) and the mean $C_{min}$ was 117 ng/mL.

At steady state, the subjects given 120 mg pseudoephedrine hydrochloride, as Sudafed® 12 Hour, every 12 hours for 11 doses, reached a steady-state maximum plasma pseudoephedrine concentration of 361 ng/mL at 4.89 hours after the last dose (124.89 hours after the first dose). The mean $AUC_{ss}$ was 3528 hr-ng/mL and the mean $C_{min}$ was 182 ng/mL. Those subjects, when given the 120 mg pseudoephedrine hydrochloride as an experimental formulation, reached a steady-state maximum plasma pseudoephedrine concentration of 365 ng/mL (103% of that of the Reference) 4.10 hours after the last dose (124.10 hours after the first dose, 99.4% of that of the Reference). The mean $AUC_{ss}$ was 3550 hr-ng/mL (102% of that of the Reference) and the mean $C_{min}$ was 173 ng/mL.

Figure 25:
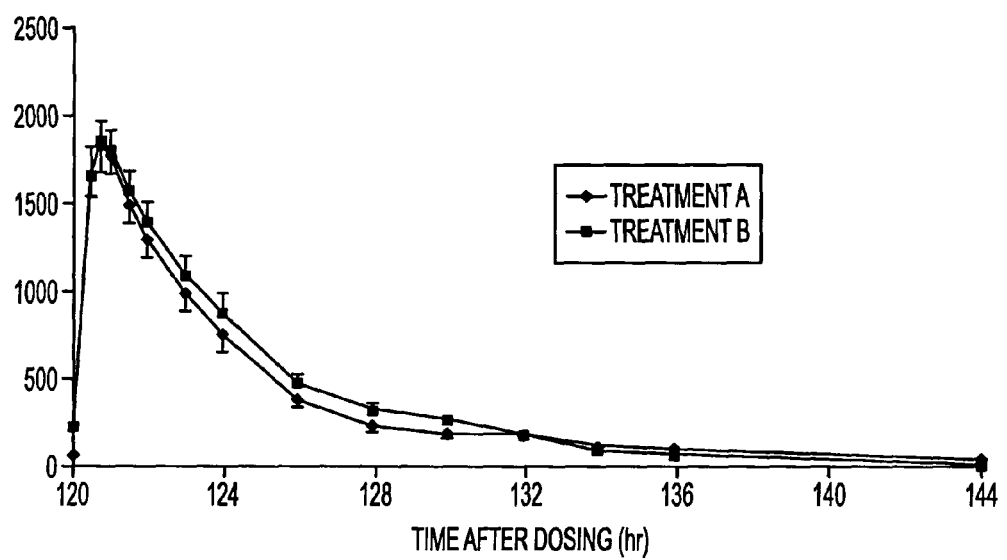
FIG. 25 depicts steady-state guaifenesin plasma concentrations following administration of 11 doses of 120 mg pseudoephedrine with 1200 mg of guaifenesin in two different formulations.

The mean plasma concentrations of guaifenesin are depicted in FIG. 25. The resulting pharmacokinetic data are shown in Tables 26 through 28. At steady state, the subjects given 1200 mg guaifenesin every 12 hours, as Reference Mucinex for 11 doses, reached a steady-state maximum plasma guaifenesin concentration of 1960±859 ng/mL (Mean±Standard Deviation) in 0.81 hours±0.305 hour after the last dose (120.81 hours after the first dose) and the steady-state AUC ($AUC_{ss}$) was 7209±3746 hr-ng/mL. At steady state, the subjects given 1200 mg guaifenesin every 12 hours, as an experimental tablet formulation for 11 doses, reached a steady-state maximum plasma guaifenesin concentration of 1983±1019 ng/mL (103%±29.6% of the Reference Mucinex) in 0.96 hours±0.645 hour after the last dose (120.96 hours after the first dose, 100%±0.494%). The $AUC_{ss}$ was 8183±5141 hr-ng/mL (114%±27.0%).

TABLE 26

Guaifenesin Steady-State Pharmacokinetic Parameters Following the Administration of 11 Doses of 1200 mg guaifenesin as Mucinex and 120 mg Pseudoephedrine Hydrochloride as Sudafed ® 12 Hour to Normal Volunteers - Treatment A (Reference)

| Subject | $AUC_{SS}$ (hr-ng/mL) | $C_{min}$ (ng/mL) | $C_{max}$ (ng/mL) | $T_{max}$ (hr) | $C_{AVERAGE}$ (ng/mL) |
|---|---|---|---|---|---|
| Mean | 7209 | 52.0 | 1960 | 120.81 | 604 |
| Median | 6554 | 28.3 | 1850 | 120.75 | 547 |
| Standard Deviation | 3746 | 48.1 | 859 | 0.305 | 311 |
| Standard Error | 633 | 8.13 | 145 | 0.052 | 52.6 |
| % CV | 52.0 | 92.5 | 43.8 | 0.253 | 51.5 |

TABLE 27 guaifenesin Steady-State Pharmacokinetic Parameters Following the Administration of 11 Doses of 1200 mg guaifenesin and 120 mg Pseudoephedrine Hydrochloride in an Experimental Formulation to Normal Volunteers - Treatment B (Test)

| Subject | $AUC_{SS}$ (hr-ng/mL) | $C_{min}$ (ng/mL) | $C_{max}$ (ng/mL) | $T_{max}$ (hr) | $C_{AVERAGE}$ (ng/mL) |
|---|---|---|---|---|---|
| Mean | 8183 | 117 | 1983 | 120.96 | 686 |
| Median | 6769 | 100 | 1750 | 120.75 | 564 |
| Standard Deviation | 5141 | 87.2 | 1019 | 0.645 | 431 |
| Standard Error | 869 | 14.7 | 172 | 0.109 | 72.8 |
| % CV | 62.8 | 74.5 | 51.4 | 0.533 | 62.7 |

TABLE 28

Ratio of Guaifenesin Steady-State Pharmacokinetic Parameters Following the Administration of 11 Doses of 1200 mg Guaifenesin and 120 mg Pseudoephedrine Hydrochloride in an Experimental Formulation Compared to Reference Formulations to Normal Volunteers (%)

| Subject | $AUC_{SS}$ | $C_{min}$ | $C_{max}$ | $T_{max}$ | $C_{AVERAGE}$ |
|---|---|---|---|---|---|
| Mean | 114 | 550 | 103 | 100 | 114 |
| Median | 116 | 261 | 104 | 100 | 113 |
| Standard Deviation | 27.0 | 712 | 29.6 | 0.494 | 26.4 |
| Standard Error | 4.57 | 120 | 5.01 | 0.084 | 4.46 |
| % CV | 23.7 | 129 | 28.6 | 0.494 | 23.2 |

Figure 26:
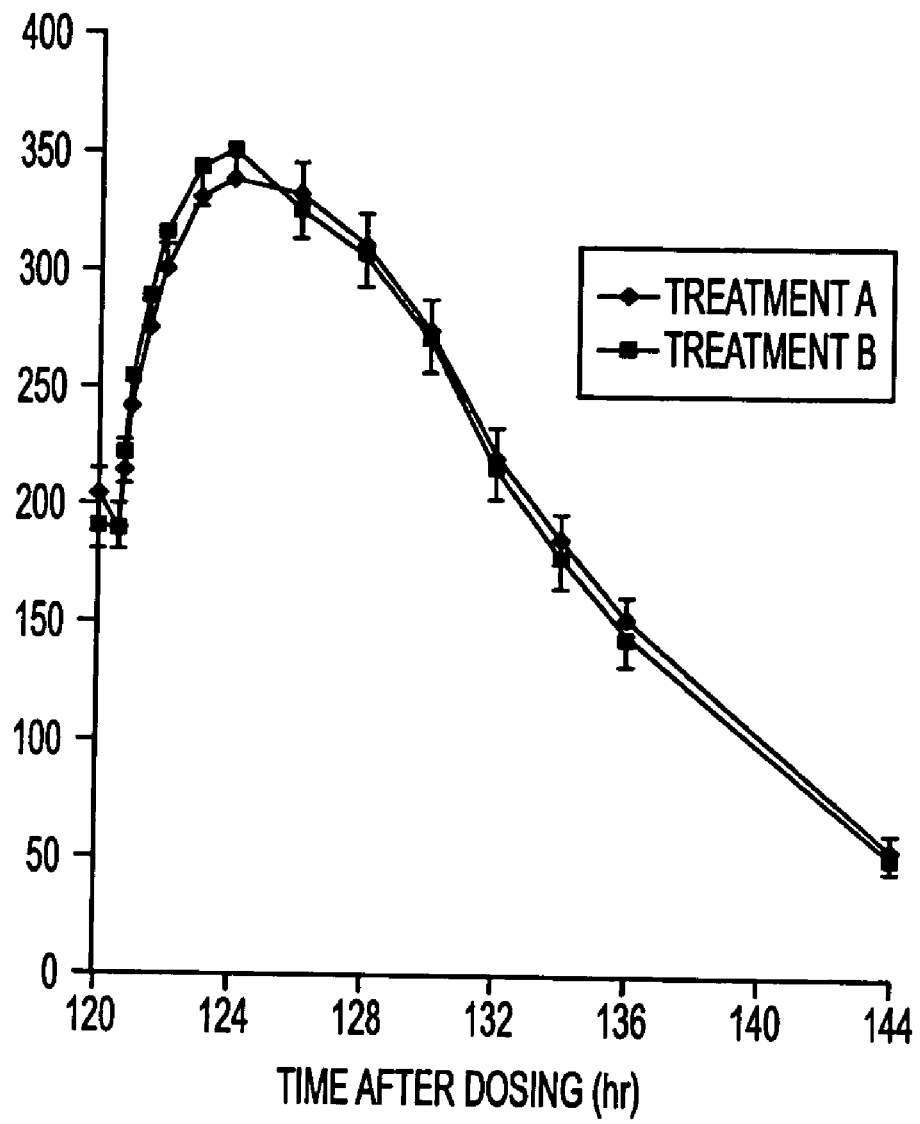
FIG. 26 depicts steady-state pseudoephedrine plasma concentrations following administration of 11 doses of 120 mg pseudoephedrine with 1200 mg of guaifenesin in two different formulations.

The mean plasma concentration of Pseudoephedrine are shown in FIG. 26. The resulting pharmacokinetic data are shown in Tables 29 through 31. At steady state, the subjects given 120 mg pseudoephedrine hydrochloride, as Sudafed® 12 Hour, every 12 hours for 11 doses, reached a steady-state maximum plasma pseudoephedrine concentration of 361±77.7 ng/mL in 4.89 hours±2.14 hour after the last dose (124.89 hours after the first dose). The $AUC_{ss}$ was 3528±862 hr-ng/mL. At steady state, the subjects given 120 mg pseudoephedrine hydrochloride every 12 hours, as an experimental tablet formulation for 11 doses, reached a steady-state maximum plasma pseudoephedrine concentration of 365±83.3 ng/mL (103%±2 1.4% of the Reference Sudafed 12-Hour) in 4.10 hours±1.85 hours after the last dose (124.10 hours after the first dose, 99.4%±2.09%). The $AUC_{ss}$ was 3550±898 hr-ng/mL (102%±19.6%).

TABLE 29

Pseudoephedrine Steady-State Pharmacokinetic Parameters Following the Administration of 11 Doses of 120 mg Pseudoephedrine Hydrochloride as Sudafed ® 12 Hour and 1200 mg Guaifenesin as Mucinex to Normal Volunteers - Treatment A (Reference)

| Subject | $AUC_{SS}$ (hr-ng/mL) | $C_{min}$ (ng/mL) | $C_{max}$ (ng/mL) | $T_{max}$ (hr) | $C_{AVERAGE}$ (ng/mL) |
|---|---|---|---|---|---|
| Mean | 3528 | 182 | 361 | 124.89 | 294 |
| Median | 3462 | 164 | 362 | 124.00 | 288 |
| Standard Deviation | 862 | 66.4 | 77.7 | 2.14 | 71.9 |
| Standard Error | 146 | 11.2 | 13.1 | 0.361 | 12.1 |
| % CV | 24.4 | 36.5 | 21.5 | 1.71 | 24.4 |

TABLE 30

Pseudoephedrine Steady-State Pharmacokinetic Parameters Following the Administration of 11 Doses of 120 mg Pseudoephedrine Hydrochloride and 1200 mg Guaifenesin in an Experimental Formulation to Normal Volunteers - Treatment B (Test)

| Subject | $AUC_{SS}$ (hr-ng/mL) | $C_{min}$ (ng/mL) | $C_{max}$ (ng/mL) | $T_{max}$ (hr) | $C_{AVERAGE}$ (ng/mL) |
|---|---|---|---|---|---|
| Mean | 3550 | 173 | 365 | 124.10 | 296 |
| Median | 3399 | 170 | 350 | 124.00 | 283 |
| Standard Deviation | 898 | 55.2 | 83.3 | 1.85 | 74.8 |
| Standard Error | 152 | 9.34 | 14.1 | 0.313 | 12.7 |
| % CV | 25.3 | 32.0 | 22.8 | 1.49 | 25.3 |

TABLE 31

Ratio of Pseudoephedrine Steady-State Pharmacokinetic Parameters Following the Administration of 11 Doses of 120 mg Pseudoephedrine Hydrochloride and 1200 mg Guaifenesin in an Experimental Formulation Compared to Reference Formulations to Normal Volunteers (%)

| Subject | $AUC_{SS}$ | $C_{min}$ | $C_{max}$ | $T_{max}$ | $C_{AVERAGE}$ |
|---|---|---|---|---|---|
| Mean | 102 | 100 | 103 | 99.4 | 102 |
| Median | 99.6 | 102 | 100 | 99.2 | 100 |
| Standard Deviation | 19.6 | 28.0 | 21.4 | 2.09 | 19.6 |
| Standard Error | 3.31 | 4.73 | 3.62 | 0.354 | 3.31 |
| % CV | 19.1 | 27.9 | 20.8 | 2.11 | 19.1 |

In conclusion, the experimental tablet formulation was bioequivalent to the Reference formulations at steady state. The experimental formulation is bioequivalent to the Reference formulations in terms of both $C_{max}$ and $AUC_{ss}$ for guaifenesin and pseudoephedrine hydrochloride.

Example 16

In another study drug interaction potential for combination drugs was examined. The interaction potential for 1200 mg guaifenesin and 120 mg Pseudoephedrine Hydrochloride was compared to reference in an open label, single dose, randomized, 3-way crossover study using 36 subjects.

The subjects were randomized and placed into one of three treatment groups. group A received a 1200 mg controlled release guaifenesin product (Mucinex) with 240 mL of room-temperature water after an overnight fast. Group B received a 120 mg controlled release pseudoephedrine product (Sudafed® 12 Hour) with 240 mL of room-temperature water after an overnight fast. Group C received a 1200 mg guaifenesin product (Mucinex) and 120 mg pseudoephedrine hydrochloride (Sudafed® 12 Hour) with 240 mL of room-temperature water after an overnight fast.

Blood (10 mL, sodium heparin anticoagulant) was obtained at the following times: Pre dose, 0.5, 0.75, 1, 1.5, 2, 3, 4, 6, 8, 10, 12, 14, 16 and 24 hours post dose (the total blood loss for guaifenesin and pseudoephedrine analysis was ~450 mL).

Subjects given 1200 mg of guaifenesin as Mucinex (Treatment A, Reference) reached a $C_{max}$ of 2009 ng/mL in 0.89 hours and had an $AUC_{inf}$ of 8138 hr-ng/mL. Subjects given 1200 mg guaifenesin as Mucinex along with 120 mg Pseudoephedrine hydrochloride as Sudafed® 12 Hour (Treatment C, Test) reached a $C_{max}$ of 1989 ng/mL (102% of that of the reference) in 0.84 hour (104% of that of the reference) and had an $AUC_{inf}$ of 8052 hr-ng/mL (100% of that of the reference).

Subjects given 120 mg pseudoephedrine hydrochloride as Sudafed® 12 Hour (Treatment B, Reference) reached a $C_{max}$ of 296 ng/mL in 6 hours and had an $AUC_{inf}$ of 4505 hr ng/mL. Subjects given 120 mg pseudoephedrine hydrochloride as Sudafed® 12 Hour, along with 1200 mg guaifenesin as Mucinex (Treatment C, Test) reached a C of 289 ng/mL (98% of that of the reference) in 6 hours (101% of that of the reference) and had an $AUC_{inf}$ of 4396 hr-ng/mL (98% of that of the reference).

Figure 27:
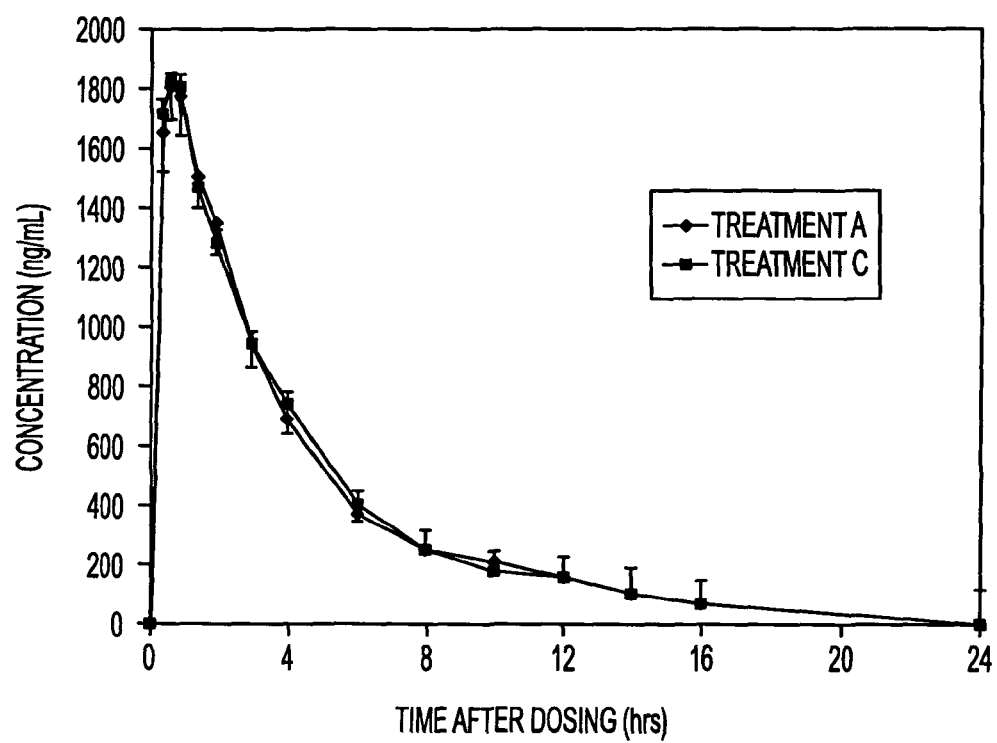
FIG. 27 depicts guaifenesin plasma concentrations following administration of 1200 mg of guaifenesin with and without the co-administration of 120 mg of pseudoephedrine.

The plasma concentrations of guaifenesin are depicted in FIG. 27. The resulting pharmacokinetic data is shown in Tables 38 through 41. The maximum plasma concentrations of guaifenesin following a 1200 mg oral dose as Mucinex (Treatment A, Reference) were 2009±819.2 ng/mL and occurred in 0.89±0.42 hours. The resulting area under the plasma concentration vs. time curve ($AUC_{inf}$ was 8138±3253 hr-ng/mL. The maximum plasma concentrations of guaifenesin following a 1200 mg oral dose as Mucinex along with 120 mg pseudoephedrine hydrochloride (Treatment C, Test) were 1989±863 ng/mL (102.33%±31.40% of that of the reference formulation) and occurred in 0.84±0.31 hours (103.94%±35.38% that of the reference formulation). The resulting $AUC_{inf}$ was 8052±3344 hr-ng/mL (100.06%±18.09% of that of the reference formulation).

TABLE 38

Guaifenesin Pharmacokinetic Parameters Following the Administration of 1200 mg Guaifenesin to Normal Volunteers (Treatment A)

| Subject | $C_{max}$ (ng/mL) | $T_{max}$ (hr) | $AUC_{0-t}$ (hr-ng/mL) | $AUC_{inf}$ (hr-ng/mL) | Half-life (hr) | Clearance (L/hr) |
|---|---|---|---|---|---|---|
| Mean | 2009 | 0.89 | 7921 | 8138 | 4.00 | 172.13 |
| Median | 1695 | 0.75 | 7063.8 | 7284.17 | 2.82 | 164.87 |
| Standard Deviation | 819.22 | 0.42 | 3196.53 | 3253.39 | 5.58 | 70.19 |
| Standard Error | 138.47 | 0.07 | 540.31 | 549.92 | 0.94 | 11.87 |
| % CV | 40.77 | 46.79 | 40.35 | 39.98 | 139.48 | 40.78 |

TABLE 39

Guaifenesin Pharmacokinetic Parameters Following the Administration of 1200 mg Guaifenesin Along with 120 mg Pseudoephedrine Hydrochloride to Normal Volunteers (Treatment C)

| Subject | $C_{max}$ (ng/mL) | $T_{max}$ (hr) | $AUC_{0-t}$ (hr-ng/mL) | $AUC_{inf}$ (hr-ng/mL) | Half-life (hr) | Clearance (L/hr) |
|---|---|---|---|---|---|---|
| Mean | 1989 | 0.84 | 7923 | 8052 | 3.41 | 175.45 |
| Median | 1770 | 0.75 | 6689 | 6745 | 3.33 | 177.93 |
| Standard Deviation | 863.36 | 0.31 | 3337 | 3344 | 1.72 | 71.07 |
| Standard Error | 145.93 | 0.05 | 564.04 | 565.25 | 0.29 | 12.01 |
| % CV | 43.41 | 36.37 | 42.12 | 41.53 | 50.56 | 40.51 |

TABLE 40

Ratio of Guaifenesin Pharmacokinetic Parameters Following the Administration of 1200 mg Guaifenesin Along with 120 mg Pseudoephedrine Hydrochloride Compared to 1200 mg Guaifenesin Alone to Normal Volunteers (%)

| Subject | $C_{max}$ (ng/mL) | $T_{max}$ (hr) | $AUC_{0-t}$ (hr-ng/mL) | $AUC_{inf}$ (hr-ng/mL) | Half-life (hr) | Clearance (L/hr) |
|---|---|---|---|---|---|---|
| Mean | 102.33 | 103.94 | 100.87 | 100.06 | 128.38 | 103.47 |
| Median | 95.79 | 100 | 103.14 | 101.71 | 107.41 | 98.32 |
| Standard Deviation | 31.40 | 35.38 | 18.01 | 18.09 | 79.38 | 20.60 |
| Standard Error | 5.31 | 5.98 | 3.05 | 3.06 | 13.42 | 3.48 |
| % CV | 30.69 | 34.04 | 17.86 | 18.08 | 61.83 | 19.91 |

TABLE 41

Pseudoephedrine Pharmacokinetic Parameters Following the Administration of 120 mg Pseudoephedrine Hydrochloride to Normal Volunteers (Treatment B)

| Subject | $C_{max}$ (ng/mL) | $T_{max}$ (hr) | $AUC_{0-t}$ (hr-ng/mL) | $AUC_{inf}$ (hr-ng/mL) | Half-life (hr) | Clearance (L/hr) |
|---|---|---|---|---|---|---|
| Mean | 295.8 | 6.17 | 4024 | 4505 | 6.05 | 23.66 |
| Median | 297.5 | 6 | 3823 | 4430 | 5.81 | 22.20 |
| Standard Deviation | 73.25 | 1.92 | 1047 | 1250 | 1.44 | 7.24 |
| Standard Error | 12.38 | 0.32 | 177 | 211 | 0.24 | 1.22 |
| % CV | 24.76 | 31.13 | 26.02 | 27.75 | 23.83 | 30.60 |

Figure 28:
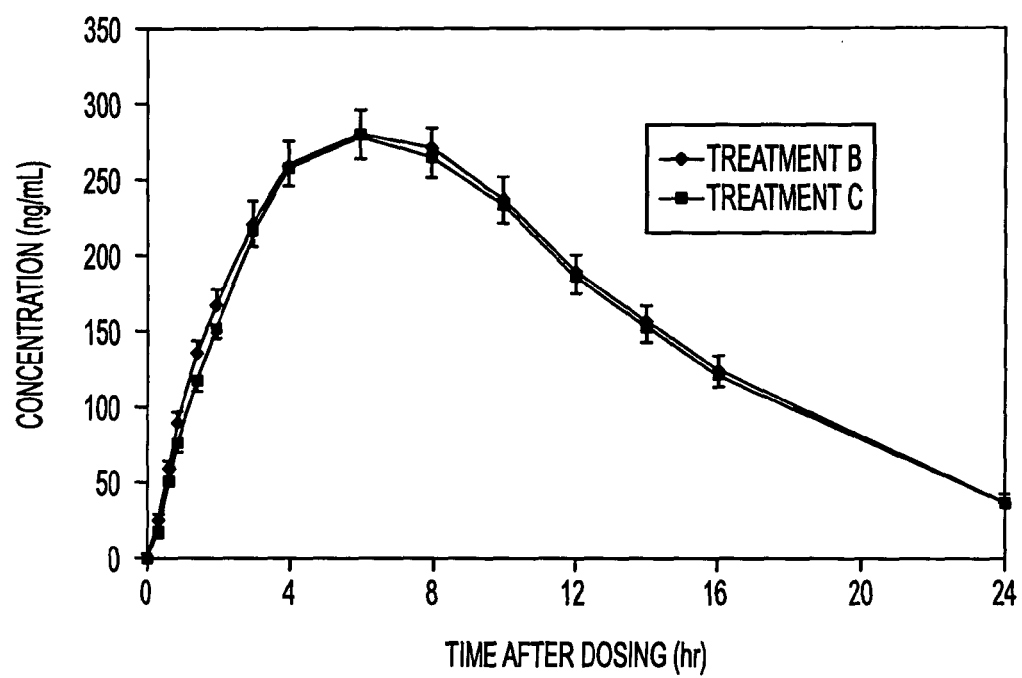
FIG. 28 depicts pseudoephedrine plasma concentrations following administration of 120 mg of pseudoephedrine with and without the co-administration of 1200 mg of guaifenesin.

The plasma concentrations of pseudoephedrine are depicted in FIG. 28. The resulting pharmacokinetic data is shown in Tables 42 through 43. The maximum plasma concentrations of pseudoephedrine following a 120 mg oral dose as Sudafed® 12 Hour (Treatment B, Reference) were 295.8±73.25 ng/mL and occurred in 6.17±1.92 hours. The resulting $AUC_{inf}$ was 4505±1250 hr-ng/mL. The maximum plasma concentrations of pseudoephedrine following a 120 mg oral dose as Sudafed® 12 Hour along with 1200 mg guaifenesin as Mucinex (Treatment C, Test) were 289.3±77.61 ng/mL (98.41%±12.77% of that of the reference formulation) and occurred in 5.75±1.54 hours (100.74%±38.65% of that of the reference formulation). The resulting $AUC_{inf}$ was 4396±1347 hr-ng/mL (98.40%±15.24% of that of the reference formulation).

TABLE 42

Pseudoephedrine Pharmacokinetic Following the Administration of 120 mg Pseudoephedrine Hydrochloride Along with 1200 mg guaifenesin to Normal Volunteers (Treatment C)

| Subject | $C_{max}$ (ng/mL) | $T_{max}$ (hr) | $AUC_{0-t}$ (hr-ng/mL) | $AUC_{inf}$ (hr-ng/mL) | Half-life (hr) | Clearance (L/hr) |
|---|---|---|---|---|---|---|
| Mean | 289.33 | 5.75 | 3925 | 4396 | 6.04 | 24.30 |
| Median | 286 | 6 | 3932 | 4247 | 5.63 | 23.16 |
| Standard Deviation | 77.61 | 1.54 | 1089 | 1347 | 1.38 | 6.95 |
| Standard Error | 13.12 | 0.26 | 184 | 228 | 0.23 | 1.17 |
| % CV | 26.82 | 26.74 | 27.75 | 30.65 | 22.79 | 28.60 |

TABLE 43

Ratio of Pseudoephedrine Pharmacokinetic Parameters Following the Administration of 120 mg Along with 1200 mg Guaifenesin Hydrochloride Compared to 120 mg Pseudoephedrine Alone to Normal Volunteers (%)

| Subject | $C_{max}$ (ng/mL) | $T_{max}$ (hr) | $AUC_{0-t}$ (hr-ng/mL) | $AUC_{inf}$ (hr-ng/mL) | Half-life (hr) | Clearance (L/hr) |
|---|---|---|---|---|---|---|
| Mean | 98.41 | 100.74 | 98.22 | 98.40 | 103.30 | 103.99 |
| Median | 98.40 | 100 | 96.90 | 97.91 | 97.46 | 102.14 |
| Standard Deviation | 12.77 | 38.65 | 13.15 | 15.24 | 30.44 | 15.96 |
| Standard Error | 2.16 | 6.53 | 2.22 | 2.58 | 5.14 | 2.70 |
| % CV | 12.97 | 38.36 | 13.39 | 15.49 | 29.47 | 15.35 |

In conclusion, the pharmacokinetics of guaifenesin and pseudoephedrine hydrochloride are unaffected by the presence or absence of one another.

Example 17

In another experiment the effect of a high-fat on the bioavailability of an of the combination of 1200 mg guaifenesin and 120 mg Pseudoephedrine Hydrochloride in normal healthy volunteers was again compared to reference drug in an open-label, single-dose, randomized, 2-way-crossover study using 36 subjects.

The subjects were randomized and placed into one of two treatment groups. Each treatment group was fasted overnight. Treatment A received an experimental formulation containing 1200 mg guaifenesin and 120 mg pseudoephedrine hydrochloride with 240 mL of water (Reference). Treatment B received an experimental controlled-release formulation containing 1200 mg guaifenesin and 120 mg pseudoephedrine hydrochloride with 240 mL of water, 30 minutes after the beginning of the consumption of a high-fat breakfast (Test).

Blood (10 mL, sodium heparin anticoagulant) was obtained at the following times: Pre dose, 0.5, 0.75, 1, 1.5, 2, 3, 4, 6, 8, 10, 12, 14, 16 and 24 hours post dose (the total blood loss for guaifenesin and pseudoephedrine analysis was 300 mL). Subjects given 1200 mg of guaifenesin and 120 mg pseudoephedrine hydrochloride as an experimental formulation following an overnight fast (Treatment A, Reference) reached a plasma guaifenesin $C_{max}$ of 1857 ng/mL in 1.06 hours and had an $AUC_{inf}$ of 8142 hr-ng/mL. Subjects given 1200 mg guaifenesin and 120 mg pseudoephedrine hydrochloride as an experimental formulation after the consumption of a high-fat meal (Treatment B, Test) reached a plasma guaifenesin $C_{max}$ of 1364 ng/mL (79.3% of that of the Reference) in 2.06 hour (238% of that of the Reference) and had an $AUC_{inf}$ of 7469 hr-ng/mL (94.1% of that of the Reference).

Subjects given 120 mg pseudoephedrine hydrochloride as an experimental formulation after an overnight fast (Treatment A, Reference) reached a plasma pseudoephedrine $C_{max}$ of 283 ng/mL in 4.6 hours and had an $AUC_{inf}$ of 3746 hr-ng/mL. Subjects given 120 mg pseudoephedrine hydrochloride as an experimental formulation following the consumption of a high-fat meal (Treatment B, Test) reached a plasma pseudoephedrine $C_{max}$ of 301 ng/mL (108% of that of the Reference) in 5.77 hours (137% of that of the Reference) and had an $AUC_{inf}$ of 3660 hr-ng/mL (99% of that of the Reference).

Figure 29:
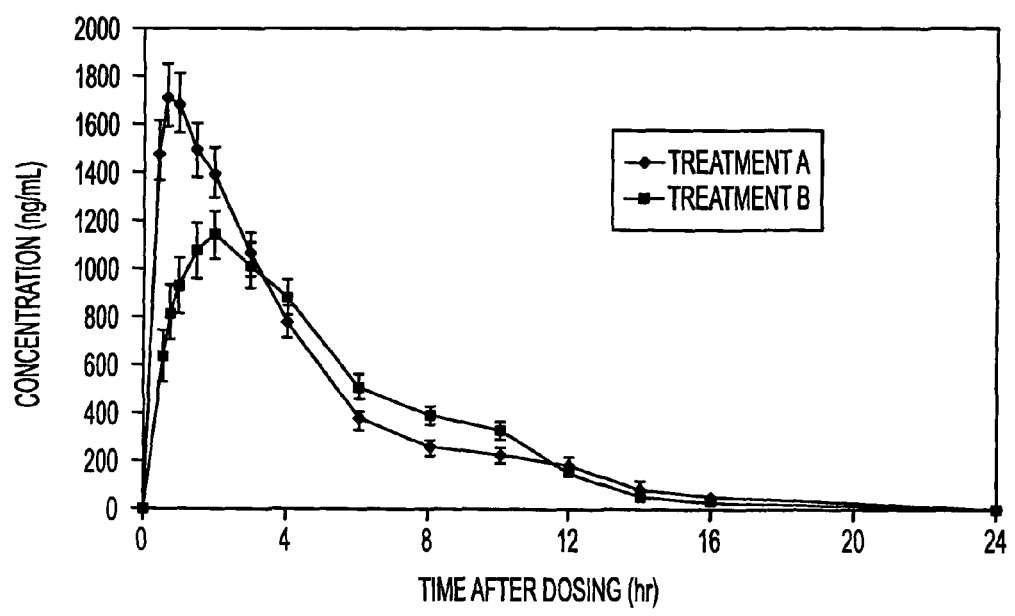
FIG. 29 depicts guaifenesin plasma concentrations following administration of an experimental 1200 mg guaifenesin-120 mg pseudoephedrine formulation to volunteers under fed and fasted conditions.
Figure 30:
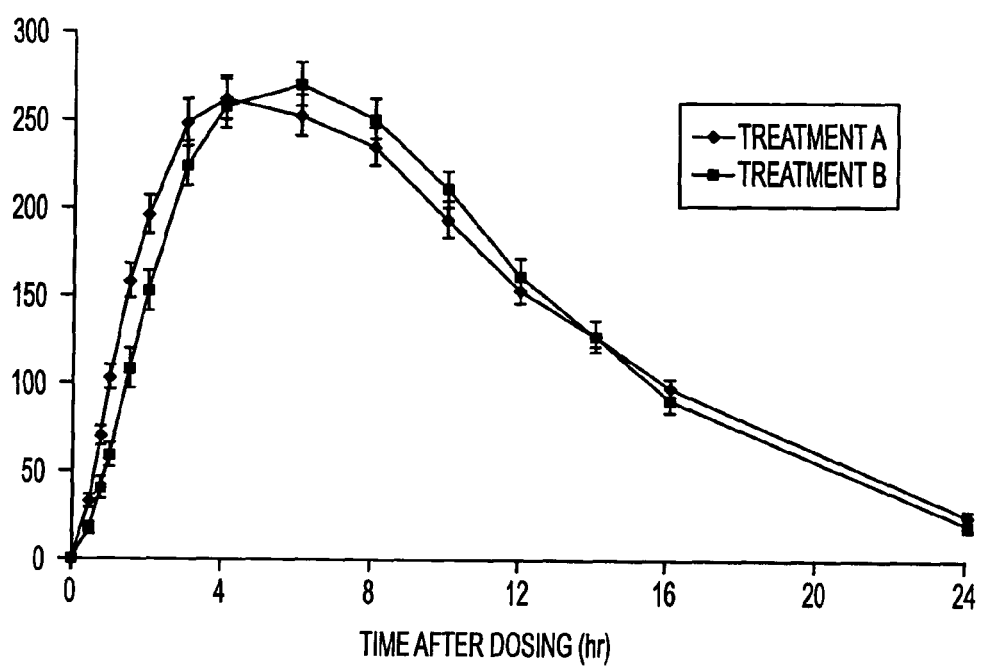
FIG. 30 depicts pseudoephedrine plasma concentrations following administration of an experimental 1200 mg guaifenesin-120 mg pseudoephedrine formulation to volunteers under fed and fasted conditions.

The plasma concentrations of guaifenesin are depicted in FIG. 29. The resulting pharmacokinetic data are shown in Tables 44 through 46. The maximum plasma concentrations of guaifenesin following 1200 mg guaifenesin and 120 mg pseudoephedrine hydrochloride after an overnight fast were 1857±838 ng/mL (Mean±Standard Deviation) and occurred in 1.06±0.582 hours. The resulting area under the plasma concentration vs. time curve ($AUC_{inf}$ was 8142±3500 hr-ng/mL. The maximum plasma concentrations of guaifenesin, following 1200 mg oral guaifenesin and 120 mg pseudoephedrine hydrochloride as an experimental formulation following the consumption of a high-fat meal (Treatment B, Test), were 1364±691 ng/mL (79.3%±34.7% of that of the Reference formulation) and occurred in 2.06±1.16 hours (238%±157% of that of the Reference formulation). The resulting $AUC_{inf}$ was 7469±3217 hr-ng/mL (94.1%±23.1% of that of the Reference formulation).

TABLE 44

Guaifenesin Pharmacokinetic Parameters Following the Administration of 1200 mg Guaifenesin and 120 mg Pseudoephedrine Hydrochloride in an Experimental Formulation to Normal Volunteers After an Overnight Fast (Treatment A, Reference)

| Subject | $C_{max}$ (ng/mL) | $T_{max}$ (hr) | $AUC_{0-t}$ (hr-ng/mL) | $AUC_{inf}$ (hr-ng/mL) | Half-life (hr) | Clearance (L/hr) |
|---|---|---|---|---|---|---|
| Mean | 1857 | 1.06 | 8091 | 8142 | 1.82 | 18.0 |
| Median | 1830 | 0.750 | 8228 | 8244 | 1.68 | 14.6 |
| Standard Deviation | 838 | 0.582 | 3501 | 3500 | 0.702 | 8.46 |
| Standard Error | 144 | 0.100 | 600 | 600 | 0.120 | 1.45 |
| % CV | 45 | 55.0 | 43.3 | 43.0 | 38.6 | 47.0 |

TABLE 45

Guaifenesin Pharmacokinetic Parameters Following the Administration of 1200 mg Guaifenesin and 120 mg Pseudoephedrine Hydrochloride in an Experimental Formulation to Normal Volunteers After the Consumption of a High-Fat Meal (Treatment B, Test)

| Subject | $C_{max}$ (ng/mL) | $T_{max}$ (hr) | $AUC_{0-t}$ (hr-ng/mL) | $AUC_{inf}$ (hr-ng/mL) | Half-life (hr) | Clearance (L/hr) |
|---|---|---|---|---|---|---|
| Mean | 1364 | 2.06 | 7403 | 7469 | 1.39 | 18.9 |
| Median | 1190 | 2.00 | 6842 | 6857 | 1.12 | 17.5 |
| Standard Deviation | 691 | 1.16 | 3185 | 3217 | 0.833 | 7.80 |
| Standard Error | 119 | 0.200 | 546 | 552 | 0.143 | 1.34 |
| % CV | 50.7 | 56.6 | 43.0 | 43.1 | 60.0 | 41.2 |

TABLE 46

Ratio of Guaifenesin Pharmacokinetic Parameters Following the Administration of 1200 mg Guaifenesin and 120 mg Pseudoephedrine Hydrochloride in an Experimental Formulation Following the Consumption of a High-Fat Meal (Treatment B, Test) Compared to that After an Overnight Fast (Treatment A, Reference) to Normal Volunteers (%)

| Subject | $C_{max}$ (ng/mL) | $T_{max}$ (hr) | $AUC_{0-t}$ (hr-ng/mL) | $AUC_{inf}$ (hr-ng/mL) | Half-life (hr) | Clearance (L/hr) |
|---|---|---|---|---|---|---|
| Mean | 79.3 | 238 | 94.0 | 94.1 | 87.2 | 112 |
| Median | 71.4 | 200 | 89.7 | 89.6 | 68.1 | 112 |
| Standard Deviation | 34.7 | 157 | 23.4 | 23.1 | 53.2 | 24.5 |
| Standard Error | 6.04 | 27.4 | 4.07 | 4.02 | 9.27 | 4.26 |
| % CV | 43.8 | 66.1 | 24.8 | 24.6 | 61.1 | 21.9 |

The resulting pharmacokinetic data are shown in Tables 47 through 49. The maximum plasma concentrations of pseudoephedrine following a 120 mg pseudoephedrine hydrochloride and 1200 mg guaifenesin, in an experimental formulation after an overnight fast (Treatment A, Reference), were 283±79.6 ng/mL and occurred in 4.60±1.56 hours. The resulting $AUC_{inf}$ was 3746±997 hr-ng/mL. The maximum plasma concentrations of pseudoephedrine following 120 mg pseudoephedrine hydrochloride and 1200 mg guaifenesin, in an experimental formulation following the consumption of a high-fat meal (Treatment B, Test), were 301±80.4 ng/mL (108%±18.5% of that of the Reference formulation) and occurred in 5.77±1.78 hours (137%±6 1.9% of that of the Reference formulation). The resulting $AUC_{inf}$ was 3660±963 hr-ng/mL (99.0%±20.1% of that of the Reference formulation).

TABLE 47

Pseudoephedrine Pharmacokinetic Parameters Following the Administration of 120 mg of Pseudoephedrine Hydrochloride and 1200 Guaifenesin in an Experimental Formulation to Normal Volunteers After an Overnight Fast (Treatment A, Reference)

| Subject | $C_{max}$ (ng/mL) | $T_{max}$ (hr) | $AUC_{0-t}$ (hr-ng/mL) | $AUC_{inf}$ (hr-ng/mL) | Half-life (hr) | Clearance (L/hr) |
|---|---|---|---|---|---|---|
| Mean | 283 | 4.60 | 3477 | 3746 | 5.01 | 28.2 |
| Median | 266 | 4.00 | 3374 | 3552 | 4.94 | 27.7 |
| Standard Deviation | 79.6 | 1.56 | 884 | 997 | 1.06 | 8.03 |
| Standard Error | 13.7 | 0.267 | 152 | 171 | 0.182 | 1.38 |
| % CV | 28.2 | 33.8 | 25.4 | 26.6 | 21.2 | 28.5 |

TABLE 48

Pseudoephedrine Pharmacokinetic Parameters Following the Administration of 120 mg of Pseudoephedrine Hydrochloride and 1200 mg guaifenesin in an Experimental Formulation to Normal Volunteers After Consumption of a High-Fat Meal (Treatment B, Test)

| Subject | $C_{max}$ (ng/mL) | $T_{max}$ (hr) | $AUC_{0-t}$ (hr-ng/mL) | $AUC_{inf}$ (hr-ng/mL) | Half-life (hr) | Clearance (L/hr) |
|---|---|---|---|---|---|---|
| Mean | 301 | 5.77 | 3403 | 3660 | 4.64 | 28.8 |
| Median | 292 | 6.00 | 3152 | 3455 | 4.45 | 28.5 |
| Standard Deviation | 80.4 | 1.78 | 915 | 963 | 1.05 | 7.91 |
| Standard Error | 13.8 | 0.306 | 157 | 165 | 0.180 | 1.36 |
| % CV | 26.7 | 30.9 | 26.9 | 26.3 | 22.6 | 27.5 |

TABLE 49

Ratio of Pseudoephedrine Pharmacokinetic Parameters Following the Administration of 120 mg Pseudoephedrine Hydrochloride and 1200 mg guaifenesin in an Experimental Formulation After the Consumption of a High-Fat Meal (Treatment B, Test) Compared to that After an Overnight Fast (Treatment A, Reference) to Normal Volunteers (%)

| Subject | $C_{max}$ (ng/mL) | $T_{max}$ (hr) | $AUC_{0-t}$ (hr-ng/mL) | $AUC_{inf}$ (hr-ng/mL) | Half-life (hr) | Clearance (L/hr) |
|---|---|---|---|---|---|---|
| Mean | 108 | 137 | 98.9 | 99.0 | 93.7 | 105 |
| Median | 109 | 133 | 96.9 | 95.9 | 88.4 | 104 |
| Standard Deviation | 18.5 | 61.9 | 20.8 | 20.1 | 17.1 | 20.2 |
| Standard Error | 3.22 | 10.8 | 3.62 | 3.50 | 2.97 | 3.52 |
| % CV | 17.1 | 45.2 | 21.0 | 20.3 | 18.2 | 19.3 |

The rate of absorption of guaifenesin from the experimental formulation, as assessed by $C_{max}$ is not bioequivalent to the Test formulation in the presence of a high-fat meal. The extent of absorption of guaifenesin from the experimental tablet, as assessed by $AUC_{inf}$, is equivalent to the Test formulation in the presence of a high-fat meal.

The rate and extent of pseudoephedrine absorption from the experimental formulation was bioequivalent to the Reference formulation in the presence of a high-fat meal.

In conclusion, the rate of guaifenesin absorption from the experimental formulation is not bioequivalent to the Reference formulation; whereas the extent of guaifenesin absorption is bioequivalent to the Reference formulation in the presence of a high-fat meal. The rate and extent of pseudoephedrine absorption from the experimental formulation are bioequivalent to the Reference formulation in the presence of a high-fat meal.

Example 18

In another experiment the relative bioavailability of guaifenesin and dextromethorphan from an experimental modified release formulation containing both guaifenesin and dextromethorphan was compared to reference guaifenesin and dextromethorphan products in normal volunteers was determined in a 36 subject open-label, randomized, 4-way crossover study.

The subjects were randomized and placed into one of four treatment groups. Group 1 received an experimental combination tablet containing 1200 mg of controlled-release guaifenesin and 60 mg of controlled-release dextromethorphan hydrobromide (Treatment A) with 240 mL of water, after an overnight fast. Group 2 received a reference controlled-release tablet containing 1200 mg guaifenesin (Mucinex, Treatment B) with 240 mL of water, after an overnight fast. Group 3 received 60 mg of dextromethorphan hydrobromide in a reference immediate-release liquid formulation according to 2 different dosing regimes (one half of the volunteers received 30 mg of dextromethorphan and a second 30 mg dose 6 hours later [Treatment C], while the other half received 20 mg dextromethorphan every 4 hours for three doses [Treatment D]) with 240 mL of water, after an overnight fast. Group 4 received 30 mg of dextromethorphan hydrobromide in a reference immediate-release liquid formulation according to 2 different dosing regimes (one half of the volunteers received 15 mg of dextromethorphan and a second 15 mg dose 6 hours later [Treatment E], while the other half received 10 mg dextromethorphan every 4 hours for three doses [Treatment F]) with 240 mL of water, after an overnight fast. Those subjects that received 30 mg dextromethorphan hydrobromide in one treatment period received 15 mg dextromethorphan in another treatment period; similarly, those that received 20 mg dextromethorphan in one treatment period received 10 mg dextromethorphan in a subsequent treatment period. In this experiment there was a 14-day washout between doses.

Blood (7 mL, sodium heparin anticoagulant) was obtained at the following times: Pre-dose, 0.5, 0.75, 1, 1.5, 2, 3, 4, 5, 6, 7, 8, 9, 10, 11, 12, 14, 16, 24, 36, 48, 72 and 96 hours post dose (the total blood loss for guaifenesin and dextromethorphan analysis was to be 644 mL).

Subjects given 1200 mg of guaifenesin as Mucinex (reference, Treatment B) reached a mean $C_{max}$ of 2145 ng/mL in 0.9 hours and had a mean $AUC_{inf}$ of 8953 hr-ng/mL. Subjects given 1200 mg guaifenesin as an experimental formulation, also containing 60 mg dextromethorphan hydrobromide (Treatment A), reached a mean guaifenesin $C_{max}$ of 2176 ng/mL in 1.4 hours and had a mean $AUC_{inf}$ of 8766 hr-ng/mL.

Subjects given 60 mg dextromethorphan hydrobromide along with 1200 mg guaifenesin in an experimental formulation (Treatment A) reached a mean dextromethorphan $C_{max}$ of 4834 pg/mL in 5 hours and had a mean $AUC_{inf}$ of 68851 hr-pg/mL. Subjects given 60 mg dextromethorphan hydrobromide as 30 mg every 6 hours (Treatment C) reached a mean dextromethorphan $C_{max}$ of 4711 pg/mL in 8.3 hours and had a mean $AUC_{inf}$ of 82655 hr-pg/mL. Subjects given 60 mg dextromethorphan hydrobromide as 20 mg every 4 hours (Treatment D) reached a mean dextromethorphan $C_{max}$ of 3344 pg/mL in 7 hours and had a mean $AUC_{inf}$ of 44683 hr-pg/mL. Subjects given 30 mg dextromethorphan hydrobromide as 15 mg every 6 hours (Treatment E) reached a mean dextromethorphan $C_{max}$ of 2180 pg/mL in 8 hours and had a mean $AUC_{inf}$ of 40324 hr-pg/mL. Subjects given 30 mg dextromethorphan hydrobromide as 10 mg every 4 hours (Treatment F) reached a mean dextromethorphan $C_{max}$ of 1286 pg/mL in 7.7 hours and had a mean $AUC_{inf}$ of 20114 hr-pg/mL.

Figure 33:
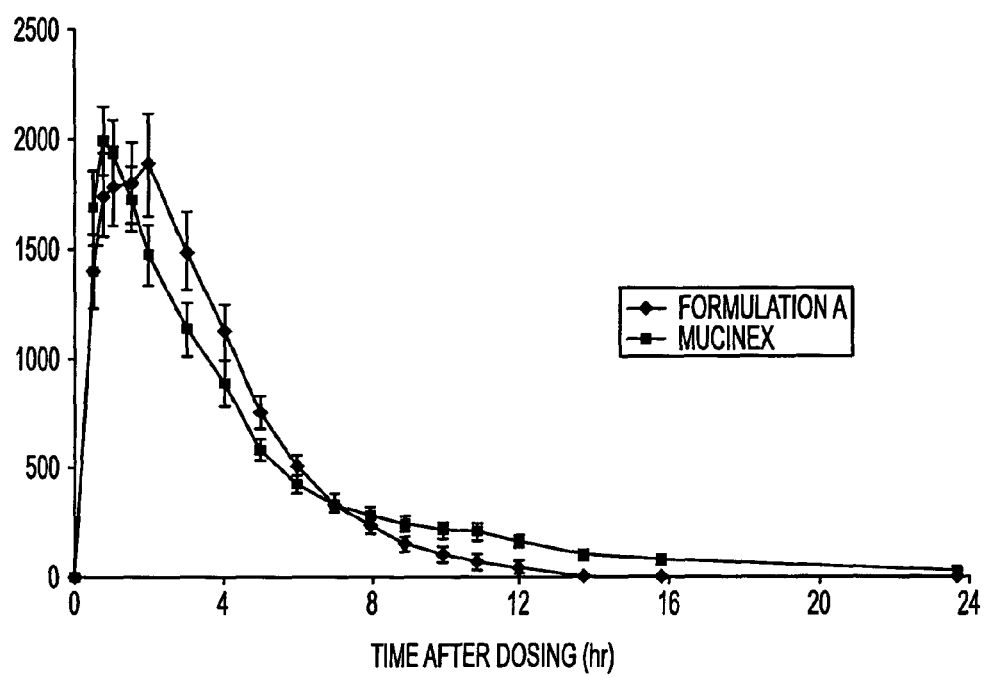
FIG. 33 depicts guaifenesin plasma concentrations following the administration of 1200 mg guaifenesin with or without the co-administration of 60 mg dextromethorphan hydrobromide.

The plasma concentrations of guaifenesin is shown in FIG. 33. The resulting pharmacokinetic data is shown in Tables 50 through 52. Subjects given 1200 mg of guaifenesin as Mucinex (Treatment B) reached a mean Coax of 2145±997 ng/mL (Mean±Standard Deviation) in 0.91±0.5 hours and had an $AUC_{inf}$ of 8953±4272 hr-ng/mL. Subjects given 1200 mg guaifenesin as an experimental formulation also containing 60 mg dextromethorphan (Treatment A) reached a mean guaifenesin $C_{max}$ of 2176±1320 ng/mL (101.36%±29.88% of that of Mucinex) in 1.44±0.67 hour (178.57%±82.70% of that of Mucinex) and had an $AUC_{inf}$ of 8761±4755 hr-ng/mL (99.57%±24.27% of that of Mucinex). These data indicate that the pharmacokinetics of guaifenesin are not affected by the presence of dextromethorphan.

TABLE 50

Guaifenesin Pharmacokinetic Parameters Following the Administration of 1200 mg Guaifenesin along with 60 mg Dextromethorphan Hydrobromide to Normal Volunteers - Treatment A

| Subject | Cmax (ng/mL) | Tmax (hr) | $AUC_{0-t}$ (hr * ng/mL) | $AUC_{inf}$ (hr * ng/mL) | Half life (hr) | Clearance (L/hr) |
|---|---|---|---|---|---|---|
| Mean | 2176 | 1.44 | 8732 | 8761 | 1.31 | 179 |
| Median | 1830 | 1.50 | 7579 | 7734 | 1.08 | 155 |
| Standard Deviation | 1320 | 0.67 | 4761 | 4755 | 1.12 | 93.93 |
| Standard Error | 237.15 | 0.12 | 855 | 854 | 0.20 | 16.87 |
| % CV | 60.67 | 46.88 | 54.52 | 54.27 | 85.67 | 52.59 |

TABLE 51

Guaifenesin Pharmacokinetic Parameters Following the Administration of 1200 mg Guaifenesin alone to Normal Volunteers - Treatment B

| Subject | Cmax (ng/mL) | Tmax (hr) | $AUC_{0-t}$ (hr * ng/mL) | $AUC_{inf}$ (hr * ng/mL) | Half life (hr) | Clearance (L/hr) |
|---|---|---|---|---|---|---|
| Mean | 2145 | 0.91 | 8657 | 8953 | 4.79 | 171 |
| Median | 1915 | 0.75 | 8346 | 8826 | 3.03 | 136 |
| Standard Deviation | 997 | 0.50 | 4268 | 4272 | 4.85 | 94.28 |
| Standard Error | 179 | 0.09 | 766 | 767 | 0.87 | 16.93 |
| % CV | 46.49 | 54.97 | 49.29 | 47.71 | 101.41 | 55.17 |

TABLE 52

Ratio of the Guaifenesin Pharmacokinetic Parameters Following the Administration of 1200 mg Guaifenesin in an Experimental Tablet along with 60 mg Dextromethorphan Hydrobromide Compared to Guaifenesin Alone (%)

| Subject | Cmax | Tmax | $AUC_{0-t}$ | $AUC_{inf}$ | Half Life | Clearance |
|---|---|---|---|---|---|---|
| Mean | 101.36 | 178.57 | 102.78 | 99.57 | 47.71 | 106.07 |
| Median | 100.00 | 200.00 | 98.64 | 95.57 | 34.50 | 104.64 |
| Standard Deviation | 29.88 | 82.70 | 23.27 | 24.27 | 39.04 | 25.35 |
| Standard Error | 5.46 | 15.10 | 4.25 | 4.43 | 7.13 | 4.63 |
| % CV | 29.48 | 46.31 | 22.64 | 24.37 | 81.83 | 23.90 |

Figure 34:
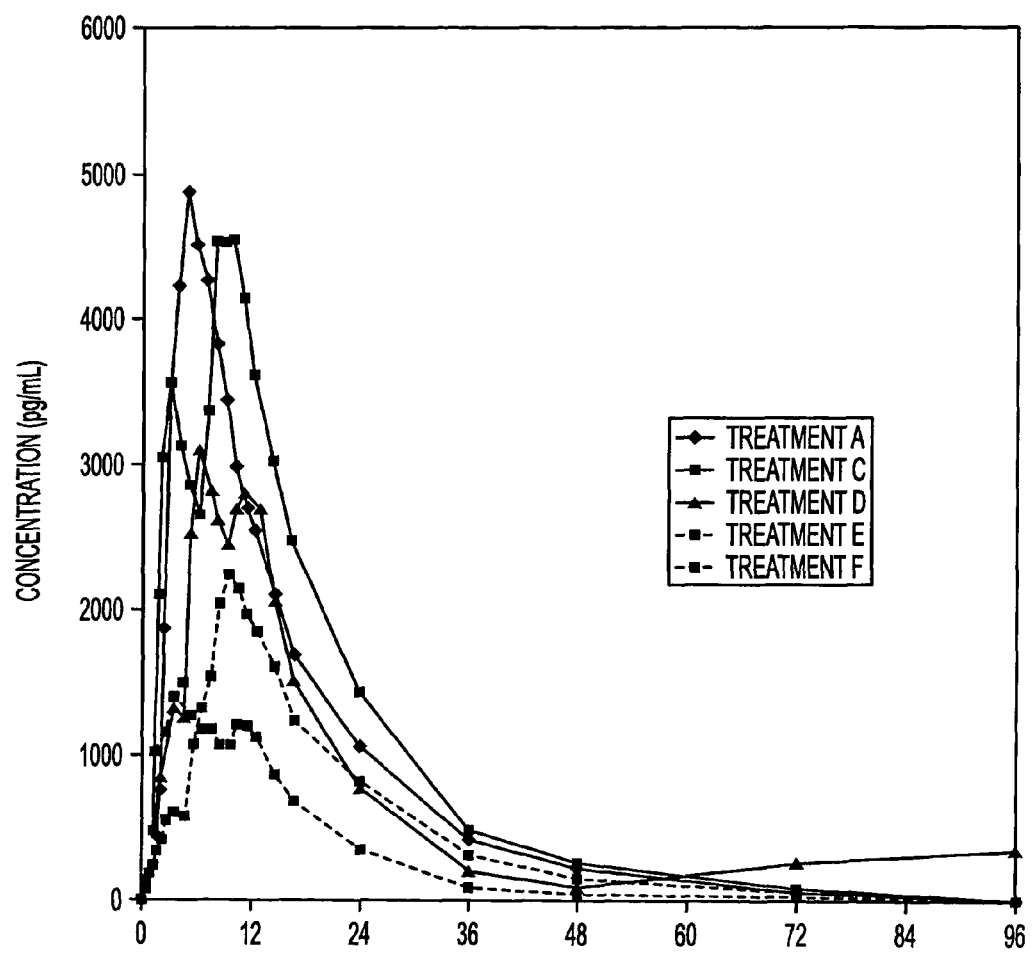
FIG. 34 depicts mean dextromethorphan plasma concentrations following the administration of dextromethorphan hydrobromide in different formulations, doses and dosing regimens.

The plasma concentrations of dextromethorphan is shown in FIG. 34. The resulting pharmacokinetic data is shown in Tables 53 through 61. Subjects given 60 mg dextromethorphan hydrobromide as an experimental formulation also containing 1200 mg guaifenesin (Treatment A) reached a mean dextromethorphan $C_{max}$ of 4834±6182 pg/mL in 5.06±0.93 hours and had an $AUC_{inf}$ of 68851±112906 hr-pg/mL. Subjects given 60 mg dextromethorphan hydrobromide as 30 mg every 6 hours (Treatment C) reached a mean dextromethorphan $C_{max}$ of 4711±6124 pg/mL (141.85%±82.73% of that of the experimental tablet, Treatment A) in 8.31±1.58 hours (62.07%±23.12% of that of Treatment A) and had an $AUC_{inf}$ of 82655±123509 hr-pg/mL (108%±44.44% of that of Treatment A). Subjects given 60 mg dextromethorphan hydrobromide as 20 mg every 4 hours (Treatment D) reached a mean dextromethorphan $C_{max}$ of 3130±2355 pg/mL (100.31%±37.06% of that of the reference) in 7.01±1.93 hours (80.02%±22.83% of that of Treatment A) and had an $AUC_{inf}$ of 44683±37119 hr-pg/mL (82.77%±22.93% of that of Treatment A). These results indicate that the tablet is not bioequivalent to either dextromethorphan dosing regimen, but is equivalent to the range generated by these two dosing regimens. These data also indicate that the pharmacokinetics of dextromethorphan are not affected by the presence of guaifenesin.

Subjects given 30 mg dextromethorphan hydrobromide as 15 mg every 6 hours (Treatment E) reached a mean dextromethorphan $C_{max}$ of 2180±2650 pg/mL (53.89%±17.62% of that of Treatment C) in 8.03±2.52 hours (96.08%±24.88% of that of Treatment C) and had an $AUC_{inf}$ of 40324±62644 hr-pg/mL (5 1.73%±16.77% of that of Treatment C). Subjects given 30 mg dextromethorphan hydrobromide as 10 mg every 4 hours (Treatment F) reached a mean dextromethorphan $C_{max}$ of 1286±903 pg/mL (53.41%±12.82% of that of Treatment D) in 7.73±2.43 hours (142.42%±67.86% of that of Treatment D) and had an $AUC_{inf}$ of 6945±16158 hr-pg/mL (54.32%±16.37% of that of Treatment D). These data suggest that the pharmacokinetics of dextromethorphan are linear over the range studied.

TABLE 53

Dextromethorphan Pharmacokinetic Parameters Following the Administration of an Experimental Tablet Formulation Containing 60 mg Dextromethorphan Hydrobromide and 1200 mg Guaifenesin to Normal Volunteers - Treatment A

| Subject | Cmax (pg/mL) | Tmax (hr) | $AUC_{0-t}$ (hr * pg/mL) | $AUC_{inf}$ (hr * pg/mL) | Half life (hr) | Clearance (L/hr) |
|---|---|---|---|---|---|---|
| Mean | 4834 | 5.06 | 68189 | 68851 | 7.73 | 1697 |
| Median | 2550 | 5.00 | 27821 | 28088 | 6.94 | 1088 |
| Standard Deviation | 6182 | 0.929 | 112242 | 112906 | 1.78 | 1585 |
| Standard Error | 1129 | 0.170 | 20493 | 20614 | 0.33 | 289 |
| % CV | 127.88 | 18.34 | 164.61 | 163.99 | 23.04 | 93.39 |

TABLE 54

Dextromethorphan Pharmacokinetic Parameters Following the Administration of 60 mg Dextromethorphan Hydrobromide as Two Doses of 30 mg Six Hours Apart to Normal Volunteers - Treatment C

| Subject | Cmax (pg/mL) | Tmax (hr) | $AUC_{0-t}$ (hr * pg/mL) | $AUC_{inf}$ (hr * pg/mL) | Half life (hr) | Clearance (L/hr) |
|---|---|---|---|---|---|---|
| Mean | 4711 | 8.31 | 82279 | 82655 | 7.46 | 1291 |
| Median | 1665 | 8.50 | 23483 | 23860 | 6.76 | 999 |
| Standard Deviation | 6124 | 1.58 | 123157 | 123509 | 1.94 | 1078 |
| Standard Error | 1581 | 0.41 | 31799 | 31890 | 0.50 | 278 |
| % CV | 129.99 | 19.01 | 149.68 | 149.43 | 25.97 | 83.45 |

TABLE 55

Dextromethorphan Pharmacokinetic Parameters Following the Administration of 60 mg Dextromethorphan Hydrobromide as Three Doses of 20 mg Four Hours Apart to Normal Volunteers - Treatment D

| Subject | Cmax (pg/mL) | Tmax (hr) | $AUC_{0-t}$ (hr * pg/mL) | $AUC_{inf}$ (hr * pg/mL) | Half life (hr) | Clearance (L/hr) |
|---|---|---|---|---|---|---|
| Mean | 3130 | 7.01 | 44287 | 44683 | 7.04 | 1335 |
| Median | 2720 | 6.00 | 26142 | 26321 | 6.60 | 1124 |
| Standard Deviation | 2355 | 1.93 | 36759 | 37119 | 1.57 | 1098 |
| Standard Error | 630 | 0.515 | 9824 | 9920 | 0.44 | 293 |
| % CV | 75.26 | 27.50 | 83.00 | 83.07 | 22.32 | 82.26 |

TABLE 56

Dextromethorphan Pharmacokinetic Parameters Following the Administration of 30 mg Dextromethorphan Hydrobromide as Two Doses of 15 mg Six Hours Apart to Normal Volunteers - Treatment E

| Subject | Cmax (pg/mL) | Tmax (hr) | $AUC_{0-t}$ (hr * pg/mL) | $AUC_{inf}$ (hr * pg/mL) | Half life (hr) | Clearance (L/hr) |
|---|---|---|---|---|---|---|
| Mean | 2180 | 8.03 | 39746 | 40324 | 7.32 | 2940 |
| Median | 1180 | 9.00 | 16061 | 16226 | 6.48 | 2735 |
| Standard Deviation | 2650 | 2.52 | 61502 | 62644 | 2.28 | 2234 |
| Standard Error | 684 | 0.65 | 15880 | 16175 | 0.59 | 577 |
| % CV | 121.59 | 31.37 | 154.74 | 155.35 | 31.13 | 75.98 |

TABLE 57

Dextromethorphan Pharmacokinetic Parameters Following the Administration of 30 mg Dextromethorphan Hydrobromide as Three Doses of 10 mg Four Hours Apart to Normal Volunteers - Treatment F

| Subject | Cmax (pg/mL) | Tmax (hr) | $AUC_{0-t}$ (hr * pg/mL) | $AUC_{inf}$ (hr * pg/mL) | Half life (hr) | Clearance (L/hr) |
|---|---|---|---|---|---|---|
| Mean | 1286 | 7.73 | 19833 | 20114 | 7.44 | 3894 |
| Median | 795 | 6.00 | 12940 | 13170 | 6.95 | 2860 |
| Standard Deviation | 903 | 2.43 | 16162 | 16158 | 2.02 | 3274 |
| Standard Error | 241 | 0.650 | 4319 | 4318 | 0.54 | 875 |
| % CV | 70.19 | 31.47 | 81.49 | 80.33 | 27.18 | 84.09 |

TABLE 58

Ratio of Dextromethorphan Pharmacokinetic Parameters
Following the Administration of 60 mg Dextromethorphan
Hydrobromide as Treatment A Compared to Two Doses of 30 mg
Six Hours Apart (Treatment C) in Normal Volunteers %

| Subject | Cmax | Tmax | $AUC_{0-t}$ | $AUC_{inf}$ | Half Life | Clearance |
|---|---|---|---|---|---|---|
| Mean | 141.85 | 62.07 | 106.81 | 108.00 | 107.71 | 122.40 |
| Median | 121.79 | 59.03 | 95.92 | 96.02 | 108.89 | 107.97 |
| Standard Deviation | 82.73 | 23.12 | 43.92 | 44.44 | 9.65 | 60.31 |
| Standard Error | 21.36 | 5.97 | 11.34 | 11.47 | 2.49 | 15.57 |
| % CV | 58.32 | 37.25 | 41.12 | 41.15 | 8.96 | 49.28 |

TABLE 59

Ratio of Dextromethorphan Pharmacokinetic Parameters
Following the Administration of 60 mg Dextromethorphan
Hydrobromide as Treatment A Compared to Three Doses of 20 mg
Four Hours Apart (Treatment D) in Normal Volunteers %

| Subject | Cmax | Tmax | $AUC_{0-t}$ | $AUC_{inf}$ | Half Life | Clearance |
|---|---|---|---|---|---|---|
| Mean | 100.31 | 80.02 | 83.01 | 82.77 | 107.26 | 164.60 |
| Median | 94.35 | 83.33 | 77.49 | 77.84 | 101.62 | 158.65 |
| Standard Deviation | 37.06 | 22.83 | 23.39 | 22.93 | 16.71 | 88.09 |
| Standard Error | 10.70 | 6.59 | 6.75 | 6.62 | 4.82 | 25.43 |
| % CV | 36.94 | 28.53 | 28.18 | 27.71 | 15.57 | 53.52 |

TABLE 60

Ratio of Dextromethorphan Pharmacokinetic Parameters Following
the Administration of 30 mg Dextromethorphan Hydrobromide as Two
Doses of 15 mg Six Hours Apart (Treatment E) Compared to
60 mg Dextromethorphan Hydrobromide as Two Doses of 30 mg
Six Hours Apart (Treatment C) (%)

| Subject | Cmax | Tmax | $AUC_{0-t}$ | $AUC_{inf}$ | Half Life | Clearance |
|---|---|---|---|---|---|---|
| Mean | 53.89 | 96.08 | 51.35 | 51.73 | 98.33 | 278.94 |
| Median | 57.20 | 100.00 | 50.70 | 50.64 | 103.29 | 214.90 |
| Standard Deviation | 17.62 | 24.88 | 16.64 | 16.77 | 14.88 | 172.08 |
| Standard Error | 4.55 | 6.42 | 4.30 | 4.33 | 3.84 | 44.43 |
| % CV | 32.70 | 25.89 | 32.40 | 32.42 | 15.14 | 61.69 |

TABLE 61

Ratio of Dextromethorphan Pharmacokinetic Parameters Following
the Administration of 30 mg Dextromethorphan Hydrobromide as
Three Doses of 10 mg Four Hours Apart (Treatment F)Compared to
60 mg Dextromethorphan Hydrobromide as Three Doses of
20 mg Four Hours Apart (Treatment D) (%)

| Subject | Cmax | Tmax | $AUC_{0-t}$ | $AUC_{inf}$ | Half Life | Clearance |
|---|---|---|---|---|---|---|
| Mean | 53.41 | 142.42 | 54.28 | 54.32 | 103.46 | 313.85 |
| Median | 56.73 | 166.67 | 52.75 | 52.23 | 89.13 | 255.28 |
| Standard Deviation | 12.82 | 67.86 | 16.26 | 16.37 | 35.81 | 143.22 |
| Standard Error | 6.41 | 33.93 | 8.13 | 8.19 | 17.91 | 71.61 |
| % CV | 24.00 | 47.65 | 29.95 | 30.14 | 34.62 | 45.63 |

In conclusion, the pharmacokinetics of guaifenesin and dextromethorphan are not affected by the presence of the other component and the pharmacokinetics of dextromethorphan are linear over the range studied.

Example 19

In another experiment the relative bioavailability of guaifenesin and dextromethorphan from an experimental modified release formulation, containing both guaifenesin and dextromethorphan was compared to reference guaifenesin and dextromethorphan was determined in normal volunteers in a 36 subject open-label, single-dose, randomized, 3-way-crossover study.

The subjects were randomized and placed into one of three treatment groups. Group 1 received a 1200-mg controlled-release guaifenesin product (Mucinex) plus 60 mg of dextromethorphan hydrobromide (administered as 30 mg every 6 hours), with 240 mL of water after an overnight fast (Reference). Group 2 received a 1200-mg controlled-release guaifenesin product (Mucinex) plus 60 mg of dextromethorphan hydrobromide (administered as 20 mg every 4 hours), with 240 mL of water after an overnight fast (Reference). Group 3 received an experimental controlled-release tablet containing 1200 mg guaifenesin and 60 mg of dextromethorphan hydrobromide, with 240 mL of water after an overnight fast (Test). In this experiment there was a 14-day washout between doses.

Blood (7 mL sodium heparin anticoagulant) was obtained at the following times: Pre-dose, 0.5, 0.75, 1, 1.5, 2, 3, 4, 4.5, 4.75, 5, 5.5, 6, 6.5, 6.75, 7, 7.5, 8, 9, 10, 11, 12, 14, 16, 24, 36, 48, 72 and 96 hours post dose (the total blood loss for guaifenesin and dextromethorphan analysis was 609 mL). Subjects given 1200 mg of guaifenesin as Mucinex, along with 60 mg dextromethorphan hydrobromide as two 30-mg doses 6 hours apart (Treatment A, Reference), reached a mean plasma guaifenesin $C_{max}$ of 1743 ng/mL in 1.25 hours and had an $AUC_{inf}$ of 7836 hr-ng/mL. Subjects given 1200 mg of guaifenesin as Mucinex, along with 60 mg dextromethorphan hydrobromide as three 20-mg doses 4 hours apart (Treatment B, Reference), reached a mean plasma guaifenesin $C_{max}$ of 1783 ng/mL in 1.27 hours and had an $AUC_{inf}$ of 7616 hr-ng/mL. Subjects given 1200 mg guaifenesin as an experimental formulation, also containing 60 mg dextromethorphan hydrobromide (Treatment C, Test), reached a mean plasma guaifenesin $C_{max}$ of 1710 ng/mL in 1.55 hour and had an $AUC_{inf}$ of 7102 hr-ng/mL.

Subjects given 1200 mg guaifenesin as Mucinex, along with 60 mg dextromethorphan hydrobromide as 30 mg Vick's Formula 44 Cough Medicine and a second 30-mg dextromethorphan hydrobromide dose 6 hours later (Treatment A, Reference), reached a mean plasma dextromethorphan $C_{max}$ of 7946 pg/mL in 8.32 hours and had an $AUC_{inf}$ of 294267 hr-pg/mL. Subjects given 1200 mg guaifenesin as Mucinex, along with 60 mg dextromethorphan hydrobromide as 20 mg Vick's Formula 44 Cough Medicine, a second 20-mg dextromethorphan hydrobromide dose 4 hours later and a third 20-mg dextromethorphan hydrobromide dose 4 hours after that (Treatment B, Reference), reached a mean plasma dextromethorphan $C_{max}$ of 8598 pg/mL in 8.90 hours and had an $AUC_{inf}$ of 339447 hr-pg/mL. Subjects given 1200 mg guaifenesin along with 60 mg dextromethorphan hydrobromide in an experimental formulation (Treatment C, Test), reached a mean plasma dextromethorphan $C_{max}$ of 7483 pg/mL in 6.30 hours and had an $AUC_{inf}$ of 316592 hr-pg/mL.

Figure 35:
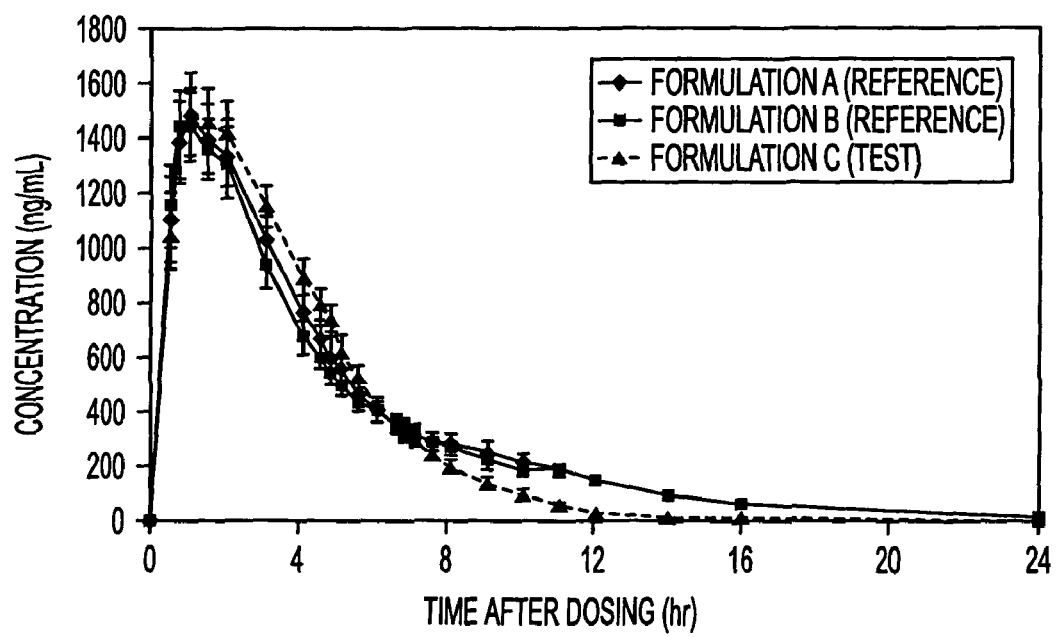
FIG. 35 depicts plasma guaifenesin concentrations following the administration of 1200 mg guaifenesin along with 60 dextromethorphan hydrobromide in three different formulations.

The plasma concentrations of guaifenesin are shown in FIG. 35. The resulting pharmacokinetic data are shown in Tables 62 through 64. Subjects given 1200 mg of guaifenesin as Mucinex, along with 60 mg dextromethorphan hydrobromide as two 30-mg doses 6 hours apart (Treatment A, Reference), reached a mean plasma guaifenesin $C_{max}$ of 1743±903 ng/mL (Mean±Standard Deviation) in 1.25±0.660 hours and had an $AUC_{inf}$ of 7836±3616 hr-ng/mL. Subjects given 1200 mg of guaifenesin as Mucinex, along with 60 mg dextromethorphan hydrobromide as three 20-mg doses 4 hours apart (Treatment B, Reference), reached a mean plasma guaifenesin $C_{max}$ of 1783±808 ng/mL in 1.27±0.833 hours and had an $AUC_{inf}$ of 7616±3398 hr-ng/mL. Subjects given 1200 mg guaifenesin as an experimental formulation, also containing 60 mg dextromethorphan hydrobromide (Treatment C, Test), reached a mean plasma guaifenesin $C_{max}$ of 1710±807 ng/mL in 1.55±0.789 hour and had an $AUC_{inf}$ of 7102±2807 hr-ng/mL.

TABLE 62

Guaifenesin Pharmacokinetic Parameters Following the Administration of 1200 mg Guaifenesin as Mucinex along with 60 mg Dextromethorphan Hydrobromide as 30 mg Vick's Formula 44 Cough Medicine and a Second 30-mg Dextromethorphan Hydrobromide Dose 6 Hours Later to Normal Volunteers - Treatment A (Reference)

| Subject | Cmax (ng/mL) | Tmax (hr) | $AUC_{0-t}$ (hr * ng/mL) | $AUC_{inf}$ (hr * ng/mL) | Half life (hr) | Clearance (L/hr) |
|---|---|---|---|---|---|---|
| Mean | 1743 | 1.25 | 7730 | 7836 | 2.60 | 192 |
| Median | 1545 | 1.00 | 6854 | 6956 | 2.27 | 173 |
| Standard Deviation | 903 | 0.660 | 3578 | 3616 | 1.37 | 109 |
| Standard Error | 147 | 0.107 | 580 | 587 | 0.221 | 17.7 |
| % CV | 51.8 | 52.7 | 46.3 | 46.1 | 52.4 | 57.0 |

TABLE 63

Guaifenesin Pharmacokinetic Parameters Following the Administration of 1200 mg Guaifenesin as Mucinex along with 60 mg Dextromethorphan Hydrobromide as 20 mg Vick's Formula 44 Cough Medicine, a Second 20-mg Dextromethorphan Hydrobromide Dose 4 Hours Later and a Third 20-mg Dextromethorphan Hydrobromide Dose 4 hours After That to Normal Volunteers - Treatment B (Reference)

| Subject | Cmax (ng/mL) | Tmax (hr) | $AUC_{0-t}$ (hr * ng/mL) | $AUC_{inf}$ (hr * ng/mL) | Half life (hr) | Clearance (L/hr) |
|---|---|---|---|---|---|---|
| Mean | 1783 | 1.27 | 7477 | 7616 | 3.19 | 191 |
| Median | 1615 | 1.00 | 6948 | 7268 | 2.77 | 165 |
| Standard Deviation | 808 | 0.833 | 3369 | 3398 | 1.81 | 90.1 |
| Standard Error | 137 | 0.141 | 570 | 574 | 0.307 | 15.2 |
| % CV | 45.3 | 65.5 | 45.1 | 44.6 | 56.9 | 47.2 |

TABLE 64

Guaifenesin Pharmacokinetic Parameters Following the Administration of 1200 mg Guaifenesin along with 60 mg Dextromethorphan Hydrobromide in an Experimental Formulation to Normal Volunteers - Treatment C (Test)

| Subject | Cmax (ng/mL) | Tmax (hr) | $AUC_{0-t}$ (hr * ng/mL) | $AUC_{inf}$ (hr * ng/mL) | Half life (hr) | Clearance (L/hr) |
|---|---|---|---|---|---|---|
| Mean | 1710 | 1.55 | 7082 | 7102 | 1.24 | 201 |
| Median | 1525 | 1.50 | 6847 | 6899 | 1.05 | 174 |
| Standard Deviation | 807 | 0.789 | 2805 | 2807 | 0.501 | 100 |
| Standard Error | 141 | 0.137 | 488 | 489 | 0.087 | 17.4 |
| % CV | 47.2 | 51.0 | 39.6 | 39.5 | 40.5 | 49.8 |

Figure 36:
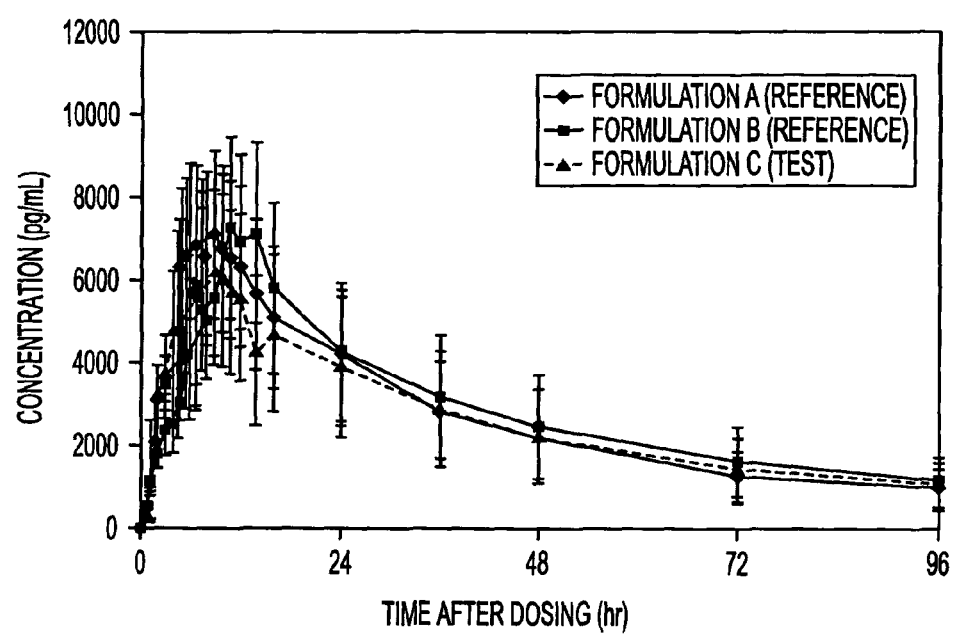
FIG. 36 depicts dextromethorphan plasma concentrations following the administration of 60 mg dextromethorphan hydrobromide at three different rates.

The plasma concentrations of dextromethorphan are shown in FIG. 36. The resulting pharmacokinetic data are shown in Tables 65 through 67. Subjects given 1200 mg guaifenesin as Mucinex, along with 60 mg dextromethorphan hydrobromide as 30 mg Vick's Formula 44 Cough Medicine and a second 30-mg dextromethorphan hydrobromide dose 6 hours later (Treatment A, Reference), reached a mean plasma dextromethorphan $C_{max}$ of 7946±12386 pg/mL in 8.32±2.88 hours and had an $AUC_{inf}$ of 294267±724235 hr-pg/mL. Subjects given 1200 mg guaifenesin as Mucinex, along with 60 mg dextromethorphan hydrobromide as 20 mg Vick's Formula 44 Cough Medicine, a second 20-mg dextromethorphan hydrobromide dose 4 hours later and a third 20-mg dextromethorphan hydrobromide dose 4 hours after that (Treatment B, Reference), reached a mean plasma dextromethorphan $C_{max}$ of 8598±13559 pg/mL in 8.90±3.62 hours and had an $AUC_{inf}$ of 339447±850232 hr-pg/mL. Subjects given 60 mg dextromethorphan hydrobromide, along with 1200 mg guaifenesin in an experimental formulation (Treatment C, Test), reached a mean plasma dextromethorphan $C_{max}$ of 7483±12332 pg/mL in 6.30±2.64 hours and had an $AUC_{inf}$ of 316592±796975 hr-pg/mL.

TABLE 65

Dextromethorphan Pharmacokinetic Parameters Following the Administration of 1200 mg Guaifenesin as Mucinex Along with 60 mg Dextromethorphan Hydrobromide as 30 mg Vick's Formula 44 Cough Medicine and a Second 30-mg Dextromethorphan Hydrobromide Dose 6 Hours Later to Normal Volunteers - Treatment A (Reference)

| Subject | Cmax (pg/mL) | Tmax (hr) | $AUC_{0-t}$ (hr * pg/mL) | $AUC_{inf}$ (hr * pg/mL) | Half life (hr) | Clearance (L/hr) |
|---|---|---|---|---|---|---|
| Mean | 7946 | 8.32 | 248123 | 294267 | 10.9 | 2044 |
| Median | 2375 | 8.00 | 31290 | 31544 | 7.57 | 1394 |
| Standard Deviation | 12386 | 2.88 | 575122 | 724235 | 9.42 | 2153 |
| Standard Error | 2009 | 0.468 | 93297 | 117486 | 1.53 | 349 |
| % CV | 156 | 34.7 | 232 | 246 | 86.2 | 105 |

TABLE 66

Dextromethorphan Pharmacokinetic Parameters Following the Administration of 1200 mg Guaifenesin as Mucinex along with 60 mg Dextromethorphan Hydrobromide as 20 mg Vick's Formula 44 Cough Medicine and a Second 20-mg Dextromethorphan Hydrobromide Dose 4 Hours Later and a Third 20-mg Dextromethorphan Hydrobromide Dose 4 Hours After That to Normal Volunteers - Treatment B (Reference)

| Subject | Cmax (pg/mL) | Tmax (hr) | $AUC_{0-t}$ (hr * pg/mL) | $AUC_{inf}$ (hr * pg/mL) | Half life (hr) | Clearance (L/hr) |
|---|---|---|---|---|---|---|
| Mean | 8598 | 8.90 | 271074 | 339447 | 11.3 | 1920 |
| Median | 2470 | 7.75 | 31698 | 31978 | 7.11 | 1374 |
| Standard Deviation | 13559 | 3.62 | 641451 | 850232 | 11.4 | 1655 |
| Standard Error | 2292 | 0.612 | 108425 | 143715 | 1.93 | 280 |
| % CV | 158 | 40.7 | 237 | 250 | 101 | 86.2 |

TABLE 67

Dextromethorphan Pharmacokinetic Parameters Following the Administration of 1200 mg Guaifenesin and 60 mg Dextromethorphan Hydrobromide in an Experimental Formulation to Normal Volunteers - Treatment C (Test)

| Subject | Cmax (pg/mL) | Tmax (hr) | $AUC_{0-t}$ (hr * pg/mL) | $AUC_{inf}$ (hr * pg/mL) | Half life (hr) | Clearance (L/hr) |
|---|---|---|---|---|---|---|
| Mean | 7483 | 6.30 | 253196 | 316592 | 12.6 | 2756 |
| Median | 2550 | 5.50 | 24730 | 24981 | 8.64 | 1760 |
| Standard Deviation | 12332 | 2.64 | 604557 | 796975 | 11.5 | 3530 |
| Standard Error | 2115 | 0.453 | 105240 | 138735 | 2.00 | 614 |
| % CV | 165 | 42.00 | 239 | 252 | 91.7 | 128 |

Dextromethorphan hydrobromide is widely recognized as a highly variable drug and therefore one can consider confidence interval width of 70% to 143% as bioequivalent rather than the classical 80% to 125%. In conclusion, guaifenesin in the experimental tablet is clearly bioequivalent to that of the Reference, Mucinex, in terms of $C_{max}$, $AUC_{0-t}$ or $AUC_{inf}$ as the 90% confidence intervals are all contained within 80% to 125%. Dextromethorphan hydrobromide in the experimental tablet can be considered bioequivalent to both 30 mg dextromethorphan hydrobromide every 6 hours, and 20 mg every 4 hours, in terms of $C_{max}$, $AUC_{0-t}$ or $AUC_{inf}$ as the 90% confidence intervals are contained within 70% to 143%.

Example 20

To determine the relative bioavailability of guaifenesin and dextromethorphan from an experimental modified release formulation containing both guaifenesin and dextromethorphan following the consumption of a high fat meal was compared to following an overnight fast in normal volunteers an open label, single dose, randomized, 2-way crossover study was conducted in 36 subjects.

The subjects were randomized and placed into one of two treatment groups. Treatment A received a 1200 mg guaifenesin and 60 mg dextromethorphan hydrobromide with 240 mL of water after an overnight fast (Reference). Treatment B received a 1200 mg guaifenesin and dextromethorphan hydrobromide experimental tablet with 240 mL of water within 30 minutes after the beginning of the consumption of a high fat meal (Test). There was a 14 day washout between doses.

Blood (7 mL, sodium heparin anticoagulant) was obtained at the following times: Pre-dose, 0.5, 0.75, 1, 1.5, 2, 3, 4, 5, 6, 8, 10, 12, 14, 16, 24, 36, 48, 72 and 96 hours post dose (the total blood loss for guaifenesin and dextromethorphan analysis will be 280 mL). Subjects given 1200 mg of guaifenesin and 60 mg dextromethorphan hydrobromide in an experimental formulation following an overnight fast (Treatment A, Reference) reached a mean $C_{max}$ of 2030 ng/mL in 1.61 hours and had an $AUC_{inf}$ of 8128 hr-ng/mL. Subjects given 1200 mg of guaifenesin and 60 mg dextromethorphan hydrobromide following the consumption of a high fat meal (Treatment B, Test) reached a mean $C_{max}$ of 1825 ng/mL (98.0% of that of Treatment A) in 2.93 hours (248% of that of Treatment A) and had an $AUC_{inf}$ of 7093 hr-ng/mL (92.9% of that of Treatment A).

Subjects given 60 mg dextromethorphan hydrobromide and 1200 mg guaifenesin in an experimental formulation following an overnight fast (Treatment A, Reference) reached a mean dextromethorphan $C_{max}$ of 10722 pg/mL in 6.23 hours and had an $AUC_{inf}$ of 466518 hr-pg/mL. Subjects given 60 mg dextromethorphan hydrobromide and 1200 mg guaifenesin in an experimental formulation after the consumption of a high fat meal (Treatment B, Test) reached a mean dextromethorphan $C_{max}$ of 12757 pg/mL (132% of that of Treatment A) in 5.74 hours (104% of that of Treatment A) and had an $AUC_{inf}$ of 472064 hr-pg/mL (117% of that of Treatment A).

Figure 37:
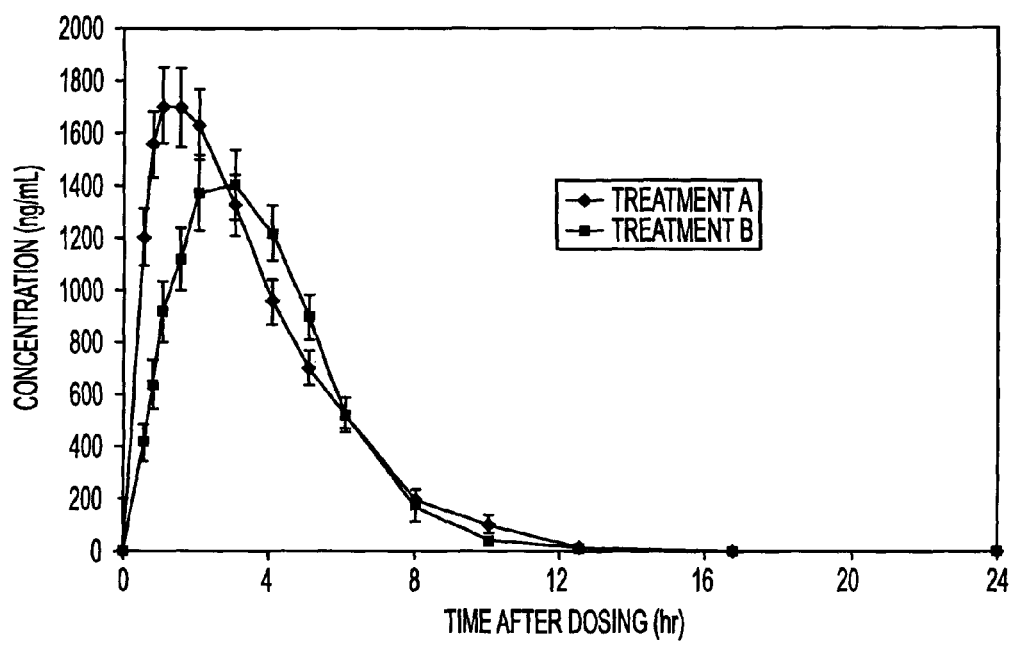
FIG. 37 depicts plasma guaifenesin concentrations following the administration of 1200 mg guaifenesin and 60 mg dextromethorphan in an experimental formulation under fed and fasted conditions.

The plasma concentrations of guaifenesin is shown in FIG. 37. The resulting pharmacokinetic data is shown in Tables 68 through 70. Subjects given 1200 mg of guaifenesin and 60 mg dextromethorphan hydrobromide in an experimental formulation following an overnight fast (Treatment A, Reference) reached a mean $C_{max}$ of 2030±882 ng/mL (Mean±Standard Deviation) in 1.61±1.15 hours and had an $AUC_{inf}$ of 8128±3497 hr-ng/mL. Subjects given 1200 mg of guaifenesin and 60 mg dextromethorphan hydrobromide in an experimental formulation after the consumption of a high fat meal (Treatment B, Test) reached a mean $C_{max}$ of 1825±789 ng/mL (98.0%±40.3% of that of Treatment A) in 2.93±1.44 hours (248%±164% of that of Treatment A) and had an $AUC_{inf}$ of 7093±2787 hr-ng/mL (92.9%±23.6% of that of Treatment A).

TABLE 68

Guaifenesin Pharmacokinetic Parameters Following the Administration of 1200 mg Guaifenesin and 60 mg Dextromethorphan Hydrobromide in an Experimental Formulation to Normal Volunteers Following an Overnight Fast - Treatment A (Reference)

| Subject | Cmax (ng/mL) | Tmax (hr) | $AUC_{0-t}$ (hr * ng/mL) | $AUC_{inf}$ (hr * ng/mL) | Half life (hr) | Clearance (L/hr) |
|---|---|---|---|---|---|---|
| Mean | 2030 | 1.61 | 8107 | 8128 | 1.15 | 172 |
| Median | 1760 | 1.5 | 777 | 7789 | 1.04 | 154 |
| Std. Dev. | 882 | 1.15 | 3485 | 3497 | 0.356 | 65.7 |
| Std. Err. | 151 | 0.198 | 598 | 600 | 0.0611 | 11.3 |
| % CV | 43.4 | 71.4 | 43.0 | 43.0 | 30.97 | 38.1 |

TABLE 69

Guaifenesin Pharmacokinetic Parameters Following the Administration of 1200 mg Guaifenesin and 60 mg Dextromethorphan Hydrobromide in an Experimental Formulation to Normal Volunteers After the Consumption of a High Fat Meal - Treatment B (Test)

| Subject | Cmax (ng/mL) | Tmax (hr) | $AUC_{0-t}$ (hr * ng/mL) | $AUC_{inf}$ (hr * ng/mL) | Half life (hr) | Clearance (L/hr) |
|---|---|---|---|---|---|---|
| Mean | 1825 | 2.93 | 7077 | 7093 | 0.849 | 190 |
| Median | 1520 | 3 | 6201 | 6228 | 0.854 | 193 |
| Std. Dev. | 789 | 1.44 | 2788 | 2787 | 0.115 | 60.6 |
| Std. Err. | 133 | 0.243 | 471 | 471 | 0.0194 | 10.2 |
| % CV | 43.2 | 49.1 | 39.4 | 39.3 | 13.5 | 31.9 |

TABLE 70

Ratio of Guaifenesin Pharmacokinetic Parameters Following the Administration of 1200 mg Guaifenesin and 60 mg Dextromethorphan Hydrobromide After the Consumption of a High Fat Meal Compared to that Following an Overnight Fast (%)

| Subject | Cmax | Tmax | AUClast | AUCtot | thalf | Clearance |
|---|---|---|---|---|---|---|
| Mean | 98.0 | 248 | 92.9 | 92.9 | 79.5 | 114 |
| Median | 89.8 | 250 | 88.9 | 88.3 | 79.5 | 113 |
| Std. Dev. | 40.3 | 163.7 | 23.7 | 23.6 | 19.4 | 26.8 |
| Std. Err. | 6.92 | 28.1 | 4.07 | 4.05 | 3.33 | 4.60 |
| % CV | 41.1 | 66.0 | 25.6 | 25.4 | 24.4 | 23.5 |

Figure 38:
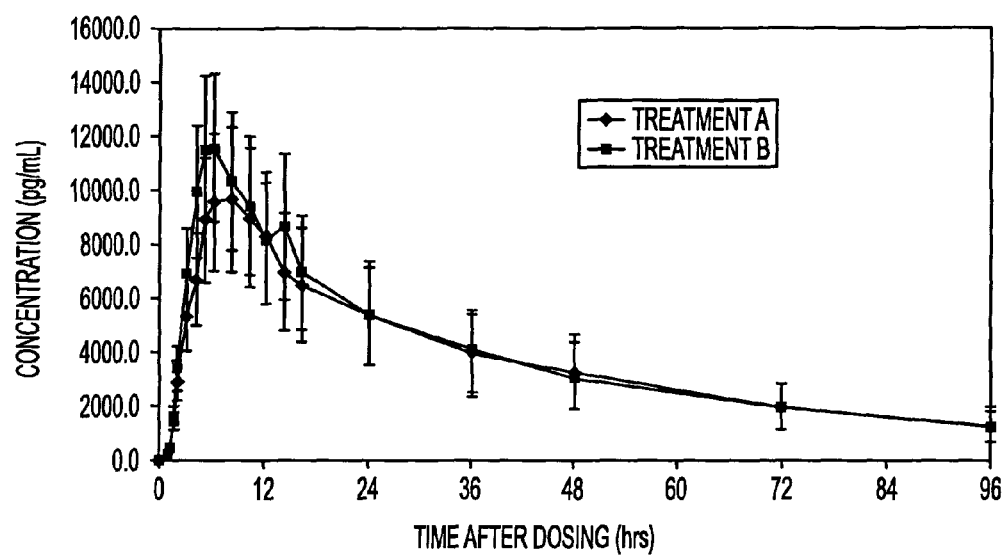
FIG. 38 depicts plasma dextromethorphan concentrations following the administration of 60 mg dextromethorphan hydrobromide and 1200 mg guaifenesin in the fed and fasted conditions.

The plasma concentrations of dextromethorphan is shown in FIG. 38. The resulting pharmacokinetic data is shown in Tables 71 to 73. Subjects given 60 mg dextromethorphan hydrobromide and 1200 mg guaifenesin in an experimental formulation following an overnight fast (Treatment A, Reference) reached a mean dextromethorphan $C_{max}$ of 10722±15966 pg/mL in 6.23±3.55 hours and had an $AUC_{inf}$ of 466518±987204 hr-pg/mL. Subjects given 60 mg dextromethorphan hydrobromide and 1200 mg guaifenesin in an experimental formulation after the consumption of a high fat meal (Treatment B, Test) reached a mean dextromethorphan $C_{max}$ of 12757±17914 pg/mL (132%±69.8% of that of Treatment A) in 5.74±2.27 hours (104%±43.4% of that of Treatment A) and had an $AUC_{inf}$ of 472064±977485 hr-pg/mL (117%±61.5% of that of Treatment A).

TABLE 71

Dextromethorphan Pharmacokinetic Parameters Following the Administration of 60 mg Dextromethorphan Hydrobromide and 1200 mg Guaifenesin in an Experimental Formulation to Normal Volunteers Following an Overnight Fast - Treatment A (Reference)

| Subject | Cmax (pg/mL) | Tmax (hr) | $AUC_{0-t}$ (hr * pg/mL) | $AUC_{inf}$ (hr * pg/mL) | Half life (hr) | Clearance (L/hr) |
|---|---|---|---|---|---|---|
| Mean | 10722 | 6.23 | 372897 | 466518 | 13.8 | 2343 |
| Median | 3020 | 6.0 | 33799 | 34134 | 8.52 | 1287 |
| Std. Dev. | 15966 | 3.55 | 753127 | 987204 | 12.8 | 3352 |
| Std. Err. | 2738 | 0.609 | 129160 | 169304 | 2.19 | 575 |
| % CV | 149 | 57.0 | 202 | 212 | 92.7 | 143 |

TABLE 72

Dextromethorphan Pharmacokinetic Parameters Following the Administration of 60 mg Dextromethorphan Hydrobromide and 1200 mg Guaifenesin to Normal Volunteers After the Consumption of a High Fat Meal - Treatment B (Test)

| Subject | Cmax (pg/mL) | Tmax (hr) | $AUC_{0-t}$ (hr * pg/mL) | $AUC_{inf}$ (hr * pg/mL) | Half life (hr) | Clearance (L/hr) |
|---|---|---|---|---|---|---|
| Mean | 12757 | 5.74 | 381391 | 472064 | 13.5 | 2246 |
| Median | 3470 | 5 | 37515 | 37808 | 7.98 | 1174 |
| Std. Dev. | 17914 | 2.27 | 753249 | 977485 | 13.3 | 2905 |
| Std. Err. | 3028 | 0.384 | 127322 | 165225 | 2.3 | 491 |
| % CV | 140 | 39.6 | 198 | 207 | 98.5 | 129 |

TABLE 73

Ratio of Dextromethorphan Pharmacokinetic Parameters Following the Administration of 60 mg Dextromethorphan Hydrobromide and 1200 mg Guaifenesin After the Consumption of a High Fat Meal Compared to that Following an Overnight Fast (%)

| Subject | Cmax | Tmax | $AUC_{0-t}$ | $AUC_{inf}$ | Half Life | Clearance |
|---|---|---|---|---|---|---|
| Mean | 132 | 104 | 118 | 117 | 98.6 | 100 |
| Median | 124 | 100 | 106 | 106 | 100 | 94.4 |
| Std. Dev. | 69.8 | 43.4 | 62.2 | 61.5 | 18.8 | 35.6 |
| Std. Err. | 12.0 | 7.5 | 10.7 | 10.5 | 3.22 | 6.10 |
| % CV | 52.8 | 41.9 | 52.8 | 52.6 | 19.0 | 35.7 |

In conclusion, there is no food effect on the absorption of guaifenesin from the experimental tablet. There is an effect of food on the rate of absorption of dextromethorphan from the experimental tablet formulation (a small increase in the rate of absorption) but not on the extent of absorption.

Example 21

To determine the relative bioavailability of guaifenesin and dextromethorphan from an experimental modified release formulation containing both guaifenesin and dextromethorphan was compared to reference guaifenesin and dextromethorphan products in normal volunteers an open-label, multiple-dose, randomized, 3-way-crossover study was conducted in 36 subjects.

The subjects were randomized and placed into one of three treatment groups. Group 1 received a 1200-mg controlled-release guaifenesin product (Mucinex) plus 60 mg of dextromethorphan hydrobromide (administered as 30 mg every 6 hours) with 240 mL of water after an overnight fast, and again 12 hours later for 11 twelve-hour dosing periods (Treatment A, Reference). Group 2 received a 1200-mg controlled-release guaifenesin product (Mucinex) plus 60 mg of dextromethorphan hydrobromide (administered as 20 mg every 4 hours) with 240 mL of water after an overnight fast, and again 12 hours later for 11 twelve-hour dosing periods (Treatment B, Reference). Group 3 received an experimental controlled-release tablet containing 1200 mg guaifenesin and 60 mg of dextromethorphan hydrobromide with 240 mL of water after an overnight fast, and again 12 hours later for 11 twelve-hour dosing periods (Treatment C, Test). There was a 14-day washout between doses.

Blood (7 mL, sodium heparin anticoagulant) was obtained at the following times: Day 1 Pre-AM dose, Day 4 Pre-AM dose and Day 5 Pre-AM dose for all three treatment groups. On Day 6 Treatment A subjects were bled at: Pre-Dose, 0.5, 0.75, 1, 1.5, 2, 3, 4, 5, 6, 6.5, 6.75, 7,7.5, 8, 9, 10, 11, 12, 14, 16, 24, 36, 48, 72, and 96 hours post dose. Treatment B subjects were bled at: Pre-dose, 0.5, 0.75, 1, 1.5, 2, 3, 4, 4.5, 4.75, 5, 5.5, 6, 7, 8, 8.5, 8.75, 9, 9.5, 10, 11, 12, 14, 16, 24, 36, 48, 72 and 96 hours post dose. On Day 6, Treatment C subjects were bled at: Pre-dose, 0.5, 0.75, 1, 1.5, 2, 3, 4, 5, 6, 8, 10, 12, 14, 16, 24, 36, 48, 72 and 96 hours post dose (the total blood loss for guaifenesin and dextromethorphan analysis was 588 mL).

Subjects given 1200 mg of guaifenesin as Mucinex, along with 60 mg dextromethorphan hydrobromide as two 30-mg doses 6 hours apart (Treatment A, Reference), reached a mean steady-state plasma guaifenesin $C_{max}$ of 1935 ng/mL in 1.27 hours after the last dose (121 hours after the first dose); had a $C_{min}$ of 75.5 ng/mL, a $C_{AVE}$ of 631 ng/mL and an $AUC_{Steady\ State}$ of 7540 hr-ng/mL. Subjects given 1200 mg of guaifenesin as Mucinex, along with 60 mg dextromethorphan hydrobromide as three 20-mg doses 4 hours apart (Treatment B, Reference), reached a mean steady-state plasma guaifenesin $C_{max}$ of 1938 ng/mL in 0.850 hours after the last dose (121 hours after the first dose), had a $C_{min}$ of 59.6 ng/mL, a $C_{AVE}$ of 618 ng/mL and an $AUC_{Steady\ State}$ of 7403 hr-ng/mL. Subjects given 1200 mg guaifenesin as an experimental formulation, also containing 60 mg dextromethorphan hydrobromide (Treatment C, Test), reached a mean steady-state plasma guaifenesin $C_{max}$ of 1780 ng/mL in 1.35 hours after the last dose (121 hours after the first dose), had a $C_{min}$ of 18.2 ng/mL, a $C_{AVE}$ of 601 ng/mL and an $AUC_{Steady\ State}$ of 7138 hr-ng/mL.

Subjects given 60 mg dextromethorphan hydrobromide as 30 mg Vick's Formula 44 Cough Medicine along with 1200 mg guaifenesin as Mucinex and a second 30-mg dextromethorphan hydrobromide dose 6 hours later (Treatment A, Reference), reached a mean steady-state plasma dextromethorphan $C_{max}$ of 17960 pg/mL in 5.03 hours after the last dose (125 hours after the first dose), had a $C_{min}$ of 11949 pg/mL, a $C_{AVE}$ of 15167 pg/mL and an $AUC_{Steady\ State}$ of 181904 hr-pg/mL. Subjects given 60 mg dextromethorphan hydrobromide as three 20-mg doses of Vick's Formula 44 Cough Medicine four hours apart, along with 1200 mg of guaifenesin as Mucinex (Treatment B, Reference), reached a mean steady-state plasma dextromethorphan $C_{max}$ of 17251 pg/mL in 5.91 hours after the last dose (126 hours after the first dose), had a $C_{min}$ of 11018 pg/mL, a $C_{AVE}$ of 14097 pg/mL and an $AUC_{Steady\ State}$ of 169160 hr-pg/mL. Subjects given 60 mg dextromethorphan hydrobromide and 1200 mg guaifenesin as an experimental formulation (Treatment C, Test), reached a mean steady-state plasma dextromethorphan $C_{max}$ of 17213 pg/mL in 5.10 hours after the last dose (125 hours after the first dose), had a $C_{min}$ of 10978 pg/mL, a $C_{AVE}$ of 14609 pg/mL and an $AUC_{Steady\ State}$ of 175309 hr-pg/mL.

Figure 39:
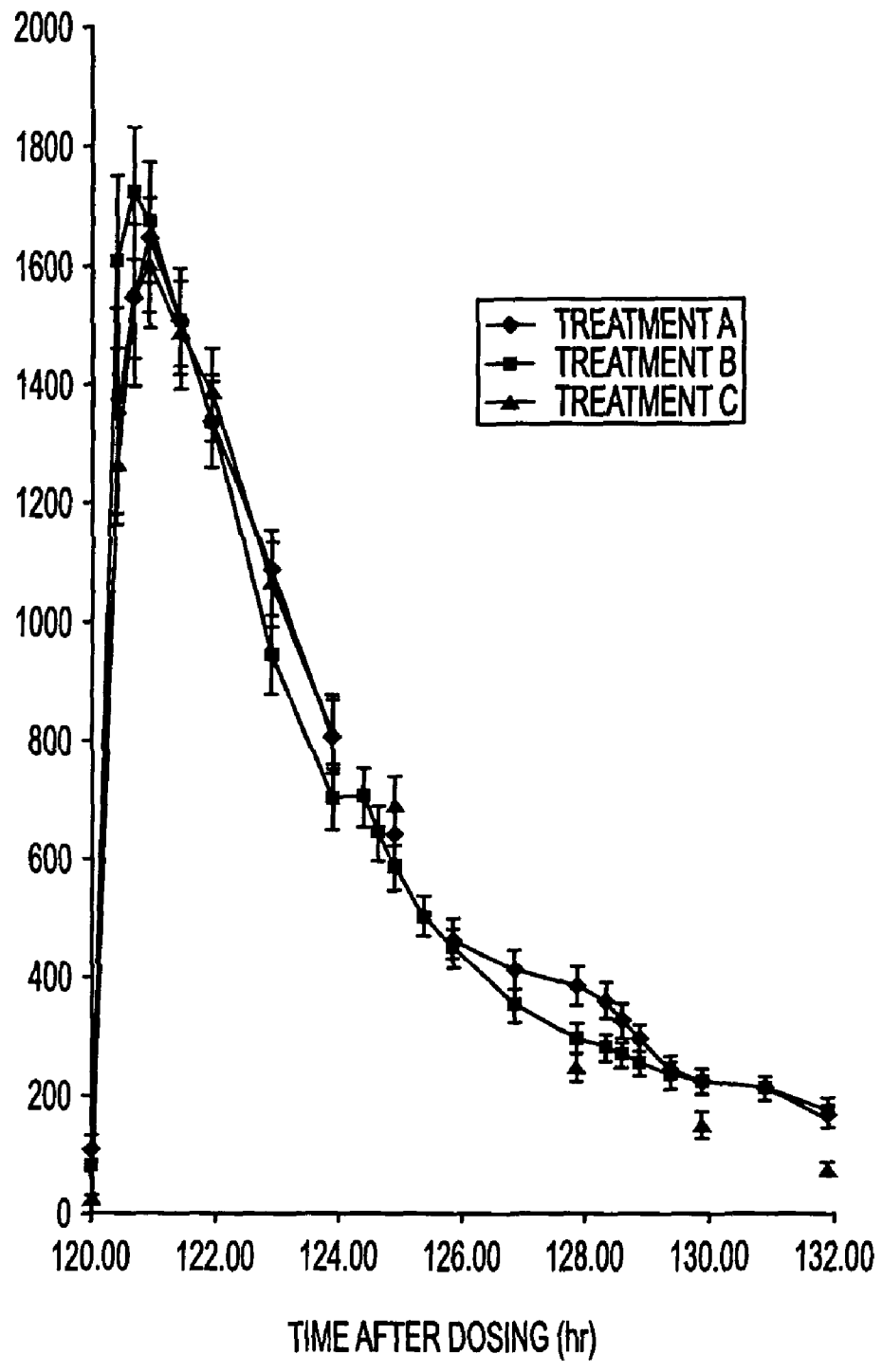
FIG. 39 depicts steady-state plasma concentrations of guaifenesin following the multiple dose administration of 1200 mg guaifenesin in different formulations.
Figure 40:
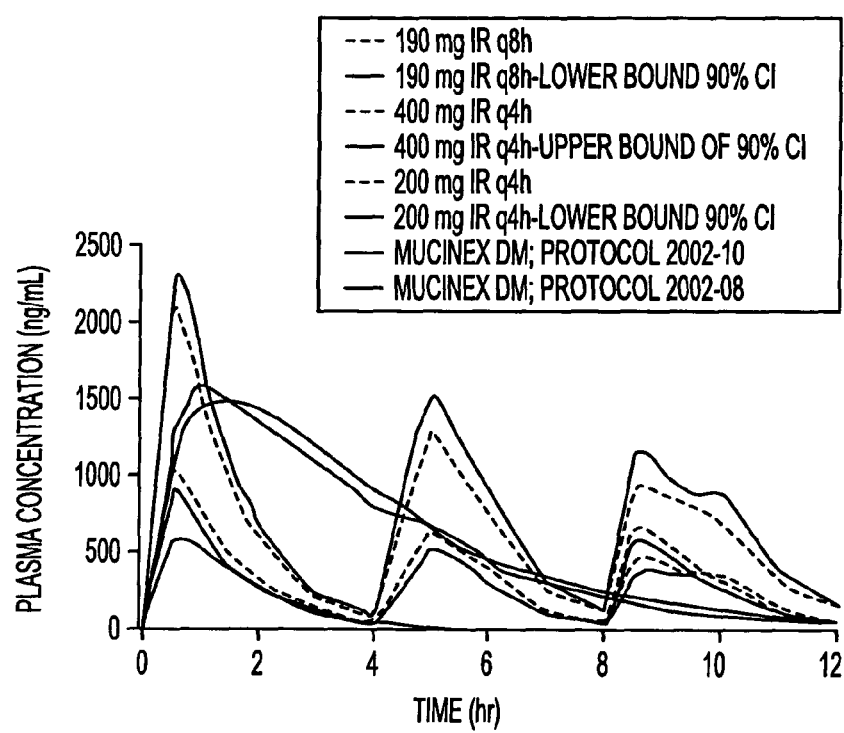
FIG. 40 depicts mean steady-state guaifenesin plasma concentration-time profiles.

The plasma concentrations of guaifenesin are shown in FIGS. 39 and 40. The resulting pharmacokinetic data are shown in Tables 74 through 76. Subjects given 1200 mg of guaifenesin as Mucinex, along with 60 mg dextromethorphan hydrobromide as two 30-mg doses 6 hours apart (Treatment A, Reference), reached a mean steady-state plasma guaifenesin $C_{max}$ of 1935±746 ng/mL at 121±0.854 hours after the first dose (1.27 hours after the last dose), had a $C_{min}$ of 75.5±73.9 ng/mL, a $C_{AVE}$ of 631±212 ng/mL and an $AUC_{Steady\ State}$ of 7540±2570 hr-ng/mL. Subjects given 1200 mg of guaifenesin as Mucinex, along with 60 mg dextromethorphan hydrobromide as three 20-mg doses 4 hours apart (Treatment B, Reference), reached a mean steady-state plasma guaifenesin $C_{max}$ of 1938±637 ng/mL at 121±0.463 hours after the first dose (0.850 hours after the last dose), had a $C_{min}$ of 59.6±51.9 ng/mL, a $C_{AVE}$ of 618±205 ng/mL and an $AUC_{Steady\ State}$ of 7403±2474 hr-ng/mL. Subjects given 1200 mg guaifenesin as an experimental formulation, also containing 60 mg dextromethorphan hydrobromide (Treatment C, Test), reached a mean steady-state plasma guaifenesin $C_{max}$ of 1780±633 ng/mL at 121±0.864 hours after the first dose (1.35 hours after the last dose), had a $C_{min}$ of 18.2±18.3 ng/mL, a $C_{AVE}$ of 601±189 ng/mL and an $AUC_{Steady\ State}$ of 7138±2268 hr-ng/mL.

TABLE 74

Steady-State Guaifenesin Pharmacokinetic Parameters Following the Administration of 1200 mg Guaifenesin as Mucinex Every 12 Hours for 11 Doses and 60 mg Dextromethorphan Hydrobromide as 30 mg Vick's Formula 44 Every 6 Hours for 22 Doses to Normal Volunteers (Treatment A, Reference)

| Subject | $AUC_{ss}$ (hr-ng/mL) | $C_{min}$ (ng/mL) | $C_{max}$ (ng/mL) | $T_{max}$ (hr) | $C_{average}$ (ng/mL) | % Ptf (%) | % Swing (%) | $L_z$ (hr$^{-1}$) | $T_{1/2}$ (hr) |
|---|---|---|---|---|---|---|---|---|---|
| Mean | 7540 | 75.5 | 1935 | 122 | 631 | 296 | 5828 | 0.270 | 3.11 |
| Median | 7366 | 59.0 | 1910 | 121 | 614 | 297 | 2962 | 0.226 | 3.07 |
| Std. Dev. | 2570 | 73.9 | 746 | 0.854 | 212 | 56.2 | 6702 | 0.151 | 1.26 |
| Std. Error | 441 | 12.7 | 128 | 0.146 | 36.4 | 9.64 | 1149 | 0.026 | 0.217 |
| % CV | 34.1 | 97.9 | 38.6 | 0.704 | 33.7 | 19.0 | 115 | 55.8 | 40.6 |

TABLE 75

Steady-State Guaifenesin Pharmacokinetic Parameters Following the Administration of 1200 mg Guaifenesin as Mucinex Every 12 Hours for 11 Doses and 60 mg Dextromethorphan Hydrobromide as 20 mg Vick's Formula 44 Every 4 Hours for 22 Doses to Normal Volunteers (Treatment B, Reference)

| Subject | $AUC_{ss}$ (hr-ng/mL) | $C_{min}$ (ng/mL) | $C_{max}$ (ng/mL) | $T_{max}$ (hr) | $C_{average}$ (ng/mL) | % Ptf (%) | % Swing (%) | $L_z$ (hr$^{-1}$) | $T_{1/2}$ (hr) |
|---|---|---|---|---|---|---|---|---|---|
| Mean | 7403 | 59.6 | 1938 | 121 | 618 | 313 | 7215 | 0.269 | 3.22 |
| Median | 7230 | 36.1 | 1910 | 121 | 603 | 294 | 3173 | 0.227 | 3.05 |
| Std. Dev. | 2474 | 51.9 | 637 | 0.463 | 205 | 72 | 8948 | 0.164 | 1.36 |
| Std. Error | 424 | 8.90 | 109 | 0.079 | 35.2 | 12.4 | 1535 | 0.028 | 0.232 |
| % CV | 33.4 | 87.1 | 32.9 | 0.383 | 33.2 | 23.2 | 124 | 61.0 | 42.1 |

TABLE 76

Steady-State Guaifenesin Pharmacokinetic Parameters Following the Administration of 1200 mg Guaifenesin and 60 mg Dextromethorphan Hydrobromide in an Experimental Formulation Every 12 Hours for 11 Doses to Normal Volunteers (Treatment C, Reference)

| Subject | $AUC_{ss}$ (hr-ng/mL) | $C_{min}$ (ng/mL) | $C_{max}$ (ng/mL) | $T_{max}$ (hr) | $C_{average}$ (ng/mL) | % Ptf (%) | % Swing (%) | $L_z$ (hr$^{-1}$) | $T_{1/2}$ (hr) |
|---|---|---|---|---|---|---|---|---|---|
| Mean | 7138 | 18.2 | 1780 | 121 | 601 | 292 | 14215 | 0.431 | 1.91 |
| Median | 6992 | 13.7 | 1770 | 121 | 583 | 291 | 10240 | 0.414 | 1.67 |
| Std. Dev. | 2268 | 18.3 | 633 | 0.864 | 189 | 45.2 | 11362 | 0.177 | 0.832 |
| Std. Error | 395 | 3.18 | 110 | 0.150 | 32.8 | 7.88 | 1978 | 0.031 | 0.145 |
| % CV | 31.8 | 101 | 35.6 | 0.712 | 31.4 | 15.5 | 79.9 | 41.1 | 43.6 |

Figure 41:
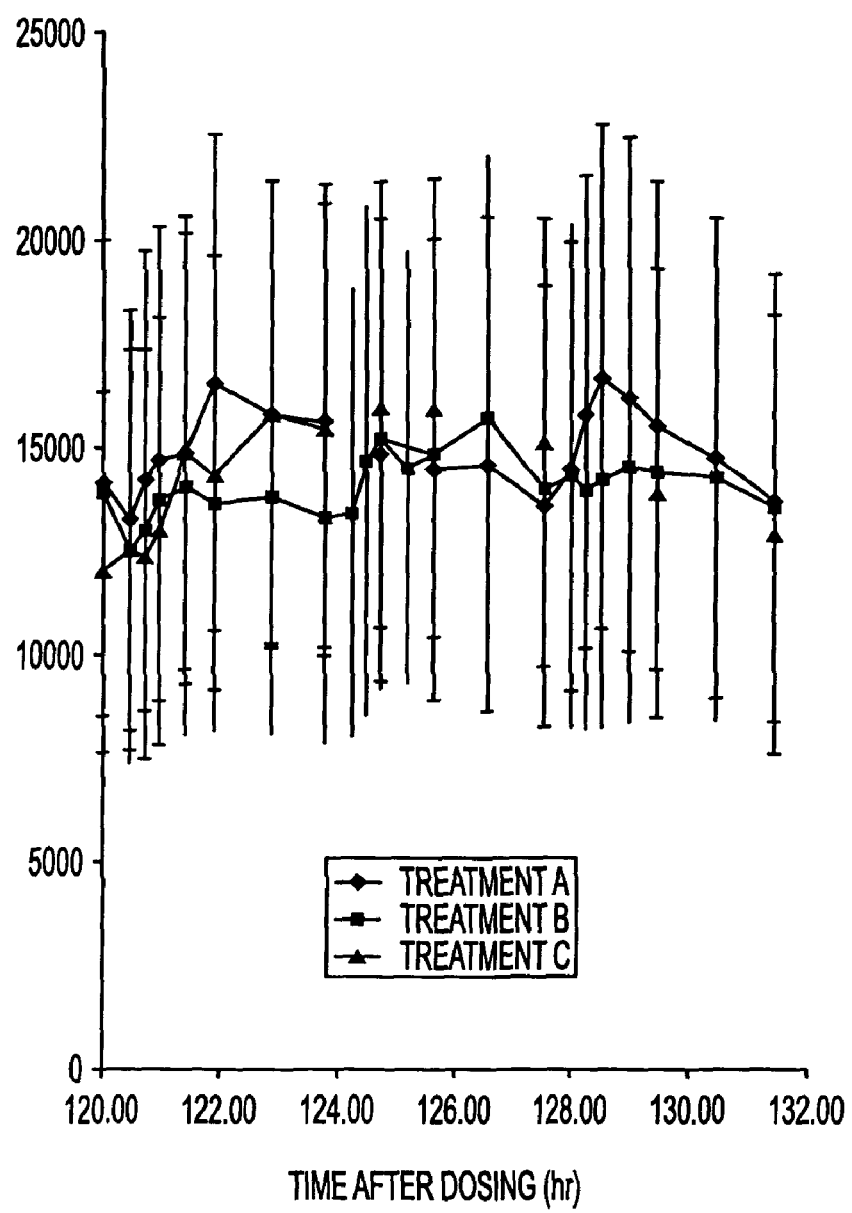
FIG. 41 depicts steady-state plasma concentrations of dextromethorphan following the multiple dose administration of 60 mg dextromethorphan hydrobromide in different formulations and/or different dosage rates.
Figure 42:
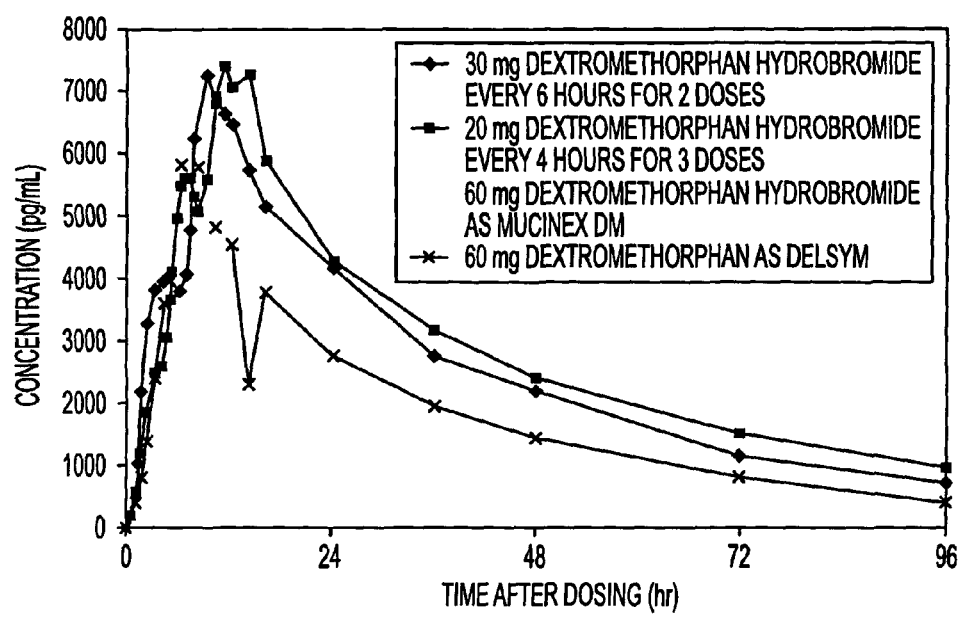
FIG. 42 depicts dextromethorphan plasma concentrations following the administration of 60 mg dextromethorphan hydrobromide in different formulations and dosage rate.
Figure 43:
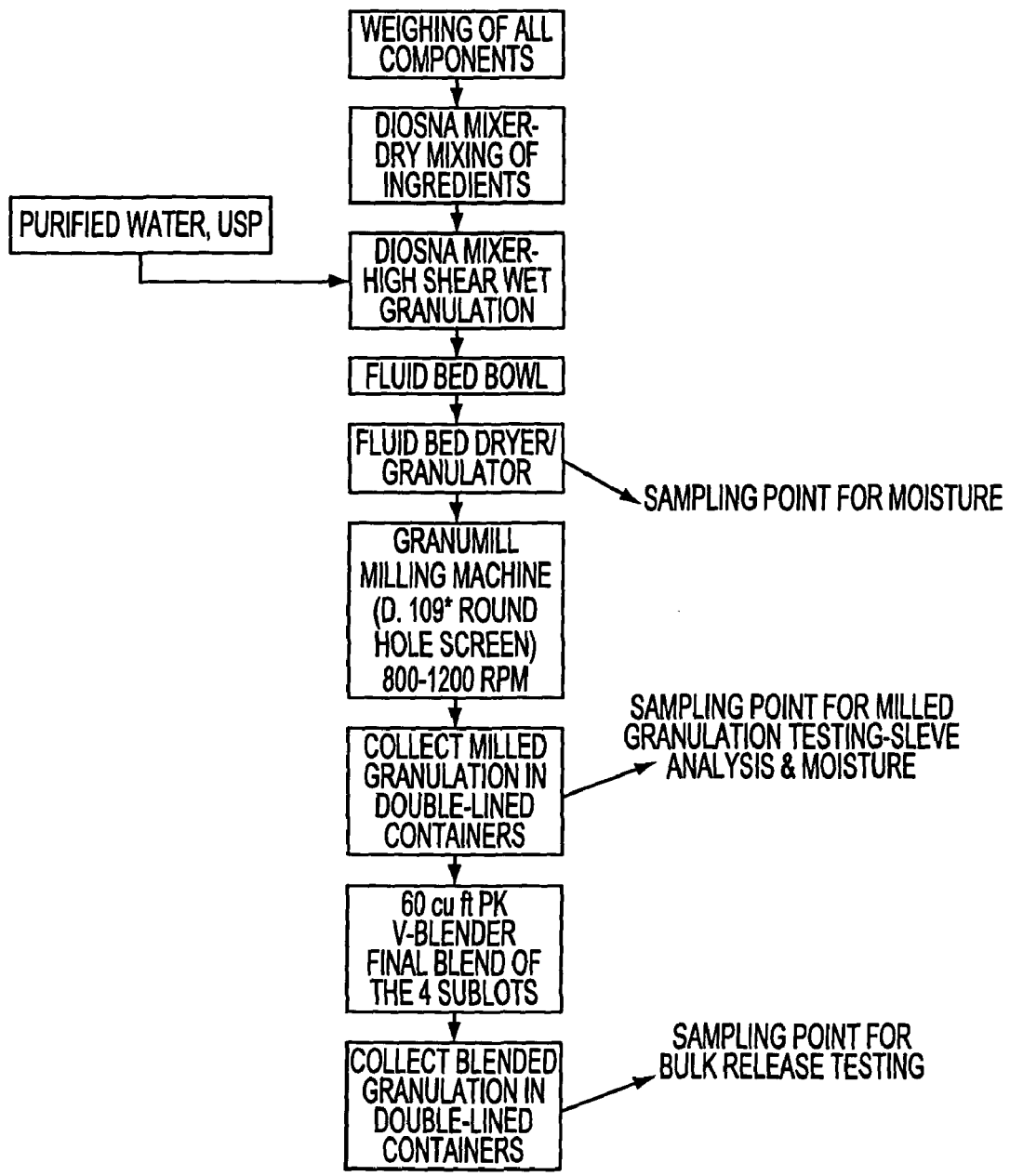
FIG. 43 depicts a process flow diagram for the manufacture of guaifenesin DC (95%).
Figure 44:
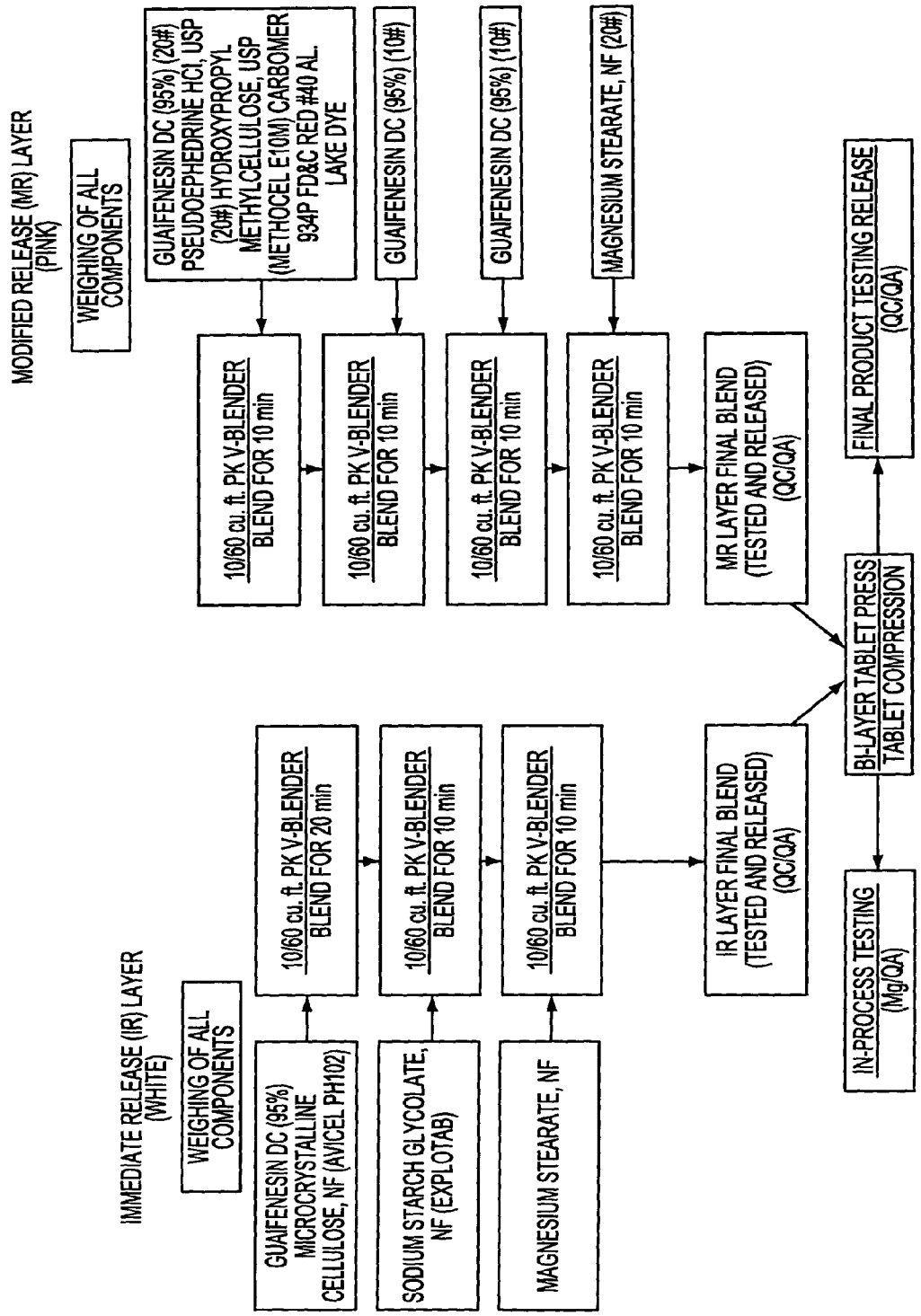
FIG. 44 depicts a process flow diagram for a guaifenesin/pseudoephedrine product (1200/120 mg) tablets.
Figure 45:
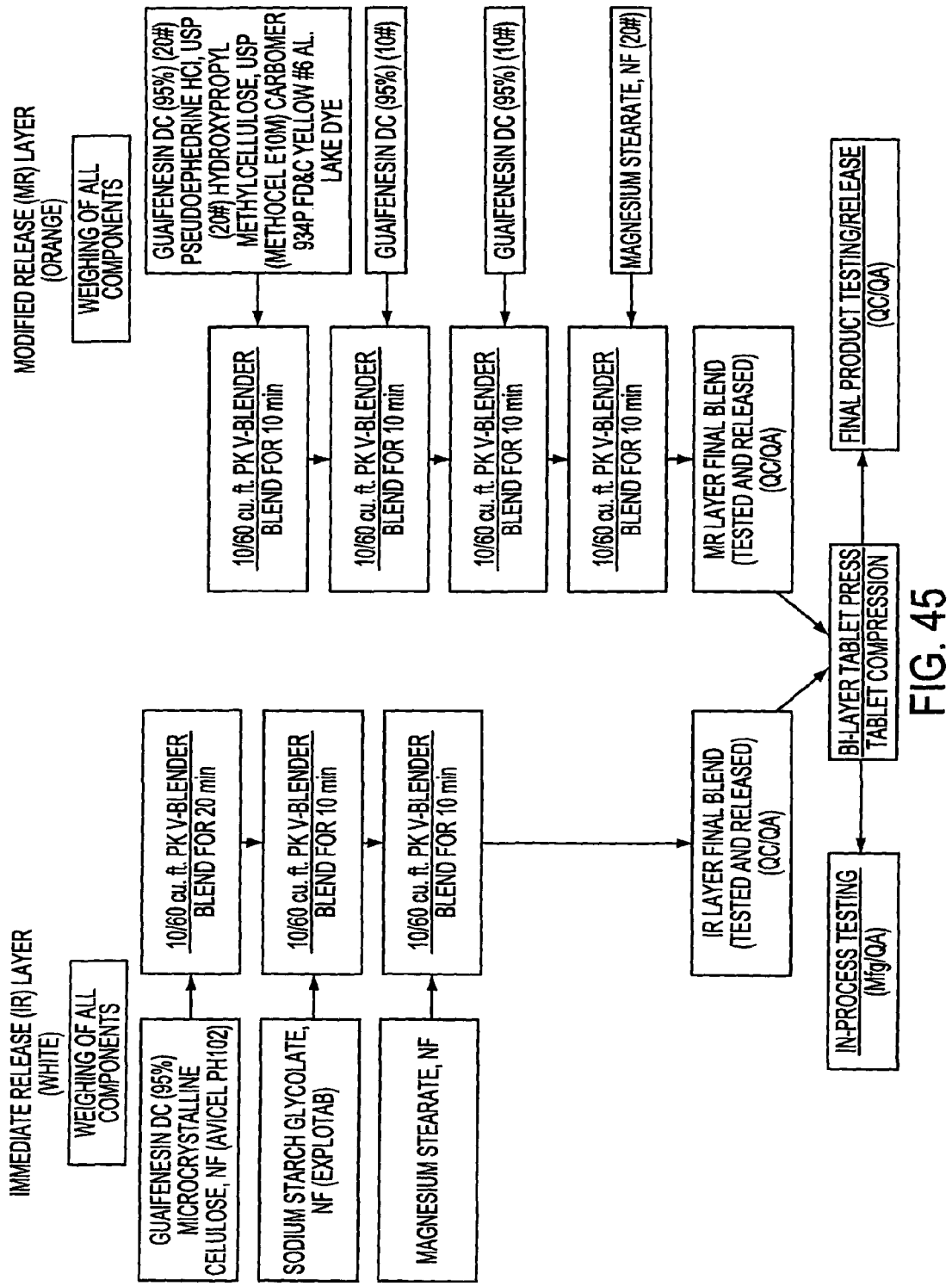
FIG. 45 depicts a process flow diagram for guaifenesin/pseudoephedrine product (600/60 mg) tablets.

The plasma concentrations of dextromethorphan are shown in FIGS. 41 and 42. The resulting pharmacokinetic data are shown in Tables 77 through 79. Subjects given 60 mg dextromethorphan hydrobromide as 30 mg Vick's Formula 44 Cough Medicine, along with 1200 mg guaifenesin as Mucinex and a second 30-mg dextromethorphan hydrobromide dose 6 hours later (Treatment A, Reference), reached a mean steady-state plasma dextromethorphan $C_{max}$ of 17960±37537 pg/mL at 125±2.94 hours after the first dose (5.03 hours after the last dose), had a $C_{min}$ of 11949±28101 pg/mL, a $C_{AVE}$ of 15167±33349 pg/mL and an $AUC_{Steady\ State}$ of 181904±400226 hr-pg/mL. Subjects given 60 mg dextromethorphan hydrobromide as three 20-mg doses of Vick's Formula 44 Cough Medicine 4 hours apart, along with 1200 mg of guaifenesin as Mucinex (Treatment B, Reference), reached a mean steady-state plasma dextromethorphan $C_{max}$ of 17251±39562 pg/mL, at 126±1.73 hours after the first dose (5.91 hours after the last dose), had a $C_{min}$ of 11018±26007 pg/mL, a $C_{AVE}$ of 14097±33537 pg/mL and an $AUC_{Steady\ State}$ of 169160±402449 hr-pg/mL. Subjects given 60 mg dextromethorphan hydrobromide and 1200 mg guaifenesin as an experimental formulation (Treatment C, Test), reached a mean steady-state plasma dextromethorphan $C_{max}$ of 17213±33703 pg/mL at 125±1.62 hours (5.10 hours after the last dose), had a $C_{min}$ of 10978±24713 pg/mL, a $C_{AVE}$ of 14609±30804 pg/mL and an $AUC_{Steady\ State}$ of 175309±369653 hr-pg/mL.

TABLE 77

Steady-State Dextromethorphan Pharmacokinetic Parameters Following the Administration of 1200 mg Guaifenesin as Mucinex Every 12 Hours for 11 Doses and 60 mg Dextromethorphan Hydrobromide as 30 mg Vick's Formula 44 Every 6 Hours for 22 Doses to Normal Volunteers (Treatment A, Reference)

| Subject | $AUC_{ss}$ (hr-pg/mL) | $C_{min}$ (pg/mL) | $C_{max}$ (pg/mL) | $T_{max}$ (hr) | $C_{average}$ (pg/mL) | % Ptf (%) | % Swing (%) | $L_z$ (hr$^{-1}$) | $T_{1/2}$ (hr) |
|---|---|---|---|---|---|---|---|---|---|
| Mean | 181904 | 11949 | 17960 | 125 | 15167 | 56.4 | 80.0 | 0.108 | 8.67 |
| Median | 39400 | 2270 | 4100 | 124 | 3312 | 53.1 | 73.1 | 0.113 | 6.13 |
| Std. Dev. | 400226 | 28101 | 37537 | 2.94 | 33349 | 19.7 | 37.7 | 0.045 | 8.50 |
| Std. Error | 68638 | 4819 | 6438 | 0.503 | 5719 | 3.38 | 6.47 | 0.008 | 1.46 |
| % CV | 220 | 235 | 209 | 2.35 | 220 | 35.0 | 47.2 | 41.4 | 98.1 |

TABLE 78

Steady-State Dextromethorphan Pharmacokinetic Parameters Following the Administration of 1200 mg Guaifenesin as Mucinex Every 12 Hours for 11 Doses and 60 mg Dextromethorphan Hydrobromide as 20 mg Vick's Formula 44 Every 4 Hours for 22 Doses to Normal Volunteers (Treatment B, Reference)

| Subject | $AUC_{ss}$ (hr-pg/mL) | $C_{min}$ (pg/mL) | $C_{max}$ (pg/mL) | $T_{max}$ (hr) | $C_{average}$ (pg/mL) | % Ptf (%) | % Swing (%) | $L_z$ (hr$^{-1}$) | $T_{1/2}$ (hr) |
|---|---|---|---|---|---|---|---|---|---|
| Mean | 169160 | 11018 | 17251 | 126 | 14097 | 57.2 | 78.4 | 0.090 | 11.8 |
| Median | 36778 | 2280 | 4250 | 126 | 3065 | 58.7 | 75.6 | 0.075 | 9.27 |
| Std. Dev. | 402449 | 26007 | 39562 | 1.73 | 33537 | 19.0 | 32.1 | 0.054 | 9.54 |
| Std. Error | 69019 | 4460 | 6785 | 0.297 | 5752 | 3.26 | 5.51 | 0.009 | 1.64 |
| % CV | 238 | 236 | 229 | 1.38 | 238 | 33.2 | 41.0 | 59.7 | 80.9 |

TABLE 79

Steady-State Dextromethorphan Pharmacokinetic Parameters Following the Administration of 1200 mg Guaifenesin and 60 mg Dextromethorphan Hydrobromide in an Experimental Formulation Every 12 Hours for 11 Doses to Normal Volunteers (Treatment C, Reference)

| Subject | $AUC_{ss}$ (hr-pg/mL) | $C_{min}$ (pg/mL) | $C_{max}$ (pg/mL) | $T_{max}$ (hr) | $C_{average}$ (pg/mL) | % Ptf (%) | % Swing (%) | $L_z$ $(hr^{-1})$ | $T_{1/2}$ (hr) |
|---|---|---|---|---|---|---|---|---|---|
| Mean | 175309 | 10978 | 17213 | 125 | 14609 | 74.0 | 129 | 0.112 | 7.84 |
| Median | 37663 | 1855 | 4355 | 125 | 3139 | 73.4 | 126 | 0.113 | 6.12 |
| Std. Dev. | 369653 | 24713 | 33703 | 1.62 | 30804 | 23.2 | 56.3 | 0.042 | 5.71 |
| Std. Error | 64348 | 4302 | 5867 | 0.282 | 5362 | 4.04 | 9.80 | 0.007 | 0.994 |
| % CV | 211 | 225 | 196 | 1.30 | 211 | 31.4 | 43.6 | 37.6 | 72.8 |

In conclusion, guaifenesin in the experimental tablet is bioequivalent to that of the Reference, Mucinex, in terms of $C_{max}$ and $AUC_{ss}$, as the 90% confidence intervals are all contained within 80% to 125%. Dextromethorphan hydrobromide in the experimental tablet is bioequivalent to both 30 mg dextromethorphan hydrobromide every 6 hours, and 20 mg every 4 hours, in terms of $C_{max}$ and $AUC_{ss}$, as the 90% confidence intervals are contained within 80% to 125%.

Other embodiments and uses of the invention will be apparent to those of skill in the art from consideration of the specification and practice of the invention disclosed herein. The specification and examples should be considered exemplary only with the true scope and spirit of the invention indicated by the following claims. As will be easily understood by those of skill in the art, variations and modifications of each of the disclosed embodiments can be easily made within the scope of this invention as defined by the following claims.

What is claimed is:

1. A drug product comprising guaifenesin and dextromethorphan and having two portions,
   wherein a first portion comprises guaifenesin in an immediate release form, which releases guaifenesin in a human's stomach, and a second portion comprises guaifenesin in a sustained release form,
   wherein the drug product contains 1200 mg of guaifenesin and provides a mean $C_{max}$ and at least one of a mean $AUC_{inf}$ and a mean $AUC_{0-12}$ for guaifenesin under fasted conditions based on single-dose administration that are from 80% to 125% of the mean $C_{max}$ and at least one of the mean $AUC_{inf}$ and the mean $AUC_{0-12}$ for guaifenesin provided by a bi-layer tablet containing 1200 mg of guaifenesin and having an immediate release layer consisting essentially of about 210.5 mg of guaifenesin dc, about 117.5 mg of microcrystalline cellulose, about 30 mg of sodium starch glycolate, and about 1 mg of magnesium stearate, and a sustained release layer consisting essentially of about 1052.7 mg of guaifenesin dc, about 25 mg of hydroxypropyl methyl cellulose, about 12.5 mg of carbomer 934P, about 5.7 mg of magnesium stearate, and a colorant, and
   wherein guaifenesin is absorbed into bloodstream such that the drug product can be appropriately dosed once in a 12-hour period.

2. The drug product according to claim 1, wherein the mean $C_{max}$ and at least one of the mean $AUC_{inf}$ and the mean $AUC_{0-12}$ for guaifenesin provided by the drug product are from 80% to 125% of the mean $C_{max}$ and at least one of the mean $AUC_{inf}$ and the mean $AUC_{0-12}$ for guaifenesin provided by the bi-layer tablet at a 90% confidence interval.

3. The drug product according to claim 1, which contains 60 mg of dextromethorphan.

4. The drug product according to claim 1, wherein the first and second portions are discrete.

5. A drug product comprising guaifenesin and dextromethorphan and having two portions,
   wherein a first portion comprises guaifenesin in an immediate release form, which releases guaifenesin in a human subject's stomach, and a second portion comprises guaifenesin in a sustained release form,
   wherein the drug product contains 600 mg of guaifenesin and provides a mean $C_{max}$ and at least one of a mean $AUC_{inf}$ and a mean $AUC_{0-12}$ for guaifenesin under fasted conditions based on single-dose administration that are from 80% to 125% of the mean $C_{max}$ and at least one of the mean $AUC_{inf}$ and the mean $AUC_{0-12}$ for guaifenesin provided by a bi-layer tablet containing 600 mg of guaifenesin and having an immediate release layer consisting essentially of about 105.25 mg of guaifenesin dc, about 58.75 mg of microcrystalline cellulose, about 15 mg of sodium starch glycolate, and about 0.5 mg of magnesium stearate, and a sustained release layer consisting essentially of about 526.35 mg of guaifenesin dc, about 12.5 mg of hydroxypropyl methyl cellulose, about 6.25 mg of carbomer 934P, about 2.85 mg of magnesium stearate, and a colorant, and
   wherein guaifenesin is absorbed into bloodstream such that the drug product can be appropriately dosed once in a 12-hour period.

6. The drug product according to claim 5, wherein the mean $C_{max}$ and at least on of the mean $AUC_{inf}$ and the mean $AUC_{0-12}$ for guaifenesin provided by the drug product are from 80% to 125% of the mean $C_{max}$ and at least one of the mean $AUC_{inf}$ and the mean $AUC_{0-12}$ for guaifenesin provided by the bi-layer tablet at a 90% confidence interval.

7. The drug product according to claim 5, which contains 30 mg of dextromethorphan.

8. The drug product according to claim 5, wherein the first and second portions are discrete.

* * * * *